United States Patent [19]

Pearson et al.

[11] Patent Number: 4,816,452
[45] Date of Patent: Mar. 28, 1989

[54] AMINOTHIAZOLE SUBSTITUTED PENICILLINS AND ANTIBACTERIAL COMPOSITIONS THEREOF

[75] Inventors: Michael J. Pearson; Richard L. Elliott, both of Betchworth, Great Britain

[73] Assignee: Beecham Group P.L.C., England

[21] Appl. No.: 890,709

[22] Filed: Jul. 25, 1986

[30] Foreign Application Priority Data

Jul. 25, 1985 [GB] United Kingdom ................. 8518869
May 3, 1986 [GB] United Kingdom ................. 8610910

[51] Int. Cl.$^4$ ..................... A61K 31/43; C01D 199/54
[52] U.S. Cl. .................................... 514/196; 540/316; 540/328
[58] Field of Search ................. 540/316, 328; 514/196; 548/194

[56] References Cited

U.S. PATENT DOCUMENTS

| | | | |
|---|---|---|---|
| 3,936,443 | 2/1976 | Gregson et al. | 540/328 |
| 4,284,631 | 8/1981 | Takaya et al. | 548/194 X |
| 4,344,939 | 8/1982 | Niemers et al. | 540/328 X |
| 4,376,203 | 3/1983 | Heyles et al. | 548/194 |
| 4,507,487 | 3/1985 | Kamachi et al. | 548/194 |

FOREIGN PATENT DOCUMENTS 0045937 2/1982 European Pat. Off. .
1399087 6/1975 United Kingdom .
1536281 12/1978 United Kingdom .

OTHER PUBLICATIONS

Chem. Abs. (1977), 87, p. 480, 53335r.

Primary Examiner—Werren B. Lone
Assistant Examiner—Vera C. Clarke
Attorney, Agent, or Firm—Jacobs & Jacobs

[57] ABSTRACT

The present invention provides a compound of formula (I) or a pharmaceutically acceptable salt or in-vivo hydrolysable ester thereof:

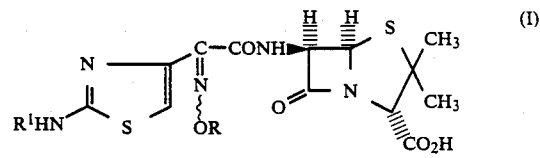

wherein $R^1$ is hydrogen or an amino protecting group and R is substituted methyl; optionally substituted $C_{2-12}$ alkyl, alkenyl or alkynyl; carbocyclyl; aryl or heterocyclyl. These compounds have antibacterial properties, and therefore are of use in the treatment of bacterial infections in humans and animals caused by a wide range of organisms.

24 Claims, No Drawings

AMINOTHIAZOLE SUBSTITUTED PENICILLINS AND ANTIBACTERIAL COMPOSITIONS THEREOF

This invention relates to novel β-lactam containing compounds, their preparation and their use, and in particular to a novel class of penicillins. These compounds have antibacterial properties, and therefore are of use in the treatment of bacterial infections in humans and animals caused by a wide range of organisms.

British Patent Specification No. 1 399 087 discloses a novel class of penicillin antibiotics containing a 6β-(α-etherified oxyimino)-acylamino group.

The present invention provides a compound of formula (I) or a pharmaceutically acceptable salt or in-vivo hydrolysable ester thereof:

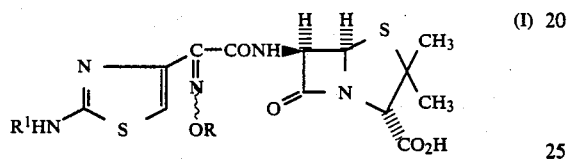

wherein $R^1$ is hydrogen or an amino protecting group and R is substituted methyl; optionally substituted $C_{2-12}$ alkyl, alkenyl or alkynyl; carbocyclyl; aryl or heterocyclyl.

Substituents that may be present on those groups R defined hereinabove as being substituted or optionally substituted include carboxyl, esterified carboxy, carbonyl, hydroxy, alkoxy, alkoxyimino, cyano, carbamoyl, N-substituted carbamoyl, aryloxy, aralkoxy, mercapto, alkylthio, arylthio, amino, substituted amino, halo, nitro, azido, formyl, acyl, acyloxy, phthalimido, acylamino, alkoxycarbonylamino, aralkoxy-carbonylamino, aryl, heterocyclyl and carbocyclyl.

When R is substituted methyl, the preferred substituents are carbocyclyl, aryl, heterocyclyl, cyano, carboxyl, esterified carboxy, carbamoyl and N-substituted carbamoyl, alkylthio, arylthio and halo.

Suitable $C_{2-12}$ alkyl groups include straight and branched chain alkyl groups containing 2 to 12 carbon atoms. Preferred alkyl groups contain 2 to 6 carbon atoms, such as t-butyl.

Suitable $C_{2-12}$ alkenyl groups include straight and branched chain alkenyl groups containing 2 to 12 carbon atoms. Preferred alkenyl groups contain 2 to 6 carbon atoms, such as propenyl and butenyl.

Suitable $C_{2-12}$ alkynyl groups include straight and branched chain alkynyl groups containing 2 to 12 carbon atoms. Preferred alkynyl groups contain 2 to 6 carbon atoms such as propynyl and butynyl.

The term "carbocyclyl" herein denotes single or fused aromatic or partly or wholly saturated carbocyclic rings, optionally substituted with one or more groups, which may be the same or different, selected from optionally substituted $C_{1-6}$ alkyl, optionally substituted $C_{2-6}$ alkenyl, optionally substituted $C_{2-6}$ alkynyl, optionally substituted exo-methylene, carboxyl, $C_{1-6}$ alkoxycarbonyl, oxo, hydroxy, $C_1$-$C_6$ alkoxyimino, oxyimino, $C_{1-6}$ alkoxy, cyano, carbamoyl, N-substituted carbamoyl, aryloxy, aralkoxy, mercapto, alkylthio, arylthio, amino, substituted amino, halo, nitro, azido, formyl, acyl, acyloxy, phthalimido, acylamino, alkoxycarbonylamino, aralkoxy-carbonylamino, aryl, heterocyclyl and carbocyclyl. Suitable substituents for $C_{1-6}$ alkyl, $C_{2-6}$ alkenyl, $C_{2-6}$ alkynyl and exo-methylene include those referred to above as substituents for R. Preferably the carbocyclic system comprises between one and four rings, attached via a non-aromatic ring carbon atom thereof.

Suitable carbocyclyl groups include optionally substituted $C_{3-12}$, preferably $C_{4-8}$, cycloalkyl; optionally substituted $C_{6-12}$, preferably $C_{7-10}$, bicycloalkyl; optionally substituted $C_{7-14}$, preferably $C_{9-12}$, tricycloalkyl; optionally substituted $C_{7-14}$, preferably $C_{10-14}$, tetracycloalkyl; optionally substituted $C_{4-12}$, preferably $C_{5-8}$, cycloalkenyl; optionally substituted $C_{6-12}$, preferably $C_{7-10}$, bicycloalkenyl; and optionally substituted $C_{8-14}$, preferably $C_{10-14}$, tricycloalkenyl. Examples of carbocyclyl groups include indan-2-yl.

Suitable $C_{3-12}$ cycloalkyl groups include cyclopentyl, cyclohexyl, cycloheptyl and cyclooctyl.

Suitable $C_{6-12}$ bicycloalkyl groups include bicyclo [2.2.1]heptyl (norbornyl) and bicyclo[2.2.2]octyl.

Suitable $C_{4-12}$ cycloalkenyl groups include cyclopentenyl and cyclohexenyl.

Examples of $C_{6-12}$ bicycloalkenyl groups include 6,6-dimethylbicyclo[3.1.1]hept-2-en-yl, and 5-norbornen-2-yl.

Suitable $C_{7-14}$ tricycloalkyl groups include adamantyl.

Suitable $C_{7-14}$ tetracycloalkyl groups include tetracyclo $[7.2.1.0^{4,11}.0^{6,10}]$dodecanyl.

Suitable $C_{8-14}$ tricycloalkenyl groups include tricyclo $[6.2.1.0^{2,7}]$undec-4-enyl.

When used herein the term 'aryl' includes phenyl and naphthyl optionally substituted with up to five, preferably up to three, groups, which are the same or different, selected from halogen, optionally substituted $C_{1-6}$ alkyl, carbocyclyl, alkylthio, acylamino, phenyl, $C_{1-6}$ alkoxy, halo($C_{1-6}$) alkyl, hydroxy, amino, nitro, carboxy, carbamoyl, N-substituted carbamoyl, $C_{1-6}$ alkoxycarbonyl, $C_{1-6}$ alkoxycarbonyl-($C_{1-6}$)-alkyl, $C_{1-6}$ alkylcarbonyloxy, $C_{-6}$ alkylcarbonyl or heterocyclyl groups.

The term "heterocyclyl" herein denotes single or fused aromatic or non-aromatic rings, at least one of which comprises up to four hetero atoms selected from oxygen, nitrogen and sulphur, each ring being optionally substituted with up to three groups, which are the same or different, selected from halogen, $C_{1-6}$ alkyl, carbocyclyl, alkylthio, acylamino, $C_{1-6}$ alkoxy, halo($C_{1-6}$)alkyl, hydroxy, amino, carboxy, carbamoyl, N-substituted carbamoyl, acyl, $C_{1-6}$ alkoxycarbonyl, $C_{1-6}$ alkoxycarbonyl($C_{1-6}$)alkyl, aryl or oxo groups. Suitably at least one heterocyclic ring comprises from 4 to 7 ring atoms, preferably 5 or 6 atoms.

Particularly suitable heterocyclyl groups consist of a 5- or 6-membered heterocyclic ring containing from one to three heteroatoms selected from oxygen, nitrogen and sulphur, for instance tetrahydrothien-3-yl, tetrahydropyran-4H-yl. The ring is optionally substituted as set out above, for instance with one or more oxo groups on carbon, as in 2-pyrrolidon-3-yl, or with up to two oxo groups on sulphur, as in 1,1 dioxo tetrahydrothien-3-yl.

The term 'halogen' refers to fluorine, chlorine, bromine and iodine.

Compounds of the invention may exist in two or more tautomeric forms, e.g. those having the partial structures below:

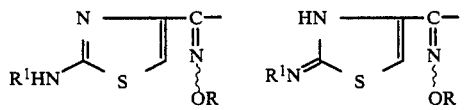

Further tautomeric forms may be present in the compounds wherein R is heterocyclyl. It should be understood that all tautomeric forms of the compound of formula (I) are included within the scope of the invention.

Suitable amino protecting groups $R^1$ are those well known in the art which may be removed under conventional conditions without disruption of the remainder of the molecule.

Examples of amino protecting groups $R^1$ include $C_{1-6}$ alkanoyl; benzoyl; benzyl optionally substituted in the phenyl ring by one or two substituents selected from $C_{1-4}$ alkyl, $C_{1-4}$ alkoxy, trifluoromethyl, halogen, or nitro; $C_{1-4}$ alkoxycarbonyl; benzyloxycarbonyl or trityl substituted as for benzyl above; allyloxycarbonyl, trichloroethoxycarbonyl or chloroacetyl Advantageously, R is joined to the oxyimino group through a secondary or tertiary carbon atom of R, more preferably a non-aromatic ring carbon atom of a carbocyclic system which may be multicyclic.

Preferred values for R within the present invention are: cyclopentyl, cyclohexyl, cycloheptyl, cyclooctyl, 4-methyl cyclohex-1-yl, 1-methyl cyclohex-1-yl, bicyclo[2.2.2]oct-1-yl, endo-bicyclo[2.2.1]hept-2-yl, t-butyl, 4-t-butyl cyclohex-1-yl, adamant-1-yl, tetrahydrothien-3-yl, 4-methylene cyclohex-1-yl, 4-oxocyclohex-1-yl, 1-methyl cyclohept-1-yl, 1-methyl cyclopent-1-yl, 2-methyl cyclohex-1-yl, 2-methoxycyclohex-1-yl, 4-methoxycarbonyl cyclohex-1-yl, 4-chlorocyclohex-1-yl, cyclohex-2-enyl, 2-fluorocyclohex-1-yl, 1-carboxycyclohex-1-yl, 4-(N,N-dimethylcarbamoyl)cyclohex-1-yl, 1-methoxycarbonyl cyclohex-1-yl, 3-methyl cyclohex-1-yl, 4-acetoxycyclohex-1-yl, 4-methoxyiminocyclohex-1-yl and 4-hydroxycyclohex-1-yl.

Particularly preferred values of R within the present invention are cyclohexyl, cyclooctyl, and tetrahydrothien-3-yl.

The term "pharmaceutically acceptable salts" as used herein in respect of compounds of formula (I) includes both mono and di- salts formed at either or both of the carboxylic groups, one of which is attached to the penicillin nucleus and the other of which is present when R is substituted by carboxyl. Similarly the term "in-vivo hydrolysable ester" when used herein applies to both mono and di- esters.

Examples of suitable pharmaceutically acceptable in vivo hydrolysable ester groups include those which break down readily in the human body to leave the parent acid or its salt. Suitable ester groups of this type include those of part formula (i), (ii), (iii), and (iv):

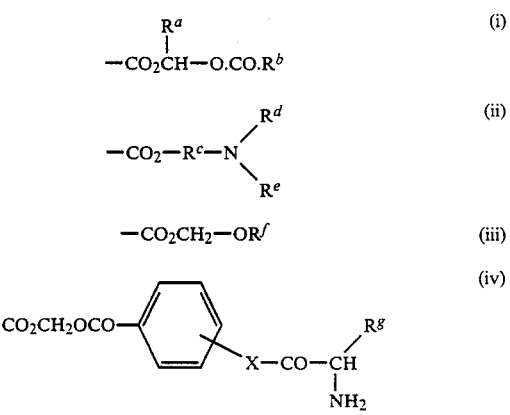

wherein $R^a$ is hydrogen, $C_{1-6}$ alkyl, $C_{3-7}$ cycloalkyl, methyl, or phenyl, $R^b$ is $C_{1-6}$ alkyl, $C_{1-6}$ alkoxy, phenyl, benzyl, $C_{3-7}$ cycloalkyl, $C_{1-6}$ alkyl $C_{3-7}$ cycloalkyl, 1-amino $C_{1-6}$ alkyl, or 1-($C_{1-6}$ alkyl)amino $C_{1-6}$ alkyl; or $R^a$ and $R^b$ together form a 1,2-phenylene group optionally substituted by one or two methoxy groups; $R^c$ represents $C_{1-6}$ alkylene optionally substituted with a methyl or ethyl group and $R^d$ and $R^e$ independently represent $C_{1-6}$ alkyl; $R^f$ represents $C_{1-6}$ alkyl; $R^g$ represents hydrogen or phenyl optionally substituted by up to three groups selected from halogen, $C_{1-6}$ alkyl, or $C_{1-6}$ alkoxy; and X is (preferably o) oxygen or (preferably o or p)NH.

Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

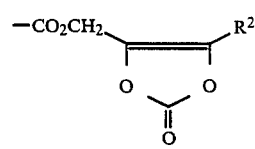

wherein $R^2$ is hydrogen, $C_{1-6}$ alkyl or phenyl.

The in-vivo hydrolysable esters of compounds of formula (I) are preferred where the antibiotic is for oral administration.

Suitable pharmaceutically acceptable salts of the carboxy group of the compound of formula (I) include metal salts, e.g. aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)amine, cycloalkylamines such as dicyclohexylamine, or with procaine, dibenzylamine, N,N-dibenzylethylenediamine, 1-ephenamine, N-ethylpiperidine, N-benzyl-β-phenethylamine, dehydroabietylamine, N,N'-bisdehydroabietylamine, ethylenediamine, or bases of the pyridine type such as pyridine, collidine or quinoline, or other amines which have been used to form salts with known penicillins and cephalosporins.

Some of the compounds of this invention may be crystallised or recrystallised from solvents such as methanol. In such cases solvates may be formed. This invention includes within its scope stoichiometric solvates including hydrates as well as compounds containing variable amounts of water that may be produced by processes such as lyophilisation.

Since the compounds of the formula (I) and their salts and in-vivo hydrolysable esters are intended for use in pharmaceutical compositions it will readily be understood that they are each provided in substantially pure form, for example at least 60% pure, more suitably at least 75% pure and preferably at least 85%, especially at least 95% pure (% are on a weight for weight basis). Impure preparations of the compounds of the formula (I) and their salts may be used for preparing the more pure forms used in the pharmaceutical compositions; these less pure preparations of the compounds of formula (I) and their salts should contain at least 1%, more suitably at least 5% and preferably from 10 to 49% of a compound of the formula (I) or salt thereof.

Compounds of the present invention may exist as either syn or anti isomers, or may exist as mixtures of syn and anti isomers containing at least 75% of one such isomer, or preferably at least 90% of one such isomer.

Herein the terms syn and anti refer to the configuration of the group OR with respect to the carboxamido group, the syn-configuration (sometimes called the Z-configuration) being denoted thus:

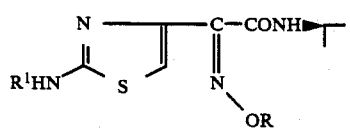

and the anti configuration (sometimes called the E-configuration) being denoted thus:

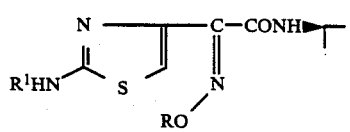

Preferred compounds of the present invention are the syn-isomers of the formula (II):

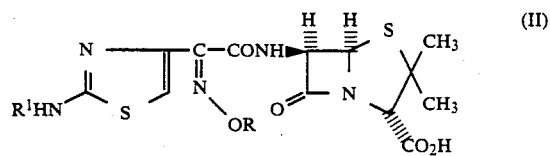

wherein R and $R^1$ are as hereinbefore defined.

A particularly preferred compound within the present invention is the syn isomer of the compound of formula (III) or a pharmaceutically acceptable salt or in vivo hydrolysable ester thereof.

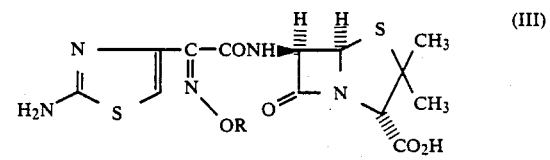

R = cyclohexyl

6β-[2-(2-aminothiazol-4-yl)-(Z)-2-cyclohexyl oxyiminoacetamido]penicillanic acid.

Other specific compounds within this invention include the following and pharmaceutically acceptable salts and in-vivo hydrolysable esters thereof:

6β-[2-(2-aminothiazol-4-yl)-(Z)-2-cyclopropylmethoxyiminoacetamido]penicillanic acid 6β-[2-(2-aminothiazol-4-yl)-(Z)-2-ethoxyiminoacetamido]penicillanic acid 6β-[2-(2-aminothiazol-4-yl)-(Z)-2-propoxyiminoacetamido]penicillanic acid 6β-[(Z)-2-allyloxyimino-2-(2-aminothiazol-4-yl)acetamido]penicillanic acid 6β-[2-(2-aminothiazol-4-yl)-(Z)-2-(iso-propyloxyimino)acetamido]penicillanic acid 6β-[2-(2-aminothiazol-4-yl)-(Z)-2-(tert-butyloxyimino)acetamido]penicillanic acid.

6β-[(Z)-2-(adamant-1-yloxyimino)-2-(2-aminothiazol-4-yl)acetamido]penicillanic acid 6β-[2-(2-aminothiazol-4-yl)-(Z)-2-(1-methylcyclohex-1-yloxyimino)acetamido]penicillanic acid 6β-[2-(2-aminothiazol-4-yl)-(Z)2-[(1S,2S,5R)-5-methyl-2-isopropylcyclohex-1-yloxyimino)acetamido]-penicillanic acid 6β-[2-(2-aminothiazol-4-yl)-(Z)-2-(2-methylpropyloxyimino)acetamido]penicillanic acid 6β-[2-(2-aminothiazol-4-yl)-(Z)-2-(indan-2-yloxyimino)acetamido]penicillanic acid 6β-[2-(2-aminothiazol-4-yl)-(Z)-2-(tetrahydrothien-3-yloxyimino)acetamido]penicillanic acid 6β-[2-(2-aminothiazol-4-yl)-(Z)-2-(1-methylcyclohept-1-yloxyimino)acetamido]penicillanic acid 6β-[2-(2-aminothiazol-4-yl)-(Z)-2-(bicyclo[2.2.2]oct-1-yloxyimino)acetamido]penicillanic acid 6β-[2-(2-aminothiazol-4-yl)-(Z)-2-((1R,2R,5S)-5-methyl-2-isopropylcyclohex-1-yloxyimino)acetamido]-penicillanic acid 6β-[2-(2-aminothiazol-4-yl)-(Z)-2-(1-methylcyclopent-1-yloxyimino)acetamido]penicillanic acid 6β-[2-(2-aminothiazol-4-yl)-(Z)-2-(1-(trans-4-methylcyclohexyl)-1-methylethoxyimino)acetanido]penicillanic acid 6β-[2-(2-aminothiazol-4-yl)-(Z)-2-(3,3-dichloroprop-2-en-1-yloxyimino)acetamido]penicillanic acid 6β-[2-(2-aminothiazol-4-yl)-(Z)-2-(1-carboxy-1-methylethoxyimino)acetamido]penicillanic acid
6β-[2-(2-aminothiazol-4-yl)-(Z)-2-(carboxymethoxyimino)acetamido]penicillanic acid
6β-[2-(2-aminothiazol-4-yl)-(Z)-2-(trans-2-methoxycyclohexyloxyimino)acetamido]penicillanic acid
6β-[2-(2-aminothiazol-4-yl)-(Z)-2-(cis-2-methylcyclohexyloxyimino)acetamido]penicillanic acid
6β-[2-(2-aminothiazol-4-yl)-(Z)-2-(trans-4-methoxycarbonylcyclohexyloxyimino)acetamido]penicillanic acid
6β-[2-(2-aminothiazol-4-yl)-(Z)-2-(1,1-dioxotetrahydrothien-3-yloxyimino)acetamido]penicillanic acid
6β-[2-(2-aminothiazol-4-yl)-(Z)-2-(decahydronapth-2-yloxyimino)acetamido]penicillanic acid
6β-[2-(2-aminothiazol-4-yl)-(Z)-2-(1-carboxycyclohexyloxyimino)acetamido]penicillanic acid
6β-[2-(2-aminothiazol-4-yl)-(Z)-2-(trans-4-(N,N-dimethylcarbamoyl)cyclohexyloxyimino)acetamido]-penicillanic acid
6β-[2-(2-aminothiazol-4-yl)-(Z)-2-(1-methoxycarbonylcyclohexyloxyimino)acetamido]penicillanic acid
6β-[2-(2-aminothiazol-4-yl)-(Z)-2-(cis-3-methylcyclohexyloxyimino)acetamido]penicillanic acid
6β-[2-(2-aminothiazol-4-yl)-(Z)-2-(trans-3-methylcyclohexyloxyimino)acetamido]penicillanic acid
6β-[2-(2-aminothiazol-4-yl)-(Z)-2-(cis-4-acetoxycyclohexyloxyimino)acetamido]penicillanic acid
6β-[2-(2-aminothiazol-4-yl)-(Z)-2-(trans-4-acetoxycyclohexyloxyimino)acetamido]penicillanic acid
6β-[2-(2-aminothiazol-4-yl)-(Z)-2-((2S,4S)-2-carboxypyrrolidin-4-yloxyimino)acetamido]penicillanic acid
6β-[2-(2-aminothiazol-4-yl)-(Z)-2-(4-oxocyclohexyloxyimino)acetamido]penicillanic acid
6β[2-(2-aminothiazol-4-yl)-(Z)-2-(4-methylenecyclohexyloxyimino)acetamido]penicillanic acid
6β-[2-(2-aminothiazol-4-yl)-(Z)-2-([R.S]-1-phenylethyloxyimino)acetamido]penicillanic acid
6β-[2-(2-aminothiazol-4-yl)-(Z)-2-(2,6-dichlorobenzyloxyimino)acetamido]penicillanic acid
6β-[2-(2-aminothiazol-4-yl)-(Z)-2-(trans-4-chlorocyclohexyloxyimino)acetamido]penicillanic acid
6β-[2-(2-aminothiazol-4-yl)-(Z)-2-(cis-4-chlorocyclohexyloxyimino)acetamido]penicillanic acid
6β-[2-(2-aminothiazol-4-yl)-(Z)-2-(phenoxyimino)acetamido]penicillanic acid
6β-[2-(2-aminothiazol-4-yl)-(Z)-2-(cyclopentyloxyimino)acetamido]penicillanic acid
6β-[2-(2-aminothiazol-4-yl)-(Z)-2-(cycloheptyloxyimino)acetamido]penicillanic acid
6β-[2-(2-aminothiazol-4-yl)-(Z)-2-(cyclooctyloxyimino)acetamido]penicillanic acid
6β-[2-(2-aminothiazol-4-yl)-(Z)-2-(endo-bicyclo[2.2.1]-hept-2-yloxyimino)acetamido]penicillanic acid
6β-[2-(2-aminothiazol-4-yl)-(Z)-2-(trans-4-methylcyclohexyloxyimino)acetamido]penicillanic acid
6β-[2-(2-aminothiazol-4-yl)-(Z)-2-(cis-4-methylcyclohexyloxyimino)acetamido]penicillanic acid
6β-[2-(2-aminothiazol-4-yl)-(Z)-2-(tetrahydro-4H-pyran-4-yloxyimino)acetamido]penicillanic acid
6β-[2-(2-aminothiazol-4-yl)-(Z)-2-(2-(1-(S)-6,6-dimethylbicyclo[3.1.1]hept-2-en-2-yl)ethoxyimino)-acetamido]penicillanic acid
6β-[2-(2-aminothiazol-4-yl)-(Z)-2-(cyclohexylmethoxyimino)acetamido]penicillanic acid
6β-[2-(2-aminothiazol-4-yl)-(Z)-2-(n-butoxyimino)acetamido]penicillanic acid
6β-[2-(2-aminothiazol-4-yl)-(Z)-2-(cyanomethoxyimino)acetamido]penicillanic acid
6β-[2-(2-aminothiazol-4-yl)-(Z)-2-(trans-2-methylcyclohexyloxyimino)acetamido]penicillanic acid
6β-[2-(2-aminothiazol-4-yl)-(Z)-2-(cyclohex-2-enyloxyimino)acetamido]penicillanic acid
6β-[2-(2-aminothiazol-4-yl)-(Z)-2-(trans-4-t-butylcyclohexyloxyimino)acetamido]penicillanic acid
6β-[2-(2-aminothiazol-4-yl)-(Z)-2-(trans-2-fluorocyclohexyloxyimino)acetamido]penicillanic acid
6β-[2-(2-aminothiazol-4-yl)-(Z)-2-(2-pyrrolidon-3-yloxyimino)acetamido]penicillanic acid
6β-[2-(2-aminothiazol-4-yl)-(Z)-2-(1-(R)-6,6-dimethylbicyclo[3.1.1]hept-2-en-2-yl)methoxyimino)acetamido]penicillanic acid
6β-[2-(2-aminothiazol-4-yl)-(Z)-2-(benzyloxyimino)acetamido]penicillanic acid Specific in vivo hydrolysable esters within this invention include the, phthalidyl, acetoxyethyl, ethoxycarbonyloxyethyl, pivaloyloxymethyl and 4-glycylaminobenzoyloxymethyl and 4-glycyloxybenzoyloxy methyl hydrochloride esters of the compound of formula (III), as well as the 2-glycylaminobenzoyloxymethyl hydrochloride esters of the compound of formula (III) and 6β-[2-(2-aminothiazol-4-yl)-(Z)-(2)-(cyclopentyl oxyimino)acetamido]penicillanic acid.

The compounds of formula (I) may be prepared by treating a compound of formula (IV) or salt thereof:

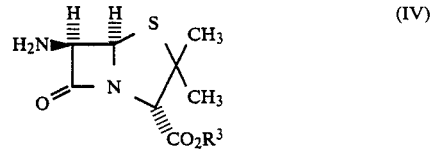

wherein the amino group is optionally substituted with a group which permits acylation to take place, and $R^3$ is hydrogen or a readily removable carboxyl blocking group; with an acylating agent derived from the acid of formula (V):

wherein Y is a group of formula:

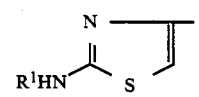

or a group which is convertable thereto, and R and $R^1$ are as defined with respect to formula (I). Any of the following reactions in any appropriate sequence may then be carried out:

(i) removal of any amino-protecting group $R^1$;
(ii) removal of any carboxyl blocking group $R^3$;
(iii) formation of a pharmaceutically acceptable salt;
(iv) conversion of a carboxyl group into an ester function such as an in vivo hydrolysable ester.
(v) conversion of group Y to a group of formula

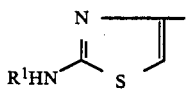

Suitable groups which permit acylation to take place and which are optionally present on the amino group of the starting material of formula (IV) include N-silyl, N-stannyl and N-phosphorus groups, for example trialkylsilyl groups such as trimethylsilyl, trialkyltin groups such as tri-n-butyltin, groups of formula—$PR^aR^b$ wherein $R^a$ is an alkyl, haloalkyl, aryl, aralkyl, alkoxy, haloalkoxy, aryloxy, aralkoxy or dialkylamino group, $R^b$ is the same as $R^a$ or is halogen or $R^a$ and $R^b$ together form a ring; suitable such phosphorus groups being

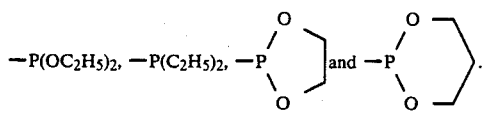

Suitable carboxyl-blocking derivatives for the group $CO_2R^3$ in formula (IV) include salts and ester derivatives of the carboxylic acid, The derivative is preferably one which may readily be cleaved at a later stage of the reaction. Suitable salts include metal salts, such as those with sodium, potassium and lithium, and tertiary amine salts, such as those with trilower-alkylamines, N-ethylpiperidine, 2,6-lutidine, pyridine, N-methylpyrrolidine, dimethylpiperazine. A preferred salt is with triethylamine.

Suitable ester-forming carboxyl-blocking groups are those which may be removed under conventional conditions. Such groups for $R^3$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl (benzhydryl), triphenylmethyl, adamantyl,2-benzyloxyphenyl, 4-methylthiophenyl, tetrahydrofuran-2-yl, tetrahydropyran-2-yl, pentachlorophenyl, p-toluenesulphonylethyl, methoxymethyl, a silyl, stannyl or phosphorus-containing group, such as described above, an oxime radical of formula —N=$CHR^4$ where $R^4$ is aryl or heterocyclic, or an in vivo hydrolysable ester radical such as defined above.

The carboxyl group may be egenerated from any of the above esters by usual methods appropriate to the particular $R^3$ group, for example, acid—and base—catalysed hydrolysis, or by enzymically—catalysed hydrolysis, or by hydrogenation under conditions wherein other parts of the molecule are unaffected.

A reactive N-acylating derivative of the acid of formula (V) is employed in the above process. The choice of reactive derivative will be influenced by the chemical nature of the group R, and of course the group $R^1$ in the acid of formula (V), when present, will be chosen such that the group $NHR^1$ does not react when the carboxy group in (V) is converted into the said N-acylating derivative. Thus, in many—although not all—of the suitable N-acylating derivatives of the acid (V) detailed below, $R^1$ cannot be hydrogen.

A preferred amino-protecting group $R^1$ in the intermediate of formula (V) is trityl, which $R^1$ group may suitably be removed from the product of formula (I) by treatment with formic acid.

Suitable N-acylating derivatives of the acid (V) include acid (V) halides, preferably the acid chloride or bromide. Acylation with an acid halide may be effected in the presence of an acid binding agent, for example a tertiary amine (such as triethylamine or dimethylaniline), an inorganic base (such as calcium carbonate or sodium bicarbonate), molecular sieves (such as type 4 Angstroms) or an oxirane, which binds hydrogen halide liberated in the acylation reaction. The oxirane is preferably a ($C_{1-6}$)- 1,2-alkylene oxide—such as ethylene oxide or propylene oxide. The acylation reaction using an acid halide may be carried out at a temperature in the range −50° C. to +50° C., preferably −20° C. to +20° C., in aqueous or non-aqueous media such as aqueous acetone, aqueous tetrahydrofuran, ethyl acetate, dimethylacetamide, dimethylformamide (DMF), acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (V) with a halogenating (e.g. chlorinating or brominating) agent such as phosphorus pentachloride, thionyl chloride or oxalyl chloride.

Alternatively, the N-acylating derivative of the acid (V) may be a symmetrical or mixed anhydride. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric or phosphorous acids) or aliphatic or aromatic sulphonic acids (such as methanesulphonic acid and p-toluenesulphonic acid respectively). When a symmetrical anhydride is employed, the acylation reaction may be carried out in the presence of an organic base such as 2,6-lutidine as catalyst.

When a mixed anhydride is employed the N-acylating derivative is preferably prepared in the presence of an organic base such as triethylamine and/or N,N-diisopropylethylamine in a suitable solvent such as DMF at between −50° C. and room temperature. Alternatively, the N-acylating derivative may be prepared from an alkali metal salt of the acid of formula (V), such as the sodium salt, in a suitable solvent such as DMF at between −50° C. and room temperature. The N-acylating derivative of the acid of formula (V) so derived may then be reacted with a compound of formula (IV). The acylation reaction may conveniently be carried out at −50° C. to +50° C. in a suitable solvent such as water, acetonitrile or DMF at a temperature of not more than 0° C. The reaction may be carried out in the presence of a suitable base such as triethylamine or sodium hydrogen carbonate.

A further method of forming the N-acylating derivative of the acid of formula (V) is to treat the acid of formula (V) with a solution or suspension preformed by addition of a carbonyl halide, preferably oxalyl chloride, or a phosphoryl halide such as phosphorus oxychloride, to a halogenated hydrocarbon solvent, preferably dichloromethane, containing lower acyl tertiary amide, preferably N,N-dimethylformamide. The N-acylating derivative of the acid of formula (V) so derived may then be caused to react with a compound of formula (IV). The acylation reaction may conveniently be carried out at $-40°$ to $+30°$ C., if desired in the presence of an acid binding agent such as triethylamine. A catalyst such as 4-dimethylaminopyridine may optionally also be added.

Other suitable acylating agents derived from the acid of formula (V) are thioesters of formula (VI)

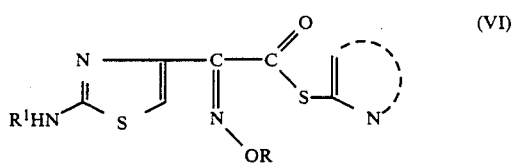

(VI)

wherein R and $R^1$ are as hereinbefore defined and

represents a 5- or 6-membered heterocyclic ring, which may contain, in addition to the nitrogen atom, one or two further heteroatoms, selected from oxygen, nitrogen and sulphur and which may be substituted or fused to a benzene ring which may itself be substituted.

Preferred acylating agents derived from the acid of formula (V) are the thio esters (VIa) or (VIb)

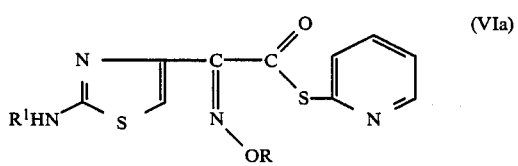

(VIa)

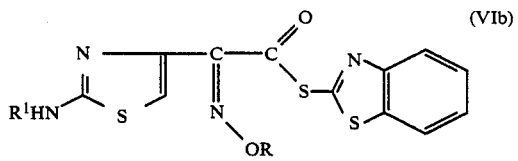

(VIb)

wherein R and $R^1$ are as hereinbefore defined.

Compounds of the formula (VIa) and (VIb) may be prepared by treatment of the acid (V) with 2,2'-dipyridyldisulohide or 2,2'-dibenzothiazolyldisulphide respectively, in the presence of triphenylphosphine, analogously to the routes described in EP-A No. 0037380. Conveniently, in compounds of the formula (VIa) and (VIb), $R^1$ may be hydrogen.

Other suitable N-acylating derivatives of acid (V) include the acid azide; the activated esters derived from cyanomethanol; p-nitrophenol; 2,4-dinitrophenol; thiophenol; halophenols, including pentachlorophenol; monomethoxyphenol; N-hydroxy succinimide; N-hydroxybenzotriazole or 8-hydroxyquinoline; or include amides such as N-acylsaccharins, N-acylthiazolidin-2-thione or N-acylphthalimides; or an alkylidene iminoester prepared by reaction of the acid (V) with an oxime.

Compounds of formula (V) may be prepared by routes analogous to those disclosed in UK patent application GB No. 2 025 398A and by Takasugi et al., J.Antibiotics [1983]36, 846 et seq.

The present invention also encompasses modifications to such routes. In particular, a process in accordance with the invention includes a step in which a compound of formula (VII)

(VII)

(wherein R and Y are as hereinbefore defined and $R^5$ is an esterifying group such as ethyl or t-butyl) is derived from the corresponding hydroxyimine by reacting the latter with the alcohol ROH in the presence of diethylazodi-carboxylate (DEAD) and triphenylphosphine. Preferred solvents are THF or toluene when Y is acetyl, and refluxing benzene, or toluene at 80° to 85°, when Y is the group of formula:

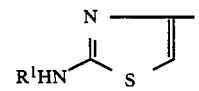

dimethylazodicarboxylate being preferred to DEAD in this case.

Inversion of stereochemistry takes place at the hydroxyl bearing carbon. This process step is advantageous in the case where the alcohol ROH cannot be converted to a corresponding halide without undesirable rearrangement of the carbon skeleton. In an alternative process of the invention a compound of formula (VII) wherein Y is acetyl is derived from the corresponding hydroxyimine by reacting the latter with a halide RX in the presence of silver trifluoromethanesulphonate or silver carbonate in an ether solvent such as dioxane. This process step is advantageous for the preparation of oximes bearing tertiary carbon atoms (for example, $RX=Me_3CBr$), for which the reaction conditions suggested in GB-A No.2,025,398 and Takasugi et al have been found to be inefficient.

Where Y is not already a group of formula:

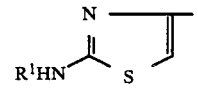

the conversion of Y may advantageously be carried out at this stage, prior to formation of the N-acylating derivative of the acid of formula (V).

Y may be any suitable group, but it is preferred that Y be an acetyl group, the conversion of which may be effected by halogenation followed by reaction with thiourea in the presence of a base such as N,N-dimethylaniline.

In a particular aspect, a compound of formula (VII) wherein $R^5$ is t-butyl and Y is acetyl is chlorinated with sulfuryl chloride in acetic acid. This causes simultaneous cleavage of the t-butyl ester linkage, removing the necessity for a separate hydrolysis step.

Certain of the compounds of formula (V) are novel, and these novel compounds and their derivatives also form a part of the present invention. Accordingly, a further aspect of this invention provides a compound of formula (Va) or a salt, ester, or acylating derivative thereof:

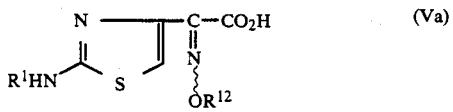

wherein $R^1$ is as defined with respect to formula (1) and $R^{12}$ is t-butyl; tetrahydrothien-3-yl; a substituted, at least partly saturated, cyclic hydrocarbon moiety having one ring; or an optionally substituted, at least partly saturated, cyclic hydrocarbon moiety having between two and four rings.

Suitable salts and esters of the compound of formula (Va) include the alkali metal salts and the ethyl and diphenylmethyl esters, respectively.

Suitable acylating derivatives of the compound of formula (Va) include those set out above in relation to the compound of formula (V).

The present invention also provides a pharmaceutical composition which comprises a compound of formula (I) or a pharmaceutically acceptable salt or in vivo hydrolysable ester thereof and a pharmaceutically acceptable carrier. The compositions of the invention include those in a form adapted for oral, topical or parenteral use and may be used for the treatment of the infection in mammals including humans.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrollidone: fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parental suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10-60% by weight, of the active material, depending on the method of administration. Where the composition comprise dosage units, each unit will preferably contain from 50-500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) is administered in the above-mentioned dosage range.

Certain compounds of the present invention are characterised by increased stability to β-lactamase producing organisms when compared to synthetic penicillins in commercial use such as amoxycillin.

The compound of the invention of formula (I) may therefore be used as the sole therapeutic agent in compositions of the invention or may be used in combination with other antibiotics or with a β-lactamase inhibitor.

Advantageously the compositions also comprise a compound of formula (VIII) or a pharmaceutically acceptable salt or ester thereof:

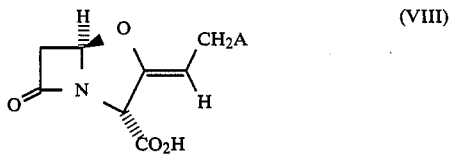

wherein A is hydroxyl; substituted hydroxyl; thiol; a group of formula $SO_2R^6$ wherein $R^6$ is $C_{1-6}$ alkyl; substituted thiol; amino; mono- or di-hydrocarbyl substituted amino; mono- or di-acylamino; an optionally substituted triazolyl group; or an optionally substituted tetrazolyl group as described in EP No. 0 053 893.

A further advantageous composition comprises an antibiotic compound according to the invention and a pharmaceutically acceptable carrier or excipient together with a β-lactamase inhibitor of formula (IX) or a pharmaceutically acceptable salt or in vivo hydrolysable ester thereof:

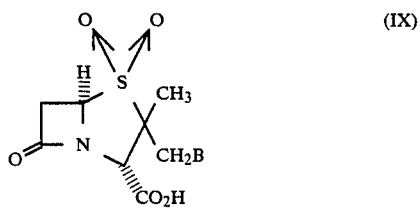

wherein B is hydrogen, halogen or a group of formula:

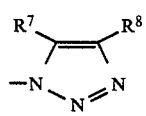

in which $R^7$ and $R^8$ are the same or different and each is hydrogen, $C_{1-6}$ alkoxycarbonyl, or carboxy or a pharmaceutically acceptable salt thereof Further suitable β-lactamase inhibitors include 6-alkylidene penem of formula X below:

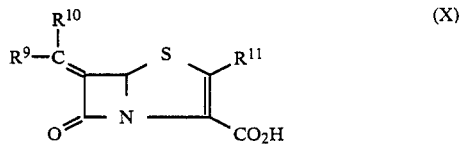

or a pharmaceutically acceptable salt or in vivo hydrolysable ester thereof, wherein $R^9$ and $R^{10}$ are the same or different and each represents hydrogen, or a $C_{1-10}$ hydrocarbon or heterocyclic group optionally substituted with a functional group; and $R^{11}$ represents hydrogen or a group of formula $R^a$ or $-SR^a$ where $R^a$ is an optionally substituted $C_{1-10}$ hydrocarbon or heterocyclic group, as described in European patent application No. 81301683.9 (Publication No. 0 041 768).

Other suitable β-lactamase inhibitors include 6β-bromopenicillanic acid and salts and in vivo hydrolysable esters thereof and 6β-iodopenicillanic acid and salts and in vivo hydrolysable esters thereof.

Such compositions of this invention comprising a β-lactamase inhibitor are formulated in conventional manner.

The present invention also includes a method of treating bacterial infections in humans and animals which comprises the administration of a therapeutically effective amount of an antibiotic compound of this invention.

Antibiotic compounds of the present invention are active against a broad range of bacteria, in particular they are useful for treatment of respiratory tract and urinary tract infections in humans and mastitis in cattle. It should be stressed that a particular advantage of certain compounds of the invention is their stability to β-lactamase enzymes and they are therefore effective against β-lactamase-producing organisms.

The antibiotic compounds of the present invention are active against both Gram-negative and Gram-positive organisms including *E.coli*, in particular ESS and NCTC 10418; *H.influenzae*, in particular Q1 and NEMC 1; *S.aureus* such as Oxford, Russell, MB 9; and methicillin resistant strains such as V.573; *S.pyogenes* such as CN10; *S.agalactiae* such as 2798; and *S.pneumoniae* such as PU7 and 1761.

The following Examples illustrate the preparation of the compounds of the present invention.

EXAMPLE 1 a.

Ethyl-2-(2-aminothiazol-4-yl)-(Z)-2-cyclopropylmethoxyiminoacetate

Ethyl (Z)-2-cyclopropylmethoxyimino-2-(2-tritylaminothiazol-4-yl)acetate (2.39 g) was dissolved in 98% formic acid (18.7 ml), water (5.6 ml) was added, and the mixture vigorously stirred. After 6 h the solvents were evaporated, toluene added to the residue and the process repeated. This was done twice more. The residual solid was chromatographed on silica to give the title compound as a white solid (1.17 g), $v_{max}$ (Nujol) 3440, 3250, 3120, 1720, and 1620 cm$^{-1}$; $\delta_H$ (CDCl$_3$) inter alia 1.35 (3H, t, J 7 Hz), 4.0 (2H, d, J 7 Hz), 4.37 (2H, q, J 7 Hz), 5.4 (2H, broad s, exch. D$_2$O), and 6.67 (1H, s).

b. 2-(2-Aminothiazol-4-yl)-(Z)-2-cyclopropylmethoxyiminoacetic acid

Ethyl 2-(2-aminothiazol-4-yl)-(Z)-2 -cyclopropylmethoxyiminoacetate (1.12 g) was suspended in ethanol (9 ml) and sodium hydroxide (1N; 9 ml) added. The mixture was stirred at room temerature for 40 h, acidified to pH2.8 and the ethanol removed. The precipitated solid was filtered off, washed with a little cold water, and dried in vacuo to give a white solid (845 mg) $v_{max}$ (Nujol) 3350, 1640 br, and 1580 cm$^{-1}$; $\delta_H$ [(CD$_3$)$_2$SO] inter alia 3.92 (2H, d, J 7 Hz), 6.82 (1H, s), and 7.20 (3H, very broad s, excn. D$_2$O).

c. 2-(2-Aminothiazol-4-yl)-(Z)-2-cyclopropylmethoxyiminoacetic acid 2-pyridyl thioester Triphenylphosphine (520 mg) was stirred in acetonitrile (3 ml) and 2,2'-dithiodipyridine (440 mg) was added. After 15 min at room temperture the solution was cooled to 0° C. and 2-(2-aminothiazol-4-yl)-(Z)-2-cyclopropylmethoxyiminoacetic acid (241 mg) added. The mixture was stirred for 3 h at 0° C. and the 2 h at room temperature. The solvent was evaporated and the residue rapidly chromatographed on silica to give the title compound, sufficiently pure for the next step, $v_{max}$ (Nujol) 1705, 1660, and 1000 cm$^{-1}$; $\delta_H$[(CD$_3$)$_2$SO] inter alia 3.87 (2H, d, J 7 Hz), 6.7 (2H, bs, exch D$_2$O), 6.92 (1H, s), and 8.07 (1H, m).

d. Sodium 6β-[2-(2-Aminothiazol-4-yl)-(Z)-2-cyclopropylmethoxyiminoacetamido]penicillanate 6-Aminopenicillanic acid (144 mg) in dichloromethane (3 ml) was treated with triethylamine (136 mg) and chlorotrimethylsilane (146 mg) under argon. The mixture was stirred under reflux for 1 h, cooled to −10° C., and 2-(2-aminothiazol-4-yl)-(Z)-2-cyclopropylmethoxyiminoacetic acid 2-pyridyl thioester (189 mg) added. The cooling-bath was removed and the solution kept 2 h at room temperature and then 16 h at +5° C. The solution was diluted with dichloromethane (5 ml) and water (5 ml) and the pH adjusted to 7. The aqueous layer was separated, washed with dichloromethane and layered with ethyl acetate. The pH was adjusted to 2 and the organic layer separated. The aqueous solution was washed (×2) with ethyl acetate and the combined extracts washed with saturated brine. Water was added to the organic solution and the pH adjusted to 7. A little acetone was added to give two layers and the aqueous layer was removed. The remaining organic layer was extracted with water (×1) and the combined water extracts evaporated to low bulk in vacuo and purified on HP20SS, using water and water/tetrahydrofuran mixtures. The relevant fractions were combined, evaporated to remove tetrahydrofuran and lyophilised to give the title compound as a white amorphous solid (105 mg), $v_{max}$ (KBr) 3193, 1766, 1668, and 1608 cm$^{-1}$; $\delta_H$ (D$_2$O) 0.3 (2H, m), 0.56 (2H, m), 1.19 (1H, m), 1.51 (3H, s), 1.61 (3H, s), 4.0 (2H, d, J 7.1 Hz), 4.23 (1H, s), 5.62 (1H, d, J 4 Hz), 5.65 (1H, d, J 4 Hz) and 7.0 (1H, s). [Mass spectrum: +ve ion (thioglycerol) [MH-Na +H]$^+$ (440), MH$^+$, (462), MNa$^+$ (484)].

EXAMPLE 2 a. Ethyl-2-(2-aminothiazol-4-yl)-(Z)-2-ethoxyiminoacetate

Ethyl (Z)-2-ethoxyimino-2-(2-tritylaminothiazol-4-yl) acetate (2.63 g) was converted into the title compound as described in Example 1a. The product (1.29 g) was isolated as a white solid, $v_{max}$ (Nujol) 3450, 3250, 3125, 1730 and 1620 cm$^{-1}$; $\delta_H$ [(CD$_3$)$_2$SO] 1.2 (6H, m), 4.16 (4H, m), 6.78 (1H, s), and 7.18 (2H, s, exch D$_2$O).

b. 2-(2-Aminothiazol-4-yl)-(Z)-2-ethoxyiminoacetic acid

Ethyl 2-(2-aminothiazol-4-yl)-(Z)-2-ethoxyiminoacetate (1.12 g) was hydrolysed as described in Example 1b. The title compound was obtained as a white solid (845 mg) $v_{max}$ (Nujol) 1660, 1620 cm$^{-1}$; $\delta_H$ [CD$_3$)$_2$SO] 1.17 (3H,t; J 7 Hz), 4.10 (2H, q, J 7 Hz), 5.5 (2H, broad s, exch. D$_2$O), 6.77 (1H,s), and 7.20 (1H, broad s, exch. D$_2$O).

c. 2-(2-Aminothiazol-4-yl)-(Z)-2-ethoxyiminoacetic acid 2-pyridyl thioester 2-(2-Aminothiazol-4-yl)-(Z)-2-ethoxyiminoacetic acid was converted into the title compound as described in Example 1c. $v_{max}$ (Nujol) 3125, 1710, 1665 cm$^{-1}$.

d. Sodium 6β-[2-(2-Aminothiazol-4-yl)-(Z)-2-ethoxyiminoacetamido]penicillanate

Method 1

6-Aminopenicillanic acid was treated with 2-(2-aminothiazol-4-yl)-(Z)-2-ethoxyiminoacetic acid 2-pyridyl thioester as described in Example 1d to give the title compound as a white freeze-dried solid, $v_{max}$ (KBr). 3160, 1764, 1663, and 1608 cm$^{-1}$; $\delta_H$(D$_2$O) 1.28 (3H, t, J 7 Hz), 1.51 (3H, s), 1.61 (3H, s), 4.22 (2H, q, J 7 Hz), 4.24 (1H, s), 5.63 (2H, s), and 7.01 (1H, s). (Mass spectrum: +ve ion (glycerol) MH$^+$ (436), MNa$^+$ (458), [M+H+G]$^+$ (528)).

Method 2

A solution of ethyl (Z)-2-ethoxyimino-2-(2-tritylaminothiazol-4-yl) acetate (1.36 g) in 1,4-dioxane (30 ml) and ethanol (9 ml) was treated with aqueous sodium hydroxide (1N, 3.5 ml). After stirring at room temperature for 16 hours, water (200 ml) was added and the pH adjusted to 2.5 with hydrochloric acid (2N). The organic solvents were evaporated under reduced pressure and the resultant precipitate collected by filtration and dried in vacuo, to afford the corresponding acid as a cream-coloured solid (0.988 g).

Oxalyl chloride (0.178 ml) was added to a stirred solution of dimethylformamide (0.183 ml) in dry dichloromethane (5 ml) at −20° C. under an argon atmosphere. After stirring for 10 minutes, the acid prepared above (0.920 g) was added, and the mixture stirred for a further 10 minutes. A solution of the triethylammonium salt of 6β-aminopenicillanic acid (0.792 g) and triethylamine (0.253 g) in dry dichloromethane (2 ml) was added and the mixture allowed to warm to 0° C. Stirring was continued at 0° C. for 4 hours.

The crude reaction mixture was evaporated under reduced pressure, the residue dissolved in ethyl acetate (10 ml) and washed with water (2×10 ml). Formic acid (98%, 10 ml) was added to the organic phase and the mixture stirred for 1.5 hours, adding a further aliquot of formic acid (5 ml) after 0.5 hours.

The solution was evaporated, toluene (25 ml) added, and the process repeated twice. The resultant foam was dissolved in ethyl acetate (20 ml), water (30 ml) added and the pH adjusted to 7.0 with saturated aqueous sodium bicarbonate. The layers were separated and the organic phase washed with water.

The combined aqueous extracts were evaporated to low bulk in vacuo and purified as described in Example 1d. The title compound was obtained as a white amorphous solid after lyophilisation (0.210 g), and was identical in all respects to the material obtained in Method 1.

EXAMPLE 3 a. Ethyl-2-(2-aminothiazol-4-yl)-(Z)-2-propoxyiminoacetate

Ethyl (Z)-2-propoxyimino-2-(2-tritylaminothiazol-4-yl) acetate (0.83 g) was converted into the title compound as described in Example 1a. The product (344 mg) was isolated as a white solid $\delta_H$ [(CD$_3$)$_2$SO] 0.85 (3H, t, J ca 7 Hz), 1.23 (3H, t, J ca 7 Hz), 1.39–1.78 (2H, m), 3.99 (2H, t, J ca 7 Hz), 4.19 (2H, q, J ca 7 Hz), 6.81 (1H, s), and 7.16 (2H, s, exch. D$_2$O).

b. 2-(2-Aminothiazol-4-yl)-(Z)-2-propoxyiminoacetic acid

Ethyl 2-(2-aminothiazol-4-yl)-(Z)-2-propoxyiminoacetate (310 mg) was hydrolysed as described in Example 1b, to give the title compound as a white solid (239 mg), $\nu_{max}$ (Nujol) 3350, 1635 (broad); $\delta_H$ ((CD$_3$)$_2$SO) 0.86 (3H, t, J 7 Hz), 1.61 (2H, m), 4.01 (2H, t, J 7 Hz), 6.78 (1H, s), and 7.0–7.64 (3H, broad s, exch. D$_2$O).

c. 2-(2-Aminothiazol-4-yl)-(Z)-2-propoxyiminoacetic acid 2-pyridyl thioester 2-(2-Aminothiazol-4-yl)-(Z)-2-propoxyiminoacetic acid was converted into the title compound as described in Example 1c $\delta_H$(CDCl$_3$) inter alia 0.97 (3H, t, J 7 Hz), 1.57–1.92 (2H, m), 4.14 (2H, t, J 7 Hz), and 6.75 (1H, s).

d. Sodium 6β-[2-(2-Aminothiazol-4-yl)-(Z)-2-propoxyiminoacetamido]penicillanate

6-Aminopenicillanic acid was treated with 2-(2-aminothiazol-4-yl)-(Z)-2-propoxyiminoacetic acid 2-pyridyl thioester as described in Example 1d to give the title compound as a white freeze-dried solid, $\nu_{max}$(KBr) 1766, 1662, and 1611 cm$^{-1}$; $\delta_H$ (D20) 0.90 (3H, t, J 7.4 Hz), 1.51 (3H, s), 1.61 (3H, s), 1.61–1.68 (2H, m), 4.14 :2H, t, J 6.5 Hz), 4.23 (1H, s), 5.62 (1H, d J 4 Hz), 5.64 (1H, d, J 4 Hz), and 7.0 (1H, s).

EXAMPLE 4 a. Ethyl (Z)-2-(cyclohexylox yimino)-3-oxobutyrate.

Method 1

A solution of ethyl (Z)-2-(hydroxyimino)-3-oxobutyrate (3.0 g) in dimethylsulphoxide (15 ml) was stirred with potassium carbonate (6.24 g) at room temperature. After 15 min cyclohexyl iodide (7.9 g) was added. The mixture was stirred vigorously for 18 h, and then partitioned between water and ethyl acetate. The organic phase was separated, washed twice with water, then brine, dried (MgSO$_4$) and evaporated. The residue was purified by flash chromatography, eluting with ethyl acetate/hexane to give the title compound as a colourless liquid (3.0 g, 67%); $\nu_{max}$ (film) 2950, 2860, 1745, 1695 cm$^{-1}$; $\delta_H$(CDCl$_3$) 1.32 (3H, t), 1.3–2.0 (10H, br m) 2.37 (3H, s) and 4.3 (3H, q+br m).

Method 2

A solution of ethyl (Z)-2-(hydroxyimino)-3-oxobutyrate (35.8 g) in dimethylsulphoxide (150 ml) was stirred with potassium carbonate (40.4 g) at room temperature. After 15 min cyclohexyl bromide (55 g) was added over 30 min. The mixture was stirred vigorously for 44 h, then partitioned between water and ethyl acetate. The organic phase was separated, washed twice with water, then brine, dried (MgSO$_4$) and evaporated. The residue was purified by flash chromatography, eluted with ethyl acetate/hexane to give the title compound as a colourless liquid (34.0 g, 64%).

Method 3

A solution of diethyl azodicarboxylate (0.495 ml) in tetrahydrofuran (5 ml) was added dropwise to a solution of ethyl (Z)-2-(hydroxyimino)-3-oxobutyrate (0.50 g), cyclohexanol (0.327 ml) and triphenylphosphine (0.825 g) in tetrahydrofuran (10 ml) over 5 min at room temperature. The mixture was stirred for 22 h, then solvent removed in vacuo. The residue was chromatographed on silica to give the title compound (0.242 g, 32%).

b. Ethyl 4-chloro-(Z)-2-(cyclohexyloxyimino)-3-oxobutyrate

Ethyl (Z)-2-(cyclohexyloxyimino)-3-oxobutyrate (1.0 g) was added to ice-cooled sulphuryl chloride (10 ml) with stirring. The mixture was allowed to warm to room temperature, stirred for 27 h, then evaporated under an argon stream. The residue was dissolved in diethyl ether, washed twice with water, then brine, dried (MgSO$_4$) and evaporated. Purification by flash chromatography, eluting with dichloromethane/carbon tetrachloride gave the title compound (0.69 g, 60%) as a colourless liquid; $\nu_{max}$ (film) 2950, 2860, 1750, 1720 cm$^{-1}$; $\delta_H$(CDCl$_3$) 1.32 (3H, t), 1.2–2.0 (10H, br m), 4.3 (1H, br m), 4.34 (2H, q), and 4.53 (2H, s), (Found: MH+ 276.0998, C$_{12}$H$_{18}$NO$_4$Cl requires M+H 276.1004).

c. Ethyl-4-bromo-(Z)-2-(cyclohexyloxyimino)-3-oxobutyrate

A solution of bromine (4.5 ml) in carbon tetrachloride (50 ml) was added dropwise to a mixture of ethyl (Z)-2-(cyclohexyloxyimino)-3-oxobutyrate (20.0 g), hydrogen bromide in acetic acid (45%, 1.0 ml) and carbon tetrachloride (150 ml) over 1.5 h, at room temperature. The mixture was stirred for 2 h, then the solvent removed in vacuo.

The residue was dissolved in ethyl acetate, washed with water, then brine, dried (MgSO$_4$) and evaporated to give the title compound as a pale yellow liquid (26.0 g, 98%); $\nu_{max}$ (film) 2940, 2860, 1740, 1700 cm$^{-1}$; δH (CDCl$_3$) 1.31 (3H t) 1.3–2.0 (10H, m) 4.29 (2H, s) 4.33 (2H, q), 4.35 (1H, m). [Mass spectrum, MH$^+$ (320) MNH$_4$$^+$ (337)].

d. Ethyl 2-(2-aminothiazol-4-yl)-(Z)-2-(cyclohexyloxyimino)acetate

Ethyl 4-chloro-(Z)-2-(cyclohexyloxyimino)-3-oxobutyrate (0.68 g) was dissolved in ethanol (6 ml) and N,N-dimethylaniline (0.30 g) and thiourea (0.19 g) added with stirring. After 18 h the mixture was evaporated and the residue partitioned between dichloromethane and water. The organic layer was separated, washed with brine, dried (MgSO$_4$) and evaporated. Purification by flash chromatography eluting with ethyl acetate/hexane gave the title compound as a cream solid (0.66 g, 90%). A sample was crystallised from cyclohexane, m.p. 133°–4° C.; $\nu_{max}$ (CHCl$_3$) 2940, 1730, 1605 cm$^{-1}$; δ$_H$(CDCl$_3$) 1.34 (3H, t), 1.3–2.0 (10H, br m), 4.3 (1H, br m), 4.36 (2H, q), 5.4 (2H, br s, exch D$_2$O), and 6.68 (1H, s).

e. 2-(2-Aminothiazol-4-yl)-(Z)-2-(cyclohexyloxyimino)acetic acid

Ethyl 2-(2-aminothiazol-4-yl)-(Z)-2-(cyclohexyloxyimino)acetate (0.536 g) was dissolved in ethanol (15 ml), and water (5 ml) and aqueous sodium hydroxide (1N, 6.4 ml) added. The mixture was stirred at room temperature for 24 h. Ethanol was removed and the residue diluted with water (25 ml), washed with ethyl acetate, and acidified to pH 2.8. The precipitate was collected by filtration, washed with cold water and dried in vacuo to give the title compound as a cream solid (0.335 g; 69%), $\nu_{max}$ (nujol) 1630 cm$^{-1}$ δ$_H$ (D$_6$DMSO) 1.2–2.0 (10H, br m), 6.78 (1H, d), and 7.14 (2H, s, exch. D$_2$O).

f. 2-(2-Aminothiazol-4-yl)-(Z)-2-(cyclohexyloxyimino)acetic acid 2-pyridyl thioester Triphenylphosphine (643 mg) was stirred in acetonitrile (4 ml) and 2,2'-dithiodipyridine (540 mg) was added. After 15min at room temperature the solution was cooled to 0° C. and 2-(2-aminothiazol-4-yl)-(Z)-2(cyclohexyloxyimino)acetic acid (330 mg) added. The mixture was stirred at room temperature for 4 h, the solvent evaporated and the residue rapidly chromatographed on silica to give the title compound (440 mg),
m.p. 154°–6° C., (Found: C, 52.9, H, 5.3, N, 15.3 C$_{16}$H$_{18}$N$_4$O$_2$S$_2$ requires C, 53.0; N, 5.0, N, 15.5%), $\nu_{max}$ (KBr) 3315, 3142, 2932, 1683, 1645, 1537cm$^{-1}$; δ$_H$ (CDCl$_3$) 1.31–1.95 (10H, m), 4.33 (1H, m), 5.69 (2H, s), 6.82 (1H, s), 7.34 (1H, m), 7.76 (2H, m), 8.66 (1H, m).

g. Sodium 6β-[2-(2-aminothiazol-4-yl)-(Z)-2-cyclohexyl oxyiminoacetamido]penicillanate 6-Aminopenicillanic acid (310 mg) was treated with 2-(2-aminothiazol-4-yl)-(Z)-2-(cyclohexyloxyimino)acetic acid 2-pyridyl thioester (440 mg) as described in Example 1d, except the reaction after the initial silylation step was stirred at room temperature for 46 h. The title compound was a white freeze-dried solid (200 mg), $\nu_{max}$(KBr) 3377, 2933, 1766, 1662, 1608, 1526cm$^{-1}$; δ$_H$ (D$_2$O) 1.33–1.91 (10H, m), 1.53 (3H, s), 1.64 (3H, s), 4.25 (2H, s+m), 5.64 (1H, d), 5.68 (1H, d), and 6.99 (1H, s), [Mass spectrum: +ve ion (thioglycerol) MH$^+$(490), MNa$^+$(512) 2M+Na+(1001)].

EXAMPLE 5 a. Ethyl (Z)-2-allyloxyimino-2-(2-tritylaminothiazol-4 yl)-acetate

Ethyl (Z)-2-hydroxyimino-2-(2-tritylaminothiazol-4-yl) acetate hydrochloride (988 mg, 2mmol) in dry dimethylsulphoxide (7.5 ml) was treated with potassium carbonate (345 mg, 2.5 mmol) followed by allyl bromide (0.173 ml, 242 mg, 2mmol) and the mixture was stirred for 18 h. Ethyl acetate layer was washed with water (3×100 ml), saturated aqueous sodium chloride (50 ml) and then was dried (MgSO$_4$) and evaporated in vacuo to leave the crude product. This was chromatographed on silica gel, eluting with ethyl acetate/hexane mixture to give the title compound as a solid foam (753 mg; 75%), $\nu_{max}$ (CH$_2$Cl$_2$) 3400, 1735 and 1215 cm$^{-1}$; δ$_H$ (CDCl$_3$, 60 MHz) 1.54 (3H, t, J 7 Hz), 4.38 (2H, q, J 7 Hz), 4.7–4.9 (2H, m), 5.1–5.55 (2H, m), 5.7–6.3 (1H, m), 6.52 (1H, s), 7.00 (1H, broad s), 7.30 (15H, s).

b. (Z)-2-Allyloxyimino-2-(2-tritylaminothiazol-4-yl) acetic acid

Ethyl (Z)-2-allyloxyimino-2-(2-tritylaminothiazol-4-yl) acetate (716 mg, 1.44 mmol) in methanol (31.5 ml) containing water (3.5 ml) was treated with anhydrous potassium carbonate (397 mg, 2.88 mmol) and the mixture was heated under reflux for 20 h. The methanol was removed by evaporation and ethyl acetate and excess 0.1N aqueous HCl were added. After separation the aqueous layer was re-extracted with ethyl acetate and the combined ethyl acetate layers were washed with saturated aqueous sodium chloride, dried (MgSO$_4$) and evaporated in vacuo. Chloroform was added to the residue and evaporated in vacuo to remove traces of ethyl acetate and leave the title compound (620 mg; 91%), δ$_H$ (CDCl$_3$, 90 MHz) 4.59 (2H, d, J ca 6 Hz), 5.0–5.35 (2H, m), 5.65–6.20 (1H, m), 6.50 (1H, s), 7.25 (15H, s), 10.09 (broad s); [Mass spectrum (+ve ion 3-NOBA) MH$^+$ (470)]. 3-NOBA is an abbreviation for 3-nitrobenzyl alcohol.

c. Sodium 6β-[(Z)-2-allyloxyimino-2-(2-aminothiazol-4-yl)acetamido]penicillanate (Z)-2-Allyloxyimino-2-(2-tritylaminothiazol-4-yl)acetic acid (583 mg, 1.24 mmol) in dry dichloromethane (10 ml) was treated with N,N-dimethylformamide (0.096 ml, 91 mg, 1.24 mmol), followed by oxalyl chloride (0.119 ml, 173 mg, 1.24 mmol). After 10 min the mixture was cooled in an ice bath and subsequently treated with a mixture of the triethylamine salt of 6-β-aminopenicillanic acid (476 mg, 1.5 mmol) and triethylamine (0.21 ml, 152 mg, 1.5 mmol) in dichloromethane (5 ml). The mixture was stirred at 0° for 45 min and then the dichloromethane was removed by evaporation in vacuo, ethyl acetate (100 ml) and water (100 ml) were added to the residue and the pH was adjusted to 2.5 by addition of dilute hydrochloric acid. The ethyl acetate layer was washed with 0.05N HCl (100 ml), then with water (100 ml), followed by saturated aqueous sodium chloride, then dried (MgSO$_4$) and evaporated in vacuo to leave the coupled product as a foam (765 mg), contaminated by ethyl acetate. This was dissolved in ethyl acetate (10 ml) and treated with 98% formic acid (15 ml) at room temperature for 1.5 h. The mixture was worked up as described in Example 2d, Method 2 and purified as described in Example 1d to give, after lyophilisation, the title compound as a white solid, $\nu_{max}$ (KBr) 1764, 1660, 1527, 1457, 1395, 1319, 1200, 1158, 1126, 1094 and 1020 cm$^{-1}$; $\delta_H$ (D$_2$O, 250 MHz), 1.51 (3H, s), 1.61 (3H, s), 4.23 (1H, s), 4.67–4.70 (2H, m), 5.25–5.42 (2H, m), 5.62 (1H, d, J 4.0 Hz), 5.64 (1H, d, J 4.0 Hz), 5.95–6.11 (1H, m), 7.03 (1H, s) [Mass spectrum (+ve ion 3NOBA/Na+) MH+ (448), MNa+ (470)].

EXAMPLE 6 a. Ethyl (Z)-2-(isopropyloxyimino)-3-oxobutyrate

Ethyl (Z)-2-hydroxyimino-3-oxobutyrate (3.2 g, 20 mmol) was converted into the title compound by reaction with 2-iodopropane in an analogous reaction to that described in Example 4a Method 1, except that reaction was complete in 3 h. After purification the title compound was obtained as an oil (3.01 g; 74%); $\nu_{max}$ (CH$_2$Cl$_2$) 1740, 1685, 1600, 1370, 1315, 1225 and 1070 cm$^{-1}$; $\delta_H$ (CDCl$_3$) 1.31 (3H, t, J 6.5 Hz), 1.33 (6H, d, J 6.5 Hz), 2.37 (3H, s), 4.38 (2H, q, J 6.5 Hz), ca 4.6 (1H, m) [Mass spectrum (+ve ion, 3NNOBA) MH+ (202)].

b Ethyl-2-(2-aminothiazol-4-yl)-(Z)-2-(isopropyloxyimino)acetate

Ethyl (Z)-2-(isopropyloximino)-3-oxobutyrate (2.86 g, 14.2 mmol) was converted into ethyl 4-bromo-(Z)-2-(isopropyloxyimino)-3-oxobutyrate by an analogous procedure to that described in Example 4c and this was converted into the title compound by an analogous procedure to that described in Example 4d. After purification and crystallisation the title compound was obtained as crystals (2.63 g; 72%) m.p. 166°–167° C. [Found: C, 46.78; H, 5.69; N, 16.35. M+, 257.0831. C$_{10}$H$_{15}$N$_3$O$_3$S requires, C, 46.68; H, 5.88; N, 16.33%; M, 257.0835]; $\nu_{max}$(Nujol) 3450, 3420, 3250, 3140, 1725, 1610, 1540, 1270, 1040 and 980 cm$^{-1}$; $\nu_{max}$ (KBr) 3451, 3425, 3258, 3145, 1724, 1609, 1539, 1381, 1270, 1191, 1116, 1040 and 983 cm$^{-1}$.

c. 2-(2-Aminothiazol-4-yl)-(Z)-2-(isopropyloxyimino) acetic acid

Ethyl 2-(2-aminothiazol-4-yl)-(Z)-2-(isopropyloxyimino) acetate (2.39 g, 993 mmol) was hydrolysed in an analogous manner to that described in Example 4e to give the title compound (1.63 g; 76%); $\nu_{max}$ (Nujol) 3350, 3050, 1650–1620 (broad) 1590, 1570 cm$^{-1}$; $\delta_H$ [(CD$_3$)$_2$CO/(CD$_3$)$_2$SO]7.10 (2H, broad s), 6.77 (1H, s), 4.33 (1H, m), 1.15 (6H, d, J 6.5 Hz).

d. 2-(2-Aminothiazol-4-yl)-(Z)-2-(isopropyloxyimino) acetic acid 2- pyridyl thioester 2-(2-Aminothiazol-4-yl)-(Z)-2-(isopropyloximino) acetic acid (1.15 g, 5 mmol) was reacted with 2,2'-dithiodipyridine and triphenyl phosphine in a similar manner to that described in Example 4f to give, after silica gel chromatography, eluting with ethyl acetate/hexane (6:4), and crystallisation the title compound (1.43 g; 89%) m.p. 171°–172° C.; (Found: C, 48.42; H, 4.32; N, 17.34. C$_{13}$H$_{14}$N$_4$O$_2$S$_2$ requires C, 48.43; H, 4.38, N 17.38%); $\nu_{max}$(KBr) 3340, 3271, 3127, 2982, 2927, 1694, 1661, 1573, 1543, 1059 and 992 cm$^{-1}$; $\delta_H$ (250 MHz, (CD$_3$)$_2$SO) 1.22 (6H, d, J 6.3 Hz), 4.35 (1H, septet, J 6.2 Hz), 6.93 (1H, s), 7.33 (2H, s), 7.50 (1H, m), 7.72 (1H, broad d, J 7.1 z), 7.94 (1H, dt, J 2.0 and 7.8 Hz), 8.63 (1H, m).

e. Sodium 6β-[2-(2-aminothiazol-4-yl)-(Z)-2-(isopropyloxyimino)acetamido]penicillanate 6-β-Aminopenicillanic acid (805 mg, 3.72 mmol) was converted into the corresponding disilyl derivative, and then reacted with 2-(2-aminothiazol-4-yl)-(Z)-2-(isopropyloxyimino)acetic acid 2-pyridyl thioester (1.18 g, 3.66 mmol) by a similar procedure to that outlined in Example 1d to give, the title compound; $\nu_{max}$ (KBr) 1766, 1662, 1609, 1526, 1457, 1396 and 1326 cm$^{-1}$; $\delta_H$ (250 MHz, D$_2$O) 1.27 (3H, d, J 6.2 Hz), 1.28 (3H, d, J 6.3 Hz), 1.52 (3H, s), 1.62 (3H, s), 4.24 (1H, s), 4.48 (1H, m), 5.63 (1H, d, J 4.0 Hz), 5.66 (1H, d, J 3.9 Hz), 6.99 (1H, s); [Mass spectrum (+ve ion, thioglycerol) MH+ (450), MNa+ (472)]

EXAMPLE 7 a. Ethyl (Z)-2-(tert-butyloxyimino)-3-oxobutyrate

Ethyl (Z)-2-hydroxyimino-3-oxobutyrate (4.77 g, 30 mmol) in 1,4-dioxane (15 ml) was treated with silver carbonate (8.27 g, 30 mmol) and the mixture was stirred in the dark and treated with tert-butyl bromide (3.37 ml, 4.11 g, 30 mmol). After stirring in the dark for 5 h more silver carbonate (8.27 g) and tert-butyl bromide (3.37 ml) were added. As the solution became warm more 1,4-dioxane (10 ml) was added, followed by tert-butyl bromide (3.37 ml). After 64 h silver carbonate (4.14 g) was added, followed by 1,4-dioxane (10 ml) and tert-butyl bromide (3.37 ml). After a further 2.5 h more tert-butyl bromide (3.37 ml) was added and stirring was continued for a further 3 h. The mixture was then filtered through Celite and the residue was washed well with 1,4-dioxane. The filtrate was evaporated in vacuo to leave an oil. Toluene was added and evaporated in vacuo to leave the crude product as an oil. Chromatography on silica gel, loading in carbon tetrachloride, and eluting with hexane/ethyl acetate mixtures gave the title compound as an oil (4.5 g; 70%); $v_{max}$ (CH$_2$Cl$_2$) 1745, 1690, 1595, 1365, 1315, 1230, 1180, 1070 and 990 cm$^{-1}$; $\delta_H$(60 MHz, CDCl$_3$) 1.36 (12H, s, superimposed on t), 2.40 (3H, s), 4.33 (2H, q, J 6.5 Hz); [Found: M$^+$-OEt 170.0813. C$_8$H$_{12}$NO$_3$ requires M-OEt 170.0817. Ammonia CI mass spectrum MH$^+$(216)].

b. Ethyl 2-(2-aminothiazol-4-yl)-(Z)-2-(tert-butyloxyimino)acetate

Ethyl (Z)-2-(tert-butyloxyimino)-3-oxobutyrate (4.30 g, 20 mmol) was converted via ethyl 4-bromo-(Z)-2-(tertbutyloxyimino)-3-oxobutyrate into the title compound (4.0 g; 74%) by procedures analogous to those described in examples 4c and 4d, m.p. 111°–112° C. (ethyl acetate/hexane). [Found: C,48.96; H, 6.18; N, 15.49. M$^+$, 271.0994. C$_{11}$H$_{17}$N$_3$O$_3$S requires C, 48.69; H, 6.32; N, 15.49%. M, 271.0991]. $\delta_H$(60 MHz, CDCl$_3$) 1.33 (9H, s), 1.35 (3H, t), 4.40 (2H, q, J 7 Hz), 6.18 (2H, s), and 6.70 (1H, s).

c. 2-(2-Aminothiazol-4-yl)-(Z)-2-(tert-butyloxyimino)acetic acid

Ethyl 2-(2-aminothiazol-4-yl)-(Z)-2-(tert-butyloxyimino)acetate (2.7 g, 10 mmol) was hydrolysed in an analogous manner to that described in Example 4e to give the title compound (1.75 g; 72%) m.p. 164°–166° (dec); $v_{max}$(KBr) 1628, 1448, 1386, 1363, 1262, 1191 and 992cm$^{-1}$; [Found: M$^+$, 243.0682. C$_9$H$_{13}$N$_3$O$_3$S requires M, 243.0678].

d. 2-(2-Aminothiazol-4-yl)-(Z)-2-(tert-butyloxyimino)acetic acid 2-pyridyl thioester 2-(2-Aminothiazol-4-yl)-(Z)-2-(tert-butyloxyimino)acetic acid (1.06 g, 4.4 mmol) was reacted with 2,2'-dithiodipyridine and triphenylphosphine in a similar manner to that described in Example 4f, except that the reaction was allowed to run for 19 h. The precipitated solid was filtered off to give the title compound (905 mg). The mother liquors were evaporated in vacuo and chromatographed on silica gel, loading in toluene and eluting with ethyl acetate/hexane mixtures to give more of the title compound (430 mg), m.p. 155°–156° C. (ethyl acetate/hexane) [Found: C, 50.00; H, 4.76; 16.80. M$^+$, 336.0704. C$_{14}$H$_{16}$N$_4$O$_2$S$_2$ requires C, 49.98; H, 4.79; N, 16.65%. M, 336.0715]; $\delta_H$ (60 MHz, CDCl$_3$+(CD$_3$)$_2$SO) 1.31 (9H, s), 6.74 (1H, s), 6.8–8.3 (6H, m).

e. Sodium 68-[2-(2-aminothiazol-4-yl)-(Z)-2-(tertbutyloxyimino)acetamido]penicillanate 6-β-Aminopenicillanic acid (648 mg, 3 mmol) was converted into the corresponding disilyl derivative and then reacted with 2-(2-aminothiazol-4-yl)-(Z)-2-(tert-butyloxyimino)acetic acid 2-pyridyl thioester (1.0 1g, 3 mmol) by a similar procedure to that described in Example 1d, except that the reaction was allowed to proceed for 44 h at room temperature. The dichloromethane was removed by evaporation in vacuo and ethyl acetate (100 ml) and water (100 ml) were added to the residue. The pH was adjusted to 7.0 by addition of aqueous NaHCO$_3$. The layers were separated and the aqueous layer was extracted with ethyl acetate (2×100 ml). The pH of the aqueous layer was adjusted to 3.0 by addition of dilute HCl, with cooling in an ice bath and the mixture was extracted with ethyl acetate (3×100 ml). The ethyl acetate layer was washed with saturated brine (50 ml) and then water (70 ml) was added and the pH adjusted to 7.5 by addition of aqueous NaHCO$_3$. The aqueous layer was reduced in volume to ca. 50 ml by evaporation in vacuo and purified on HP20SS to give the title compound. $v_{max}$ (KBr) 1766, 1607, 1516, 1456, 1398, 1365, 1323, 1186, 985 and 909 cm$^{-1}$; $\delta_H$(250 MHz, D$_2$O) 1.33 (9H, s), 1.51 (3H, s), 1.62 (3H, s), 4.23 (1H, s), 5.62 (IH, d, J 4.1Hz), 5.67 (1H, d, J 4.0 Hz), 6.95 (1H, s); [Mass spectrum. +ve ion (thioglycerol). MH$^+$ (464)].

EXAMPLE 8 a. Ethyl (Z)-2-(adamant-1-vloxyimino)-3-oxobutyrate

Ethyl (Z)-2-hydroxyimino-3-oxobutyrate (4.77 g, 30 mmol) was reacted with 1-bromoadamantane in an analogous manner to that described in Example 7a to give after purification the title compound (3.8 g; 40%). $v_{max}$ 2830, 2750, 1745, 1730 and 1700 cm$^{-1}$; $v_{max}$(CH$_2$Cl$_2$) 2820, 2750, 1735, 1700 (sh) and 1680 cm$^{-1}$; $\delta_H$(60 MHz, CDCl$_3$) 1.31 (3H, t, J 7 Hz), 1.67 (6H, broad s), 1.94 (6H, broad s), 2.21 (3H, broad s), 2.35 (3H, s), 4.30 (2H, q, J 7 Hz).

b. Ethyl (Z-2-(adamant-1-yloxyimino)-4-bromo-3oxobutyrate

Ethyl (Z)-2-(adamant-1-yloxyimino)-3-oxobutyrate (3.8 g, 11.8 mmol) was converted into the title compound by a similar procedure to that described in Example 4c. The title compound was obtained as an oil, $v_{max}$ (neat) 2945, 2915, 1750, 1710, 1250, 1030 and 990 cm$^{-1}$; $\delta_H$ (60 MHz, CDCl$_3$) 1.37 (3H, t, J6.5 Hz), 1.73 (6H, broad s) 1.97 (3H, broad s), 2.0–2.4 (6H, broad m), and 4.33 (4H, m).

c. Ethyl (Z)-2-(adamant-1-yloxyimino)-2-(2-aminothiazol-4-yl)acetate

The ethyl (Z)-2-(adamant-1-yloxyimino)-4-bromo-3-oxobutyrate was converted into the title compound (1.67 g, 43%), as described in example 4d. m.p.152°–153° C. (ethyl acetate/hexane); [Found: C, 58.68; H, 6.63; N, 11.91; M$^+$ 349.1461.C$_{12}$H$_{23}$N$_3$O$_3$S requires C, 58.43; H, 6.63; N, 12.02%; M, 349.1461]; $v_{max}$(CH$_2$Cl$_2$) 2915, 2855, 1735, 1605, 1530, 1305, 1075, 1040 and 975 cm$^{-1}$. $\delta_H$(9.0 MHz, CDCl$_3$) 1.35 (3H, t, J 7 Hz), 1.65 (6H, broad s), 1.90 (6H, broad s), 2.16 (3H, broad s), 4.37 (2H, q, J 7 Hz) 5.65 (2H, s), 6.71 (1H, s).

d. (Z)-2-(Adamant-1-yloxyimino)-2-(2-aminothiazol-4-yl)acetic acid

Ethyl (Z)-2-(adamant-1-yloxyimino)-2-(2-aminothiazol-4-yl)acetate (1.2 g, 3.79 mmol) was hydrolysed to the title compound using a similar procedure to that described in Example 4e; m.p. 203°–204° C.; $\nu_{max}$(KBr) 3362, 3218, 2907, 2851, 1628, 1450, 1393, 1351, 1300 and 973 cm$^{-1}$; $\delta_H$ [(CD$_3$)$_2$SO] 1.73 (6H, broad s), 1.92 (6H, broad s), 2.23 (3H broad s), 6.85 (1H, s), 7.37 (2H, broad s).

c. (Z)-2-(Adamant-1-yloxyimino)-2-(2-aminothiazol-4-yl)acetic acid 2-pyridyl thioester (Z)-2-(Adamant-1-yloxyimino)-2-(2-aminothiazol-4-yl) acetic acid (641 mg, 2.2 mmol) was converted into the title compound using a similar procedure to that described in Example 4f, except that the reaction was allowed to proceed for 24 h. The product crystallised from the reaction mixture, and was filtered off and washed with ether; m.p. >307° C.; $\nu_{max}$ (Nujol) 3290, 3125, 1680, 1645, 1530, 1345, 1070, 990, 925, 915 and 775 cm$^{-1}$; $\delta_H$ (250 MHz, (CD$_3$)SO) 1.61 (6H, broad s), 1.81 (6H, broad s), 2.15 (3H, broad s), 6.9 (1H, s), 7.36 (2H, s), 7.5 (1H, m), 7.7 (1H, d, J 7.9 Hz), 7.94 (1H, m), 8.64 (1H, m).

f. Sodium 6β-[(Z)-2-(adamant-1-yloxyimino)-2-(2-aminothiazol-4-yl)acetamido]penicillanate (Z)-2-(Adamant-1-yloxyimino)-2-(2-aminothiazol-4-yl) acetic acid 2-pyridyl thioester (706 mg, 1.7 mmol) was converted into the title compound as described in Example 1d, except that the coupling reaction was allowed to run for 80 h at room temperature. The dichloromethane was then removed by evaporation in vacuo and water and ethyl acetate were added. The mixture was cooled in an ice-bath and the pH adjusted to 3.0 by addition of dilute HCl. The ethyl acetate layer was treated with water and then with aqueous NaHCO$_3$. The combined pH 7.0 extracts were lyophilised and chromatographed on HP20SS to give the title compound as a white solid; $\nu_{max}$ (KBr) 3366 (broad), 2907, 2852, 176, 1685, 1608, 1515, 1351, 1397, 1070 and 964 cm$^{-1}$; $\delta_H$(250 MHz, D$_2$O) 1.52 (3H, s), 1.63 (9H, broad s), 1.90 (6H, m), 2.17 (3H, broad s), 4.24 (1H, s), 5.63 (1H, d, J 4.0 Hz), 5.68 (1H, d, J 4.1Hz), 6.96 (1H, s). [Mass spectrum, +ve ion (thioglycerol). MNa+564, MH+ (542), and M-Na+ (520)].

EXAMPLE 9 a. Ethyl (Z)-2-(1-methylcyclohex-1-yl)oxyimino-3-oxobutyrate

Ethyl (Z)-2-hydroxyimino-3-oxobutyrate (3.18 g, 20 mmol) and 1-bromo-1-methylcyclohexane (3.54 g, 20 mmol) in dry dioxane (15 ml) were stirred together in the dark and silver trifluoromethanesulphonate (5.13 g, 20 mmol) was added portionwise over 4 h. After a total of 100 h the mixture was filtered through Kieselguhr and the residue was washed well with dioxane. The filtrate was evaporated in vacuo, toluene was added and evaporated in vacuo and the residual oil was dissolved in ethyl acetate and washed with dilute aqueous NaHCO$_3$, followed by water and brine. Ater drying (MgS$_4$) the ethyl acetate was evaporated in vacuo and the residual oil was chromatographed on silica gel, to give the title compound as a yellow oil (3.49 g; 69%); $\nu_{max}$ (CH$_2$Cl$_2$) 2945, 1740, 1685, 1370, 1320, 1235, 1070 and 1005 cm$^{-1}$; $\delta_H$ (60 MHz, CDCl$_3$) 1.35 (6H, s superimposed on t), 1.4–2.0 (10H, m), 2.37 (3H, s), 4.55 (2H, q, J 7 Hz).

b. Ethyl 4-bromo-(Z)-2-(1-methylcyclohex-1-yl)oxyimino-3-oxobutyrate

Ethyl (Z)-2-(1-methylcyclohex-1-yl)oxyimino-3-oxobutyrate (3.19 g, 12.5 mmol) was converted into the title compound by an analogous procedure to that of Example 4c. The title compound was obtained as an oil: $\nu_{max}$ (neat) 2980, 2860, 1740, 1690, 1590, 1445, 1370, 1330, 1275, 1020 and 790 cm$^{-1}$; $\delta_H$ (60 MHz, CDCl$_3$) 1.0–2.1 (16H, m), 4.31 (2H, s), 4.36 (2H, q, J 7 Hz).

c. Ethyl 2-(2-aminothiazol-4-yl)-(Z)-2-[(1-methylcyclohex-1-yl)oxyimino]acetate The ethyl 4-bromo-(Z)-2-(1-methylcyclohex-1-yl)oxyimino-3-oxobutyrate was transformed into the title compound (2.75 g; 71%) as described in example 4d; m.p.125.5° C. (cyclohexane-hexane); [Found: M+, 311.1303, Cl$_{14}$H$_{21}$N$_3$O$_3$S requires M, 311.1303]. $\nu_{max}$ (CH$_2$Cl$_2$) 3470, 3380, 1735, 1605, 1530, 1375, 1240, 1045 and 975 cm$^{-1}$; $\delta_H$ (90 MHz, CDCl$_3$) 1.0–2.0 (16H, m), 4.35 (2H, q, J 7 Hz), 5.85 (2H broad s), 6.67 (1H, s).

d. 2-(2-Aminothiazol-4-yl)-(Z)-2-[(1-methylcyclohex-1-yl)oxyimino]acetic acid Hydrolysis of ethyl 2-(2-aminothiazol-4-yl)-(Z)-2-[1-methylcyclohex-1-yl)oxyimino]acetate (1.13 g, 3.6 mmol) by a similar method to that described in Example 4e gave the title compound (704 mg; 69%) as a solid, m.p. 203°–204° C.; [Found; M+, 283.0991, C$_{12}$H$_{17}$N$_3$O$_3$S requires M, 283.0991]; $\nu_{max}$ (KBr) 3369, 3055, 2928, 1639, 1573, 1395, 987, 972, 843 and 738 cm$^{-1}$; $\delta_H$ [250 MHz, (CD$_3$)$_2$SO] 1.23 (3H, s), 1.31–1.51 (8H, m), 1.78 (H, broad d, J 12.6 Hz), 6.80 (1H, s), 7.28 (2H,.broad s).

e. 2-(2-Aminothiazol-4-yl)-(Z)-2-[(1-methylcyclohex-1-yl)oxyimino]acetic acid 2-pyridyl thioester 2-(2-Aminothiazol-4-yl)-(Z)-2-[(1-methylcyclohex-1-yl)oxyimino]acetic acid was converted into the title compound as described in Example 4f except the reaction was left to proceeed for 18 h. The title compound (574 mg) crystallised from the reaction mixture. A further quantity (95 mg) was obtained by evaporating in vacuo the mother liqours and chromatography on silica gel, eluting with dichloromethane, followed by ethyl acetate/hexane mixtures. The title compound was obtained as pale yellow crystals; (Found: C, 54.36; H, 5.28; N, 14.86; M+, 376.1029. C$_{17}$H$_{20}$N$_4$O$_2$S$_2$ requires C, 54.23; H, 5.35; N, 14.88%, M, 376.1028); $\nu_{max}$ (KBr)

3287, 3141, 2931, 1694, 1652, 1623, 1538, 1419, 1059, 989, 936 and 918 cm$^{-1}$; $\delta_H$ [250 MHz, (CD$_3$)$_2$SO]1.23 (3H, s), 1.43 (8H, m), 1.84 (2H, broad d, J 12.8 Hz), 6.91 (1H, s), 7.36 (2H, s), 7.50 (1H, m), 7.71 (1H, d, J 7.8 Hz), 7.96 (1H, dt J 1.8 and 7.7 Hz), 8.64 (1H, m).

f. Sodium 6β-8-[2-(2-aminothiazol-4-yl)-(Z)-2-(1-methylcyclohex-1-yloxyimino)acetamido]penicillanate 2-(2-Aminothiazol-4-yl)-(Z)-2-[(1-methylcyclohex-1-yl)oxyimino]acetic acid 2-pyridyl thioester (706 mg, 1.7 mmol) was converted into the title compound using a similar procedure to that described in Example 8f. After purification and lyophilisation the title compound was obtained as a colourless solid, $\nu_{max}$ (KBr) 3375, 2969, 1766, 1662, 1608, 1515, 1398 and 1322 cm$^{-1}$; $\delta_H$ (250 MHz, D$_2$O) 1.28 (6H, s), 1.41 (5H, broad d, J 3.1Hz), 1.51 (3H, s), 1.61 (3H, s), 1.87 (2H, m), 4.22 (1H, s), 5.62 (1H, d, J 3.9 Hz), 5.69 (1H, d, J 4.0 Hz), 6.93 (1H, s), [Mass spectrum, +ve ion (thioglycerol) MH$^+$ (504) and MNa$^+$ (526)].

EXAMPLE 10 a. Ethyl (Z)-2-[(1S, 2S, 5R)-5-methyl-2-isopropylcyclohex-1-yl]oxyimino-3-oxobutyrate (1R, 2S, 5R-)-(−)-Menthol (7.3 g, 45 mmol) and triphenylphosphine (8.65 g, 33 mmol) in dry tetrahydrofuran under argon were cooled in an ice bath and diethyl azodicarboxylate (5.2 ml, 5.7 g, 33 mmol) in dry tetrahydrofuran (30 ml) was added dropwise over 15 minutes. The ice bath was removed and ethyl 2-hydroxyimino-3-oxobutyrate (4.77 g, 33 mmol) in dry tetrahydrofuran (30 ml) was added dropwise over 20 min. The mixture was stirred at room temperature for 18 h and then warmed at 50° C. for 1.5 h. The mixture was cooled and the tetrahydrofuran was removed by evaporation in vacuo. Toluene was added to the residue and evaporated in vacuo. The residual yellow oil was chromatographed on silica gel, eluting with carbon tetrachloride, followed by hexane, followed by hexane/ethyl acetate mixtures. After evaporation of relevant fractions the title compound was obtained as an oil, $\nu_{max}$ (CH$_2$Cl$_2$) 2945, 2920, 2860, 1740, 1685, 1365, 1315, 1235, 1070 and 1005 cm$^{-1}$; $\delta$ (250 MHz, CDCl$_3$) 0.87 (3H, d, J 7.3 Hz), 0.90 (3H, d, J 6.8 Hz), 0.92 (3H, d, J 6.3 Hz), 0.95-1.14 (2H, m), 1.14-1.35 (1H, m), 1.32 (3H, t, J 7.2 Hz), 1.49-1.63 (2H, m), 1.63-1.80 (2H, m), 2.13 (1H, m), 2.40 (3H, s), 4.34 (2H, q, J 7.1 Hz), 4.70 (1H, broad s).

b. Ethyl 2-(2-aminothiazol-4-yl)-(Z)-2-[(1S, 2S, 5R)-5-methyl-2-isopropylcyclohex-1-yl]oxyiminoacetate Ethyl (Z)-2-[(1S, 2S,5R)-5-methyl-2-isopropylcyclohex-1-yl]oxyimino-3-oxobutyrate (1.3 g, 4.37 mmol) was converted into ethyl 4-bromo-2-[(1S, 2S, 5R)-5-methyl-2-isopropylcyclohex-1-yl]oxyimino-3-oxobutyrate by an analogous method to that described in Example 4c and this was converted into the title compound (1.17 g; 75%) by an analogous procedure to that described in example 4d. The product was obtained as a solid [Found: M$^+$ 353.1768. C$_{17}$H$_{27}$N$_3$O$_3$S requires M, 353.1773], $\nu_{max}$ (CH$_2$Cl$_2$) 3470, 3380, 3250, 3110, 2940, 2920, 2860, 1735, 1605, 1530, 1190 and 980 cm$^{-1}$; $\delta$ (400 MHz, CDCl$_3$) 0.85 (3H, d, J 6.5 Hz) 0.89 (3H, d, J 6.7 Hz), 0.93 (3H, d, J 6.7 Hz), 0.8-1.1 (3H, m), 1.24 (1H, approx dq J ca 3 Hz and 12.8 Hz), 1.36 (3H, t, J 7.2 Hz), 1.5-1.7 (4H, m), 2.17 (1H approx ddd, J ca 14 Hz, ca 3 Hz and ca 2 Hz), 4.37 (2H, dq J ca 1.2 Hz and 7.2 Hz), 4.63 (1H, broad s), 5.33 (2H, s), 6.69 (1H, s).

c. 2-(2-Aminothiazol-4-yl)-(Z)-2-[(1S, 2S, 5R)-5-methyl-2-isopropylcyclohex-1-yl]oxyiminoacetic acid Ethyl 2-(2-aminothiazol-4-yl)-(Z)-2-[1S, 2S, 5R)-5-methyl-2-isopropylcyclohex-1-yl]oxyiminoacetate (1.16 g, 3.28 mmol) was hydrolysed to the solid title compound as described in Example 4e; [Found: M$^+$, 325.1464. C$_{15}$H$_{23}$N$_3$O$_3$S requires 325.1460]; $\nu_{max}$ (KBr) 3296, 3121, 2945, 2866, 2843, 1704, 1622, 1451, 1382, 1195 and 1011 cm$^{-1}$; $\delta_H$ [(CD$_3$)$_2$SO, 250 MHz], 0.82 (3H, d, J 6.4 Hz), 0.86 (3H, d, J6.5 Hz), 0.89 (3H, d, J ca 6 Hz), 0.9-1.3 (4H, m), 1.3-1.8 (4H, m), 2.02 (1H, broad d, J ca 14 Hz), 1.3-1.8 (4H, m), 2.02 (1H, broad d, J ca 14 Hz), 4.42 (1H, broad s), 6.81 (1H, s), 7.24 (2H, s), 10.3-11.0 (1H, broad).

d. 2-(2-Aminothiazol-4-yl)-(Z)-2-[(1S, 2S, 5R)-5-methyl-2-isopropylcyclohex-1-yl]oxyiminoacetic acid 2-pyridyl thioester 2-(2-Aminothiazol-4-yl)-Z)-2-[(1S, 2S, 5R)-5-methyl-2-isopropylcyclohex-1-yl]oxyiminoacetic acid (1.07 g,3.3 mmol) was converted into the title compound (1.03 g; 74%) as described in Example 9e, m.p. 158°-159° C. [Found: C, 57.49; H, 6.29; N, 13.49. C$_{20}$H$_{26}$N$_4$O$_2$S$_2$ requires C, 57.39; H, 6.26; N, 13.39%]; $\nu_{max}$ (KBr) 3302, 3145, 1693, 1653, 1622, 1571, and 1538 cm$^{-1}$; $\delta$H (250 MHz, CDCl$_3$) 0.86 (3H, d, J 6.3 Hz), 0.92 (3H, d, J 6.8 Hz), 0.95 (3H, d, J 6.8 Hz), 0.9-1.2 (3H, m), 1.2-1.5 (1H, m), 1.5-1.9 (4H, m), 2.10-2.3 (1H, m), 4.66 (1H, broad s), 6.26 (2H, s), 6.81 (1H, s), 7.3-7.45 (1H, m), 7.6-7.9 (2H, m), 8.65-8.70 (1H, m).

e. Sodium 6β-([2-(2-aminothiazol-4-yl)-(Z)-2-[(1S,2S,5R)-5-methyl-2-isopropylcyclohex-1-yl]oxyimino]acetamido)-penicillanate 2-(2-Aminothiazol-4-yl)-(Z)-2-[(1S, 2S, 5R)-5-methyl-2-isopropylcyclohex-1-yl]oxyiminoacetic acid 2-pyridyl thioester was converted into the title compound as described in Example 8f. $\nu_{max}$ (KBr) 1768, 1668, 1608, 1514, 1455 and 1396 cm$^{-1}$; $\delta_H$ (250 MHz, D$_2$O) 0.83 (3H, d, J 6.6 Hz), 0.87 (3H, d, J 6.7 Hz), 0.88 (3H, d, J 6.6 Hz), 0.9-1.4 (4H, m), 1.51 (3H, s), 1.61 (3H, s), 1.5-1.75 (4H, m), 2.10 (1H, broad d, J ca 12 Hz), 4.22 (1H, s), 4.57 (1H, broad s), 5.62 (1H, d, J 4.2 Hz), 5.68 (1H, d, J 4.1 Hz), 6.93 (1H s)

EXAMPLE 11 a. Ethyl (Z)-2-(2-methylpropyloxyimino)-2-(2-tritylaminothiazol-4-yl)acetate Ethyl (Z)-2-(hydroxyimino)-2-(2-tritylaminothiazol-4-yl)acetate hydrochloride (1 g) was alkylated with 1-bromo-2-methylpropane (0.48 ml) as described in Example 5a to give the title compound (0.8 g), $\nu_{max}$ (CHCl₃) 3400, 2960, 1725, 1520 and 1025 cm⁻¹m; $\delta_H$ (CDCl₃) 1.09 (6H, d, J 7 Hz), 1.30 (3H, t), 1.90 (1H, m), 3.95 (2H, d, J 7 Hz), 4.30 (2H, q), 6.42 (1H, s), 6.93 (1H, br.s), 7.22 (15H, m). [Mass spectrum: +ve ion (3NOBA) MH⁺ (514)].

b. (Z)-2-(2-Methylpropyloxyimino)-2-(2-tritylaminothiazol-4-yl)acetic acid

Ethyl (Z)-2-(2-methylpropyloxyimino)-2-(2-tritylaminothiazol-4-yl)acetate (0.8 g) was hydrolysed as described in Example 5b to give the title compound (0.6 g) m.p. 168°–9° C. (acetone-light petroleum); $\nu_{max}$ (CHCl₃) 3400, 2960, 1710, 1525 and 1025 cm⁻¹, $\delta_H$ [(CD₃)₂SO] 0.87 (6H, d, J 7 Hz), 1.85 (1H, m), 3.78 (2H, d J 7 Hz), 4.16 (1H, br.s), 6.75 (1H, s), 7.26 (15H, m), 8.68 (1H, s), [Mass spectrum: +ve ion (3NOBA) MNa⁺ (508)].

c. Sodium 6β-[2-(2-aminothiazol-4-yl)-(Z)-2-(2-methylpropyloxyimino)acetamido]penicillanate (Z)-2-(2-Methylpropyloxyimino)-2-(2-tritylaminothiazol-4-yl)acetic acid (0.512 g), was coupled to 6β-aminopenicillanic acid and the product deprotected as described in Example 5c to give the title compound (67 mg), $\nu_{max}$ (KBr) 3321 (br), 1765, 1610, 1526 and 1027 cm⁻¹, $\delta_H$ (D₂O) 0.90 (6H, d J 7 Hz), 1.52 (3H, s), 1.63 (3H, s), 1.99 (1H, m), 3.97 (2H q J 7 Hz), 4.24 (1H, s), 5.63 (1H, d J 4 Hz), 5.67 (1H, d J 4 Hz), 7.01 (1H, s), [Mass spectrum: +ve ion (thioglycerol) MNa⁺ (486)].

EXAMPLE 12

Ethyl (Z)-2-(hydroxyimino)-3-oxobutyrate (2.4 g) was reacted with 2-indanol as described in Example 4a, method 3 to give the title compound (2.4 g), $\nu_{max}$ (film) 2970, 1740, 1685, 1235 and 1010 cm⁻¹; $\delta_H$ (CDCl₃) 1.27 (3H, t), 2.32 (3H, s), 3.26 (4H, m), 4.25 (2H, q), 5.30 (1H, m), 7.23 (4H, m). [Mass spectrum: +ve ion (3NOBA/Na⁺) MH⁺ (276), MNa⁺ (298)].

b. Ethyl 4-bromo-(Z)-2-(indan-2-yloxyimino)-3-oxobutyrate

Ethyl (Z)-2-(indan-2-yloxyimino)-3-oxobutyrate (2.4 g) was brominated as described in Example 4c to give the title compound (3.1 g).

c. Ethyl 2-(2-aminothiazol-4-yl)-(Z)-2-(indan-2-yl-oxyimino)acetate

Ethyl 4-bromo-(Z)-2-(indan-2-yloxyimino)-3-oxobutyrate (3.1 g) was converted into the title compound (0.8 g) as described in Example 4d after crystallisation from toluene, [Found: M⁺, 331.0998, C₁₆H₁₇N₃O₃S requires M, 331.0991); $\nu_{max}$ (KBr) 3433, 1734, 1622, 1533 and 1095 cm⁻¹, $\delta_H$(CDCl₃) 1.08 (3H, t), 3.08 (4H, m), 4.17 (2H, q), 5.22 (1H, m), 5.52 (2H, br s), 6.63 (1H, s), 7.12 (4H, m).

d. 2-(2-Aminothiazol-4-yl)-(Z)-2-(indan-2-yloxyimino)acetic acid

Ethyl 2-(2-aminothiazol-4-yl)-(Z)-2-indan-2-yloxyimino)acetate (0.8 g) was hydrolysed as described in Example 4e to give the title compound (0.285 g), $\nu_{max}$ (KBr) 3068, 2952, 1622, 1369 and 1014 cm⁻¹; $\delta_H$ [(CD₃)₂SO]3.18 (4H, m), 3.88 (3H, br s, exch. D₂O), 5.06 (1H, m), 6.79, 7.32 (1H, 2 x s), 7.15 (4H, m).

e. 2-(2-Aminothiazol-4-yl)-(E,Z)-2-(indan-2-yloxyimino)acetic acid 2-pyridyl thioester 2-(2-Aminothiazol-4-yl)-(E,Z)-2-(indan-2-yloxyimino)acetic acid (230 mg) was converted into the title compound as described in example 4f (300 mg).

f. Sodium 6β-[2-(2-aminothiazol-4-yl)-(Z)-2-(indan-2-yloxyimino)acetamido]penicillanate 2-(2-Aminothiazol-4-yl)-(E,Z)-2-(indan-2-yloxyimino)acetic acid 2-pyridyl thioester (300 mg) was coupled to 6β-aminopenicillanic acid as described in Example 1d and the (Z)-isomer separated during the HP20SS chromatography to give the title compound (48 mg), $\nu_{max}$ (KBr) 3369, 1765, 1662, 1616 and 1017 cm⁻¹, $\delta_H$(D₂O) 1.42 (3H, s), 1.46 (3H, s), 3.22 (4H, m), 4.12 (1H, s), 5.17 (1H, m), 5.44 (1H, d, J 4 Hz), 5.47 (1H, d, J 4 Hz), 6.97 (1H, s), 7.27 (4H, m). [Mass spectrum: +ve ion (thioglycerol), MH⁺ (524), MNa⁺(546)].

EXAMPLE 13 a. Ethyl (Z)-2-(cyclopentyloxyimino)-3-oxobutyrate

Ethyl (Z)-2-(hydroxyimino)-3-oxobutyrate (7.9 g) was treated with cyclopentyl bromide as described in Example 4a, Method 2, except that the reaction was stirred overnight to give the title compound as a colourless liquid (9.0g, 80%), (Found: M⁺+H, 228.1241. C₁₁H₁₇NO₄ requires M+H, 228.1236); $\nu_{max}$ (film) 2960 1745, 1700 cm⁻¹; $\delta_H$ (CDCl₃) 1.30 (3H, t), 1.6-2.0 (8H, m), 2.37 (3H, s), 4.31 (2H, q), and 4.87 (1H, m).

b. Ethyl 4-bromo-(Z)-2-(cyclopentyloxyimino)-3-oxobutyrate

Ethyl (Z)-2-(cyclopentyloxyimino)-3-oxobutyrate (4.0g) was brominated as described in Example 4c to give the title compound (5.37 g, 99%).

c. Ethyl 2-(2-aminothiazol-4-yl)-(Z)-2-(cyclopentyloxyimino)acetate

Ethyl 4-bromo-(Z)-2-(cyclopentyloxyimino)-3-oxybutyrate (5.23 g) was treated with thiourea as described in Example 4d. Crystallisation from cyclohexane gave the title compound as a white solid (3.69 g, 76%), m.p. 136°–8° C.; (Found: C: 51.01, H: 6.22, N: 14.59%., C₁₂H₁₇N₃O₃S requires C: 50.87, H: 6.05, N: 14.83%); $\nu_{max}$ (CHCl₃) 3500, 3400, 2960, 1730, 1600, 1525 cm⁻¹; $\nu_H$ (CDCl₃) 1.33 (3H, t), 1.5–1.9 (8H, m), 4.34 (2H, q), 4.81 (1H, m) 5.65 (2H, br s, exch D₂O), 6.64 (1H, s).

d. 2-(2-Aminothiazol-4-yl)-(Z)-2-(cyclopentyloxyimino)acetic acid

Ethyl 2-(2-aminothiazol-4-yl)-(Z)-2-(cyclopentyloxyimino)acetate (2.0g) was hydrolysed as described in Example 4e to give the title compound as a white solid (1.44 g, 80%). $\nu_{max}$ (KBr) 3342, 2957, 1639 cm⁻¹, $\delta_H$ (d₆-DMSO) 1.65 (8H, m), 4.5 (2H, br s) 4.66 (1H, m), 6.79 (1H, s), 7.2 (1H, br s).

e. 2-(2-Aminothiazol-4-yl)-(Z)-2-(cyclopentyloxyimino)acetic acid 2-pyridyl thioester 2-(2-Aminothiazol-4-yl)-(Z)-2-(cyclopentyloxyimino)acetic acid (0.50 g) was treated with triphenylphosphine and 2,2'-dithiodipyridine as described in Example 4f to give the title compound (0.59 g, 87%).

f. Sodium 6β-[2-(2-aminothiazol-4-yl)-(Z)-2-(cyclopentyloxyimino)acetamido]penicillanate 6β-Aminopenicillanic acid (0.44 g) was treated with 2-(2-aminothiazol-4-yl)-(Z)-2-(cyclopentyloxyimino)acetic acid 2-pyridyl thioester (0.59 g) as described in Example 1d to give the title compound as a white freeze-dried solid (0.28 g, 35%), $\nu_{max}$ (KBr) 3337, 2963, 1764, 1662, 1526 cm$^{-1}$; $\delta_H$(D₂O) 1.52 (3H, s) 1.59 (2H, m), 1.63 (3H, s), 1.81 (2H, m), 4.23 (1H, s), 4.80 (1H, m), 5.62 (1H, d), 5.64 (1H, d), 6.98 (1H, s). [Mass spectrum: +ve ion (thioglycerol) MH+ (476) MNa+ (498) 2M+Na+(973)].

EXAMPLE 14 a. Ethyl (Z)-2-(cycloheptyloxyimino)-3-oxobutyrate

Ethyl (Z)-2-(hydroxyimino)-3-oxobutyrate (5.0g) was treated with cycloheptyl bromide as described in Example 13a to give the title compound as a colourless liquid (6.36 g, 80%). (Found: M+ +H, 256.1547, C₁₃H₂₁NO₄ requires M+H 256.1550), $\nu_{max}$ (film) 2940, 1750, 1690 cm$^{-1}$; $\delta_H$(CDCl₃): 1.31 (3H, t) 1.4–2.0 (12H, m), 2.35 (3H, s) 4.32 (3H, q+m).

b. Ethyl 4-bromo-(Z)-2-(cycloheptyloxyimino)-3-oxobutyrate

Ethyl (Z)-2-(cycloheptyloxyimino)-3-oxobutyrate (5.0 g) was brominated as described in Example 4c to give the title compound (6.4 g, 98%), $\nu_{max}$ (film) 2940, 1745, 1700 cm$^{-1}$.

c. Ethyl 2-(2-aminothiazol-4-yl)-(Z)-2-(cycloheptyloxyimino)acetate

Ethyl 4-bromo-(Z)-2-(cycloheptyloxyimino)-3-oxobutyrate (6.3 g) was treated with thiourea as described in Example 4d. Crystallisation from dichloromethane/hexane gave the title compound as a white solid (4.1 g, 69%), m.p. 107°–8° C. (Found: C: 54.24, H: 6.72, N: 13.33. C₁₄H₂₁N₃O₃S requires C: 54.00, H: 6.80, N:13.49%). $\nu_{max}$ (KBr) 3433, 2930, 1723, 1611, 1540 cm$^{-1}$; $\delta_H$(CDCl₃) 1.33 (3H, t) 1.4–2.0 (12H, m), 4.35 (3H, q+m) 5.60 (2H, br s, exch. D₂O), 6.64 (1H,ss).

d. 2-(2-Aminothiazol-4-yl)-(Z)-2-(cycloheptyloxyimino)acetic acid

Ethyl 2-(2-aminothiazol-4-yl)-(Z)-2-(cycloheptyloxyimino) acetate (2.17 g) was hydrolysed as described in Example 4e to give the title compound as a white solid (1.50 g, 76%). $\nu_{max}$ (KBr) 2927, 1633 cm$^{-1}$. $\delta_H$ (d₆-DMSO): 1.5–1.9 (12H, m), 4.0 (3H, br m), 6.76 (1H, s), 7.14 (1H, br s).

e. 2-(2-Aminothiazol-4-yl)-(Z)-2-(cycloheptyloxyimino)acetic acid 2-pyridyl thioester 2-(2-Aminothiazol-4-yl)-(Z)-2-(cycloheptyloxyimino) acetic acid was converted into the title compound as described in Example 4f.

f. Sodium 6β-[2-(2-aminothiazol-4-yl)-(Z)-2-(cycloheptyloxyimino)acetamido]penicillanate 6β-Aminopenicillanic acid (0.154 g) was treated with 2-(2-aminothiazol-4-yl)-(Z)-2-(cycloheptyloxyimino) acetic acid 2-pyridyl thioester (0.244 g) as described in Example 1d to give the title compound as a white freeze-dried solid (0.132 g, 44%), $\nu_{max}$ (KBr) 3329, 2928, 1767, 1668, 1610, 1522 cm$^{-1}$; $\delta_H$(D₂O) 1.51 (3H, s), 1.62 (3H, s), 1.43–1.91 (12H, m), 4.23 (1H, s), 4.44 (1H, m), 5.62 (1H, d), 5.65 (1H, d), 6.96 (1H, s). [Mass spectrum: +ve ion (thioglycerol) MH+ (504), MNa+ (526)].

EXAMPLE 15 a. Ethyl (Z)-2-(cyclooctyloxyimino)-3-oxobutyrate

Ethyl (Z)-2-(hydroxyimino)-3-oxobutyrate (2.0g) was treated with cyclooctyl iodide as described in Example 4a, Method 1, to give the title compound as a colourless liquid (2.35 g, 69%). $\nu_{max}$ (film) 2930, 1740, 1695 cm$^{-1}$, $\delta_H$(CDCl₃) 1.31 (3H, t), 1.4–2.0 (14H, m), 2.38 (3H, s), 4.33 (2H, q), 4.4 (1H, m). [Mass spectrum, +ve ion, MH+ (270)].

b. Ethyl 4-bromo-(Z)-2 (cyclooctyloxyimino)-3-oxobutyrate

Ethyl (Z)-2-(cyclooctyloxyimino)-3-oxobutyrate (2.17 g) was brominated as described in Example 4c to give the title compound (2.8 g, 99%).

c. Ethyl 2-(2-aminothiazol-4-yl)-(Z)-2-(cyclooctyloxyimino)acetate

Ethyl 4-bromo-(Z)-2-(cyclooctyloxyimino)-3-oxobutyrate (2.8 g) was treated with thiourea as described in Example 4d. Crystallisation from cyclohexane gave the title compound as colourless needles (1.9 g, 72%), m.p. 117°–8° C. [Found, C: 55.66, H: 7.16, N: 12.45. C₁₅H₂₃N₃O₃S requires C: 55.36, H: 7.12, N: 12.91%]. $\nu_{max}$ (KBr) 3428, 2926, 1718, 1610, 1541 cm$^{-1}$: $\delta_H$ (CDCl₃) 1.35 (3H, t) 1.4–2.0 (14H, m), 4.36 (3H, q+m) 5.65 (2H, br s, exch D₂O), 6.66 (1H, s).

d. 2-(2-Aminothiazol-4-yl)-(Z)-2-(cyclooctyloxyimino) acetic acid

Ethyl 2-(2-aminothiazol-4-yl)-(Z)-2-(cyclooctyloxyimino) acetate (1.5 g) was hydrolysed as described in Example 4e to give the title compound as a white solid (1.28 g, 93%).

e. 2-(2-Aminothiazol-4-yl)-(Z)-2-(cyclooctyloxyimino) acetic acid 2-pyridyl thioester 2-(2-Aminothiazol-4-yl)-(Z)-2-(cyclooctyloxyimino) acetic aid (1.0 g) was converted into the title compound (1.24 g, 94%) as described in Example 4f.

f. Sodium 6β-[2-(2-aminothiazol-4-yl)-(Z)-2-(cyclooctyloxyimino)acetamido]penicillanate 6β-Aminopenicillanic acid (0.816 g) was treated with 2-(2-aminothiazol-4-yl)-(Z)-2-(cyclooctyloxyimino) acetic acid 2-pyridyl thioester (1.23 g) as described in Example 1d to give the title compound as a white freeze-dried solid (0.48 g, 29%), $\nu_{max}$ (KBr) 3365, 2921, 1766, 1670, 1608, 1526 cm$^{-1}$, $\delta_H$ (D$_2$O) 1.50 (3H, s), 1.60 (3H, s), 1.50–1.84 (14H, m), 4.19 (1H, s), 4.36 (1H, m), 5.59 (1H, d), 5.63 (1H, d), 6.90 (1H, s). [Mass spectrum: +ve ion (thioglycerol) MH$^+$ (518), MNa$^+$ (540)].

EXAMPLE 16 a. Ethyl (Z)-2-(endo-bicyclo[2.2.1]hept-2-yloxyimino)-3-oxobutyrate

Ethyl (Z)-2-(hydroxyimino)-3-oxobutyrate (4.6 g) was treated with exo-2-bromobicyclo[2.2.1]heptane as described in Example 4a, Method 2, except that the reaction was stirred for 11 days to give the title compound as a colourless liquid (2.06 g, 28%). $\nu_{max}$ (film) 2960, 1745, 1700 cm$^{-1}$, $\delta_H$ (CDCl$_3$) 1.32 (3H, t), 1.0–2.6 (10H, m), 2.36 (3H, s), 4.34 (2H, q), 4.8 (1H, m).

b. Ethyl 4-bromo-(Z)-2-(endo-bicyclo[2.2.1]hept-2-yloxyimino)-3-oxobutyrate

Ethyl (Z)-2-(endo-bicyclo[2.2.1]hept-2-yloxyimino)-3-oxobutyrate (1.0 g) was brominated as described in Example 4c to give the title compound (1.37 g, 95%). $\delta_H$ (CDCl$_3$) 1.35 (3H, t), 1.0–2.6 (10H, m), 4.34 (4H, s+q), 4.8 (1H, m).

c. Ethyl 2-(2-aminothiazol-4-yl)-(Z)-2-(endo-bicylo[2.2.1]hept-2-yloxyimino)acetate Ethyl 4-bromo-(Z)-2-(endo-bicyclo[2.2.1]hept-2-yloxyimino)-3-oxobutyrate (1.37 g) was treated with thiourea as described in Example 4d to give the title compound as a foam (0.915 g, 72%). A sample was crystallised from cyclohexane, m.p. 91°–5° C. [Found: M$^+$, 309.1150. C$_{14}$H$_{19}$N$_3$O$_3$S requires M 309.1147]. $\nu_{max}$ (CHCl$_3$) 3400, 2905, 1720, 1605 cm$^{-1}$, $\nu_H$ (CDCl$_3$) 1.35 (3H, t), 1.0–2.6 (10H, m), 4.36 (2H, q), 4.75 (1H, m), 5.55 (2H, br s, exch. D$_2$O), 6.66 (1H, s).

d. 2-(2-Aminothiazol-4-yl)-(Z)-2-(endo-bicyclo[2.2.1]hept-2-yloxyimino)acetic acid Ethyl 2-(2-aminothiazol-4-yl)-(Z)-2-(endo-bicyclo[2.2.1]hept-2-yloxyimino) acetate (0.778 g) was hydrolysed as described in Example 4e to give the title compound as a cream solid (0.236 g, 33%).

e. 2-(2-Aminothiazol-4-yl)-(Z)-2-(endo-bicyclo[2.2.1]hept-2-yloxyimino)acetic acid 2-pyridyl thioester 2-(2-Aminothiazol-4-yl)-(Z)-2-(endo-bicyclo[2.2.1]hept-2-yloxyimino) acetic acid (0.20 g) was converted into the title compound (0.26 g, 98%) as described in Example 4f.

f. Sodium 6β[2-(2-aminothiazol-4-yl)-(Z)-2-(endobicyclo[2.2.1]hept-2-yloxyimino)acetamido]penicillanate 6β-Aminopenicillanic acid (0.184 g) was treated with 2-(2-aminothiazol-4-yl)-(Z)-2-(endo-bicyclo[2.2.1]hept-2-yloxyimino) acetic acid 2-pyridyl thioester (0.26 g) as described in Example 1d to give the title compound as a white freeze-dried solid (0.126 g, 35%), $\nu_{max}$ (KBr) 3393, 2959, 1765, 1662, 1607, 1526 cm$^{-1}$, $\delta_H$ (D$_2$O) 1.08 (1H, m), 1.26–1.62 ($\delta_H$, m), 1.51 (3H, s), 1.62 (3H, s), 1.92 (1H, m), 2.19 (1H, m), 2.52 (1H, m), 4.23 (1H, s), 4.73 (1H, m), 5.64 (2H, m), 6.97 (1H, d). [Mass spectrum: +ve ion (thioglycerol) MH$^+$ (480), MNa$^+$ (502)].

EXAMPLE 17 a. Ethyl (Z)-2-(trans-4-methylcyclohexyloxyimino)-3-oxobutyrate

Ethyl (Z)-2-(hydroxyimino)-3-oxobutyrate (3.0 g) was reacted with cis-4-methylcyclohexanol as described in Example 4a, Method 3, to give the title compound as a colourless liquid (1.2 g, 25%), $\nu_{max}$ (film) 2950, 1745, 1695 cm$^{-1}$, $\delta_H$ (CDCl$_3$) 0.91 (3H, d), 1.02 (2H, m), 1.32 (3H, t), 1.41 (3H, m), 1.78 (2H, m), 2.10 (2H, m), 2.39 (3H, s), 4.20 (1H, m), 4.34 (2H, q); $\delta_C$ (CDCl$_3$) 14.1, 21.7, 25.1, 31.2 (2C), 31.7, 32.9 (2C), 61.8, 85.2, 149.9, 161.5, 193.0.

b. Ethyl 4-bromo-(Z)-2-(trans-4-methylcyclohexyloxyimino)-3-oxobutyrate

Ethyl (Z)-2-(trans-4-methylcyclohexyloxyimino)-3-oxobutyrate (1.13 g) was brominated as described in Example 4c to give the title compound (1.46 g, 98%).

c. Ethyl 2-(2-aminothiazol-4-yl)-(Z)-2-(trans-4-methylcyclohexyloxyimino)acetate Ethyl 4-bromo-(Z)-2-(trans-4-methylcyclohexyloxyimino)-3-oxobutyrate (1.46 g) was treated with thiourea as described in Example 4d. Crystallisation from cyclohexane gave the title compound as a cream solid (0.80 g, 58%), m.p. 133°–5° C. [Found: M$^+$, 311.1300, C$_{14}$H$_{21}$N$_3$O$_3$S requires M, 311.1303]. $\nu_{max}$ (KBr) 3447, 3119, 2940, 1723, 1616, 1538 cm$^{-1}$, $\delta_H$ (CDCl$_3$) 0.89 (3H, d), 0.98 (2H, m), 1.36 (6H, t+m), 1.72 (2H, m), 2.11 (2H, m), 4.16 (1H, m), 4.39 (2H, q), 5.44 (2H, s, exch. D$_2$O) 6.68 (1H, s).

d. 2-(2-Aminothiazol-4-yl)-(Z)-2-(trans-4-methylcyclohexyloxyimino)acetic acid Ethyl 2-(2-aminothiazol-4-yl)-(Z)-2-(trans-4-methylcyclohexyloxyimino) acetate (0.622 g) was hydrolysed as described in Example 4e, except that after acidification the aqueous solution was freeze-dried and the residue extracted with acetone. Evaporation of the acetone gave the title compound as a cream solid (0.31 g, 55%).

e.
2-(2-Aminothiazol-4-yl)-(Z)-2-(trans-4-methylcyclohexyloxyimino)acetic acid-2-pyridylthioester 2-(2-Aminothiazol-4-yl)-(Z)-2-(trans-4-methylcyclohexyloxyimino)acetic acid (0.31 g) was converted into the title compound (0.32 g, 78%) as described in Example 4f.

f. Sodium 6β-[2-(2-aminothiazol-4-yl)-(Z)-2-(trans-4-methylcyclohexyloxyimino)acetamido]penicillanate 6β-Aminopenicillanic acid (0.22 g) was treated with 2-(2-aminothiazol-4-yl)-(Z)-2-(trans-4-methylcyclohexyl oxyimino)acetic acid 2-pyridyl thioester (0.32 g) as described in Example 1d to give the title compound as a white freeze-dried solid (0.134 g, 31%), $\nu_{max}$ (KBr) 3338, 2929, 1765, 1668, 1608, 1526 cm$^{-1}$. $\delta_H$ (D$_2$O) 0.86 (3H, d), 1.03 (2H, m), 1.35 (3H, m), 1.51 (3H, s), 1.62 (3H, s), 1.74 (2H, m), 2.04 (2H, m), 4.14 (1H, m), 4.22 (1H, s), 5.61 (1H, d), 5.65 (1H, d), 6.97 (1H, s). [Mass spectrum; +ve ion (thioglycerol) [M+2H-Na]+(482), MH+ (504)].

EXAMPLE 18 a. Ethyl (Z)-2-(cis-4-methylcyclohexyloxyimino)-3-oxobutyrate

Ethyl (Z)-2-(hydroxyimino)-3-oxobutyrate (3.61 g) was reacted with trans-4-methylcyclohexanol as described in Example 4a, Method 3, to give the title compound as a colourless liquid (1.66 g, 29%).[Found: M$^+$+H, 256.1555. C$_{13}$H$_{21}$NO$_4$ requires M+H, 256.1549]. $\nu_{max}$ (film) 2930, 2850, 1745, 1690 cm$^{-1}$; $\delta_H$ (CDCl$_3$) 0.89 (3H, d), 1.20 (2H, m), 1.35 (3H, t), 1.47 (3H, m), 1.60 (2H, m), 2.03 (2H, m), 2.40 (3H, s), 4.36 (2H, q), 4.51 (1H, m); $\delta_C$ (CDCl$_3$) 14.3, 22.2, 25.1, 29.1 (2C), 29.4 (2C), 31.5, 61.8, 81.2, 150.2, 161.5, 193.1.

b. Ethyl 4-bromo-(Z)-2-(cis-4-methylcyclohexyloxyimino)-3-oxobutyrate

Ethyl (Z)-2-(cis-4-methylcyclohexyloxyimino)-3-oxobutyrate (1.50 g) was brominated as described in Example 4c to give the title compound (0.78 g, 40%) [Found; M$^+$+H,334.0657. C$_{13}$H$_{20}$NO$_4$Br requires M+H 334.0654]. $\nu_{max}$ (film) 2930, 2850, 1745, 1695 cm$^{-1}$; $\delta_H$ (CDCl$_3$) 0.90 (3H, d), 1.20 (2H, m), 1.36 (3H, t), 1.60 (5H, m), 2.04 (2H, m), 4.35 (2H, s), 4.38 (2H, q), 4.55 (1H, m).

c. Ethyl 2-(2-aminothiazol-4-yl)-(Z)-2-(cis-4-methylcyclohexyloxyimino)acetate

Ethyl 4-bromo-(Z)-2-(cis-4-methylcyclohexyloxyimino)-3-oxobutyrate (0.78 g) was treated with thiourea as described in Example 4d. Crystallisation from cyclohexane gave the title compound as colourless platelets (0.30 g, 41%), m.p. 123°–6° C. $\nu_{max}$ (KBr) 3464, 2925, 1727, 1609, 1537 cm$^{-1}$. $\delta_H$ (CDCl$_3$) 0.88 (3H, d), 1.23 (2H, m), 1.40 (3H, t), 1.46 (5H, m), 2.03 (2H, m),4.41 (2H, q), 4.50 (1H, m), 5.36 (2H, br s, exch. D$_2$O), 6.70 (1H, s).

d.
2-(2-Aminothiazol-4-yl)-(Z)-2-(cis-4-methylcyclohexyloxyimino)acetic acid

Ethyl 2-(2-aminothiazol-4-yl)-(Z)-2-(cis-4-methylcyclohexyloxyimino)acetate (0.247 g) was hydrolysed as described in Example 17d to give the title compound (0.13 g, 57%).

e.
2-(2-Aminothiazol-4-yl)-(Z)-2-(cis-4-methylcyclohexyloxyimino)acetic acid 2-pyridyl thioester 2-(2-Aminothiazol-4-yl)-(Z)-2-(cis-4-methylcyclohexyloxyimino)acetic acid (0.129 g) was converted into the title compound (0.13 g, 76%) as described in Example 4f.

f. Sodium 6β-[2-(2-aminothiazol-4-yl)-(Z)-2-(cis-4-methylcyclohexyloxyimino)acetamido]penicillanate 6β-Aminopenicillanic acid (90 mg) was treated with 2-(2-aminothiazol-4-yl)-(Z)-2-(cis-4-methylcyclohexyloxyimino)acetic acid 2-pyridyl thioester (0.13 g) as described in Example 1d to give the title compound as a white freeze-dried solid (87 mg, 50%) $\nu_{max}$ (KBr) 3351, 2925, 1766, 1661, 1606, 1526 cm$^{-1}$, $\delta_H$(D$_2$O) 0.87 (3H, d), 1.17 (2H, m), 1.5 (5H, m), 1.52 (3H, s), 1.62 (3H, s), 1.93 (2H, m), 4.24 (1H, s), 4.43 (1H, m), 5.64 (1H, d), 5.68 (1H, d), 6.98 (1H, s). [Mass spectrum: +ve ion (thioglycerol) MH+ (504) MNa+ (526)].

EXAMPLE 19 a. Ethyl (Z)-2-(tetrahydro-4H-pyran-4-yloxyimino)-3-oxobutyrate

Ethyl (Z)-2-(hydroxyimino)-3-oxobutyrate (3.0 g) was reacted with tetrahydro-4H-pyran-4-ol as described in Example 4a, Method 3, to give the title compound as a colourless liquid (1.69 g, 37%). $\nu_{max}$ (film) 2950, 1740, 1695 cm$^{-1}$. $\delta_H$ (CDCl$_3$) 1.34 (3H, t), 1.82 (2H, m), 2.03 (2H, m), 2.40 (3H, s), 3.57 (2H, m), 3.91 (2H, m), 4.37 (2H, q), 4.54 (1H, m).

b. Ethyl 4-bromo-(Z)-2-(tetrahydro-4H-pyran-4-yloxyimino)-3-oxobutyrate

Ethyl (Z)-2-(tetrahydro-4H-pyran-4-yloxyimino)-3-oxobutyrate (1.0 g) was brominated as described in Example 4c to give the title compound (0.55 g, 42%). $\nu_{max}$ (film) 2950, 2850, 1740, 1695 cm$^{-1}$; $\delta_H$ (CDCl$_3$) 1.32 (3H, t), 1.7–2.0 (4H, m), 3.5 (2H, m), 3.8 (2H, m), 4.26 (2H, s), 4.34 (2H, q), 4.50 (1H, m).

c. Ethyl 2-(2-aminothiazol-4-yl)-(Z)-2-(tetrahydro-4H-pyran-4-yloxyimino)acetate Ethyl 4-bromo-(Z)-2-(tetrahydro-4H-pyran-4-yloxyimino)-3-oxobutyrate (0.52 g) was treated with thiourea as described in Example 4d. Crystallisation from diisopropyl ether gave the title compound as a pale yellow solid (0.34 g, 70%), m.p. 110.0°–110.5° C. [Found: C: 48.37, H: 5.99, N: 13.59. C$_{12}$H$_{17}$N$_3$O$_4$S requires C: 48.15, H: 5.72, N: 14.04%]. $\nu_{max}$ (KBr) 3138, 1733, 1616, 1538 cm$^{-1}$. $\delta_H$ (CDCl$_3$) 1.39 (3H, t), 1.76 (2H, m), 2.01 (2H, m), 3.56 (2H, m), 3.88 (2H, m), 4.42 (2H, q), 4.53 (1H, m), 5.29 (2H, br s, exch. D$_2$O), 6.73 (1H, s).

d. 2-(2-Aminothiazol-4-yl)-(Z)-2-(tetrahydro-4H-pyran-4-yloxyimino)acetic acid Ethyl 2-(2-aminothiazol-4-yl)-(Z)-2-(tetrahydro-4H-pyran-4-yloxyimino)acetate (0.308 g) was hydrolysed as described in Example 17d to give the title compound (0.243 g, 87%).

e. 2-(2-Aminothiazol-4-yl)-(Z)-2-(tetrahydro-4H-pyran-4-yloxyimino)acetic acid 2-pyridyl thioester 2-(2-Aminothiazol-4-yl)-(Z)-2-(tetrahydro-4H-pyran-4-yloxyimino)acetic acid (0.24 g) was converted, as described in Example 4f, into the title compound contaminated with triphenylphosphine oxide.

f. Sodium 6β-[2-(2-aminothiazol-4-yl)-(Z)-2-(tetrahydro-4H-pyran-4-yloxyimino)acetamido]penicillanate 6β/Aminopenicillanic acid (0.229 g) was treated with 2-(2-aminothiazol-4-yl)-(Z)-2-(tetrahydro-4H-pyran-4-yloxyimino)acetic acid 2-pyridyl thioester as described in Example 1d to give the title compound as a white freeze-dried solid (0.173 g, 40%, 2 steps). $\nu_{max}$ 3404, 2961, 1766, 1662, 1608, 1528 cm$^{-1}$; $\delta_H$ (D$_2$O) 1.52 (3H, s), 1.62 (3H, s), 1.79 (2H, m), 2.02 (2H, m), 3.63 (2H, m), 3.89 (2H, m), 4.24 (1H, s), 4.50 (1H, m), 5.63 (1H, d), 5.68 (1H, d), 7.01 (1H, s). [Mass spectrum, +ve ion (thioglycerol) [M+2H-Na]$^+$ (470), MH$^+$ (492) MNa$^+$ (514)].

EXAMPLE 20 a. Ethyl (Z)-2-(2-(1-(S)-6,6-dimethylbicyclo[3.1.1]hept-2-en-2-yl)ethoxyimino)-2-(2-tritylaminothiazol-4-yl)acetate Ethyl (Z)-2-(hydroxyimino)-2-(2-tritylaminothiazol-4-yl)acetate hydrochloride (3.57 g) was reacted with 2-(1-(S)-6,6-dimethylbicyclo[3.1.1]hept-2-en-2-yl)ethyl iodide as described in Example 5a, to give the title compound as a foam (2.34 g, 53%). [Found: M$^+$, 605.2718. C$_{37}$H$_{39}$N$_3$O$_3$S requires M, 605.2712); $\nu_{max}$ (CHCl$_3$) 3400, 2990, 1735, 1525 cm$^{-1}$; $\delta_H$ (CDCl$_3$) 0.81 (3H, s), 1.14 (1H, d), 1.25 (3H, s), 1.31 (3H, t), 2.0–2.4 (7H, m), 4.22 (2H, t), 4.30 (2H, q), 5.24 (1H, m), 6.43 (1H, s), 6.90 (1H, s), 7.25 (15H, brs).

b. 2-(2-Aminothiazol-4-yl)-(Z)-2-(2-(1-(S)-6,6-dimethylbicyclo[3.1.1]hept-2-en-2-yl)ethoxyimino)acetic acid Ethyl (Z)-2-(2-(1-(S)-6,6-dimethylbicyclo[3.1.1]hept-2-en-2-yl)ethoxyimino)-2-(2-tritylaminothiazol-4-yl)acetate (1.26 g) was deprotected with formic acid as described in Example 1a. Crystallisation from cyclohexane gave the title compound as a white solid (0.40 g, 53%) m.p. 84°–50° C. [Found: M$^+$, 363.1612. C$_{18}$H$_{25}$N$_3$O$_3$S requires M, 363.1616; $\nu_{max}$ (film) 3450, 3100, 2950, 1730, 1610, 1530 cm$^{-1}$; $\delta_H$ (CDCl$_3$) 0.81 (3H, s), 1.14 (1H, d), 1.25 (3H, s), 1.32 (3H, t), 2.0–2.4 (7H, m), 4.20 (2H, t), 4.34 (2H, q), 5.25 (1H, m), 5.33 (2H, brs), 6.65 (1H, s).

c. 2-(2-Aminothiazol-4-yl)-(Z)-2-(2-(1-(S)-6,6-dimethylbicyclo[3.1.1]hept-2-en-2-yl)ethoxyimino)acetic acid Ethyl 2-(2-aminothiazol-4-yl)-(Z)-2-(2-(1-(S)-6,6-dimethylbicyclo[3.1.1]hept-2-en-2-yl)ethoxyimino)acetate (0.347 g) was hydrolysed as described in Example 4e to give the title compound as a white solid (0.254 g, 79%); $\delta_H$ (d$_6$-DMSO) 0.79 (3H, s), 1.08 (1H, s), 1.22 (3H, s), 2.0–2.4 (7H, m), 4.03 (2H, t), 5.25 (1H, m), 6.78 (1H, s), 7.14 (2H, br s, exch. D$_2$O).

d. 2-(2-Aminothiazol-4-yl)-(Z)-2-(2-(1-(S)-6,6-dimethylbicyclo[3.1.1]hept-2-en-2-yl)ethoxyimino)acetic acid 2-pyridyl thioester 2-(2-Aminothiazol-4-yl)-(Z)-2-(2-(1-(S)-6,6-dimethylbicyclo[3.1.1]hept-2-en-2-yl)ethoxyimino)acetic acid (0.22 g) was converted into the title compound as described in Example 4f. $\delta_H$ (CDCl$_3$) 0.83 (3H, s), 1.17 (1H, d), 1.26 (3H, s), 2.0–2.4 (7H, m), 4.28 (2H, t), 5.31 (1H, m), 5.85 (2H, brs), 6.83 (1H, s), 7.34 (1H, m), 7.74 (2H, m), 8.66 (1H, m).

e. Sodium 6β-[2-(2-aminothiazol-4-yl)-(Z)-2-(2-(1-(S)-6,6-dimethylbicyclo[3.1.1]hept-2-en-2-yl)ethoxyimino)acetamido]penicillanate 2-(2-Aminothiazol-4-yl)-(Z)-2-(2-(1-(S)-6,6-dimethylbicyclo[3.1.1]hept-2-en-2-yl)ethoxyimino)acetic acid 2-pyridyl thioester was treated with 6β-aminopenicillanic acid as described in Example 1d to give the title compound as a white freeze-dried solid (14 mg, 4%, 2 steps); $\nu_{max}$ (KBr) 2930, 1772, 1673, 1610, 1532 cm$^{-1}$; $\delta_H$ (D$_2$O) 0.78 (3H, s), 1.09 (1H, d), 1.25 (3H, s), 1.51 (3H, s), 1.61 (3H, s), 2.07–2.37 (7H, m), 4.23 (3H, s +m), 5.32 (1H, m), 5.59 (1H, d), 5.62 (1H, d), 7.01 (1H, s). [Mass spectrum, +ve ion (thioglycerol) MH$^+$ (556) MNa$^+$ (578)].

EXAMPLE 21 a. Ethyl 2-(2-aminothiazol-4-yl)-(Z)-2-(cyclohexylmethoxyimino)acetate

Ethyl (Z)-2-(hydroxyimino)-2-(2-tritylaminothiazol-4-yl)acetate hydrochloride (3.08 g) was reacted with cyclohexylmethyl bromide as described in Example 5a. The product was deprotected with formic acid as described in Example 1a. Crystallisation from cyclohexane/hexane gave the title compound as a white solid (1.2 g, 62%), m.p. 107.0°–107.5° C. [Found: C: 54.21; H: 6.58; N: 13.31. C$_{14}$H$_{21}$N$_3$O$_3$S requires C: 54.00; H: 6.80; N: 13.49%]. $\nu_{max}$(CHCl$_3$) 3400, 2920, 1730, 1600 cm$^{-1}$; $\delta_H$ (CDCl$_3$) 1.0 (2H, m), 1.2 (3H, m), 1.33 (3H, t), 1.7 (6H, m), 3.97 (2H, d), 4.35 (2H, q), 5.60 (2H, br s, exch. D$_2$O), 6.63 (1H, s).

b. 2-(2-Aminothiazol-4-yl)-(Z)-2-(cyclohexylmethoxyimino)acetic acid

Ethyl 2-(2-aminothiazol-4-yl)-(Z)-2-(cyclohexylmethoxyimino)acetate (0.971 g) was hydrolysed as described in Example 4e to give the title compound as a white solid (0.679 g, 77%); $\delta_H$ (d$_6$-DMSO) 1.1 (5H, m), 1.6 (6H, m), 3.9 (2H, d), 6.8 (1H, s), 7.2 (2H, br s, exch. $D_2O$).

c. 2-(2-Aminothiazol-4-yl)-(Z)-2-(cyclohexylmethoxyimino)acetic acid 2-pyridyl thioester 2-(2-Aminothiazol-4-yl)-(Z)-2-(cyclohexylmethoxyimino) acetic acid (0.60 g) was converted into the title compound (0.56 g, 70%) as described in Example 4f.

d. Sodium 6β-[2-(2-aminothiazol-4-yl)-(Z)-2-(cyclohexylmethoxyimino)acetamido]penicillanate 6β-Aminopenicillanic acid was treated with 2-(2-aminothiazol-4-yl)-(Z)-2-(cyclohexylmethoxyimino)acetic acid 2-pyridyl thioester (0.56 g) as described in Example 1d to give the title compound as white freeze-dried solid (0.315 g, 42%); $v_{max}$ (KBr) 3385, 2924, 1766, 1668, 1608, 1526 cm$^{-1}$; $\delta_H$ ($D_2O$) 0.97 (2H, m), 1.20 (3H, m), 1.51 (3H, s), 1.62 (3H, s), 1.68 (6H, m), 4.01 (2H, dd), 4.22 (1H, s), 5.61 (1H, d), 5.64 (1H, d), 6.97 (1H, s). [Mass spectrum, +ve ion (thioglycerol), MH+ (504), MNa+ (526), 2M+Na+ (1029)].

EXAMPLE 22 a. Ethyl (Z)-2-n-butoxyimino-2-(2-tritylaminothiazol-4-yl)acetate

Ethyl (Z)-2-hydroxyimino-2-(2-tritylaminothiazol-4-yl) acetate hydrochloride (lg) was alkylated with n-butyl bromide (0.55 g) as described in Example 5a to give the title compound (0.706 g); (Found: M+, 513.2083. $C_{30}H_{31}N_3O_3S$ requires M, 513.2088); $v_{max}$ ($CH_2Cl_2$) 3400, 1735 and 1525 cm$^{-1}$; $\delta_H$ ($CDCl_3$) 0.92–1.80 (10H, m), 4.07 (4H, m), 6.55 (1H, s), 7.06 (1H, broad s) and 7.34 (15H, s).

b. (Z)-2-n-Butoxyimino-2-(2-tritylaminothiazol-4-yl) acetic acid

Ethyl (Z)-2-n-butoxyimino-2-(2-tritylaminothiazol-4-yl) acetate (0.7 g) was hydrolysed to the title compound (0.596 g) as described in Example 5b; $v_{max}$ ($CH_2Cl_2$) 3400–2500 (broad), 1730, 1590, 1570, 1520 and 1490 cm$^{-1}$; $\delta_H$($CDCl_3$) 4.16 (2H, t, J 6Hz), 6.59 (1H, s), 7.34 (15H, s) and 8.85 (2H, broad s). [Mass spectrum: +ve ion (3NOBA/Na+) MNa+ (508), MNa+ (sodium salt) (530)].

c. Sodium 6β-[2-(2-aminothiazol-4-yl)-(Z)-2-(n-butoxyimino)acetamido]penicillanate (Z)-2-n-Butoxyimino-2-(2-tritylaminothiazol-4-yl)acetic acid (0.56 g) was converted into the title compound (0.094 g) using a similar procedure to that described in Example 2d Method 2; $v_{max}$ (KBr) 1766, 1662, 1608, 1527, 1459 and 1395 cm$^{-1}$; $\delta_H$ ($D_2O$) 0.89 (3H, t, J 7 Hz), 1.37 (2H, m), 1.51 (3H, s), 1.61 (3H, s), 1.55–1.70 (2H, m), 4.20 (2H, t, J 6 Hz), 4.23 (1H, s), 5.62 (1H, d, J 4 Hz), 5.63 (1H, d, J 4 Hz), and 6.99 (1H, s). [Mass spectrum: +ve ion (3NOBA/Na+).MNa+ (486)].

EXAMPLE 23 a. (Z)-2-Hydroxyimino-2-(2-tritylaminothiazol-4-yl) acetic acid

Ethyl (Z)-2-hydroxyimino-2-(2-tritylaminothiazol-4-yl)acetate hydrochloride (5 g) as a suspension in dioxane (50ml) was treated at room temperature with 1M aqueous sodium hydroxide (23 ml). After stirring for 12 h, water (50 ml) was added. The pH was adjusted to 1–2 with dilute hydrochloric acid. The resulting precipitate was filtered off, washed with water and dried over $P_2O_5$ to give the title compound (4.2 g) as a white solid; $\delta_H$ (($CD_3$)$_2$SO) 6.73 (1H, s), 7.30 (15H, s).

b. Diphenylmethyl (Z)-2-hydroxyimino-2-(2-tritylaminothiazol-4-yl)acetate (Z)-2-Hydroxyimino-2-(2-tritylaminothiazol-4-yl)acetic acid (4.2 g) as a suspension in dichloromethane (150 ml) was treated with a solution of diphenyldiazomethane (1.91 g) in dichloromethane (50 ml) in a dropwise fashion, over 5 min. After 2 h stirring at room temperature, acetic acid (1 ml) was added and stirred for a further 30 min. The solution was washed with saturated sodium bicarbonate and water, dried and filtered. Removal of solvent in vacuo gave a yellow crisp foam which was purified by chromatography on silica gel eluting with ethyl acetate/hexane. The title compound was obtained as a white solid; $v_{max}$ ($CH_2Cl_2$) 1735, 1520 and 1490 cm$^{-1}$; $\delta_H$($CDCl_3$) 6.16 (1H, s), 7.17 (1H, s). 7.22–7.50 (25H, m). [Mass spectrum: +ve ion (thioglycerol) MNa+ (596)].

c. Diphenylmethyl (Z)-2-(cyanomethoxyimino)-2-(2-tritylaminothiazol-4-yl)acetate Diphenylmethyl (Z)-2-hydroxyimino-2-(2-tritylaminothiazol-4-yl)acetate (1.5 g) was alkylated with chloroacetonitrile (0.38 g) as described in Example 5a to give the title compound as a white solid (1.23 g); $v_{max}$ ($CH_2Cl_2$) 3400, 1740, 1535 and 1490 cm$^{-1}$; $\delta_H$ ($CDCl_3$) 4.82 (2H, s), 6.45 (1H, s), 6.98 (1H, broad s), 7.17 (1H, s) and 7.26–7.52 (25H, m). [Mass spectrum: +ve ion (3NOBA) MH+ (635) and (3NOBA/Na+) MNa+ (657)]

d. 2-(2-Aminothiazol-4-yl)-(Z)-2-cyanomethoxyiminoacetic acid

Diphenylmethyl (Z)-2-cyanomethoxyimino-2-(2-tritylaminothiazol-4-yl)acetate (lg) was dissolved in formic acid (98%, 40 ml) and water (10 ml) at room temperature and stirred for 12 h. The solvent was removed in vacuo and the residue triturated with ether to give the title compound as an off-white solid (0.39 g). The product was sufficiently pure for the next step; $v_{max}$ (nujol) 3700–2500, 1605 (broad), 1465 and 1380 cm$^{-1}$; $\delta_H$ inter alia 5.09 (2H, s), 7.04 (1H, s). [Mass spectrum: EI M+ (226)].

e. 2-(2-Aminothiazol-4-yl)-(Z)-2-(cyanomethoxyimino)acetic acid 2-pyridyl thioester 2-(2-Aminothiazol-4-yl)-(Z)-2-cyanomethoxyimino acetic acid (0.32 g) was treated with triphenylphosphine (0.557 g) and 2,2′-dithiodipyridine (0.467 g) as described in Example 1c, to give the title compound as a white solid (0.423 g); $\nu_{max}$ (KBr) 3405, 3263, 1681, 1626, 1569 and 1543 cm$^{-1}$; $\delta_H$ (CDCl$_3$) 4.85 (2H, s), 6.94 (2H, s+broad s), 7.33–7.92 (m, PPh$_3$ impurities), 8.70 (1H, m).

f. Sodium 6β-[2-(2-aminothiazol-4-yl}-(Z)-2-(cyanomethoxyimino)acetamido]penicillanate 2-(2-Aminothiazol-4-yl)-(Z)-2-cyanomethoxyimino acetic acid 2-pyridyl thioester (0.323 g) was reacted with 6β-aminopenicillanic acid as described in Example 1d, to give the title compound as a freeze-dried white solid (149 mg); $\nu_{max}$ (KBr) 1764, 1662, 1606 and 1531 cm$^{-1}$; $\delta_H$ (D$_2$O) 1.51 (3H, s), 1.61 (3H, s), 4.25 (1H, s), 5.00 (2H, s), 5.62 (1H, d, J 4 Hz), 5.64 (1H, d, J 4 Hz), 7.17 (1H, s). [Mass spectrum: +ve ion (glycerol) MH$^+$ (447)].

Example 24 a. Ethyl (Z)-2-(trans-2-methylcyclohexyloxy-imino)-3-oxobutyrate

Ethyl (Z)-2-hydroxyimino-3-oxobutyrate (1.59 g) was alkylated with cis-2-methylcyclohexan-1-ol (1.71 g) as described in Example 4, method 3. The pure title compound was otained as a pale yellow oil (0.506 g). (Found: M$^+$, 256.1552. C$_{13}$H$_{21}$NO$_4$ requires M 256.1549); $\nu_{max}$ (film) 1745, 1695 and 1595 cm$^{-1}$; $\delta_H$ (CDCl$_3$) 1.02 (3H, d, J 6 Hz), 1.35 (3H, t, J 7 Hz), ca 1.2–2.3 (9H, m), 2.40 (3H, s), 3.95 (1H, m) and 4.42 (2H, q, J 7 Hz).

b. Ethyl 4-bromo-(Z)-2-(trans-2-methylcyclohexyloxyimino)-3-oxobutyrate

Ethyl (Z)-2-(trans-2-methylcyclohexyloxyimino)-3-oxobutyrate (1.91 g) was brominated according to the procedure outlined in Example 4c to give the crude title compound.

c. Ethyl 2-(2-aminothiazol-4-yl)-(Z)-2-(trans-2-methylcyclohexyloxyimino)acetate Ethyl 4-bromo-(Z)-2-(trans-2-methylcyclohexyloxyimino)-3-oxobutyrate (2.5 g) was treated with thiourea (0.57 g) and N,N-dimethylaniline (0.95 ml) as described in Example 4d to give the title compound as a yellow gum (1.07 g) after silica gel chromatography. (Found: M$^+$, 311.1297. C$_{14}$H$_{21}$N$_3$O$_3$S requires M, 311.1305); $\nu_{max}$ (CH$_2$Cl$_2$) 3475, 3380, 1735, 1600 and 1525 cm$^{-1}$; $\delta_H$ (CDCl$_3$) 0.98 (3H, d, J 6 Hz), 1.35 (3H, t, J 7 Hz), ca 1.1–2.4 (9H, m), 3.84 (1H, m), 4.40 (2H, q, J 7 Hz), 5.88 (2H, broad s), 6.71 (1H, s).

d. 2-(2-Aminothiazol-4-yl)-(Z)-2-(trans-2-methylcyclohexyloxyimino)acetic acid Ethyl 2-(2-aminothiazol-4-yl)-(Z)-2-(trans-2-methylcyclohexyloxyimino)acetate (1.07 g) was hydrolysed as described in Example 4e to give the title compound as a buff coloured solid (0.802 g); $\nu_{max}$ (nujol) 3500–2300, 1615 (broad), 1460 and 1375 cm$^{-1}$; $\delta_H$ ((CD$_3$)$_2$SO) inter alia 0.95 (3H, d, J 6 Hz), 0.95–2.1 (9H, m), 6.83 (1H, s). [Mass spectrum: +ve ion (thioglycerol) MH$^+$ (284)].

e. 2-(2-Aminothiazol-4-yl)-(E,Z)-2-(trans-2-methylcyclohexyloxyimino)acetic acid 2-pyridyl thioester 2-(2-Aminothiazol-4-yl)-(Z)-2-(trans-2-methylcyclohexyloxyimino)acetic acid (0.5 g) was converted to the corresponding 2-pyridyl thioester as described in Example 1c. The title compound was isolated as a mixture of (E) and (Z) isomers (0.472 g). (Found: M$^+$, 376.1024. C$_{17}$H$_{20}$N$_4$O$_2$S$_2$ requires M, 376.1028); $\nu_{max}$ (KBr) 3343, 3128, 1688, 1652, 1622, 1572, 1562, 1537, 1449 and 1418 cm$^{-1}$; $\delta_H$ ((CD$_3$)$_2$SO) 0.99 (3H, d, J 6 Hz), 1.15–2.3 (9H, m), ca 3.5–4.20 (1H, m), 6.97 (1H, s), ca 7.2–8.20 (4H, m), 8.72 (1H, m).

f. Sodium 6β-[2-(2-aminothiazol-4-yl)-(Z)-2-(trans-2-methylcyclohexyloxyimino)acetamido]penicillanate 2-(2-Aminothiazol-4-yl)-(E,Z)-2-(trans-2-methylcyclohexyloxyimino)acetic acid 2-pyridyl thioester (0.43 g) was coupled with 6β-aminopenicillanic acid (0.247 g) as described in example 1d. The title compound was obtained (0.112 g) as a freeze-dried solid after separation from its (E)-isomer; $\nu_{max}$ (KBr) 1766, 1668, 1608 and 1526 cm$^{-1}$; $\delta_H$ (D$_2$O) 0.93 and 0.96 (3H, 2d, J 6 Hz), 1.03–1.41 (4H, m), 1.51 (3H, s), 1.56–1.75 (4H, m), 1.62 (3H, s), 2.06 (1H, m), 3.71–3.83 (1H, m), 4.21 and 4.22 (1H, 2s), 5.61–5.66 (2H, m), 6.95 (1H, s). [Mass spectrum: +ve ion (thiolglycerol) MH$^+$ (504)].

EXAMPLE 25 a. Ethyl (Z)-2-(cyclohex-2-enyloxyimino)-2-(2-tritylamrnothiazol-4-yl)acetate Ethyl (Z)-2-hydroxyimino-2-(2-tritylaminothiazol-4-yl) acetate (4.58 g) was suspended in dry ethanol (120 ml), with stirring at room temperature. This was treated with a solution of sodium (0.23 g) in ethanol to give a yellow homogeneous solution. After 15 min at room temperature, freshly distilled 3-bromocyclohexene (4.83 g) was added and the reaction mixture left to stir at room temperature for ca 3 h. The solvent was removed in vacuo. The residue was taken up in ethyl acetate, and washed successively with portions of water and brine. Drying over anhydrous sodium sulphate and evaporating gave a brown gum. Flash silica gel chromatography eluting with 10% ethyl acetate/hexane afforded the title compound as a colourless foam (1.35 g). (Found: M$^+$, 537.2075. C$_{32}$H$_{31}$N$_3$O$_3$S requires M, 537.2088); $\nu_{max}$ (CH$_2$Cl$_2$) 3380 and 1730 cm$^{-1}$; $\delta_H$ (CDCl$_3$) 1.46 (3H, t, J 7 Hz), 1.6–2.3 (6H, m), 4.42 (2H, q, J 7 Hz), 4.93 (1H, m), 5.96 (2H, broad s), 6.55 (1H, s), 7.37 (15H, s).

b. (Z)-2-(Cyclohex-2-enyloxyimino)-2-(2-tritylaminothiazol-4-yl)acetic acid

Ethyl (Z)-2-(cyclohex-2-enyloxyimino)-2-(2-tritylaminothiazol-4-yl)acetate (1.35 g) was hydrolysed as described in Example 5b. The title compound was obtained as a white solid (0.944 g); $\nu_{max}$ 3397, 1727 (broad), 1590, 1569, 1526, 1490 and 1446 cm$^{-1}$; $\delta_H$ ((CD$_3$)$_2$SO) 1.5–2.2 (6H, m), 4.64 (1H, m), 5.90 (2H, m), 6.89 (1H, s), 7.36 (15H, s). [Mass spectrum: +ve ion (thioglycerol) MH+ (510)].

c. Sodium 6β-[2-(2-aminothiazol-4-yl)-(Z)-2-(cyclohex-2-enyloxyimino)acetamido]penicillanate (Z)-2-(Cyclohex-2-enyloxyimino)-2-(2-tritylaminothiazol-4-yl)acetic acid (0.85 g) was converted into the title compound (0.112 g) as described in Example 2d, method 2; $\nu_{max}$ (KBr) 3351, 1766, 1662, 1608, 1526 and 1396 cm$^{-1}$; $\delta_H$(D$_2$O) 1.50 (3H, s), 1.61 (3H, s), 1.84 (2H, m), 2.02 (2H, m), 4.22 (1H, s), 5.59 (1H, d, J 4 Hz), 5.60 (1H, d, J 4 Hz), 5.63 (1H, d, J 4 Hz), 5.64 (1H, d, J 4 Hz), 5.83 (1H, m), 6.05 (1H, m), 6.98 and 6.99 (1H, 2s). [Mass spectrum: +ve ion (3NOBA/Na+) MH+ (488) and MNa+ (510)].

EXAMPLE 26 a. Ethyl (Z)-2-(trans-4-t-butylcyclohexyloxyimino)-3-oxobutyrate

Ethyl (Z)-2-hydroxyimino-3-oxobutyrate (1.59 g) was converted to the title compound using 4-t-butylcyclohexanol as described in Example 4a, method 3. The product was obtained as a pale yellow oil (0.973 g). [Found: M+, 298.2014 C$_{16}$H$_{28}$NO$_4$ requires M, 298.2020; $\nu_{max}$ (CH$_2$Cl$_2$) 1735 and 1685 cm$^{-1}$; $\delta_H$ (CDCl$_3$) 0.67 (9H, s), 0.9–2.1 (8H, m), 1.13 (3H, t, J 7 Hz), 2.20 (3H, s), 3.8–4.3 (3H, m).

b. Ethyl 4-bromo-(Z)-2-(trans-4-t-butylcyclohexyloxyimino)-3-oxobutyrate

Ethyl (Z)-2-(trans-4-t-butylcyclohexyloxyimino)-3-oxobutyrate (5.19 g) was brominated as outlined in Example 4c to give the unpurified title compound.

c. Ethyl 2-(2-aminothiazol-4-yl)-(Z)-2-(trans-4-t-butylcyclohexyloxyimino)acetate Ethyl-4-bromo-(Z)-2-(trans-4-t-butylcyclohexyloxyimino)-3-oxobutyrate was converted to the pure title compound (1.577 g) as described in Example 4d. [Found: M+, 353.1781. C$_{17}$H$_{27}$N$_3$O$_3$S requires M, 353.1773]; $\nu_{max}$ (CH$_2$Cl$_2$) 3480, 3380, 1735, 1600 and 1525 cm$^{-1}$; $\delta_H$ (CD$_3$OD) 0.88 (9H, s), ca 0.9–1.5 (4H, m), 1.36 (3H, t, J 7 Hz), ca 1.8–2.4 (4H, m), ca 4.1 (1H, broad m), 4.41 (2H, q, J 7 Hz), 6.77 (1H, s).

d. 2-(2-Aminothiazol-4-yl)-(Z)-2-(trans-4-t-butylcyclohexyloxyimino)acetic acid Ethyl 2-(2-aminothiazol-4-yl)-(Z)-2-(trans-4-t-butylcyclohexyloxyimino)acetate (1.52 g) was hydrolysed as described in Example 4e to give the title compound as a white amorphous solid (1.11 g); $\nu_{max}$ (KBr) 3214, 1610 (very broad), 1450 and 1389 cm$^{-1}$; $\delta_H$ ((CD$_3$)$_2$SO) 0.78 (9H, s), ca 0.8–1.3 (4H, m), ca 1.5–2.3 (4H, m), 3.8 (1H, broad m), 6.70 (1H, s), 7.13 (3H, broad s). [Mass spectrum: +ve ion (thioglycerol) MH+ (326)].

e. 2-(2-Aminothiazol-4-yl)-(Z)-2-(trans-4-t-butylcyclohexyloxyimino)acetic acid 2-pyridyl thioester 2-(2-Aminothiazol-4-yl)-(Z)-2-(trans-4-t-butylcyclohexyloxyimino)acetic acid (1.05 g) was converted to the title compound (1.22 g) as described in Example 1c. [Found: M+, 418.1507. C$_{20}$H$_{26}$N$_4$O$_2$S$_2$ requires M 418.1497]; $\nu_{max}$ (KBr) 3313, 3155, 1700, 1641, 1573 and 1538 cm$^{-1}$; $\delta_H$((CD$_3$)$_2$CO) 0.90 (9H, s), ca 1.4–1.9 (4H, m), ca 2.0–2.7 (4H, m), 7.00 (2H, broad s), 7.20 (1H,s), 7.70 (1H, m), 8.10 (2H, m), 8.87 (1H, m).

f. Sodium 6β-[2-(2-aminothiazol-4-yl)-(Z)-2-(trans-4-t-butylcyclohexyloxyimiino)acetamido]penicillanate 2-(2-Aminothiazol-4-yl)-(Z)-2-(trans-4-t-butylcyclohexyloxyimino)acetic acid 2-pyridyl thioester (1.19 g) was converted to the title compound (0.656 g) as described in Example 1d; $\nu_{max}$ (KBr) 3369, 1767, 1668, 1608 and 1526 cm$^{-1}$; $\delta_H$ (D$_2$O) 0.83 (9H, s), 1.02 (3H, m), 1.33 (2H, m), 1.51 (3H, s), 1.62 (3H, s), 1.81 (2H, m), 2.12 (2H, m), 4.07 (1H, m), 4.21 (1H, s), 5.60 (1H, d, J4 Hz), 5.66 (1H, d, J 4 Hz), 6.90 (1H, s). [Mass spectrum: +ve ion (thioglycerol) MH+ (546) and MNa+ (568)].

EXAMPLE 27 a. Ethyl (Z)-2-(trans-2-fluorocyclohexyloxyimino-3-oxobutyrate

Ethyl (Z)-2-hydroxyimino-3-oxobutyrate was treated with cis-1-bromo-2-fluorocyclohexane (prepared according to the method of T. Ando et al., J. Org. Chem., 1981, 46, 4446) as described in Example 4a (method 2), to give the title compound as a colourless oil (15%); $\nu_{max}$ (CH$_2$Cl$_2$) 2950, 2350, 1740 and 1685 cm$^{-1}$; $\delta_H$ (CDCl$_3$) 1.28–1.78 (9H, m, incl. 1.33, t, J 7 Hz), 2.00–2.18 (2H, m), 2.40 (3H, s), 4.30–4.52 (3.5H, m), 4.68 (0.5H, ddd, J 4.8, 7.9, 9.5 Hz).

b. Ethyl 4-bromo-(Z)-2-(trans-2-fluorocyclohexyloxyimino)-3-oxobutyrate

Ethyl (Z)-2-(trans-2-fluorocyclohexyloxyimino)-3-oxobutyrate was converted to the title compound using the procedure described in Example 4c, (69%); $\nu_{max}$ (CH$_2$Cl$_2$) 2940 and 1735 cm$^{-1}$; $\delta_H$ (CDCl$_3$) 1.33–1.80 (9H, m, incl. 1.33, t, J=7 Hz), 2.05–2.20 (2H, m), 4.30–4.52 (5.5H, m), 4.68 (0.5H, ddd, J=4.9, 8.1, 9.7 Hz).

c. Ethyl 2-(2-aminothiazol-4-yl)-(Z)-2-(trans-2-fluorocyclohexyloxyimino)acetate Ethyl 4-bromo-(Z)-2-(trans-2-fluorocyclohexyloxyimino)-3-oxobutyrate was converted to the title compound following the procedure of Example 4d, (76%), $\nu_{max}$ (CH$_2$Cl$_2$) 3460, 3380, 1735, 1610, 1525 cm$^{-1}$; $\delta_H$ (CDCl$_3$) 1.22–2.30 (11H, m, incl. 1.34, t, J=7 Hz), 4.25–4.60 (3.5H, m), 4.80–5.25 (0.5H, m), 5.85 (2H, br s), 6.76 (1H, s).

d. 2-(2-Aminothiazol-4-yl)-(Z)-2-(trans-2-fluorocyclohexyloxyimino)acetic acid Ethyl 2-(2-aminothiazol-4-yl)-(Z)-2-(trans-2-fluorocyclohexyloxyimino)acetate was converted to the title compound following the procedure of Example 4e, (60%), $v_{max}$ (Nujol) 3350 (br), 1640 cm$^{-1}$; $\delta_H$ (D$_6$-DMSO) 1.20–2.30 (8H, m), 4.00–4.50 (1.5H, m), 4.60–5.30 (2.5H, m), 6.88 (1H, s).

e. 2-(2-Aminothiazol-1-yl)-(Z)-2-(trans-2-fluorocyclohexyloxyimino)acetic acid-2-pyridyl thioester 2-(2-Aminothiazol-4-yl)-(Z)-2-(trans-2-fluorocyclohexyloxyimino)acetic acid was converted to the title compound following the procedure of Example 4f. The product was obtained as a pale yellow crystalline solid, (73%), m.p. 159°–160° C. (ethyl acetate), $v_{max}$ (CH$_2$Cl$_2$) 3460, 3380, 1730, 1690, 1610, 1525 cm$^{-1}$; $\delta_H$ (D$_6$-DMSO) 1.20–1.70 (6H, m), 1.95–2.10 (2H, m), 4.16–4.28 (1H, m), 4.60 (1H, dddd, J=4.9, 9.6, 9.6, 5.3 Hz), 6.96 (1H, s), 7.35 (2H, br s), 7.48–7.53 (1H, m), 7.75 (1H, dd, J=0.9, 7.9 Hz), 7.96 (1H, ddd, J=1.9, 7.7, 7.7 Hz), 8.62–8.66 (1H, m).

f. Sodium 6β-[2-(2-aminothiazol-4-yl)-(Z)-2-(trans-2-fluorocyclohexyloxyimino)acetamido]penicillanate.

2-(2-Aminothiazol-4-yl)-(Z)-2-(trans-2-fluorocyclohexyloxyimino)acetic acid 2-pyridyl thioester and 6β-aminopenicillanic acid was converted to the title compound as described in Example 1d. $v_{max}$ (KBr) 1767, 1663, 1615, 1529 cm$^{-1}$, $\delta_H$(D$_2$O) 1.15–1.75 (12H, m, incl. 1.25, 3H, t, J=7.5 Hz), 2.02–2.18 (2H, m), 4.24 (1H, s), 4.21–4.38 (1H, m), 4.51–4.62 (0.5H, m) (remainder of this signal hidden under HOD peak), 5.63–5.69 (2H, m), 7.02 (1H, s); [Mass spectrum: (+ve ion FAB) MH$^+$ (508), MH$^+$-Na (486)].

EXAMPLE 28 a. Benzhydryl-6β-aminopenicillanate

To a suspension of 6β-aminopenicillanic acid (2.16 g) in dry acetonitrile (50 ml) was added diphenyl diazomethane (1.94 g) and the reaction mixture heated to 50° C. for 68 h. The solution was filtered, the solvent evaporated, and the residue chromatographed on Kieselgel 60 (<230 mesh ASTM) eluting with 70% ethyl acetate/hexane, to afford the title compound as a white foam (1.84 g, 46%); $v_{max}$ (CH$_2$Cl$_2$) 3400, 1780, 1740 cm$^{-1}$. To a solution of the title compound (1.80 g) in acetone (10 ml) was added a solution of p-toluenesulphonic acid hydrate (0.863 g) in acetone (10 ml). The resultant white crystals of benzhydryl-6-aminopenicillanate p-toluene sulphonic acid salt were collected by filtration and dried in vacuo, (1.92 g); m.p. 165° C., (Found: C, 60.50; H, 5.39; N, 4.92. C$_{28}$H$_{30}$S$_2$O$_6$N$_2$ requires C, 60.63; H, 5.45; N, 5.05%); $\delta_H$(D$_6$-DMSO) 1.48 (3H, s), 1.83 (3H, s), 2.25 (3H, s), 4.68 (1H, s), 5.10 (1H, d, J=5 Hz), 5.54 (1H, d, J=5 Hz), 6.89 (1H, s), 7.05–7.52 (14H, m).

b. Benzhydryl 6β-([2-(2-tritylaminothiazol-4-yl)-(Z)-2-(2-pyrrolidon-3-yloxyimino)]aetamido)-penicillanate To a suspension of (Z)-2-(2-tritylaminothiazol-4-yl)-2-(2-pyrrolidon-3-yloxyimino)acetic acid (0.130 g) (prepared according to the procedure described in European Patent No. 0101265) in dry tetrahydrofuran (8 ml) were added benzhydryl 6β-aminopenicillanic acid (0.120 g), 1-hydroxybenzotriazole (0.042 g) and 1,3-dicyclohexylcarbodiimide (0.063 g). The reaction mixture was stirred at room temperature under an argon atmosphere for 2 h, filtered and the filtrate evaporated under reduced pressure and the residue dissolved in ethyl acetate (10 ml). The organic solution was washed with dilute HCl (0.1N, 5 ml), 5% NaHCO$_3$ (5 ml), saturated aqueous NaCl (5 ml), dried (MgSO$_4$) and evaporated under reduced pressure. Chromatography on Keiselgel 60 (<250 mesh ASTM) eluting with ethyl acetate afforded the title compound as a white foam (0.082 g; contaminated with a small amount of 1,3-dicyclohexyl urea); $v_{max}$ (CH$_2$Cl$_2$) 3430, 3380, 1785, 1710, 1680, 1520 cm$^{-1}$; $\delta_H$(CDCl$_3$) inter alia 1.23 (3H, s), 1.58 (3H, s), 2.30–2.65 (2H, m), 3.20–3.55 (2H, m), 4.48 (1H, s), 4.99 (1H, t, J=9 Hz), 5.55–5.78 (2H, m), 6.75 (1H, s), 7.27 (25H, m).

c. Sodium 6β-[2-(2-aminothiazol-4-yl)-(Z)-2-(2-pyrrolidon-3-yloxyimino)acetamido]penicillanate Benzhydryl 6β-([2-(2-tritylaminothiazol-4-yl)-(Z)-2-(2-pyrrolidon-3-yloxyimino)]acetamido)penicillanate (0.030 g) was dissolved in dry dichloromethane (1 ml) and treated with anisole (2.5 μl) and trifluoroacetic acid (50 μl) at 0° C. After 20 mins at 0° C., the reaction mixture was diluted with toluene (3 ml), the solvent evaporated to low volume under reduced pressure, further toluene (3 ml) added, and the process repeated twice. The residue was partitioned between water (3 ml) and ethyl acetate (3 ml), and the pH adjusted to 8.0 with saturated aqueous sodium bicarbonate. The aqueous phase was separated, concentrated to low volume and applied to a column of HP20 SS. Elution with water followed by 0.5% tetrahydrofuran/water afforded the title compound which was lyophilised to a pale yellow solid (2.5 mg); $v_{max}$ (KBr) 1772, 1690 (br), 1610 (br), 1532 cm$^{-1}$; $\delta_H$ (D$_2$O) 1.51 (3H, s), 1.59 (3H, s), 2.20–2.38 (1H, m), 2.50–2.65 (1H, m), 3.35–5.53 (2H, m), 4.25 (1H, s), 5.00–5.06 (1H, m), 5.61 (2H, dd, J=3.2, 5.4 Hz), 7.07 (1H, s). ([Mass spectrum: (+ve ion-FAB) M$^+$ (491, sodium salt), MH$^+$ (469, free acid)].

EXAMPLE 29 a. Ethyl 2-(2-aminothiazol-4-yl)-(Z)-2-(1-(R)-6,6-dimethylbicyclo[3.1.1]hept-2-en-2-yl)methoxyimino)acetate Ethyl (Z)-2-(hydroxyimino)-2-(2-tritylaminothiazol-4-yl)acetate hydrochloride (4.93 g) was reacted with 2-(1-(R)-6,6-dimethylbicyclo[3.1.1]hept-2-en-2-yl)-methyl bromide as described in Example 5a, to give the title compound as a foam (3.5 g, 59%), $v_{max}$ (CHCl$_3$) 3380, 1730 and 1525 cm$^{-1}$; $\delta_H$(CDCl$_3$) 0.8 (3H, s), 1.25

(3H, s), 1.16 (1H, d, J8 Hz), 1.32 (3H, t, J7 Hz), 2.25 (5H, m), 4.3 (2H, q, J7 Hz), 4.58 (1H, s showing undefined fine coupling), 5.54 (1H, m), 6.45 (1H, s), 6.88 (1H, s, exch. $D_2O$), and 7.25 (15H, m).

b. 2-(2-Aminothiazol-4-yl)-(Z)-2-(1-(R)-6,6-dimethylbicyclo[3.1.1]hept-2-en-2-yl)methoxyimino)acetic acid Ethyl 2-(2-aminothiazol-4-yl)-(Z)-2-(1-(R)-6,6-dimethylbicyclo[3.1.1]hept-2-en-2-yl)methoxyimino)acetate (1.18 g) was hydrolysed as described in Example 5b to give the title compound as a pale yellow foam (100%), $\nu_{max}$ ($CHCl_3$) ca. 3000 (very broad), 1720 cm$^{-1}$, $\delta_H$ ($CDCl_3$), 0.75 (3H, s), 1.08 (1H, d, J8 Hz), 1.2 (3H, s), 2.17 (5H, m), 4.49 (2H, slightly broadened s), 5.47 (1H, br s), 6.5 (1H, s), 7.25 (16H, m), and ca. 10.2 (1H, very broad signal, exch. $D_2O$). [Found: +ve ion (3NOBa/Na) MNa+ (586), M+ +2Na (608)].

c. Sodium 6β-[2-(2-aminothiazol-4-yl)-(Z)-2-(1-(R)-6,6-dimethylbicyclo[3.1.1]hept-2-en-2yl)methoxyimino)acetamido]penicillanate 2-(2-Aminothiazol-4-yl)-(Z)-2-(1-(R)-6,6-dimethylbicyclo[3.1.1]hept-2-en-2-yl)methoxyimino)acetic acid was converted to the title compound (37 mg, 9%) as described in Example 2d, method 2, $\nu_{max}$ (KBr) 2969, 2915, 2830, 1766, 1668, 1608 and 1528 cm$^{-1}$; $\delta_H$($D_2O$) 0.79 (3H, s), 1.12 (1H, d, J8.6 Hz), 1.52 (3H, s), 1.63 (3H, s), 1.9 (1H, m), 2.16–2.33 (3H, m), 2.4 (1H, m), 4.24 (1H, s), 4.6 (2H, AA' system), 5.62 (2H, s), 5.66 (1H, br s) and 7.0 (1H, s). [Mass spectrum: +ve ion (thioglycerol) MH+ (542), MNa+ (564)]

EXAMPLE 30 a. Ethyl (Z)-2-(benzyloxyimino)-3-oxobutyrate

Ethyl (Z)-2-(hydroxyimino)-3-oxobutyrate (2.4 g) was alkylated with benzyl bromide as described in Example 4a, method 1, to give the title compound (2.94 g). (Found: M+, 249.0994. $C_{13}H_{15}NO_4$ requires M 249.1001). $\nu_{max}$ (film) 2980, 1740 and 1695 cm$^{-1}$, $\delta_H$ ($CDCl_3$) 1.28 (3H, t), 2.33 (3H, s), 4.26 (2H, q), 5.23 (2H, s), 7.27 (5H, m).

b. Ethyl 4-bromo-(Z)-2-(benzyloxyimino)-3-oxobutyrate

Ethyl (Z)-2-(benzyloxyimino)-3-oxobutyrate (2.84 g) was brominated as described in Example 4c to give the title compound (3.24 g) $\nu_{max}$ (film) 2980, 1740, 1700 and 1010 cm$^{-1}$, $\delta_H$ ($CDCl_3$) 1.30 (3H, t), 4.29 (2H, s), 4.36 (2H, q), 5.37 (2H, s), 7.40 (5H, m). [Mass spectrum; +ve ion (ammonia) MH+ (328), MNH4+ (348)].

c. Ethyl 2-(2-aminothiazol-4-yl)-(Z)-2-(benzyloxyimino)acetate

Ethyl 4-bromo-(Z)-2-(benzyloxyimino)-3-oxobutyrate (3.14 g) was converted into the title compound (2.0 g) as described in Example 4d, m.p. 133°–4° C. (acetone-light petroleum), $\nu_{max}$ ($CHCl_3$) 3450, 1730, 1605 and 1020cm$^-$, $\delta_H$[($CD_3$)$_2$CO] 1.29 (3H, t), 4.36 (2H, q), 5.24 (2H, s), 6.88 (1H, s), 7.40 (7H, m).

d. 2-(2-Aminothiazol-4-yl)-(E,Z)-2-(benzyloxyimino)acetic acid.

Ethyl 2-(2-aminothiazol-4-yl)-(Z)-2-(benzyloxyimino)acetate (1.9 g) was hydrolysed as described in Example 4e to give the title compound (0.43 g), $\nu_{max}$ (KBr) 3029, 1623, 1364 and 1010 cm$^{-1}$, $\delta_H$ [($CD_3$)$_2$SO] 4.18 (3H, br s, exch. $D_2O$), 5.13, 5.23 (1H, 2xs)), 6.82, 7.50 (1H, 2 xs), 7.33 (5H, m). [Mass spectrum: +ve ion (3NOBA/Na+) MNa+ (300), MNa+ sodium salt (322)].

e. 2-(2-Aminothiazol-4-yl)-(E,Z)-2-(benzyloxyimino)acetic acid 2-pyridyl thioester 2-(2-Aminothiazol-4-yl)-(E,Z)-2-(benzyloxyimino)acetic acid (0.4 g) was converted into the title compound (0.575 g) as described in Example 4f.

f. Sodium 6β-([2-(2-aminothiazol-4-yl)-(Z)-2-(benzyloxyimino)-]acetamido)penicillanate 2-(2-Aminothiazol-4-yl)-(E,Z)-2-(benzyloxyimino)acetic acid 2-pyridyl thioester (285 mg) was coupled to 6β-aminopenicillanic acid as described in Example 1d and the (Z) isomer separated during the HP2OSS chromatography to give the title compound (50 mg), $\nu_{max}$ (KBr), 3322, 1766, 1668, 1608 and 1015 cm$^{-1}$, $\delta_H$($D_2O$) 1.47 (3H, s), 1.56 (3H, s), 4.20 (1H, s), 5.23 (2H, s), 5.56 (1H, d, J4 Hz), 5.61 (1H, d, J4 Hz), 6.99 (1H, s), 7.43 (5H, m). [Mass spectrum +ve ion (thioglycerol) MH+ (498), MNa+ (520)].

EXAMPLE 31 a. Ethyl (Z)-2-(1-methylcyclohept-1-yloxyimino)-3-oxobutyrate

Ethyl (Z)-2-hydroxyimino-3-oxobutyrate (795 mg, 5 mmol) and 1-bromo-1-methylcycloheptane (1.1g, 5.76 mmol) in dry 1,4-dioxan (5 ml) under an atmosphere of argon in the dark were treated portionwise with silver trifluoromethanesulphonate (1.48 g, 5.76 mmol), with stirring, over 5 h. The mixture was stirred for a further 18 h in the dark and then worked up using a similar procedure to that described in Example 7a to give the title compound as an oil (878 mg; 65%); $\nu_{max}$ ($CH_2Cl_2$) 3430, 3350, 1740, 1685, 1595, 1370, 1320, 1230, 1070, and 1,000cm$^{-1}$; $\delta_H$(250 MHz, $CDCl_3$) 1.33 (3H, t, J 7.1Hz), 1.33 (3H, s), 1.4–1.8 (10H, m), 1.99 (2H, dd, J ca 13.5 and 7.5 Hz), 2.40 (3H, s), and 4.35 (2H, q, J 7.1 Hz); [Found: M$^{30}$ -OEt 224.1273. $C_{12}H_{18}NO_3$ requires M-OEt 224.1287. Ammonia CI mass spectrum MH+ (270)].

b. Ethyl 2-(2-aminothiazol-4-yl)-(Z)-2-(1-methylcyclohept-1-yloxyimino)acetate Ethyl (Z)-2-(1-methylcyclohept-1-yloxyimino)-3-oxobutyrate (3.4 g, 12.6 mmol) was converted via ethyl 4-bromo-(Z)-2-(1-methylcyclohept-1-yloxyimino)-3-oxobutyrate, using analogous procedures to those outlined in Examples 4c and 4d, to the title compound (3.0 g; 73%); [Found: M$^{30}$ 325.1468. $C_{15}H_{23}N_3O_3S$ requires M 325.1460]. $\nu_{max}$ ($CH_2Cl_2$) 3470, 3380, 3260, 3110, 2930, 1730, 1605, 1520, 1210, 1175, and 1030 cm$^{-1}$; $\delta_H$ (60 MHz, CDCl$_3$) 1.35 (3H, s), 1.1–2.0 (15H, m), 4.33 (2H, q, J 7 Hz), 6.18 (2H, s), and 6.61 (1H, s).

c. 2-(2-Aminothiazol-4-yl)-(Z)-2-(1-methylcyclohept-1-yloxyimino)acetic acid Ethyl 2-(2-aminothiazol-4-yl)-(Z)-2-(1-methylcyclohept-1-yloxyimino)acetate (3.0 g, 9.2 mmol) was hydrolysed in an analogous manner to that described in Example 4e to give the title compound (1.8 g; 66%) m.p. 173°–179° (dec); $\nu_{max}$(KBr) 3290, 3119, 2927, 2856, and 1626 cm$^{-1}$; $\delta_H$ (400 MHz, (CD$_3$)$_2$SO) 1.26 (3H, s), 1.27–2.0 (12H, m), 6.79 (1H, s), and 7.27 (2H, s) [Ammonia CI mass spectrum MH+ (298)].

d. 2-(2-Aminothiazol-4-yl)-(Z)-2-(1-methylcyclohept-1-yloxyimino)acetic acid 2-pyridyl thioester 2-(2-Aminothiazol-4-yl)-(Z)-2-(1-methylcyclohept-1-yl-oxyimino)acetic acid (320 mg, 1.08 mmol) was reacted with 2,2′-dithiodipyridine and triphenylphosphine in a similar manner to that described in Example 4f, except the reaction was allowed to run for 20 min. Work up and chromatography gave the title compound (370 mg; 88%). $\nu_{max}$ (CH$_2$Cl$_2$) 3300, 3130, 2920, and 1690 cm$^{-1}$.

e. Sodium 6β-[2-(2-aminothiazol-4-yl)-(Z)-2-(1-methylcyclohept-1-yloxyimino)acetamido]penicillanate 6β-Aminopenicillanic acid (216 mg, 1 mmol) was converted into the corresponding disilyl derivative and then reacted with 2-(2-aminothiazol-4-yl)-(Z)-2-(1-methylcyclohept-1-yloxyimino)acetic acid 2-pyridyl thioester (360 mg, 0.92 mmol) by a similar procedure to that described in Example 1d, except the reaction was allowed to run for 4 days at room temperature. Work up and chromatography by a similar method to that described in Example 7e gave the title compound. $\nu_{max}$ (KBr) 3376, 2967, 2926, 2855, 1766, 1675, 1609, and 1515 cm$^{-1}$; $\lambda_{max}$ (H$_2$O) 288 ($\epsilon$ 8,050), 232 (13,130)nm; $\delta_H$(250 MHz, D$_2$O) 1.32 (3H, s), 1.52 (3H, s), 1.62 (3H, s), 1.3–1.7 (10H, m), 1.85–2.05 (2H, m), 4.22 (1H, s), 5.63 (1H, d, J 4.1Hz), 5.68 (1H, d, J 4.0 Hz), and 6.93 (1H, s); [FAB mass spectrum +ve ion (thioglycerol) MH+ (518), MNa+ (540)].

EXAMPLE 32 a. Ethyl (Z)-2-(bicyclo[2.2.2]oct-1-yloxyimino)-3-oxobutyrate

1-Bromobicyclo[2.2.2]octane (4.6 g, 24.3 mmol), ethyl (Z)-2-hydroxyimino-3-oxobutyrate (3.78 g, 24.3 mmol) and silver trifluoromethanesulphonate (6.32 g, 24.6 mmol) were reacted under similar conditions to that described in Example 31a to give the title compound (1.47 g, 22%); $\nu_{max}$ (CH$_2$Cl$_2$) 2950, 2925, 2860, 1735, 1685, 1370 and 1325 cm$^{-1}$; $\delta_H$(60 MHz, CDCl$_3$) 1.30 (3H, t, J ca 7 Hz), 1.64 (S) and 1.75 (s) (together 13H), 2.36 (3H, s), and 4.30 (2H, q); [Ammonia CI mass spectrum Found MH+ (288)].

b. Ethyl 2-(2-aminothiazol-4-yl)-(Z)-2-(bicyclo[2.2.2]oct-1-yloxyimino)acetate Ethyl (Z)-2-(bicyclo[2.2.2]oct-1-yloxyimino)-3-oxobutyrate (1.47 g, 5.4 mmol) was converted to the title compound (1.03 g, 69%) via ethyl 4-bromo-(Z)-2-(bicyclo[2.2.2]oct-1-yloxyimino)-3-oxobutyrate using analogous procedures to those outlined in Examples 4c and 4d. Recrystallisation from dichloromethane/hexane gave the title compound as crystals m.p. 139°–140° [Found C, 6.06; H, 6.39; N, 12.81% C$_{15}$H$_{21}$N$_3$O$_3$S requires C, 5.71; H, 6.55; N, 12.99%]; $\nu_{max}$(CH$_2$Cl$_2$) 3480, 3390, 2960, 2930, 2780, 1605, 1530, 1185, 1035, and 975 cm$^{-1}$; $\delta_H$(250 MHz, CDCl$_3$) 1.35 (3H, t, J 7.1 Hz), 1.57 (1H, m), 1.6–1.9 (12H, m), 4.37 (2H, q, J 7.1 Hz), 5.49 (2H, s), and 6.73 (1H, s).

c. 2-(2-Aminothiazol-4-yl)-(Z)-2-(bicyclo[2.2.2]oct-1-yloxyimino)acetic acid Ethyl 2-(2-aminothiazol-4-yl)-(Z)-2-(bicyclo[2.2.2]oct-1-yloxyimino)acetate (760 mg, 2.35 mmol) was converted into the title compound by a similar procedure to that described in Example 4e, except the product was extracted into ethyl acetate from the acidified solution. After drying (MgSO$_4$) and removal of the ethyl acetate under reduced pressure, trituration with diethyl ether gave the title compound (316 mg, 45%), $\nu_{max}$ (KBr) 3363, 2293, 3067, 2947, 2920, 2866, 1640, 1571, 1396, and 976 cm$^{-1}$; $\delta_H$[250 MHz, (CD$_3$)$_2$SO] 1.53 (1H, broad s), 1.66 (12H broad s), 6.77 (1H, s), and 7.24 (2H, s).

d. Sodium 6β-[2-(2-aminothiazol-4-yl)-(Z)-2-(bicyclo[2.2.2]oct-1-yloxyimino)acetamido]penicillanate 2-(2-Aminothiazol-4-yl)-(Z)-2-(bicyclo[2.2.2]oct-1-yloxyimino)acetic acid (300 mg, 1.02 mmol) in dry N,N-dimethylformamide (2 ml) was treated with N-ethyl-N,N-diisopropylamine (0.194 ml, 144 mg, 1.12 mmol), cooled to −50° C. to −60° C. and then treated with methanesulphonyl chloride (0.086 ml, 128 mg, 1.12 mmol) and the mixture was stirred at −50° to −60° for 40 min. The mixed anhydride thus formed was added to a mixture of 6β-aminopenicillanic acid (200 mg, 0.92 mmol) and triethylamine (0.354 ml, 257 mg, 2.55 mmol) in water (2 ml) at 0° C. After 10 min. water (50 ml) and ethyl acetate (50 ml) were added and the pH was adjusted to 2.5 with ice cooling. The layers were separated and the aqueous layer was re-extracted with ethyl acetate (25 ml). The combined ethyl acetate layers were washed with water (20 ml) and then treated with water and, while cooling in ice and stirring, the pH was adjusted to 8.0 by addition of aqueous sodium hydrogen carbonate. After separation the ethyl acetate was washed with water (30 ml) at pH 8.0 a further two times. The combined pH 8.0 extracts were evaporated in vacuo to ca 80 ml, treated with a little sodium chloride, and loaded onto Diaion HP2OSS (3×12 cm). The column was eluted with water, followed by water-tetrahydrofuran mixtures. The relevant fractions were combined and the volume was reduced by evaporation under reduced pressure. Lyophilisation then gave the title compound (300 mg, 55%); $\nu_{max}$ (KBr) 3349, 3196, 2949, 2921, 2866, 1768, 1669, 1601, and 1517 cm$^{-1}$; $\delta_H$(250 MHz, D$_2$O) 1.49 (3H, s) 1.50 (1H, broad s), 1.61 (3H, s), 1.72 (12H, broad s), 4.20 (1H, s), 5.59 (1H, d, J 4.0 Hz), 5.64 (1H, d, J 4.0 Hz), and 6.92 (1H, s).

EXAMPLE 33 a. Ethyl (Z)-2-[(1R, 2R, 5S)-5-methyl-2-isopropylcyclohex-1-yl]oxyimino-3-oxobutyrate (1S, 2R, 5S)-(+)-Menthol (7.03 g, 45 mmol), triphenylphosphine (8.65 g, 33 mmol), ethyl (Z)-2-hydroxyimino-3-oxobutyrate (4.77 g, 33 mmol) and diethyl azodicarboxylate (5.7 g, 33 mmol) were reacted by analogy with Example 4a Method 3 to give the title compound (1.37 g, 14%), $\nu_{max}$ (CH$_2$Cl$_2$) 2960, 2930, 2870, 1745, 1690, 1370, 1320, 1235, 1075, and 1010cm$^{-1}$; $\delta_H$(400 MHz, CDCl$_3$) 0.87 (3H, d, J 6.6 Hz), 0.90 (3H, d, J 6.8 Hz), 0.92 (3H, d, J 6.7 Hz), ca 0.9 (1H, m), 1.02–1.12 (2H, m), 1.1–1.3 (1H, m), 1.32 (3H, t, J 7.1 Hz), 1.50–1.65 (2H, m), 1.67–1.78 (2H, m), 2.06–2.18 (1H, m), 2.40 (1H, s), 4.34 (2H, dq, J 7.1 and 1.0 Hz), and 4.70 (1H, broad s); $\delta$13$_C$ (100 MHz, CDCl$_3$), 14.24 (CH$_3$), 20.70 (CH$_3$), 20.97 (CH$_3$), 22.26 (CH$_3$) 25.04 (CH$_2$), 25.11 (CH$_3$) 26.06 (CH), 29.10 (CH), 34.77 (CH$_2$), 39.44 (CH$_2$) 46.98 (CH), 61.70 (CH$_2$), 83.43 (CH), 150.28, 161.53, 192.94 [Ammonia CI mass spectrum Found: MH+ (298); MNH+ (315)].

b. Ethyl 2-(2-aminothiazol-4-yl)-(Z)-2-[(1R, 2R, 5S)-methyl-2-isopropylcyclohex-1-yl]oxyiminoacetate Ethyl (Z)-2-[(1R, 2R, 5S)-5-methyl-2-isopropylcyclohex-1-yl]oxyimino-3-oxobutyrate (2.31 g, 7.77 mmol) was converted via ethyl 4-bromo-2-[(1R, 2R, 5S)-5-methyl-2-isopropylcyclohex-1-yl]oxyimino-3-oxobutyrate into the title compound (0.5 g, 18%), by analogous methods to those described in Examples 4c and 4d. $\nu_{max}$ (CH$_2$Cl$_2$) 480, 3380, 2930, 2870, 1735, 1605, 1530, 1180, and 980 cm$^{-1}$; $\delta_H$(400 MHz, CDCl$_3$) 0.85 (3H, d, J 8.5 Hz), 0.89 (3H, d, J 6.7 Hz), 0.93 (3H, d, J 6.7 Hz), 0.8–1.1 (3H, m), 1.25 (1H, m), 1.36 (3H, t, J 7.1Hz), 1.5–1.8 (4H, m), 2.18 (1H, m), 4.38 (2H, approx q, J 7.1 Hz), 4.63 (1H, broad s), 5.46 (2H, s), and 6.69-(1H, s); $\delta$13$_C$(100 MHz, CDCl$_3$) 14.26 (CH$_3$), 20.85 (CH$_3$) 21.05 (CH$_3$), 22.35 (CH$_3$), 25.24 (CH$_2$), 25.96 (CH), 29.30 (CH), 34.96 (CH$_2$), 39.36 (CH$_2$), 47.01 (CH), 61.6 (CH$_2$), 80.83 (CH), 109.06 (CH), 142.32, 146.11, 163.49, 168.78.

c. 2-(2-Aminothiazol-4-yl)-2-[(1R,2R,5S)-5-methyl-2-isopropylcyclohex-1-yl]oxyiminoacetic acid Ethyl 2-(2-aminothiazol-4-yl)-2-[(1R,2R,5S)-5-methyl-2-isopropylcyclohex-1-yl]oxyiminoacetate (ca 500 mg) was hydrolysed to the title compound (440 mg,1 by an analogous method to that described in Example 4e. $\nu_{max}$ (KBr) 3304, 3123, 2947, 2867, and 1625 cm$^{-1}$; $\delta_H$(250 MHz, (CD$_3$)$_2$SO), 0.7–1.3 (13H, m), 1.4–1.8 (4H, m), 2.08 (1H, broad d, J ca 6 Hz), 4.42 (1H, s), 6.81 (1H,s), 7.25 (2H, s), and 13.53 (1H, s).

d. Sodium 6$\beta$-[2-(2-aminothiazol-4-yl)-(Z)-2-[(1R,2R,5S)-5-methyl-2-isopropylcyclohex-1-yl]oxyiminoacetamido]-penicillanate 2-(2-Aminothiazol-4-yl)-2-[(1R,2R,5S)-5-methyl-2-isopropylcyclohex-1-yl]oxyiminoacetic acid (440 mg, 1.35 mmol) in dry N,N-dimethylformamide (DMF) (3 ml) at −50° to −60° C. was treated with N-ethyl-N,N-diisopropylamine (0.235 ml, 1.48 mmol) followed by methane chloride (0.115 ml, 170 mg, 1.48 mmol). More DMF (3 ml) was added followed by dry dichloromethane (4 ml) and the mixture was stirred at −50° for 40 min. The bis-trimethylsilyl derivative of 6-aminopenicillanic acid, (prepared by treatment of 6-aminopenicillanic acid (321 mg) with triethylamine (298 mg) and chloromethylsilane (322 mg) in dichloromethane (10 ml) under reflux for 1 h), in dichloromethane (10 ml) was added and the reaction mixture was allowed to warm to 0° C. over 1 h. The dichloromethane was removed by evaporation under reduced pressure. Ethyl acetate (50 ml) and water (50 ml) were added and, cooling in an ice bath, the pH was adjusted to 2.5. The aqueous layer was washed with ethyl acetate and the combined ethyl acetate layers were washed with water followed by saturated brine. Water (50 ml) was then added to the ethyl acetate and, cooling in an ice bath, the pH of the stirred mixture was adjusted to 8.0. The ethyl acetate layer was extracted a further two times with water (50 ml) at pH 8.0. The combined pH 8.0 extracts were adjusted to pH 7.5, reduced in volume to ca 120 ml, treated with some sodium chloride and loaded on to Diaion HP2OSS (3×10 cm). The column was eluted with water, followed by water/tetrahydrofuran mixtures to give the title compound (244 mg) after freeze-drying. $\nu_{max}$ (KBr) 3368, 3197, 2947, 2925, 2868, 1772, 1670, 1611, and 1513 cm$^{-1}$; $\delta_H$(250 MHz, D$_2$O) 0.81 (3H, d, J 6.1 Hz), 0.88 (6H, d, J ca 6 Hz), 0.88–1.35 (4H, m), 1.50 (3H, s), 1.60 (3H, s), 1.4–1.7 (4H, m), 2.06 (1H, broad d, J ca 12.2 Hz), 4.21 (1H, s), 4.58 (1H, broad s), 5.61 (1H, d, J 4.0 Hz), 5.67 (1H, d, J 4.0 Hz), and 6.91 (1H, s), [FAB mass spectrum (thioglycerol) MH+(546), MNa+ (568)].

EXAMPLE 34 a. Ethyl (Z)-2-(1-methylcyclopent-1-yloxyimino)-3-oxobutyrate

Ethyl (Z)-2-(hydroxyimino)-3-oxobutyrate (5.86 g, 36.8 mmol), 1-bromo-1-methylcyclohexane (6.01 g 36.8 mmol), and silver trifluoromethanesulphonate (9.45 g, 36.8 mmol) were reacted together by a similar method to that described in Example 9a to give the title compound (4.45 g, 50%); $\nu_{max}$ (film) 2970, 1745, 1690, 1590, 1370, 1320, 1230, 1070, and 990 cm$^{-1}$; $\delta_H$(60 MHz, CDCl$_3$), 1.31 (3H, t, J 7 Hz), 1.48 (3H, s), 1.1–2.2 (8H, m), 2.35 (3H, s), and 4.30 (2H, q, J 7 Hz).

b. Ethyl 4-Bromo-(Z)-2-(1-methylcyclopent-1-yloxyimino)-3-oxobutyrate

Ethyl (Z)-2-(1-methylcyclopent-1-yloxyimino)-3-oxobutyrate (3.9 g, 16 mmol) was converted into the title compound by an analogous procedure to that described in Example 4c. $v_{max}$ (film) 2970, 1745, 1690, 1370, 1325, 1245, and 1005 cm$^{-1}$.

c. Ethyl 2-(2-aminothiazol-4-yl)-(Z)-2-(1-methylcyclopent-1-yloxyimino)acetate Ethyl 4-bromo-(Z)-2-(1-methylcyclopent-1-yloxyimino)-3-oxobutyrate prepared above was converted into the title compound (1.39 g, 64%) by an analogous procedure to that described in Example 4d. m.p. 94°-95° C. (ethyl acetate-hexane), [Found: C, 52.82; H, 6.41; N, 14.11. C$_{13}$H$_{19}$N$_3$O$_3$S requires C, 52.50; H, 6.44; N, 14.13%]. $v_{max}$(CH$_2$Cl$_2$) 3475, 3380, 2960, 1735, 1605, 1530, 1175, and 970 cm$^{-1}$; $\delta_H$(60 MHz, CDCl$_3$) 1.34 (3H, t, J 7 Hz), 1.45 (3H, s), 1.0-2.2 (8H, m), 4.31 (2H, q, J 7 Hz), 5.95 (2H, s), and 6.62 (1H, s).

d. 2-(2-Aminothiazol-4-yl)-(Z)-2-(1-methylcyclopent-1-yloxyimino)acetic acid Hydrolysis of ethyl 2-(2-aminothiazol-4-yl)-(Z)-2-(1-methylcyclopent-1-yloxyimino)acetate (2.94 g, 10.4 mmol) by similar method to that described in Example 4e gave the title compound (1.46 g, 52%), m.p. 182°-3° C.; $v_{max}$ (KBr) 3365, 2963, 1636, 1574, 1391, and 984 cm$^{-1}$; $\delta_H$(250 MHz, (CD$_3$)$_2$SO) 1.37 (3H, s), 1.54-1.61(6H, m), 1.80-1.95 (2H, m), 6.81 (1H, s), and 7.27 (2H, s).

e. 2-(2-Aminothiazol-4-yl)-(Z)-2-(1-methylcyclopent-1-yloxyimino)acetic acid 2-pyridyl thioester 2-(2-Aminothiazol-4-yl)-(Z)-2-(1-methylcyclopent-1-yl-oxyimino)acetic acid (680 mg, 2.5 mmol) was converted into the title compound (516 mg, 57%) using a similar procedure to that described in Example 4f, except that the reaction time was 20 min. m.p. 146°-9° C. (ethyl acetate-hexane) -rFound: C,52.93; H, 4.92; N, 15.46. C$_{16}$H$_{18}$N$_4$O$_2$S$_2$ requires C, 53.02; H, 5.00; N, 15.46%]. $v_{max}$(KBr) 3295, 3144, 2965, 1697, 1649, 1624, 1573, 1539, 1421, 1207, 990, and 924 cm$^{-1}$; $\delta_H$(250 MHz, (CD$_3$)$_2$SO) 1.39 (3H, s), 1.63 (6H, m), 1.92 (2H, m), 6.92 (1H, s), 7.37 (2H, s), 7.71 (1H, dd, J 7.8 and 0.8 Hz), 7.96 (1H, dt, J 1.9 and 7.7 Hz), and 8.64 (1H, m).

f. Sodium 6β-[2-(2-aminothiazol-4-yl)-(Z)-2-(1-methylcyclopent-1-yloxyimino)acetamido]penicillanate 2-(2-Aminothiazol-4-yl)-(Z)-2-(1-methylcyclopent-1-yloxyimino)acetic acid 2-pyridyl thioester (483 mg, 1.33 mmol) was converted into the title compound (190 mg) using a similar procedure to that described in Example 4 g. $v_{max}$(KBr) 3337, 2965, 1765, 1608, 1525, 1397, and 1323 cm$^{-1}$; $\delta_H$(250 MHz, D$_2$O) 1.43 (3H, s), 1.51 (3H, s), 1.62 (9H, s superposed on m), 1.98 (2H, m), 4.22 (1H, s), 5.62 (1H, d, J 4.0 Hz), 5.66 (1H, d, J 4.0 Hz), and 6.94 (H, s). $\lambda_{max}$(H$_2$O) 290 ($\epsilon$7730) and 232 nm (12580). [Mass spectrum: +ve ion (thioglycerol) FAB MNa$^+$ (512)].

EXAMPLE 35 a. 2-(4-Methylcyclohexyl)propan-2-ol

α-Terpineol (6.17 g) in ethanol (130 ml) was hydrogenated for 1 h at atmospheric pressure using 10% Pd-C catalyst (290 mg). The catalyst was then removed by filtration through Kieselguhr and the solvent was removed under reduced pressure to leave the title compound as an oil (5.93 g). Distillation gave an oil (4.56 g) b.p. (13 mm) 98°; $v_{max}$ (film) 3375, 2940, 1445, 1160, 1140, and 910 cm$^{-1}$; $\delta_H$(60 MHz, CDCl$_3$) 0.6-2.0(m).

b. 2-Bromo-2-(4-methylcyclohexyl)propane 2-(4-Methylcyclohexyl)propan-2-ol (0.99 g, 6.39 mmol) was added to a mixture of anhydrous zinc bromide (0.72 g, 3.2 mmol) and 48% HBr (aq). The mixture was stirred at room temperature for 2 h. The mixture was then extracted with diethyl ether (2×20 ml) and the combined extracts were washed with water, dried (MgSO$_4$/K$_2$CO$_3$) and evaporated under reduced pressure to give the crude title compound as an oil (1.12 g, 80%), $v_{max}$ (film) 2940, 2915, 2860, 1450, and 1370 cm$^{-1}$; $\delta_H$(60 MHz, CDCl$_3$) 0.8-2.2 (m), 7.2 (s). Distillation from K$_2$CO$_3$ under reduced pressure removed the impurity resonating at δ7.2.

c. Ethyl (Z)-2-[1-(trans-4-methylcyclohexyl)-1-methylethoxyimino]-3-oxobutyrate 2-Bromo-2-(4-methylcyclohex-1-yl)propane (1.99 g, 9.06 mmol), ethyl (Z)-2-hydroxyimino-3-oxobutyrate (1.44 g, 9.06 mmol) and silver trifluoromethanesulphonate (2.33 g) were reacted together in dry dioxane (8 ml) using a similar method to Example 9a. The title compound was obtained as an oil (1.31 g, 51%), $v_{max}$ (CH$_2$Cl$_2$) 2920, 2860, 1740, 1685, 1370, 1320, 1235, 1070, and 1000 cm$^{-1}$. $\delta_{13C}$ (100 MHz, CDCl$_3$) 14.14 (CH$_3$), 22.55 (CH$_3$), 23.24 (2×CH$_3$), 25.11 (CH$_3$), 26.8 (2×CH$_2$), 32.76 (CH), 35.36 (2×CH$_2$), 46.25 (CH), 61.7 (CH$_2$) 87.6, 149.7, 161.6 (C=O), 193.1 (C=O); $\delta_H$(400 MHz, CDCl$_3$), 0.86 (3H, d, J 6.5 Hz), 0.8-0.95 (2H, m), 0.95-1.15 (2H, m), 1.29 (6H, s), 1.32 (3H, t, J 7.1 Hz), 1.2-1.35 (1H, m), 1.45-1.65 (2H, m), 1.65-1.80 (3H, m), 2.40 (3H, s), and 4.34 (2H, q, J 7.1 Hz).

d. Ethyl 4-Bromo-(Z)-2-[1-(trans-4-methylcyclohexyl)-1-methylethoxyimino]-3-oxobutyrate Ethyl (Z)-2-[1-(trans-4-methylcyclohexyl)-1-methylethoxyimino]-3-oxobutyrate (1.31 g, 4.65 mmol) was converted into the title compound using a similar method to that described in Example 4c. The title compound was obtained as an oil, $v_{max}$ (film) 2980, 2945, 2860, 1745, 1690, 1590, 1370, 1330, 1250, 1025, and 790 cm$^{-1}$; $\delta_H$ (60 MHz, CDCl$_3$) 0.65-2.0 (16H, m), 1.37 (6H, s), 4.37 (2H, q, J 7 Hz), and 4.30 (2H, s).

e. Ethyl 2-(2-Aminothiazol-4-yl)-(Z)-2-[1-(trans-4-methylcyclohexyl)-1-methylethoxyimino]acetate Ethyl 4-bromo-(Z)-2-[1-(trans-4-methylcyclohexyl)-1-methylethoxyimino]-3-oxobutyrate was converted into the title compound (1.24 g, 76%), by the method f. 2-(2-Aminothiazol-4-yl)-(Z)-2-[1-(trans-4-methylcyclohexyl)-1-methylethoxyimino]acetic acid Ethyl 2-(2-aminothiazol-4-yl)-(Z)-2-[1-(trans-4-methylcyclohexyl)-1-methylethoxyimino]acetate (630 mg, 1.78 mmol) in ethanol (14 ml) and water (2 ml) was treated with 1M NaOH (1.78 ml) and the mixture was stirred at room temperature for 5 days. The ethanol was removed by evaporation in vacuo and the residual mixture was treated with ethyl acetate (100 ml) and water (100 ml) and the pH was adjusted to 3.0. The aqueous layer was extracted with ethyl acetate (3×30 ml). The combined ethyl acetate layers were dried (MgSO$_4$) and evaporated to leave the title compound (390 mg, 67%), $\nu_{max}$(KBr) 3290, 3120, 2942, 1724, 1616, 1447, 1380, and 985 cm$^{-1}$; $\delta_H$ (250 MHz, (CD$_3$)$_2$SO), 0.84 (3H, d, J 6.4 Hz), 1.17 (6H, s), 0.7–1.9 (10 H, m), 6.78 (1H, s), 7.25 (2H, s), and 13.5 (1H, broad s).

g. 2-(2-Aminothiazol-4-yl)-(Z)-2-[1-(trans-4-methylcyclohexyl)-1-methylethoxyimino)acetic acid 2-pyridyl thioester 2-(2-Aminothiazol-4-yl)-(Z)-2-[1-(trans-4-methylcyclohexyl)-1-methylethoxyimino]acetic acid (382 mg, 1.17 mmol) was converted into the title compound by an analogous method to that described in Example 4f, except the mixture was stirred for 17 h. Filtration gave the title compound (291 mg, 54%). Work-up and chromatography of the material from the mother liquors gave a further quantity of product (68 mg, 14%). m.p.164°–5° C.; [Found: C, 57.60; H, 6.43; N, 13.50. C$_{20}$H$_{26}$N$_4$O$_2$S$_2$ requires C,57.39, H, 6.26; N, 13.39%]. $\nu_{max}$ (KBr) 3125, 2923, 1702, 1660, 1546, 1452, 1421, 1055, 994, and 931 cm$^{-1}$; $\delta_H$(250 MHz, (CD$_3$)$_2$SO) 0.84 (3H, d, J 6.3 Hz), 0.8–1.4 (5H, m), 1.19 (6H, s), 1.46–1.75 (5H, m), 6.89 (1H, s), 7.35 (2H, s), 7.49 (1H, m), 7.68 (1H, d, J 7.9 Hz), 7.95 (1H, dt J 1.9 Hz and 7.8 Hz), and 8.63 (1H, m).

h. Sodium 6β-[2-(2-aminothiazol-4-yl)-(Z)-2-[1-(trans-4-methylcyclohexyl)-1-methylethoxyimino]acetamido]penicillanate 2-(2-Aminothiazol-4-yl)-(Z)-2-[1-(trans-4-methylcyclohexyl)-1-methylethoxyimino]acetic acid 2-pyridyl thioester (215 mg) was converted into the title compound (134 mg) by an analogous procedure to that described in Example 4g. $\nu_{max}$ (KBr) 3369, 2975, 2944, 1769, 1610, 1517, 1321, 969, and 902 cm$^{-1}$; $\lambda_{max}$(H$_2$O) 288, 231 nm; $\delta_H$ (250 MHz, D$_2$O), 0.81 (3H, d, J ca 6 Hz), 0.9–1.75 (10H, m), 1.22 (6H, s), 1.49 (3H, s), 1.59 (3H, s), 4.20 (1H, s), 5.58 (1H, d, J 3.7 Hz), 5.66 (1H, d, J 3.7 Hz), and 6.85 (1H, s). [FAB mass spectrum (thioglycerol) MH+ (524), MNa+ 546].

EXAMPLE 36 a. Ethyl (Z)-2-(3,3-dichloroprop-2-en-1-yloxyimino)-2-(2-triphenylmethylaminothiazol-4-yl)acetate Ethyl (Z)-2-hydroxyimino-2-triphenylmethylaminothiazol-4-yl)acetate (1.231 g, 2.69 mmol) was converted into the title compound (0.65 g 43% yield) using 1-bromo-3,3-dichloroprop-2-ene by an analogous method to that outlined in Example 25a. $\nu_{max}$ (CH$_2$Cl$_2$) 3380, 1735, 1620, 1545, 1180, and 1025 cm$^{-1}$; $\delta_H$(60 MHz, CDCl$_3$) 1.37 (3H, t, J 7 Hz), 4.45 (2H, q, J 7 Hz), 4.87 (2H, d, J 6.5 Hz), 6.23 (1H, t, J 6.5 Hz), 6.62 (1H, s), 7.02 (1H, broad s), and 7.35 (15H, m). [FAB mass spectrum (3NOBA/Na+) MH+ (566), MNa+ (588)].

b. Ethyl 2-(2-aminothiazol-4-yl)-(Z)-2-(3,3-dichloroprop-2-en-1-yloxyimino)acetate Ethyl (Z)-2-(3,3-dichloroprop-2-en-1-yloxyimino)-2-(2-triphenylmethylaminothiazol-4-yl)acetate (622 mg, 1.09 mmol) was dissolved in 98% formic acid (5 ml) and treated with water (1.5 ml). After stirring for 2 h the formic acid and water were removed under reduced pressure. Toluene was added and the process repeated. The residue was chromatographed on silica-gel eluting with ethyl acetate/hexane mixtures to give the title compound (298 mg, 84%) m.p. 135°–136°; [Found C, 37.25; H, 3.46; N, 13.12. C$_{10}$H$_{11}$Cl$_2$N$_3$O$_3$S requires C, 37.05; H, 3.42; N, 12.96%]. $\nu_{max}$ (CH$_2$Cl$_2$) 3475, 3380, 3110, 1735, 1605, 1530, 1375, 1180, and 1025 cm$^{-1}$; $\delta_H$ (60 MHz, CDCl$_3$) 1.30 (3H, t, J ca 7 Hz), 4.37 (2H, q, J ca 7 Hz), 4.72 (2H, d, J ca 6.5 Hz), 5.83 (2H, broad s), 6.1 (1H, t, J ca 6.5 Hz), and 6.66 (1H, s).

c. 2-(2-Aminothiazol-4-yl)-(Z)-2-(3,3-dichloroprop-2-en-1-yloxyimino)acetic acid Ethyl 2-(2-aminothiazol-4-yl)-(Z)-2-(3,3-dichloroprop-2-en-1-yloxyimino)acetate (285 mg, 0.88 mmol) was hydrolysed in an analogous way to that described in Example 4e to give the title compound (167 mg, 64%). $\nu_{max}$(KBr) 3114, 2935, 1623, 1387, 1017, 883, and 853 cm$^{-1}$; $\delta_H$ (250 MHz, (CD$_3$)$_2$SO), 4.69 (2H, d, J 6.5 Hz), 6.35 (1H, t, J 6.3 Hz), 6.91 (1H, s), 7.28 (2H, s), and 14.0 (1H, broad s).

d. Sodium 6β-[2-(2-aminothiazol-4-yl)-(Z)-2-(3,3-di-chloroprop-2-en-1-yloxyimino)acetamido]penicillanate 2-(2-Aminothiazol-4-yl)-(Z)-2-(3,3-dichloroprop-2-en-1-yloxyimino)acetic acid (155 mg, 0.52 mmol) was converted to the title compound (123 mg, 45%) using an analogous procedure to that described in Example 32d, $\nu_{max}$ (KBr) 3331, 2971, 1767, 1664, 1611, 1529, 1398, 1323, and 1024 cm$^{-1}$; $\delta_H$ (250 MHz, D$_2$O) 1.50 (3H, s), 1.61 (3H, s), 4.22 (1H, s), 4.78 (2H, d, J 6.9 Hz), 5.60 (2H, s), 6.27 (1H, t, J 6.9 Hz), and 7.02 (1H, s).

EXAMPLE 37 a. Diphenylmethyl (Z)-2-[1-methyl-1-(4-nitrobenzyloxycarbonylethoxyimino]-2-(2-tritylaminothiazol-4-yl)acetate A solution of diphenylmethyl (Z)-2-hydroxyimino-2-(2-tritylaminothiazol-4-yl)acetate (1.20 g) in dry dimethylsulphoxide (12 ml) was stirred with potassium carbonate (0.552 g) and p-nitrobenzyl-2-bromo-2-methyl propionate (0.600 g) at room temperature for 1.5 h. The mixture was poured into water (120 ml), the precipitate collected by filtration, washed with water, and dissolved in ethyl acetate. The solution was washed with water, brine, dried ($MgSO_4$), and evaporated. The residue was purified by flash chromatography, eluting with ethyl acetate-hexane to afford the title compound as a pale yellow foam (1.41 g, 88%); $\nu_{max}$ ($CH_2Cl_2$) 3370, 1740, 1520, and 1350 cm$^{-1}$; $\delta_H$(CDCl$_3$) 1.48 (6H, s), 5.17 (2H, s), 6.34 (1H, s), 6.65 (1H, br. s), 7.08 (1H, s), 7.15–7.32 (26H, m), 7.38 and 7.95 (4H, ABq, J 9 Hz).

b. 2-(2-Aminothiazol-4-yl)-(Z)-2-[1-methyl-1-(4-nitrobenzyloxycarbonyl)ethoxyimino]acetic acid Diphenylmethyl (Z)-2-[1-methyl-1-(4-nitrobenzyloxy-carbonyl)ethoxyimino]-2-(2-tritylaminothiazol-4-yl)-acetate (1.0 g) was treated with formic acid under the conditions described in Example 23d. The title compound was obtained as a white solid (0.355 g, 75%); $\nu_{max}$ (Nujol) 3300 (br), 3100 (br), 1740, 1625 (br). 1610, 1520, and 1350 cm$^{-1}$; $\delta_H$((CD$_3$)$_2$SO) 1.50 (6H, s), 5.30 (2H, s), 6.74 (1H, s), 7.15–7.40 (3H, m), and 7.59 and 8.08 (4H, ABq, J 9 Hz).

c. 2-(2-Aminothiazol-4-yl)-(Z)-2-(1-methyl-1-(4-nitrobenzyloxycarbonyl)ethoxyimino]acetic acid 2-pyridyl thioester 2-(2-Aminothiazol-4-yl)-(Z)-2-[1-methyl-1-(4-nitrobenzyloxycarbonyl)ethoxyimino] acetic acid (0.325 g) was treated with triphenylphosphine (0.87 g) and 2,2′-di-thiodipyridine (0.741 g) as described in Example 1c, increasing the reaction time to 16 h at 7° C. to give the title compound as a white solid (0.230 g, 59%); $\nu_{max}$ ($CH_2Cl_2$) 3420, 3380, 1735, 1685, 1610, 1525, and 1350 cm$^{-1}$; $\delta_H$ (CDCl$_3$) 1.65 (6H, s), 5.35 (2H, s), 6.78 (1H, s), 7.32–8.18 (7H, m), and 8.70–8.80 (1H, m).

d. Sodium 6β-[2-(2-aminothiazol-4-yl)-(Z)-2-[1-methyl-1-(4-nitrobenzyloxycarbonyl)ethoxyimino]acetamido]-penicillanate 6β-Aminopenicillanic acid (0.100 g) was treated with 2-(2-aminothiazol-4-yl)-(Z)-2-[1-methyl-1-(4-nitrobenzyloxycarbonyl)ethoxyimino]acetic acid 2-pyridyl thioester (0.220 g) as described in Example 4g. The title compound was obtained as a white freeze-dried solid (28 mg); $\nu_{max}$ (KBr) 3378, 1773, 1739, 1680, 1606, 1522, and 1347 cm$^{-1}$; $\delta_H$(D$_2$O) 1.49 (3H, s), 1.58 (9H, s), 4.21 (1H, s), 5.28 and 5.37 (2H, ABq, J 12.8 Hz), 5.60 and 5.66 (2H, ABq, J 3.99 Hz), 6.93 (1H, s), and 7.53 and 8.06 (4H, ABq, J 8.7 Hz); [Mass spectrum: +ve ion (thioglycerol) MH$^+$ (629), MNa$^+$ (651)].

e. Disodium 6β-[2-(2-aminothiazol-4-yl)-(Z)-2-(1-carboxylato-1-methylethoxyimino)acetamido]penicillanate Sodium 6β-[2-(2-aminothiazol-4-yl)-(Z)-2-[1-methyl-1-(4-nitrobenzyloxycarbonyl)ethoxyimino]acetamido]-penicillanate (60 mg) was dissolved in water (10 ml) and 1,4-dioxan (10 ml), 5% palladium on activated carbon (60 mg) added, and the mixture subjected to hydrogenolysis at room temperature and pressure for 1 h. Sodium hydrogen carbonte (8.8 mg) in wa-ter (2 ml) was added, the mixture filtered through Kieselguhr and the 1,4-dioxan removed under reduced pressure. The resultant aqueous solution was washed twice with ethyl acetate, evaporated to low volume and purified on HP20SS using water as eluant. The product-containing fractions were combined and lyophilised to give the title compound as a white amorphous solid (22 mg); $\nu_{max}$ (KBr) 3417, 1766, 1594, 1530, and 1401 cm$^{-1}$; $\delta_H$ (D$_2$O) 1.44 (3H, s), 1.47 (3H, s), 1.51 (3H, s), 1.61 (3H, s), 4.25 (1H, s), 5.63–5.68 (2H, m), and 6.99 (1H, s). [Mass spectrum: +ve ion (thioglycerol) MH$^+$ (516), MNa$^+$ (538)].

EXAMPLE 38 a. Diphenylmethyl (Z)-2-[(4-nitrobenzyloxycarbonyl)methoxyimino]-2-(2-tritylaminothiazol-4-yl)acetate Diphenylmethyl (Z)-2-hydroxyimino-2-(2-tritylaminothiazol-4-yl) acetate (5.95 g) was treated with potassium carbonate (2.76 g) and p-nitrobenzyl bromoacetate (3.014 g) under the conditions described in Example 1a. The title compound was obtained as a pale yellow solid (6.64 g, 84%), m.p. 176°–178° C.; $\nu_{max}$ (KBr) 3390, 3070, 3030, 1765, 1740, 1605, 1525, and 1490 cm$^{-1}$; $\delta_H$(CDCl$_3$) 4.80 (2H, s), 5.23 (2H, s), 6.01 (1H, s), 6.85 (1H, br. s), 7.06 (1H, s), 7.17–7.33 (25H, m), 7.38 and 8.12 (4H, ABq, J 10 Hz).

b. 2-(2-Aminothiazol-4-yl)-(Z)-2-[(4-nitrobenzyloxycarbonyl)methoxyimino]acetic acid Diphenylmethyl (Z)-2-(4-nitrobenzyloxycarbonyl)-methoxyimino-2-(2-tritylaminothiazol-4-yl)acetate (2.5 g) was treated with formic acid under the conditions described in Example 23d, increasing the reaction time to 26 h. The title compound was obtained as a white solid (1.13 g); $\nu_{max}$ (Nujol) 3520, 1745, 1605, and 1510 cm$^{-1}$; $\delta_H$((CD$_3$)$_2$SO) inter alia 4.85 (2H, s), 5.37 (2H, s), 6.86 (1H, s), 7.23 (2H, br. s), 7.57 and 8.23 (4H, ABq, J 8 Hz).

c. 2-(2-Aminothiazol-4-yl)-(Z)-2-[(4-nitrobenzyloxycarbonyl)methoxyimino]acetic acid 2-pyridyl thioester 2-(2-Aminothiazol-4-yl)-(Z)-2[(4-nitrobenzyloxycarbonyl)methoxyimino]acetic acid was converted to the title compound (40%) under the conditions described in Example 1c, increasing the reaction time to 16 h at 7° C.; $\nu_{max}$ (Nujol) 3425, 3100, 1760, 1690, 1630, 1545, and 1510 cm$^{-1}$; $\delta_H$ [(CD$_3$)$_2$SO] 4.95 (2H, s), 5.37 (2H, s), 7.00 (1H, s), 7.37–8.25 (12H, m), and 8.50–8.68 (1H, m).

d. Sodium 6β-[2-(2-aminothiazol-4-yl)-(Z)-2-[(4-nitrobenzyloxycarbonyl)methoxyimino]acetamido]penicillanate 6β-Aminopenicillanic acid was treated with 2-(2-aminothiazol-4-yl)-(Z)-2-[(4-nitrobenzyloxycarbonyl)-methoxyimino] acetic acid 2-pyridyl thioester as described in Example 4g. The title compound was obtained as a white freeze-dried solid (15%); $v_{max}$ (KBr) 3369, 1761, 1670, 1606, and 1521 cm$^{-1}$; $\delta_H$(D$_2$O) 1.48 (3H, s), 1.55 (3H, s), 4.22 (1H, s), 5.36 (2H, s), 5.57 and 5.73 (2H, ABq, J 3.9 Hz), 7.04 (1H, s), 7.53 and 8.15 (4H, ABq, J 8.7 Hz).

e. Disodium 6β-[2-(2-aminothiazol-4-yl)-(Z)-2-(carboxylatomethoxyimino)acetamido]penicillanate Sodium 6β-[2-(2-aminothiazol-4-yl)-(Z)-2-[(4-nitrobenzyloxycarbonyl)methoxyimino]acetamido]-penicillanate (50 mg) was subject to hydrogenolysis under the conditions described for Example 37e. The product was obtained as a white freeze-dried solid (32 mg); $v_{max}$ (KBr) 3405, 1765, 1600, and 1531 cm$^{-1}$; $\delta_H$(D$_2$O) 1.52 (3H, s), 1.59 (3H, s), 4.27 (1H, s), 4.54 (2H, s), 5.62 and 5.65 (2H, ABq, J 4 Hz), and 7.07 (1H, s).

EXAMPLE 39 a. Ethyl (Z)-2-(trans-2-methoxycyclohexyloxyimino)-3-oxobutyrate

Ethyl (Z)-2-hydroxyimino-3-oxobutyrate (0.98 g) was alkylated with cis-2-methoxycyclohexanol (0.89 g) as described in Example 4, method 3. The pure title compound was obtained as a colourless oil (0.3 g). $v_{max}$ (film) 1745, 1695, and 1595 cm$^{-1}$; $\delta_H$(CDCl$_3$) 1.30–2.30 (13H, m), 2.39 (3H, s), 3.42 (3H, s), and 4.20–4.60 (3H, m). [Mass spectrum: CI MH$^+$ (272)].

b. Ethyl 4-bromo-(Z)-2-(trans-2-methoxycyclohexyloxyimino)-3-oxobutyrate

Ethyl (Z)-2-(trans-2-methoxycyclohexyloxyimino)-3-oxobutyrate (2.82 g) was brominated according to the procedure outlined in Example 4c to give the crude title compound.

c. Ethyl 2-(2-aminothiazol-4-yl)-(Z)-2-(trans-2-methoxycyclohexyloxyimino)acetate Ethyl 4-bromo-(Z)-2-(trans-2-methoxycyclohexyloxyimino)-3-oxobutyrate was treated with thiourea (0.79 g) and N,N-dimethylaniline (1.318 ml) as described in Example 4d to give the title compound as an orange gum (1.78 g) after silica gel chromatography. $v_{max}$ (CH$_2$Cl$_2$) 3460, 3370, 3250, 3100, 1730, 1605, and 1530 cm$^{-1}$; $\delta_H$(CDCl$_3$) inter alia 1.10–1.20 (11H, m), 3.32 (1H, m), 3.43 (3H, s), 4.00–4.50 (3H, m), 6.55 (2H, br. s), and 6.66 (1H, s). [Mass spectrum: EI M$^+$ (327)].

d. 2-(2-Aminothiazol-4-yl)-(Z)-2-(trans-2-methoxycyclohexyloxyimino)acetic acid Ethyl 2-(2-aminothiazol-4-yl)-(Z)-2-(trans-2-methoxycyclohexyloxyimino)acetate (1.79 g) was hydrolysed with 1M sodium hydroxide (10.75 ml) in ethanol (20 ml) as described in Example 4e. After acidification of the aqueous phase to pH 2–3 the water was removed under reduced pressure. The residue was extracted with hot ethanol and concentrated to dryness to give a brown foam. Trituration with ethyl acetate gave the title compound as a buff coloured solid (0.904 g). $v_{max}$ (KBr) 3302, 3207, 1628, 1534, and 1450 cm$^{-1}$; $\delta_H$((CD$_3$)$_2$SO) inter alia 1.00–2.00 (8H, m), 3.00–3.33 (4H, m and s), 3.90–4.30 (1H, m), 6.87 (1H, s), and 7.28 (3H, br. s). [Mass spectrum: +ve ion (thioglycerol) MH$^+$ (300), MNa$^+$ (322)].

e. 2-(2-Aminothiazol-4-yl)-(Z)-2-(trans-2-methoxycyclohexyloxyimino)acetic acid 2-pyridyl thioester 2-(2-Aminothiazol-4-yl)-(Z)-2-(trans-2-methoxycyclohexyloxyimino)acetic acid (0.8 g was converted to the corresponding 2-pyridyl thioester (0.319 g) as described in Example 1c. m.p. 158° C. (ethanol); $v_{max}$ (KBr) 3326, 3108, 1688, 1626, 1570, 1562, and 1540 cm$^{-1}$; $\delta_H$((CD$_3$)$_2$SO) 1.10–2.20 (8H, m), 3.20–3.50 (4H, m and s), 4.15 (1H, m), 7.05 (1H, s), 7.41–8.10 (3H, m), and 8.76 (1H, m). [Mass spectrum: +ve ion (thioglycerol) MH$^+$ (393)].

f. Sodium 6β-[2-(2-aminothiazol-4-yl)-(Z)-2-(trans-2-methoxycyclohexyloxyimino)acetamido]penicillanate 2-(2-Aminothiazol-4-yl)-(Z)-2-(trans-2-methoxycyclohexyloxyimino)acetic acid 2-pyridyl thioester (0.277 g) was coupled with 6β-aminopenicillanic acid (0.153 g) as described in Example 1d. The title compound was obtained as a white freeze-dried solid (0.139 g); $v_{max}$ (KBr) 3377, 3196, 1767, 1668, 1608, 1528, and 1453 cm$^{-1}$; $\delta_H$(D$_2$O) 1.25 (3H, m), 1.42 (1H, m), 1.51 (3H, s), 1.62 (3H, s), 1.66 (2H, m), 2.09 (2H, m), 3.39 (3H, s), 3.43 (1H, m), 4.12 (1H, m), 4.22 and 4.23 (together 1H, 2s), 5.62–5.67 (2H, m), 6.98 and 6.99 (together 1H, 2s). [Mass spectrum: +ve ion (thioglycerol) MH$^+$ (520), MNa$^+$ (542)].

EXAMPLE 40 a. Ethyl (Z)-2-(tetrahydrothien-3-yloxyimino)-3-oxobutyrate

Ethyl (Z)-2-hydroxyimino-3-oxobutyrate (1.68 g) was treated with 3-bromotetrahydrothiophene as described in Example 4a, method 2, to give the title compound (1.7 g, 68%) as a colourless liquid; [Found M$^+$ 245.0719, C$_{10}$H$_{15}$NO$_4$S requires M 245.0722]. $v_{max}$ (film) 2890, 2940, 1745, 1695, and 1600 cm$^{-1}$. $\delta_H$ (CDCl$_3$) 1.33 (3H, t), 2.02 (1H, m), 2.41 (3H, s), 2.47 (1H, m), 2.89 (2H, m), 3.13 (2H, m), 4.35 (2H, q), and 5.14 (1H, m). $\delta_C$ (CDCl$_3$) 14.1, 25.2, 28.6, 35.7, 62.0, 88.3, 150.8, 60.7, and 192.6.

b. Ethyl 4-bromo-(Z)-2-(tetrahydrothien-3-yl-oxyimino)-3-oxobutyrate

Ethyl (Z)-2-(tetrahydrothien-3-yloxyimino)-3-oxobutyrate (1.29 g) was dissolved in a mixture of carbontetrachloride (15 ml), dichloromethane (5 ml) and methanol (2 ml). The mixture was cooled to −26°, a solution of hydrogen bromide in acetic acid (0.05 ml, 45% w/v) was added followed by bromine (0.29 ml). The mixture was allowed to warm to room temperature and stirred for 3 dyys. The solvents were removed under reduced pressure, the residue was partitioned between ethyl acetate and water. The organic layer was washed successively with saturated aqueous sodium bicarbonate, water and brine, then dried (MgSO4) and evaporated. Purification by flash chromatography with dichloromethane elution gave the title compound (0.4 g, 23%) as a pale yellow liquid. $\nu_{max}$ (film) 2970, 2940, 1740, 1695, and 1600 cm$^{-1}$. $\delta_H$ (CDCl$_3$) 1.34 (3H, t), 2.04 (1H, m), 2.48 (1H, m), 2.90 (2H, m), 3.13 (2H, m), 4.33 (2H, s), 4.37 (2H, q), and 5.18 (1H, m). [Mass spectrum: +ve ion MH$^+$ (324)].

c. Ethyl 2-(2-aminothiazol-4-yl)-(Z)-2-(tetrahydrothien-3-yloxyimino)acetate Ethyl 4-bromo-(Z)-2-(tetrahydrothien-3-yloxyimino)-3-oxobutyrate (0.39 g) was converted into the title compound (0.24 g, 66%) as described in Example 4d, m.p. 151°-2° C. (toluene), $\nu_{max}$ (KBr) 3113, 1734, 1610, and 1538 cm$^-$, $\delta_H$(CDCl$_3$) 1.38 (3H, t), 1.93 (1H, m), 2.48 (1H, m), 2.86 (2H, m), 3.09 (2H, d), 4.4 (2H, q), 5.15 (1H, m), 5.20 (2H, br s), and 6.75 (1H, s). [Mass spectrum, +ve ion (ammonia) MH$^+$ (302)].

d. 2-(2-Aminothiazol-4-yl)-(Z)-2-(tetrahydrothien-3-yloxyimino)acetic acid

Ethyl 2-(2-aminothiazol-4-yl)-(Z)-2-(tetrahydrothien-3-yloxyimino)acetate (0.17 g) was hydrolysed as described in Example 17d, to give the title compound (86 mg).

e. 2-(Aminothiazol-4-yl)-(Z)-2-(tetrahydrothien-3-yloxyimino)acetic acid 2-pyridyl thioester 2-(2-Aminothiazol-4-yl)-(Z)-2-(tetrahydrothien-3-yloxyimino)acetic acid (86 mg) was converted into the title compound, contaminated with 2-mercaptopyridine, as described in Example 4f.

f. Sodium 6β-[2-(2-aminothiazol-4-yl)-(Z)-2-(tetrahydrothien-3-yloxyimino)acetamido]penicillanate 2-(2-Aminothiazol-4-yl)-(Z)-2-(tetrahydrothien-3-yloxyimino)acetic acid 2-pyridyl thioester was coupled to 6β-aminopenicillanic acid as described in Example 1d to give the title compound (50 mg, 33% 2 steps) as a white freeze-dried solid, $\nu_{max}$ (KBr) 3325, 1762, 1668, 1607, and 1527 cm$^{-1}$, $\delta_H$ (D$_2$O) 1.52 (3H, s), 1.63 (3H, s), 1.94 (1H, m), 2.48 (1H, m), 2.91 (2H, m), 3.12 (2H, m), 4.24 (1H, s), 5.12 (1H, m), 5.6 (1H, d), 5.66 (1H, d), and 7.02 (1H, d). [Mass spectrum: +ve ion (thioglycerol) MH$^+$ (494), MNa$^+$ (516)].

EXAMPLE 41 a. Ethyl (Z)-2-(cis-2-methylcyclohexyloxyimino)-3-oxobutyrate

Ethyl (Z)-2-hydroxyimino-3-oxobutyrate (3.48 g) was reacted with trans-2-methylcyclohexanol as described in Example 4a, method 3 to give the title compound (0.476 g, 8.5%), as a colourless liquid, $\nu_{max}$ (film) 2930, 1740 and 1690 cm$^{-1}$, $\delta_H$ (CDCl$_3$) 0.95 (3H, d, J 6.9 Hz), 1.34 (3H, t), 1.3–2.1 (9H, m), 2.40 (3H, s), 4.36 (2H, q), and 4.39 (1H, m).

b. Ethyl 4-bromo-(Z)-2-(cis-2-methylcyclohexyloxyimino)-3-oxobutyrate

Ethyl (Z)-2-(cis-2-methylcyclohexyloxyimino)-3-oxobutyrate (0.46 g) was treated with bromine as described in Example 4c to give the title compound (0.41 g, 68%), $\nu_{max}$ (film) 2930, 1740, and 1695 cm$^{-1}$, $\delta_H$ (CDCl$_3$) 0.95 (3H, d, J 6.7 Hz), 1.35 (3H, t), 1.3–2.1 (9H, m), 4.35 (2H, s), 4.38 (2H, q), and 4.40 (1H, m). [Mass spectrum: +ve ion (ammonia) MH$^+$ (334)].

c. Ethyl 2-(2-aminothiazol-4-yl)-(Z)-2-(cis-2-methylcyclohexyloxyimino)acetate Ethyl 4-bromo-(Z)-2-(cis-2-methylcyclohexyloxyimino)-3-oxobutyrate was converted into the title compound (0.24 g, 66%) as described in Example 4d, m.p. 123°–126° C. (cyclohexane/hexane), [Found: M$^+$311.1309, C$_{14}$H$_{21}$N$_3$O$_3$S requires M 311.1303]. $\nu_{max}$ (KBr) 3453, 3117, 2927, 1730, 1610, and 1538 cm$^{-1}$, $\delta_H$(CDCl$_3$) 0.95 (3H, d, J 7.0 Hz), 1.38 (3H, t), 1.3–2.1 (9H, m), 4.36 (1H, m), 4.39 (2H, q), 5.35 (2H, br s), and 6.69 (1H, s).

d. 2-(2-Aminothiazol-4-yl)-(Z)-2-(cis-2-methylcyclohexyloxyimino)acetic acid Ethyl 2-(2-aminothiazol-4-yl)-(Z)-2-(cis-2-methylcyclohexyloxyimino)acetate 0.227 g) was hydrolyesd as described in Example 17d to give the title compound (0.159 g, 77%).

e. 2-(2-Aminothiazol-4-yl)-(Z)-2-(cis-2-methylcyclohexyloxyimino)acetic acid 2-pyridyl thioester 2-(2-Aminothiazol-4-yl)-(Z)-2-(cis-2-methylcyclohexyloxyimino) acetic acid (0.159 g) was converted into the title compound (0.17 g, 80%) as described in Example 4f.

f. Sodium 6β-[2-(2-aminothiazol-4-yl)-(Z)-2-(cis-2-methylcyclohexyloxyimino)acetamido]penicillanate 2-(2-Aminothiazol-4-yl)-(Z)-2-(cis-2-methylcyclohexyloxyimino)acetic acid 2-pyridyl thioester (0.17 g) coupled to 6β-aminopenicillanic acid as described in Example 1d to give the title compound (57 mg, 25%), as a white freeze-dried solid, $\nu_{max}$ (KBr) 3385, 2928, 1767, 1668, 1609, and 1514 cm$^{-1}$, $\delta_H$ (D$_2$O) 0.91 (3H, d+d), 1.2–2.0 (9H, m), 1.50 (3H, s), 1.60 (3H, s), 4.21 (1H, s), 4.28 (1H, m), 5.62 (1H, d+d), 5.68 (1H, d+d), and 6.94 (1H, s). [Mass spectrum +ve ion (thioglycerol) MH$^+$ (504), MNa$^+$ (526)].

EXAMPLE 42 a. tert-Butyl-(Z)-2-(trans-4-methoxycarbonylcyclohexyloxyimino)-3-oxobutyrate A solution of diethyl azodicarboxylate (1.62 ml) in tetrahydrofuran (5 ml) was added dropwise to a solution of tert-butyl (Z)-2-hydroxyimino-3-oxobutyrate (1.6 g), methyl cis-4-hydroxycyclohexanecarboxylate (1.9 g) and triphenylphosphine (2.7 g) in tetrahydrofuran (20 ml) over 15 min at room temperature. The mixture was stirred for 18h, then the solvent removed under reduced pressure. The residue was chromatographed on silica to give the title compound (0.93 g, 33%) as a colourless liquid. $\nu_{max}$ (film) 2950, 1730, and 1690 cm$^{-1}$. $\delta_H$ (CDCl$_3$) 1.47–1.64 (3H, m), 1.53 (9H, s), 1.56 (3H, d, J 5.3 Hz), 2.05 (2H, m), 2.17 (2H, m), 2.35 (1H, m), 2.37 (3H, s), 3.69 (3H, s), and 4.24 (1H, tt, J 4.1, 10.0 Hz), $\delta$C (CDCl$_3$) 25.2, 26.3 (2C), 28.1 (3C), 29.9 (2C), 41.6, 51.7, 82.9, 84.0, 160.6, 175.5, and 193.0. [Mass spectrum +ve ion (ammonia) MH$^+$ (328), MNH$_4^+$ (345)].

b. 2-(2-Aminothiazol-4-yl)-(Z)-2-(trans-4-methoxycarbonylcyclohexyloxyimino) acetic acid Sulphuryl chloride (0.55 ml) was added to a solution of tert-butyl (Z)-2-(trans-4-methoxycarbonylcyclohexyloxyimino)-3-oxobutyrate (0.50 g) in acetic acid (1.5 ml).

The mixture was stirred at 45°–50° C. for 3.5 h, then evaporated to dryness. Toluene (2 ml) was added and evaporated, the process was repeated two more times to leave a residue of 4-chloro-(Z)-2-(trans-4-methoxycarbonylcyclohexyloxyimino)-3-oxobutyric acid. $\delta_H$ (CDCl$_3$) inter alia 3.7 (3H, s) and 4.5 (2H, s). This residue was dissolved in ethanol (5 ml), thiourea (0.14 g) and N,N-dimethylaniline (0.22 g) were added with stirring. After 18h the mixture was evaporated and the residue dissolved in a mixture of ethyl acetate and water. The pH was adjusted to 8.0 by addition of aqueous sodium bicarbonate. The aqueous layer was separated, adjusted to pH 2.8 with IM aqueous hydrochloric acid and lyophilised. The resulting solid was extracted with a mixture of acetone and methanol to give the title compound as a gum. $\delta_H$ (CDCl$_3$) inter alia 3.7 (3H, s) and 6.9 (1H, s).

c. 2-(2-Aminothiazol-4-yl)-(Z)-2-(trans-4-methoxycarbonylcyclohexyloxyimino) acetic acid 2-pyridyl thioester.

2-(2-Aminothiazol-4-yl)-(Z)-2-(trans-4-methoxycarbonylcyclohexyloxyimino) acetic acid was converted into the title compound (0.177 g, 28%, 3 steps) as described in Example 4f. m.p. 156°–158° (toluene), [Found: C, 51.80; H, 4.95; N, 13.10. C$_{18}$H$_{20}$N$_4$O$_4$S$_2$ requires C, 51.41; H, 4.79 N, 13.32%], $\nu_{max}$ (KBr) 3428, 3125, 2942, 1714, 1684, and 1611 cm$^{-1}$, $\delta_H$(CDCl$_3$) 1.56 (4H, m), 2.0–2.4 (5H, m), 3.68 (3H, s), 4.26 (1H, m), 5.83 (2H, brs), 6.82 (1H, s), 7.35 (1H, m), 7.76 (2H, m), and 8.67 (1H, m).

d. Sodium 6β-[2-(2-aminothiazol-4-yl)-(Z)-2-(trans-4-methoxycarbonylcyclohexyloxyimino)acetamido]penicillanate 2-(2-Aminothiazol-4-yl)-(Z)-2-(trans-4-methoxycarbonylcyclohexyloxyimino) acetic acid 2-pyridyl thioester (0.138 g) was coupled to 6β-aminopenicillanic acid as described in Example 1d to give the title compound (80 mg, 45%) as a white freeze-dried solid, $\theta_{max}$(KBr) 3335, 2945, 1767, 1723, 1668, 1609, and 1527 cm$^{-1}$, $\delta_H$(D$_2$O) 1.48 (4H, m), 1.52 (3H, s), 1.63 (3H, s), 2.06 (4H, m), 2.43 (1H, m), 3.68 (3H, s), 4.21 (1H, m), 4.23 (1H, s), 5.63 (1H, d), 5.66 (1H, d), and 6.99 (1H, s). [Mass spectrum: +ve ion (thioglycerol) MH+ (548), MNa+ (570)].

EXAMPLE 43 a. Ethyl (Z)-2-(1,1-dioxotetrahydrothien-3-yloxyimino)-3-oxobutyrate

A solution of 3-chloroperbenzoic acid (2.49 g) in chloroform (20 ml) was added to a solution of ethyl (Z)-2-(tetrahydrothien-3-yloxyimino)-3-oxobutyrate (1.37 g) in chloroform (30 ml) over 5 min at 0° C. After stirring at room temperature for 30 min, then at 50° C. for 1h, the solution was washed successively with saturated aqueous sodium bicarbonate, water and brine and dried (MgSO$_4$). The residue after evaporation was chromatographed on silica to give the title compound (1.55 g, 100%); [Found: MH+278.0701, C$_{10}$H$_{15}$NO$_6$S +H$^+$ requires 278.0698]. $\nu_{max}$ (film) 2980, 1740, 1700, 1305, and 1000 cm$^{-1}$; $\nu_H$(CDCl$_3$) 1.35 (3H, t), 2.42 (3H, s), 2.60 (2H, m), 3.17 (2H, m), 3.42 (2H, m), 4.38 (2H, q), and 5.22 (1H, m).

Ethyl 4-chloro-(Z)-2-(1,1-dioxotetrahydrothien-3-oxobutyrate

Sulphuryl chloride (3 ml) was added to a solution of ethyl (Z)-2-(1,1-dioxotetrahydrothien-3-yloxyimino)-3-oxobutyrate (1.55 g) in acetic acid (6 ml). The mixture was stirred at 50° for 5h, then evaporated to dryness. The residue was chromatographed on silica to give the title compound (0.87 g, 50%) as a white solid. m.p. 86°–88° C. (ethanol), $\nu_{max}$ (KBr) 3012, 1741, 1714, 1302, and 993 cm$^{-1}$, $\delta_H$ (CDCl$_3$)) 1.36 (3H, t), 2.62 (2H, m), 3.17 (2H, m), 3.42 (2H, m), 4.40 (2H, q), 4.56 (2H, s), and 5.25 (1H, m).

c. Ethyl 2-(2-aminothiazol-4-yl)-(Z)-2-(1,1-dioxotetra-hydrothien-3-yloxyimino)acetate Ethyl 4-chloro-(Z)-2-(1,1-dioxotetrahydrothien-3-yloxyimino)-3-oxobutyrate (0.467 g) was converted into the title compound (0.34 g, 68%) as described in Example 4d, m.p. 147°–148° C. (ethanol). [Found: C, 39.80; H, 4.42; N, 12.35. C$_{11}$H$_{15}$N$_3$O$_5$S$_2$ requires C, 39.63; H, 4.54; N, 12.60%]. $\nu_{max}$ (KBr) 1735, 1618, 1537, 1307, and 999 cm$^{-1}$, $\delta_H$ (CDCl$_3$) 1.40 (3H, t), 2.45 (1H, m), 2.66 (1H, m), 3.14 (2H, m), 3.37 (2H, d, J 4.3 Hz) 4.43 (2H, q), 5.21 (1H, m), 5.44 (1H, br s), and 6.80 (1H, s).

d. 2-(2-Aminothiazol-4-yl)-(Z)-2-(1,1-dioxotetrahydrothien-3-yloxyimino) acetic acid Ethyl 2-(2-aminothiazol-4-yl)-(Z)-2-(1,1-dioxotetrahydrothien-3-yloxyimino) acetate (0.34 g) was hydrolysed as described in Example 17d to give the title compound (0.15 g, 48%).

e. 2-(2-Aminothiazol-4-yl)-(Z)-2-(1,1-dioxotetrahydrothien-3-yloxyimino)acetic acid 2-pyridyl thioester 2-(2-Aminothiazol-4-yl)-(Z)-2-(1,1-dioxotetrahydrothien -3-yloximino) acetic acid (80 mg) was converted into the title compound (20 mg, 19%) as described in Example 4f.

f. Sodium 6β-[2-(2-aminothiazol-4-yl)-(Z)-2-(1,1-dioxotetrahydrothien-3-yloxyimino)acetamido]-penicillanate 2-(2-Aminothiazol-4-yl)-(Z)-2-(1,1-dioxotetrahydrothien -3-yloxyimino)acetic acid 2-pyridyl thioester (20 mg) was coupled to 6β-aminopenicillanic acid as described in Example 1d to give the title compound (2.1 mg, 8%) as a white freeze-dried solid. $\delta_H$ (D$_2$O) 1.54 (3H, s), 1.64 (3H, s), 2.56 (1H, m), 2.69 (1H, m), 3.34 (2H, m), 3.59 (2H, m), 4.27 (1H, s), 5.23 (1H, m), 5.66(2H, m), and 7.11 (1H, d). [Mass spectrum, +ve ion (thioglycerol) MH$^+$ (526), MNa$^+$ (548)].

EXAMPLE 44 a. Ethyl (Z)-2-(decahydronapth-2-yloxyimino)-3-oxo-butyrate

Ethyl (Z)-2-hydroxyimino-3-oxobutyrate (2.4 g) was reacted with cis, trans-decahydronapth-2-ol as described in Example 4a, method 3 to give the title compound (1.7 g). (Found: M$^+$, 296.1868. C$_{16}$H$_{26}$NO$_4$ requires M, 296.1861), $\nu_{max}$ (film) 2930, 1745, 1690, and 1005 cm$^{-1}$, $\delta_H$ (CDCl$_3$) 0.8–2.2 (16H, m), 1.35 (3H, t), 2.4 (3H, s), 4.28 (1H, m), and 4.35 (2H, q).

b. Ethyl 4-bromo-(Z)-2-(decahydronaphth-2-yloxyimino)-3-oxobutyrate

Ethyl (Z)-2-(decahydronapht-2-yloxyimino)-3-oxobutyrate (1.7 g) in carbon tetrachloride (10 ml) was treated with bromine (0.29 ml). The mixture was stirred at room temperature for 1h, then the solvent was evaporated under reduced pressure. The residue was dissolved in ether, washed with water, dried (MgSO$_4$) and evaporated under reduced pressure. The title compound (0.7 g) was isolated by flash chromatography on silica eluting with chloroform:carbon tetrachloride. $\delta_H$ (CDCl$_3$) 1.33 (3H, t), 1.10–2.00 (16H, m), 6.35 (2H, s), 4.40 (2H, q), and 4.40 (1H, m).

c. Ethyl 2-(2-aminothiazol-4-yl)-(Z)-2-(decahydronaphth-2-yloxyimino)acetate Ethyl 4-bromo-(Z)-2-(decahydronaphth-2-yloxyimino)-3-oxobutyrate (0.7 g) was converted into the title compound (0.48 g) as described in Example 4d. (Found: M$^+$, 351.1618. C$_{17}$H$_{25}$N$_3$O$_3$S requires M, 351.1616), $\nu_{max}$ (CHCl$_3$) 2930, 1730, 1605, 1530, and 1005 cm$^{-1}$, $\delta_H$ [(CD$_3$)$_2$CO]0.8–2.1 (16H, m), 1.33 (3H, t), 4.20 (1H, m), 4.33 (2H, q), 6.8 (1H, s), and 6.98 (2H, br s).

d. 2-(2-Aminothiazol-4-yl)-(Z)-2-(decahydronaphth-2-yloxyimino) acetic acid

Ethyl 2-(2-aminothiazol-4-yl)-(Z)-2-(decahydronaphth-2-yloxyimino)acetate (0.48 g) was hydrolysed as described in Example 4e to give the title compound (0.35 g), $\nu_{max}$ (KBr) 3118, 2920, 1625, and 1013 cm$^{-1}$, $\delta_H$[(CD$_3$)$_2$SO]0.8–2.1 (16H, m), 4.06 (1H, m), 6.82 (1H, s), and 7.26 (3H, br s).

e. 2-(2-Aminothiazol-4-yl)-(Z)-2-(decahydrona-phth-2-yloxyimino)acetic acid 2-pyridyl thioester 2-(2-Aminothiazol-4-yl)-(Z)-2-(decahydronaphth-2-yloxy mino)acetic acid (348 mg) was converted to the title compound (450 mg) as described in Example 4f.

f. 6β-[2-(2-Aminothiazol-4-yl)-(Z)-2-(decahydronapth-2-yloxyimino)acetamido]penicillanic acid 2-(2-Aminothiazol-4-yl)-(Z)-2-(decahydronaphth-2-yloxyimino)acetic acid 2-pyridyl thioester (450 mg) was coupled to 6β-aminopenicillanic acid as described in Example 1d except that the title compound (20 mg) was isolated as the zwitterion, by flash chromatography on silica eluting with ethyl acetate: propan-2-ol:water, $\nu_{max}$(KBr) 3344, 1773, 1638, 1610, and 1526 cm$^{-1}$, $\delta_H$ [(CD$_3$)$_2$SO]1.10–1.85 (16H, m), 1.44 (3H, s), 1.56 (3H, s), 3.95 (1H, s), 4.03 (1H, m), 5.47 (2H, m), 6.74 (1H, s), 7.21 (3H, s), and 9.22 (1H, m) [Mass spectrum: (thioglycerol) MH$^+$ (522)].

EXAMPLE 45 a. Ethyl (Z)-2-([R,S]-1-phenylethyloxyimino)-3-oxobutyrate

Ethyl (Z)-2-hydroxyimino-3-oxobutyrate (2.4 g) was reacted with [R,S]-1-phenylethanol (1.81 ml) as described in Example 4a, method 3 to give the title compound (1.4 g), $\nu_{max}$ (film) 1740, 1685, and 1230 cm$^{-1}$, $\delta_H$(CDCl$_3$) 1.32 (3H, t), 1.61 (3H, d J 7 Hz), 4.30 (2H, q), 5.41 (1H, q, J 7 Hz), and 7.27 (5H, s), [Mass spectrum: (ammonia) MH$^+$ (264), MNH$_4^+$ (281)].

b. Ethyl 4-bromo-(Z)-2-([R,S]-1-phenylethyloxyimino)-3-oxobutyrate

Ethyl (Z)-2-([R,S]-1-phenylethyloxyimino)-3-oxobutyrate (1.3 g) was brominated as described in Example 4c to give the title compound (1.65 g), $\delta_H$(CDCl$_3$) 1.34 (3H, t), 1.61 (3H, d, J 7 Hz), 4.21 (2H, s), 4.37 (2H, q), 5.43 (1H, q, J 7 Hz), and 7.29 (5H, s).

c. Ethyl 2-(2-aminothiazol-4-yl)-(Z)-2-([R,S]-1-phenyloxyimino)acetate

Ethyl 4-bromo-(Z)-2-([R,S]-1-phenylethyloxyimino)-3-oxobutyrate (1.6 g) was converted into the title compound (0.5 g) as described ih Example 4d after crystallisation from toluene, $\nu_{max}$ (KBr) 3439, 3101, 1729, and 1612 cm$^{-1}$, $\delta_H$ [(CD$_3$)$_2$CO]1.33 (3H, t), 1.50 (3H, d, J 7

Hz), 4.34 (2H, q), 5.32 (1H, q, J 7 Hz), 6.52 (2H, br s), 6.77 (1H, s), and 7.30 (5H, m), [Mass spectrum: M+ (319)].

d. 2-(2-Aminothiazol-4-yl)-(Z)-2-([R,S]-1-phenylethyloxyimino)acetic acid

Ethyl 2-(2aminothiazol-4-yl)-(Z)-2-([R,S]-1-phenylethoxy imino) acetate (0.45 g) was hydrolysed as described in Example 4e to give the title compound (0.12 g), $\nu_{max}$ (KBr) 2975 (br), 1616 (br), and 1385 cm$^{-1}$; $\delta_H$ ((CD$_3$)$_2$SO) 1.45 (3H, d, J 7 Hz), 5.28 (1H, q, J 7 Hz), 6.81 (1H, s), 7.23 (2H, br s), and 7.32 (5H, m), [Mass spectrum: M+ (291)].

e. 2-(2-Aminothiazol-4-yl)-(Z)-2-([R,S]-1-phenylethyloxyimino)acetic acid 2-pyridyl thioester 2-(2-Aminothiazol-4-yl)-(Z)-2-([R,S]-1-phenylethyloxyimino)acetic acid (120 mg) was converted into the title compound (175 mg) as described in Example 4f, $\nu_{max}$ (KBr) 3441, 3113, 1688, 1614, 1570, and 929 cm$^{-1}$, $\delta_H$ (CDCl$_3$) 1.56 (3H, d), 5.34 (1H, q), 6.48 (2H, br s), 6.72 (1H, s), 7.32 (1H, m), 7.44 (5H, m), 7.76 (2H, m), and 8.72 (1H, m), [Mass spectrum: M+ (384)].

f. 6β-[2-(2-Aminothiazol-4-yl)-(Z)-2-([R,S]-1-phenylethyloxyimino)dacetamido]penicillanic acid 2-(2-Aminothiazol-4-yl)-(Z)-2-([R,S]-1-phenylethyloxyimino)acetic acid 2-pyridyl thioester (170 mg) was coupled to 6β-aminopenicillanic acid as described in Example 1d except that the title compound (90 mg) was isolated as its zwitterion, by flash chromatography on silica eluting with ethyl acetate:propan-2-ol:water, $\nu_{max}$ (KBr) 3351 1773 1671 1615 1525 and 1317 cm$^{-1}$, $\delta_H$[(CD$_3$)$_2$CO]1.45 (3H, d, J 6.6 Hz), 1.46 , 1.48, 1.67, 1.68 (6H, 4s), 4.12, 4.14 (1H, 2s), 5.23 (1H, q, J 6.6 Hz), 5.57 (2H, m), 6.72, 6.73 (1H, 2s), 7.20 (3H, s), 7.32 (5H, m), 9.48 and 9.50 (1H, 2d), [Mass spectrum: (thioglycerol) MH+ (490)].

EXAMPLE 46 a. (Z)-2-(2,6-dichlorobenzyloxyimino)-3-oxobutyrate

Ethyl (Z)-2-hydroxyimino-3-oxobutyrate (3.33 g) was alkylated with 2,6-dichlorobenzylchloride (4.39 g) as described in Example 4a to give the title compound (6 g) $\delta_H$(CDCl$_3$) 1.27 (3H, t), 2.34 (3H, s), 4.36 (2H, q), 5.68 (2H, s), and 7.4 (3H, m). [Mass spectrum: M+ (317)].

b. Ethyl 4-bromo-(Z)-2-(2,6-dichlorobenzyloxyimino)-3-oxobutyrate

Ethyl (Z)-2-(2,6-dichlorobenzyloxyimino)-3-oxobutyrate (5.8 g) was reacted with bromine (0.94 ml) as described in Example 4c to give the title compound (7.2 g), $\delta_H$ (CDCl$_3$) 1.31 (3H, t), 4.35 (2H, s), 4.45 (2H, q), 5.73 (2H, s), and 7.43 (3H, m).

c. Ethyl 2-(2-aminothiazol-4-yl)-(Z)-2-(2,6-dichlorobenzyloxyimino)acetate

Ethyl 4-bromo-(Z)-2-(2,6-dichlorobenzyloxyimino)-3-oxobutyrate (7.2 g) was dissolved in ethanol (20 ml) and N,N-dimethylaniline (2.33 ml) and thiourea (1.4 g) added with stirring. After 18 h the title compound was filtered off, washed with ethanol and dried (4.9 g), m.p. 171°-2° C., $\nu_{max}$ (KBr) 3423, 1722, 1619, 1529, 1284, 1188, 1021, and 995 cm$^{-1}$, $\delta_H$ [(CD$_3$)$_2$SO]1.22 (3H, t), 4.33 (2H, q), 5.51 (2H, s), 6.96 (1H, s), 7.24 (2H, br s), and 7.54 (3H, m), [Mass spectrum: M+ (373/375)].

d. 2-(2-Aminothiazol-4-yl)-(Z)-2-(2,6-dichlorobenzyloxyimino)acetic acid

Ethyl 2-(2-aminothiazol-4-yl)-(Z)-2-(2,6-dichlorobenzyloxyimino)acetate (4.8 g) was hydrolysed with aqueous sodium hydroxide (1N, 25.6 ml) in ethanol (40 ml), acetone (20 ml) as described in Example 4e to give the title compound (1.9 g), $\nu_{max}$ (KBr) 3123 (br), 1610 (br), and 992 cm$^{-1}$, $\delta_H$ [(CD$_3$)$_2$SO]5.32 (2H, s), 6.81 (1H, s), 7.17 (2H, br s), and 7.44 (3H, m), [Mass spectrum: +ve ion (thioglycerol) MH+ (346)].

e. 2-(2-Aminothiazol-4-yl)-(Z)-2-(2,6-dichlorobenzyloxyimino)acetic acid 2-pyridyl thioester 2-(2-Aminothiazol-4-yl)-(Z)-2-(2,6-dichlorobenzyloxyimino)acetic acid (0.69 g) was treated with triphenylphosphine (0.79 g) and 2,2'-dithiodipyridine (0.66 g) as described in Example 4f to give the title compound (0.72 g), $\nu_{max}$ (KBr) 3125, 1690, 1658, 1623, and 990 cm$^{-1}$, $\delta_H$[(CD$_3$)$_2$SO]inter alia 5.38 (2H, s), 6.98 (1H, s), 7.25 (2H, br s), 7.45 (3H, m), 7.30–8.00 (3H, m), and 8.65 (1H, m).

f. 6β-[2-(2-Aminothiazol-4-yl)-(Z)-2-(2,-6-dichlorobenzyloxyimino)acetamido]penicillanic acid 2-(2-Aminothiazol-4-yl)-(Z)-2-(2,6-dichlorobenzyloxyimino)acetic acid 2-pyridyl thioester (0.59 g), was treated with 6β-aminopenicillanic acid (0.32 g) as described in Example 1d, except that the title compound (0.012 g) was isolated as its zwitterion after flash chromatography on silica eluting with ethyl acetate:propan-2-ol: water, $\nu_{max}$(KBr) 3328, 1773, 1671, 1610, and 1523 cm$^{-1}$, $\delta_H$(CD$_3$OD) 1.46 (3H, s), 1.57 (3H, s), 4.18 (1H, s), 5.4–5.6 (4H, m), 6.89 (1H, s), and 7.25–7.50 (3H, m).

EXAMPLE 47 a. 2-(2-Aminothiazol-4-yl)-(Z)-2-(cyclohexyloxyimino)acetic acid 2-benzothiazolyl thioester Triphenylphosphine (643 mg, 2.45 mmol) and 2,2'-dithiobis-benzothiazole (815 mg, 2.45 mmol) in dry acetonitrile (8 ml) under argon were stirred for 25 min. 2-(2-Aminothiazol-4-yl)-(Z)-2-(cyclohexyloxyimino)acetic acid (330 mg, 1.22 mmol) was then added, followed by dry acetonitrile (2 ml) and the resultant mixture was stirred overnight. The solid was filtered off to give the title compound (218 mg, 43%). The mother liquors were evaporated to leave an oil which was chromatographed on silica gel, eluting with ethyl acetate/hexane mixtures to give further title compound (168 mg, 33%). m.p. 125°–126° C. (ethyl acetate-hexane). [Found: C, 51.81; H, 4.52; N, 13.15, $C_{18}H_{18}N_4O_2S_3$ requires C, 51.65; H, 4.33; N, 13.39%]. $\nu_{max}$(KBr) 3317, 3159, 2931, 2855, 1706, 1645, 1616, and 1538 cm$^{-1}$; $\delta_H$ (400 MHz, CDCl$_3$) 1.2–1.4 (3H, m), 1.5 (1H, m), 1.55–1.65 (2H, m), 1.7–1.8 (2H, m), 1.9–2.0 (2H, m), 4.34 (1H, m), 5.74 (2H, s), 6.84 (1H, s), 7.4–7.6 (2H, s), 7.93 (1H, broad d, J ca 7 Hz), and 8.07 (1H, broad d, J ca 8 Hz).

b. Sodium 6β-[2-(2-aminothiazol-4-yl)-(Z)-2-(cyclohexyloxyimino)acetamido]penicillanate 8β-Aminopenicillanic acid (130 mg, 0.6 mmol) in dry dichloromethane (3 ml) was treated with triethylamine (0.167 ml, 121 mg, 1.2 mmol), followed by chlorotrimethylsilane (0.152 ml, 130 mg, 1.2 mmol) and the mixture was heated under reflux for 30 min. The mixture was then allowed to cool to room temperature and treated with 2-(2-aminothiazol-4-yl)-(Z)-2-(cyclohexyloxyimino)-acetic acid 2-benzothiazolylthioester (239 mg, 0.57 mmol), followed by dry dichloromethane (2 ml). After stirring for 18 h the dichloromethane was removed under reduced pressure and ethyl acetate (50 ml) and water (30 ml) were added. The pH was adjusted to 8.0 (cooling in ice) and the layers were separated. The ethyl acetate layer was extracted with water (20 ml) at pH 8.0 and the combined aqueous layers were treated with ethyl acetate (30 ml) and the pH was adjusted to 3.0 (ice cooling) by addition of dilute HCl. The aqueous layer was washed with ethyl acetate and these ethyl acetate extracts (pH 3) were treated with water (20 ml) and the pH was adjusted (ice cooling) to pH 7.7 by addition of aqueous NaHCO$_3$. The ethyl acetate layer was again extracted with water at pH 7.7 and the combined aqueous extracts (pH 7.7) were treated with 1,4-dioxan (2 ml) and evaporated under reduced pressure to ca 15 ml. A little sodium chloride was added and the resultant solution was chromatographed on HP20SS to give the title compound (233 mg, 83%), which exhibited identical spectroscopic properties to those described in Example 4 g.

c. A solution of 2-(2-aminothiazol-4-yl)-(Z)-2-cyclohexyloxyimino)acetic acid (0.5 g; 1.9 mmol) and N-ethyl diisopropylamine (0.36 ml; 2 mmol) in- dimethyl formamide (5 ml) cooled to −50° C. under dry argon was treated with methanesulphonyl chloride (0.16 ml; 2 mmol) The mixture was stirred at −50° C. for 40 min then added to a solution of 6β-aminopenicillanic acid (0.36 g; 1.8 mmol) and triethylamine (0.58 ml); 4.2 mmol) in water (3 ml) at 0° C. The resulting reaction mixture was stirred at 0° C. for 10 min then water (50 ml) was added and the pH of the solution adjusted to 7.5 (1N HCl). The aqueous phase was washed with ethyl acetate (2×), then a further quantity of ethyl acetate (70 ml) was added and the pH of the mixture adjusted to 2.3 (5N HCl). The organic phase was separated and washed with water. Water (70 ml) was added and the pH adjusted to 7.5 (5N NaOH). The aqueous phase was concentrated and chromatographed on HP20SS to give the title compound (0.53 g; 58%).

d. A solution of 2-(2-aminothiazol-4-yl)-(Z)-2-(cyclohexyloxyimino)acetic acid (0.5 g; 1.9 mmol) and N-ethyl diisopropylamine (0.36 ml; 2mmol) in dimethylformamide (5 ml) cooled to −50° C. under dry argon was treated with methane sulphonylchloride (0.16 ml; 2 mmol). The mixture was stirred at −50° C. for 40 min. then allowed to warm to −30° C. and a solution of 6β-aminopenicillanic acid (0.36 g; 1.8 mmol) and triethylamine (0.58 ml; 4.2 mmol) in water (3 ml) at 0° C. added. The reaction mixture was stirred at 0° C. for 10 min. then treated as in part c of this example to give the title compound (0.51 g, 52%).

EXAMPLE 48

[R,S]-Phthalid-3-yl 6β-[2-(2-aminothiazol-4-yl)-(Z)-2-(cyclohexyloxyimino)acetamido]penicillanate A mixture of [R,S]-3-bromophthalide (44 mg) and sodium 6β-[2-(2-aminothiazol-4-yl)-(Z)-2-(cyclohexyloxyimino)-acetamido]penicillanate (100 mg) in dry N,N-dimethylformamide was stirred at room temperature for 1 h. The solution was diluted with ethyl acetate, washed with water, dried (MgSO$_4$) and the solvent evaporated under reduced pressure. The title compound (80 mg) was isolated by flash chromatography on silica eluting with ethyl acetate: cyclohexane, $\nu_{max}$ (KBr) 3351, 2932, 1786, 1677, 1611, and 980 cm$^{-1}$, $\delta_H$ [(CD$_3$)$_2$CO]1.20–2.05 (10H, m), 1.61, 1.62 (3H, 2s), 1.65, 1.67 (3H, 2s), 4.13 (1H, m), 4.57, 4.58 (1H, 2s), 5.77 (2H, m), 6.58 (2H, s), 6.83, 6.84 (1H, 2s), 7.63 (1H, s), 7.88 (4H, m), and 8.14 (1H, d). [Mass spectrum: +ve ion (thioglycerol) MH+ (600)].

EXAMPLE 49

[R,S]-1-Acetoxyethyl 6β-[2-(2-aminothiazol-4-yl)-(Z)-2-(cyclohexyloxyimino)-acetamido]penicillanate Sodium 6β-[2-(2-aminothiazol-4-yl)-(Z)-2-(cyclohexyloxyimino)acetamido]penicillanate (245 mg) was esterified with [R,S]-1-acetoxy-1-bromoethane (84 mg) as described in Example 48 to give the title compound (100 mg), $\nu_{max}$ (KBr) 3342, 2934, 1790, 1763, 1676, 1614, and 1527 cm$^{-1}$, $\delta_H$ [(CD$_3$)$_2$CO]1.2–2.05 (22H, m), 4.15 (1H, m), 4.39, 4.43 (1H, 2s), 5.68 (1H, 2d J 4 Hz) 5.85 (1H, 2dd, J 4 and 9 Hz), 6.67 (2H, s), 6.84, 6.86 (1H, 2s), 6.91 (1H, 2q), and 8.13 (1H, d, J 9 Hz) [Mass spectrum: +ve ion (thioglycerol) MH+ (554)].

EXAMPLE 50

[R,S]-1-Ethoxycarbonyloxyethyl 6β-[2-(2-aminothiazol-4-yl)-(Z)-2-(cyclohexyloxyimino)acetamido]penicillanate Sodium 6β-[2-(2-aminothiazol-4-yl)-(Z)-2-(cyclohexyloxyimino)acetamido]penicillanate (490 mg) was esterified with [R,S]-1-ethoxycarbonyloxy-1-iodoethane (153 mg) as described in Example 48 to give the title compound (60 mg), $\nu_{max}$ (KBr) 3352, 2935, 1767, 1678, 1616, 1373, and 1077 cm$^{-1}$, $\delta_H$ [(CD$_3$)$_2$CO]1.20–2.05 (2H, m), 4.14 (1H, m), 4.22 (2H, q), 4.41, 4.45 (1H, 2s), 5.67 (1H, 2d, J 4 Hz), 5.86 (1H, dd, J 4 and 9 Hz) 6.57 (2H, s), 6.82 (1H, m), 6.84, 6.85 (1H, 2s), and 8.13 (1H, d J 9 Hz), [Mass spectrum: +ve ion (thioglycerol), MH+ (584)].

EXAMPLE 51

Pivaloyloxymethyl 6β-[2-(2-aminothiazol-4-yl)-(Z)-2-(cyclohexyloxyimino)acetamido]penicillanate A solution of pivaloyloxymethyl 6β-aminopenicillanate (1.13 g) in dry dichloromethane (10 ml) was treated with triethylamine (0.48 ml) and chlorotrimethylsilane (0.44 ml). After 40 min at room temperature the mixture was cooled to 5° C. 2-(2-Aminothiazol-4-yl)-(Z)-2-(cyclohexyloxyimino)acetic acid 2-pyridyl thioester (1.13 g) was added and the reaction allowed to warm to room temperature. After 5 h the solvent was evaporated under reduced pressure and the title compound (0.1 g) isolated by flash chromatography on silica eluting with ethyl acetate:cyclohexane, $\nu_{max}$ (KBr) 3347, 2933, 1790, 1756, 1676, 1614, and 1529 cm$^{-1}$, $\delta_H$ [(CD$_3$)$_2$CO]1.22 (9H, s), 1.23-2.05 (10H, m), 1.53 (3H, s), 1.65 (3H, s), 4.15 (1H, m), 4.46 (1H, s), 5.67 (1H, d, J 4 Hz), 5.85 (1H, dd J 4 and 9 Hz), 5.88 (2H, ABq J 4 Hz), 6.70 (2H, s), 6.83 (1H, s), and 8.15 (1H, d J 9 Hz) [Mass spectrum: +ve ion (thioglycerol), MH+ (582)].

EXAMPLE 52 a. cis-4-Chlorocyclohexanol trans-4-Chlorocyclohexanol (2.67 g) (R. S. Monson, J. Chem. Education, 1971, 48(3), 197), triphenylphosphine (7.86 g), and formic acid (2.8 g; 2.3 ml) were dissolved in dry tetrahydrofuran (100 ml) and the solution cooled in an ice-bath. Diethyl azodicarboxylate (5.24 g) was added to the stirred solution and the cooling-bath was removed. After 30 min the solvent was evaporated under reduced pressure and the residue partitioned between ethyl acetate and aqueous sodium hydrogencarbonate. The organic layer was separated, washed with brine, dried, and evaporated. Chromatography on silica gel gave cis-4-chloro-1-formyloxycyclohexane (680 mg), $\nu_{max}$ (film) 1715 cm$^{-1}$, $\delta_H$ (CDCl$_3$) inter alia 4.12 (1H, m), 4.96 (1H, m), and 8.01 (1H, s). The formate (598 mg) in ethanol (10 ml) was treated with 1N sodium hydroxide (3.6 ml). After 10 min the solvent was removed under reduced pressure and the residue partitioned between ethyl acetate and water. The organic layer was separated, washed with brine, dried and evaporated. Chromatography on silica gel gave the title compound as an oil (358 mg) which slowly crystallised m.p. 27°-29° C. (Found; M+, 134.0507. C$_6$H$_{11}$OCl requires M, 134.0499), $\delta_H$ (CDCl$_3$) inter alia 1.58 (1H, s, exch. D$_2$O), 3.76 (1H, m), and 4.20 (1H, m), $\delta_C$ (CDCl$_3$) 30.62, 32.00, 58.45, and 67.67.

b. Ethyl (Z)-2-(trans-4-chlorocyclohexyloxyimino)-3-oxobutyrate

Ethyl (Z)-2-hydroxyimino-3-oxobutyrate (95 mg) was treated with cis-4-chlorocyclohexanol as described in Example 4a, Method 3, to give the title compound as a colourless liquid (37 mg, 21%), (Found: M+, 276.1011. C$_{12}$H$_{19}$NO$_4$Cl requires M, 276.1002) $\nu_{max}$ (film) 1735, 1685, 1360, 1310, and 950 cm$^{-1}$, $\nu_H$ (CDCl$_3$), 1.32 (3H, t, J 7.1 Hz), 1.76 (4H, m), 2.14 (4H, m), 2.4 (3H, s), 4.19 (1H, m), 4.35 (2H, q, J 7.1 Hz), and 4.44 (1H, m).

c. Ethyl 4-bromo-(Z)-2-(trans-4-chlorocyclohexyloxyimino)-3-oxobutyrate

Ethyl (Z)-2-(trans-4-chlorocyclohexyloxyimino)-3-oxobutyrate (673 mg) was brominated as described in Example 4c to give the title compound (730 mg; 84%).

d. Ethyl 2-(2-aminothiazol-4-yl)-(Z)-2-(trans-4-chlorocyclohexyloxyimino)acetate Ethyl 4-bromo- (Z)-2-(trans-4-chlorocyclohexyloxyimino)-3-oxobutyrate (730 mg) was treated with thiourea as described in Example 4d, to give the title compound (579 mg, 85%) m.p. 155° C. (ethyl acetate-hexane) (Found: C, 47.05; H, 5.02; N, 12.75; Cl, 10.8; S, 9.73. C$_{13}$H$_{18}$N$_3$ClO$_3$S requires C,47.1; H, 5.4; N, 12.7; Cl, 10.7; S, 9.7%). $\nu_{max}$ (Nujol) 3450, 3430, 3250, 3125, 1720, 1615, 1610, and 1540 cm$^{-1}$, $\nu_H$(CDCl$_3$), 1.36 (3H, t, J 7.1 Hz), 1.73 (4H, m), 2.13 (4H, m), 4.18 (1H, m), 4.39 (2H, q, J 7.1 Hz), latter signal obscures single hydrogen multiplet, 5.5 (2H, s, exch. D$_2$O), and 6.71 (1H, s).

e. 2-(2-Aminothiazol-4-yl)-(Z)-2-(trans-4-chlorocyclohexyloxymino)acetic acid Ethyl-2-(2-aminothiazol-4-yl)-Z-2-(trans-4-chlorocyclohexyloxyimino)acetate (497 mg) was hydrolysed as described in Example 4e to give the title compound as a very pale yellow solid (411 mg, 91%). $\nu_{max}$ (KBr) 2947, 1613, 1390, and 987 cm$^{-1}$ $\delta_H$ [(CD$_3$)$_2$SO]1.61 (4H, m), 2.03 (4H, m), 4.23 (2H, m), 6.84 (1H, s), 7.25 (2H, s, exch. D$_2$O), and 13.69 br (1H, s, exch. D$_2$O) [Mass spectrum: +ve ion (thioglycerol) MH+ (304)].

f. Sodium 6β-[2-(2-aminothiazol-4-yl)-(Z)-2-(trans-4-chlorocyclohexyloxyimino)acetamido]penicillanate 2-(2-Aminothiazol-4-yl)-Z-2-(trans-4-chlorocyclohexyloxyimino)acetic acid (302 mg) was suspended in dry DMF (2 ml) under argon and di-isopropylethylamine (142 mg) added. The solution was cooled to −50° C. and methane sulphonyl chloride (126 mg) added. After 45 min at −50° C., triethylammonium 6β-aminopenicillanate (348 mg) in dichloromethane (1 ml) containing triethylamine (111 mg) was added, and the temperature raised to 0° C. After 1h the reaction mixture was poured into ethylacetate-water and the pH adjusted to 3. The aqueous layer was separated and re-extracted with ethyl acetate. The combined organic extracts were washed with brine, water added, and the pH adjusted to 7. The aqueous layer was evaporated under reduced pressure and the residue purified on HP20SS to give the title compound as a white freeze-dried solid (191 mg 37%) (Found: M+ +H, 524.0815. C$_{19}$H$_{23}$N$_5$O$_5$S$_2$ClNa requires M+H, 524.0816), $\nu_{max}$ (KBr), 3345, 2951, 1768, 1669, 1611, and 1527cm$^{-1}$, $\nu_H$(D$_2$O), 1.51 (3H, s), 1.61 (3H, s), 1.71 (4H, m), 2.09 (4H, m), 4.22 (1H, s), 4.32 (2H, m), 5.61 (1H, d, J 4 Hz), 5.67 (1H, d, J 4 Hz), and 6.98(1H, s).

EXAMPLE 53 a. Ethyl (Z)-2-(cis-4-chlorocyclohexyloxyimino)-3-oxobutyrate

Ethyl (Z)-2-(hydroxyimino)-3-oxobutyrate (3.18 g) was treated with trans-4-chlorocyclohexanol as described in Example 4a, method 3 to give the title compound as a colourless oil (2.02 g). (Found: MH+, 276.0995. $C_{12}H_{19}ClNO_4$ requires MH+, 276.1002; $\delta_H$ (CDCl$_3$) 1.36 (3H, t, J 7Hz), 1.79, 1.96 and 2.09 (8H, 3m), 2.40 (3H, s), 4.11 (1H, qt, J 6 Hz), 4.38 (2H, q, J 7 Hz), and 4.41 (1H, qt, J 6 Hz). A small quantity of the trans-isomer was obtained from faster-eluting column fractions.

b. Ethyl 4-bromo-(Z)-2-(cis-4-chlorocyclohexyloxyimino)-3-oxobutyrate

Ethyl (Z)-2-(cis-4-chlorocyclohexyloxyimino-3-oxobutyrate (2.42 g) was treated with bromine (0.50 ml) in chloroform (20 ml) as described in Example 4c. Workup afforded the bromo-compound (3.15 g) which was sufficiently pure to use directly; $\delta_H$(CDCl$_3$) (3H, t, J 7 Hz), 1.83, 1.96 and 2.10 (8H, 3m), 4.13 (1H, qt, J 6 Hz), 4.34 (2H, s), 4.40 (2H, q, J 7 Hz), and 4.44 (1H, qt, J 6 Hz).

c. Ethyl 2-(2-aminothiazol-4-yl)-(Z)-2-(cis-4-chlorocyclohexyloxyimino)acetate Ethyl 4-bromo-(Z)-2-(cis-4-chlorocyclohexyloxyimino)-3-oxobutyrate (3.15 g) was treated witn thiourea (0.67 g) as in Example 4d. The product was obtained as a crystalline solid (2.03 g), m.p. 143°–144° C. (ethyl acetate-hexane) (Found: C, 46.8; H, 5.5; N, 12.4. $C_{13}H_{18}ClN_3O_3S$ requires C, 47.1; H, 5.4; N, 12.7%); $\nu_{max}$ (KBr) 1723, 1601, 1534, and 1383 cm$^{-1}$; $\delta_H$ (CDCl$_3$) 1.42 (3H, t, J 7 Hz), 1.72, 1.95 and 2.06 (8H, 3m), 4.06 (1H, qt, J 6.5 Hz), 4.40–4.50 (3H, 2m), 5.25 (2H, brs, D$_2$O exch.) and 6.73 (1H, s).

d. Ethyl 2-(2-tritylaminothiazol-4-yl)-(Z)-2-(cis-4-chlorocyclohexyloxyimino)acetate Ethyl 2-(2-tritylaminothiazol-4-yl)-(Z)-2-(hydroxyimino)acetate (0.91 g), triphenylphosphine (0.58 g) and trans-4-chlorocyclohexanol (0.54 g) were dissolved together in anhydrous benzene (20 ml). Diethyl azodicarboxylate (0 35 ml) was added and the solution heated at reflux for 16 h with exclusion of moisture. Evaporation of solvent followed by chromatography afforded the title compound as a near colourless gum (225 mg, 20%); $\nu_{max}$ (KBr) 1737, 1595 (w), 1529, 1491 and 1446 cm$^{-1}$; $\delta_H$H (CDCl$_3$) 1.39 (3H, t, J 7 Hz), 1.69, 1.96 and 2.06 (8H, 3m), 4.04 (1H, qt, J 6 Hz), 4.39(2H, q, J 7Hz), 4.44 (1H, qt, J 3 Hz), 6.49 (1H, s), 6.97 (1H, brs, D$_2$O exch), and 7.32 (15H, s). [Mass spectrum: +ve ion (thioglycerol) MH+ (574), MNa+ (596)].

e. Ethyl 2-(2-aminothiazol-4-yl)-(Z)-2-(cis-4-chlorocyclohexyloxyimino)acetate Ethyl 2-(2-tritylaminothiazol-4-yl)-(Z)-2-(cis-4-chlorocyclohexyloxyimino)acetate (205 mg) was de-protected using formic acid as described in Example 1a. After chromatography the crystalline title compound (81 mg) was obtained, having identical m.p. and spectroscopic data to Example 53c.

f. 2-(2-Aminothiazol-4-yl)-(Z)-2-(cis-4-chorocyclohexyloxyimino)acetic acid

Ethyl 2-(2-aminothiazol-4-yl)-(Z)-2-(cis-4-chlorocyclohexyloxyiminoacetate (1.33 g) was hydrolysed as described in Example 4e. The title acid was obtained as a solid (0.72 g); $\nu_{max}$(Nujol) 1640, 1570 and 1470 cm$^{-1}$; $\delta_H$ [(CD$_3$)$_2$SO]1.88 (8H, m), 3.35 (2H, brs, D$_2$O exch), 4.23 (2H, m), and 6.86 (1H, s). [Mass spectrum: +ve ion (thioglycerol) MH+ (304), MNa+ (326)].

g. Sodium 6β-[2-(2-Aminothiazol-4-yl)-(Z)-2-(cis-4-chlorocyclohexyloxyimino)acetamido[penicillanate 2-(2-Aminothiazol-4-yl)- (Z)-2-(cis-4-chlorocyclohexyloxyimino)acetic acid (202 mg) was coupled to 6β-aminopenicillanic acid as described in Example 52f to give the title compound as a white amorphous solid (66 mg); $\nu_{max}$(KBr) 1777, 1671, 1611 and 1529 cm$^{-1}$ $\delta_H$ (D$_2$O) 1.55 and 1.66 (6H, 2s), 1.70–2.10 (8H , m), 4.28 (1H, s), 4.28 (1H, m), 4.38 (1H, m), 5.67 (1H, d, J 4 Hz), 5.70 (1H, d, J 4 Hz), and 7.03 (1H, s), [Mass spectrum: +ve ion (thioglycerol) MH+ (524), MNa+ (546), M-Na+ (502)].

EXAMPLE 54 a. 2-(2-Chloroacetamidothiazol-4-yl)-2-phenpxyiminoacetic acid

2-Chloroacetamidothiazol-4-ylglyoxylic acid (3.6 g) (S. Kishimoto et. al., Chem. Pharm. Bull., 1984, 32, 2649) was dissolved in tetrahydrofuran (40 ml)and water (70 ml). Phenoxyammonium chloride (2.5 g) was added, and the solution adjusted to pH 5 by the addition of 2.5M sodium hydroxide solution. The solution was stirred and maintained at pH 5–6 by the dropwise addition of 5M hydrochloric acid. The reaction (monitored by the rate of addition of HCl) became very slow after 7.5 h; it was refrigerated (2°–3° C.) overnight, and then adjusted to pH 8 with sodium hydroxide, extracted with toluene (50 ml) and with ether (50 ml). The aqueous solution was layered with ethyl acetate (100 ml) and toluene (10 ml) and acidified to pH 1.5 by the addition of 5M hydrochloric acid. The solvent layer was separated, dried (Na$_2$SO$_4$) and evaporated to near dryness, whereupon the compound crystallized. The mixture was slurried with ethr, filtered off, washed with hexane and dried in vacuo, to afford the title compound (3.4 g) as a fluffy solid. A further crop (0.5 g) of less pure material was obtained from the mother liquors m.p. >170° C. (decomp.) $\nu_{max}$ (Nujol) 3385, 1735, 1730, 1535, and 703 cm$^{-1}$; $\delta_H$[(CD$_3$)$_2$CO]4.52 (2H, s) 7.0–7.5 (5H, m), and 7.85 (1H, s).

b. Sodium 6β-[2-(2-chloroacetamidothiazol-4-yl)-Z-2-(phenoxyimino)acetamido]penicillanate To a solution of N,N-dimethylformamide (0.25 ml) in dry dichloromethane (5 ml), stirred and cooled at −10° C., was added oxalyl chloride (0.29 ml). A crystalline precipitate formed with evolution of gas. To this was added 2-(2-chloroacetamidothiazol-4-yl)-2-phenoxyiminoacetic acid (1.02 g). The mixture was stirred at −10° C. for ½ h, then allowed to warm gradually to 5° C. Triethylammonium 6β-aminopenicillanate (2.08 g) and triethylamine (0.42 ml) were added. The reaction mixture maintained at about 0° C. for 1 h, and was then added to water and neutralised to pH 7.2. The separated organic layer was discarded. The aqueous phase was layered with ethyl acetate and toluene (50 ml, 1:1), acidified to pH 1.5 and separated. The solvent layer was washed with a little water and then brine, dried ($Na_2SO_4$), filtered and added to water 100 ml). The mixture was stirred and adjusted to pH 7.2 with dilute sodium hydroxide solution The layers were separated, the aqueous layer washed with a little toluene and evaporated to partial solidification under reduced pressure. The residue was re-evaporated with 1-propanol and then with acetone. Acetone and ether were then added to precipitate the product as an off-white solid. This material was filtered off, washed with acetone-ether, then with hexane and dried in vacuo to yield the title product (1.2 g), $\nu_{max}$(KBr) 3351, 1772, 1672, 1607, 1592, and 689 cm$^{-1}$; $\delta_H$(D$_2$O) 1.44, 1.51 (2×3H, 2s), 4.18 (1H, s), 4.24 (2H, s), HOD at 4.78, 5.58 (1H, d, J 4 Hz), 5.62 (1H, d, J 4 Hz) 7.0–7.35 (5H, m), and 7.45 (1H, s).

c. Sodium 6β-[2-(2-aminothiazol-4-yl)-Z-2-(phenoxyimino)acetamido]penicillanate Sodium 6β-[2-(2-chloroacetamidothiazol-4yl)-Z-2-(phenoxyimino)acetamido]penicillanted (0.86 g) dissolved in water (30 ml). Sodium N-methyldithiocarbamate (0.24 g) was added, and the mixture allowed to stir at ambient temperature for 1.5 h. A further aliquot of sodium N-methyldithiocarbamate was added and the mixture stirred for 1 h. The solution was extracted with ether, evaporated under reduced pressure to a syrup and leached witn acetone. A trace of gummy insoluble material was discarded and the remainder evaporated to dryness (0.45 g). This was subjected to column chromatography on HP20SS resin, eluting with water graded to 6% v/v tetrahydrofuran-water water. Fractions containing the desired penicillin (by tlc) were combined and evaporated to dryness to yield 0.18 g of a slightly impure product. This was rechromatographed on silica gel using water-isopropanol-ethyl acetate (1:3:6) as eluent. Fractions containing the desired product were combined, evaporated to dryness and then dried overnight in vacuo, to yield the title product as an off-white solid (65 mg). $\nu_{max}$(KBr) 3332, 3204, 1772, 1670, 1592, and 690 cm$^{-1}$; $\delta_H$(D$_2$) 1.52, 1.58 (2 x 3H, 2s) 4.26 (1H, s), HOD at 4.80, 5.69 (1H, d,J 4 Hz) 5.72 (1H, d, J 4 Hz) and 7.1–7.5 (6H, m); the thiazole singlet is at δ7.23. [Mass spectrum +ve ion thioglycerol MH$^+$ (484)].

EXAMPLE 55 a. 4-[N-(4-Nitrobenzyloxycarbonyl)glycylamino]-benzoic acid

Oxalyl chloride (1.74 ml) was added to a solution of dry dimethylformamide (1.70 ml) in dry dichloromethane (40 ml) at −20° C. with stirring under argon. After stirring for 10 mins at −20° C.-0° C. the mixture as recooled to −20° C. and N-(4-nitrobenzyloxycarbonyl)-glycine (5.08 g) added. Stirring was continued at −20° C.-0° C. for 10 min and the solution recooled to −20° C. A suspension of the triethylammonium salt of p-amino benzoic acid (4.96 g) in dichloromethane (20 ml) was added together with triethylamine (2.22 g and the reaction mixture stirred at −20° C.-0° C. for 20 minutes. The solvent was evaporated and the resultant solid partitioned between ethyl acetate (100 ml) and water (100 ml). The aqueous layer was separated and the organic phase washed with water (60 ml), saturated aqueous NaCl (60 ml) and dried (MgSO$_4$). Evaporation under reduced pressure afforded the crude product as a pale yellow solid. This was dissolved in hot ethyl acetate (60 ml). Hexane (300 ml) was added to precipitate the title compound which was collected by filtration and dried in vacuo, (4.63 g, 62%); $\nu_{max}$ (Nujol) 3300, 1680, 1600, and 1580 cm$^{-1}$; $\delta_H$(D$_6$-DMSO) 3.86 (2H, d, J 6.5 Hz), 5.23 (2H, s), and 7.45–8.23 (10H, m).

b. Chloromethyl-4[N-(4-nitrobenzyloxycarbonyl)-glycylamino]benzoate

A solution of chloromethylchlorosulphate (2.21 g) in dichloromethane (5 ml) was added dropwise to a stirred mixture of 4-[N-(4-nitrobenzyloxycarbonyl)-glycylamino]-benzoic acid (4.00 g), sodium bicarbonate (3.00 g) and tetrabutylammonium hydrogen sulphate (0.493 g) in dichloromethane-water (1:1, 50 ml). The mixture was stirred at room temperature for 3 h. The organic phase was separated and the aqueous phase washed with dichloromethane (50 ml). The combined organic extracts were dried (MgSO$_4$), concentrated to low volume and applied to a column of Kieselgel 60. Elution with 50% ethyl acetate/hexane afforded the title compound as a white solid (46%); m.p. 163°–5° (ethyl acetate), (Found: C, 51.49; H, 3.79; N, 9.76. $C_{18}H_{16}N_3O_7Cl$ requires C, 51.26; H, 3.82; N, 9.96%); $\nu_{max}$(Nujol) 3400, 3300, 1740, 1685, and 1610 cm$^{-1}$; $\delta_H$ (CDCl$_3$/D$_6$-DMSO) 3.95 (2H, d, J 6.0 Hz), 5.25 (2H, s), 5.97 (2H, s), and 7.35–8.20 (10H, m).

c. Iodomethyl-4[N-(4-nitrobenzyloxycarbonyl)-glycylamino]benzoate

A solution of chloromethyl-4[N-(4-nitrobenzyloxycarbonyl)glycylamino]benzoate (1.0 g) in dry acetone (30 ml) was treated with finely-ground sodium iodide (3.6 g) and the mixture stirred at room temperature for 16 h. The mixture was filtered, the filtrate evaporated under reduced pressure and the residue dissolved in dichloromethane (50 ml) and washed with sodium thiosulphate (10%. aq. solution) until colourless. The organic phase was washed with water (20 ml), saturated aqueous NaCl (20 ml) and dried (MgSO$_4$). The solvent was evaporated and the residue crystallised from ethyl acetate to afford the title compound as a white solid (0.600 g), m.p. 162°–4° C.; $\nu_{max}$ (Nujol) 3300, 1735, 1690, 1610, and 1525 cm$^{-1}$; $\delta_H$ (CDCl$_3$/D$_6$-DMSO) 3.90 (2H, d, J 6 Hz), 5.23 (2H, s), 6.18 (2H, s), 6.18 (2H, s), and 7.35–8.20 (10H, m).

d. 4-[N-(4-Nitrobenzyloxycarbonyl)glycylamino]-benzoyloxymethyl 6β-[2-(2-aminothiazol-4yl)-(Z)-2-(cyclohexyloxyimino)acetamido]penicillanate A solution of iodomethyl-4[N-(4-nitrobenzyloxycarbonyl)glycylamino]benzoate (0.600 g) in dry dimethylformamide (6 ml) was added to a stirred solution of sodium 6β-[2-(2-aminothiazol-4-yl)-(Z)-2-(cyclohexyloxyimino)acetamido]penicillanate (0.380 g) in dry dimethylformamide (5 ml) under an argon atmosphere at −20° to −10° C. The reaction mixture was stirred at this temperature for 1.5h. The resultant solution was poured into ethyl acetate (30 ml), washed with sodium bicarbonate solution (10%, 20 ml), and saturated aqueous NaCl (20 ml) and dried (MgSO$_4$). The solvent was evaporated and the residue chromatographed on Kieselgel 60, eluting with 80% ethyl acetate/hexane. The title compound was obtained as a pale yellow foam (0.500 g, 75%); $\nu_{max}$ (CH$_2$Cl$_2$) 3400, 1780, 1735, 1610, and 1525 cm$^{-1}$; $\delta_H$ (D$_6$-DMSO) 1.15–1.90 (16H, m), 3.86 (2H, d, J, 6.0 Hz), 4.00–4.08 (1H, m), 4.48 (1H, s) 5.23 (2H, s), 5.58 (1H, d, J 4.2 Hz), 5.67 (1H, dd,J 4.1, 7.6 Hz ), 6.04 (2H, ABq, J 6.1, 19.1 Hz), 7.20 (2H, s, D$_2$O exch), 7.64 (2H, d, J 8.8 Hz), 7.80 (3H, m), 7.95 (2H, d, J 8.8 Hz), 8.24 (2H, d, J 6.8 Hz), and 9.45 (1H d, J 5.6 Hz, D$_2$O exch); [Mass spectrum: +ve ion (thioglycerol) MH$^+$ (853)].

e. 4-Glycylaminobenzoyloxymethyl 6β-[2-(2-aminothiazol-4-yl)-(Z)-2-(cyclohexyloxyimino)acetamido]penicillanate hydrochloride (4[N-(4-Nitrobenzyloxycarbonyl)glycylamino]benzoyloxymethyl) 6β-2-(2-aminothiazol-4-yl)-(Z)-2-(cyclohexyloxyimino)acetamido]penicillanate (0.200 g) was dissolved in 1,4-dioxane (40 ml) and water (4 ml), 5% palladium on activated carbon (0.200 g) added, and the mixture subjected to hydrogenation at room temperature and pressure for 2 h. The reaction mixture was filtered through Kieselguhr, water (40 ml) added, and the solution treated with dilute hydrochloric acid (0.1N, 2.3 ml, 1 equiv). The mixture was stirred at room temperature for 4 h, the 1,4-dioxan removed under reduced pressure, and the resultant aqueous solution washed with ethyl acetate (3×30 ml). Lyophilisation of the aqueous phase afforded the title compound as a white amorphous solid (0.075 g. 45%); $\nu_{max}$(KBr) 3399, 1775, 1736, 1701, 1626, 1602, and 1541 cm$^{-1}$; $\delta_H$(D$_6$-DMSO) 1.20–1.80 (16H, m), 4.00–4.08 (1H, m), 4.27 (2H, d, J 7.4 Hz), 4.45 (1H, s), 5.57 (1H, d, J 4.1 Hz), 5.65 (1H, dd, J 4.0, 7.5 Hz), 6.03 (2H, ABq, J 5.9, 19 Hz), 6.72 (1H, s), 7.22 (2H, br. s, D$_2$O exch), 7.83 and 7.98 (4H, ABq, J 8.8 Hz), 8.40 (3H, br. s, D$_2$O-exch), 9.44 (1H, d, J 7.5 Hz, D$_2$O exch), and 11.45 (1H, br,. s, D$_2$O exch); [Mass spectrum: +ve ion, (thioglycerol) MH$^+$ (free base) (674)].

EXAMPLE 56 a. Benzhydryl 2-(2-tritylaminothiazol-4-yl)-(Z)-2-(1-(4-nitrobenzyl)oxycarbonylcyclohexyloxyimino)acetate Benzhydryl 2-(2-tritylaminothiazol-4-yl)-(Z)-2(hydroxyimino)acetate (3.44 g) was treated with 4-nitrobenzyl 1-bromocyclohexanecarboxylate as described in Example 5a to give the title compound (3.0 g, 61%) as a foam. $\delta_H$(CDCl$_3$) 1.26–2.30 (10H, m), 5.22 (2H, s), 6.39 (1H, s), 6.77 (1H, br s), 7.14 (1H, s), 7.28 (25H, s), 7.46 (2H, d), and 8.01 (2H, d).

b. 2-(2-Aminothiazol-4-yl)-(Z)-2-(1-(4-nitrobenzyl)oxycarbonylcyclohexyloxyimino)acetic acid Benzhydryl 2-(2-tritylaminothiazol-4-yl)-(Z)-2-(1-(4-nitrobenzyl)oxycarbonylcyclohexyloxyimino)acetate (1.3 g) was treated with aqueous formic acid as described in Example 23d to give the title compound (0.58 g, 85%) as a white solid. m.p. 184°–185° C., [Found: C: 50.94; H: 4.56; N: 12.48. C$_{19}$H$_{20}$N$_4$O$_7$S requires C: 50.89; H: 4.50; N: 12.49%] $\nu_{max}$(KBr) 3358, 2939, 1735, 1608, 1515, and 1346 cm$^{-1}$, $\delta_H$(CDCl$_3$) 1.28 (1H, m), 1.52 (5H, m), 1.78 (2H, m), 2.01 (2H, m), 5.34 (2H, s), 6.80 (1H, s), 7.31 (2H, br s), 7.63 (2H, d), and 8.13 (2H, d).

c. Sodium 6β-[2-(2-aminothiazol-4-yl)-(Z)-2-(1-(4-nitrobenzyl)oxycarbonylcyclohexyloxyimino)acetamido]penicillanate 2-(2-Aminothiazol-4-yl)-(Z)-2-(1-(4-nitrobenzyl)oxycarbonylcyclohexyloxyimino) acetic acid was coupled to 6β-aminopenicillanic acid as described in Example 47c to give the title compound as a white freeze-dried solid. $\nu_{max}$ (KBr) 3362, 2938, 1774, 1740, 1676, 1607, 1522, and 1347cm$^{-1}$; $\delta_H$(D$_2$O) 1.32 (1H, m), 1.54 (3H, s), 1.57 (5H, m), 1.62 (3H, s), 1.90 (2H, m), 2.13 (2H, m), 4.25 (1H, s), 5.37 (2H, d), 5.67 (1H, d), 5.75 (1H, d), 6.97 (1H, s), 7.59 (2H, d), and 8.11 (2H, d). [Mass spectrum; +ve ion (thioglycerol) MH$^+$ (free acid) (647)].

d. Disodium 6β[2-(2-aminothiazol-4-yl)-(Z)-2-(1-carboxylatocyclohexyloxyimino)acetamido]penicillanate Sodium 6β-[2-(2-aminothiazol-4-yl)-(Z)-2-(1-(4-nitrobenzyl)oxycarbonylcyclohexyloxyimino)acetamido]penicillanate in aqueous dioxan was hydrogenated over 5% palladium on carbon. After 2 h the mixture was filtered through celite, diluted with water, and the dioxan removed under reduced pressure. The resulting suspension was adjusted to pH 8 by the addition of aqueous sodium hydroxide to give a clear solution, this was washed with ethyl acetate, then chromatographed on HP20SS to give the title compound as a white freeze-dried solid. $\nu_{max}$(KBr) 3401, 2935, 1768, 1596, 1529, and 1400cm$^{-1}$; $\delta_H$(D$_2$O) 1.27–1.81 (8H, m), 1.55 (3H, s), 1.65 (3H, s), 2.05 (2H, m), 4.28 (1H, s), 5.68 (1H, d), 5.74 (1H, d), and 7.02 (1H, s). [Mass spectrum +ve ion (thioglycerol) MH$^+$ (556), MNa$^+$ (578)].

EXAMPLE 57 a. tert-Butyl (Z)-2-(trans-4-(4-nitrobenzyl)oxycarbonylcyclohexyloxyimino)-3-oxobutyrate tert-Butyl (Z)-2-(hydroxyimino)-3-oxobutyrate (7.36 g) was treated with 4-nitrobenzyl 4-hydroxycyclohexanecarboxylate as described in Example 4, Method 3 to give the title compound (5.1 g, 29%) as a gum. $\nu_{max}$ (film) 2950, 1740, 1695, and 1525cm$^{-1}$, $\delta_H$(CDCl$_3$) 1.53 (9H, s), 1.62 (3H, m), 1.82 (1H, m), 2.14 (4H, m), 2.37 (3H, s), 2.45 (1H, tt, J 3.7 Hz, 10.7 Hz), 4.26 (1H, tt, J 3.8, 9.8 Hz), 5.22 (2H, s), 7.51 (2H, d), and 8.24 (2H, d). $\delta_C$ (CDCl$_3$) 25.2, 26.2, 28.1 (3C), 29.8, 41.6, 64.7, 82.7, 84.0, 123.8 (2C), 128.3 (2C), 143.3, 147.7, 150.7, 160.6, 174.5 and 193.0. [Mass spectrum (ammonia) MNH$_4^+$ (466)].

b. trans-4-[(Z)-Acetyl-(tert-butoxycarbonyl)methyliminooxy]cyclohexanecarboxylic acid A solution of tert-butyl (Z)-2-(trans-4-(4-nitrobenzyl)oxycarbonylcyclohexyloxyimino)-3-oxobutyrate (2.0 g) in ethanol (30 ml) and water (6 ml) was hydrogenated at atmospheric pressure and room temperature over 5% palladium on carbon (0.10 g). After 20 min the mixture was filtered through celite and the solvents evaporated. The residue was dissolved in ethyl acetate and extracted into water at pH 10. The aqueous layer was acidified, extracted with ethyl acetate and the extract washed with water, then brine, dried (MgSO$_4$), and evaporated under reduced pressure to give the title compound (1.33 g, 95%). $\nu_{max}$ (film) 2950, 1740, 1705, and 1600cm$^{-1}$, $\delta_H$(CDCl$_3$) 1.53 (9H, s), 1.58 (4H, m), 2.14 (4H, m), 2.37 (3H, s), 2.40 (1H, m), and 4.26 (1H, tt, J 4.3, 9.8 Hz).

c. tert-Butyl (Z)-2-(trans-4-(N,N-dimethylcarbamoyl)cyclohexyloxyimino)-3-oxobutyrate N,N'-Dicyclohexylcarbodiimide (0.88 g), 4-dimethylaminopyridine (0.04 g) and dimethylamine (1.0 ml) were added successively to an ice-cool solution of trans-4-[(Z)-acetyl-(tert-butoxycarbonyl)methyliminooxy]cyclohexanecarboxylic acid (1.20 g). The mixture was stirred at room temperature for 4 days, the solid removed by filtration and the filtrate chromatographed on silica gel to give the title compound (0.52 g, 40%) as colourless plates. m.p. 109°–110° C. (hexane), [Found: C: 60.10, H: 8.38, N: 8.21. C$_{17}$H$_{28}$N$_2$O$_5$ requires C: 59.98; N: 8.29; N: 8.23%]. $\nu_{max\ (KBr)}$ 2937, 1735, 1695, and 1634cm$^{-1}$, $\delta_H$(CDCl$_3$) 1.53 (9H, s), 1.42–1.71 (4H, m), 1.85 (2H, m), 2.24 (2H, m), 2.37 (3H, s), 2.52 (1H, tt, J 3.7, 11.1 Hz), 2.95 (3H, s), 3.06 (3H, s), and 4.26 (1H, tt, J 4.4, 10.8 Hz).

d. Sodium 2-(2-aminothiazol-4-yl)-(Z)-2-(trans-4-(N,N-dimethylcarbamoyl)cyclohexyloxyimino)acetate Sulphuryl chloride (1.0 ml) was added to a solution of tert-butyl (Z)-2-(trans-4-(N,N-dimethylcarbamoyl)cyclohexyloxyimino)-3-oxobutyrate (0.409 g) in acetic acid (2 ml) and the mixture stirred at 50°. After 3.5 h excess reagent and solvent were evaporated under reduced pressure. Toluene (2 ml) was added to the residue and evaporated, this process was repeated twice more to leave a residue of 4-chloro-(Z)-2-(trans-4-(N,N-dimethylcarbomoyl)cyclohexyloxyimino)-3-oxobutyric acid. This was dissolved in ethanol (4 ml), thiourea (0.091 g) and N,N-dimethylaniline (0.145 g) were added. After stirring for 3 h the solvent was removed under reduced pressure, ethyl acetate was added and the product was extracted into water at pH 8. Purification by HP20SS chromatography gave the title compound (0.185 g, 42%) as a white freeze-dried solid. $\nu_{max}$ (KBr) 3313, 2939, 1611, 1531 and 1400 cm$^{-1}$, $\delta_H$(D$_2$O) 1.49 (4H, m), 1.87 (2H, m), 2.23 (2H, m), 2.77 (1H, m), 2.95 (3H, s), 3.16 (3H, s), 4.13 (1H, m), and 6.87 (1H, s). [Mass spectrum: +ve ion (thioglycerol) MH$^+$ (363), MNa$^+$ (385)].

e. Sodium 6β[2-(2-aminothiazol-4-yl)-(Z)-2-(trans-4-(N,N-dimethylcarbamoyl)cyclohexyloxyimino)acetamido]penicillanate Methanesulphonyl chloride (35 μl) was added to a suspension of sodium 2-(2-aminothiazol-4-yl)-(Z)-2-(trans-4-(N,N-dimethylcarbamoyl)cyclohexyloxyimino) acetate (163 mg) in dimethylformamide (3 ml) at −60° C. The mixture was stirred at −60° to −50° C. for ½ h, then at −40° to −30° for a further ½ h. In the meantime a mixture of 6β-aminopenicillanic acid (107 mg) and sodium bicarbonate (41 mg) was stirred in water (2 ml) at 0° C. until a clear solution was obtained This solution was added to the dimethylformamide suspension and allowed to warm to 0°. After 15 min water was added, the pH adjusted to 7.5 and the mixture washed with ethyl acetate. Butan-1-ol was added and the pH taken to 3.0. The butan-1-ol extract was diluted with ethyl acetate, washed with brine, added to water and the pH taken to 7.5 with aqueous sodium hydroxide. The resulting aqueous solution was concentrated, then chromatographed on HP20SS to give the title compound (80 mg, 32%) as a white freeze-dried solid. $\nu_{max}$ (KBr) 3399, 2937, 1768, 1610, and 1529cm$^{-1}$, $\delta_H$ (D$_2$O) 1.53 (4H, m), 1.58 (3H, s), 1.68 (3H, s), 1.89 (2H, m), 2.24 (2H, m), 2.76 (1H, m), 2.96 (3H, s), 3.17 (3H, s), 4.27 (1H, m), 4.29 (1H, s), 5.69 (1H, d), 5.71 (1H, d), and 7.05 (1H, s). [Mass spectrum, +ve ion (thioglycerol) MH$^+$ (561). MNa$^+$ (583)].

EXAMPLE 58 a. Benzhydryl 2-(2-tritylaminothiazol-4-yl)-(Z)-2-(1-methoxycarbonylcyclohexyloxyimino)acetate Benzhydryl 2-(2-tritylaminothiazol-4-yl)-(Z)-2-(hydroxyimino)acetate (2.0 g) was treated with methyl 1-bromocyclohexane carboxylate as described in Example 5a to give the title compound (1.7 g, 69%) as a white solid, m.p. 180°–182° C. (ethyl acetate/hexane). [Found: C: 73.73; H: 5.60; N: 5.69. C$_{45}$H$_{41}$N$_3$O$_5$S requires C: 73.45; H: 5.62; N: 5.71%] $\nu_{max}$ (KBr) 3406, 2945, 1751, and 1528cm$^{-1}$, $\delta_H$(CDCl$_3$) 1.36 (5H, m), 1.72 (3H, m), 2.00 (2H, m), 3.69 (3H, s), 6.46 (1H, s), 6.71 (1H, s), 7.15 (1H, s), 7.29 and 7.34 (25H, m).

b. Sodium 2-(2-aminothiazol-4-yl)-(Z)-2-(1-methoxy carbonylcyclohexyloxyimino)acetate A solution of benzhydryl 2-(2-tritylaminothiazol-4-yl)-(Z)-2-(1-methoxycarbonylcyclohexyloxyimino)acetate (1.03 g) in a mixture of formic acid (15 ml) and water (3.5 ml) was stirred for 5 h. The solvents were evaporated, then toluene was added to the residue and evaporated. Water and ethyl acetate were added and the pH adjusted to 9 with sodium hydroxide, the aqueous layer was concentrated and chromatographed on HP20SS to give the title compound (0.103 g, 21%), as a white freeze-dried solid. $\nu_{max}$ (KBr) 3310, 2940, 1727, 1617, and 1531cm$^{-1}$, $\delta_H$(D$_2$O) 1.32 (1H, m), 1.58 (5H, m), 1.84 (2H, m), 2.08 (2H, m), 3.82 (3H, s), and 6.90 (1H, s). [Mass spectrum, +ve ion (thioglycerol) MH+ (350), MNa+ (372)].

c. Sodium 6β[2-(2-aminothiazol-4-yl)-(Z)-2-(1-methoxycarbonylcyclohexyloxyimino)acetamido]penicillanate Sodium 2-(2-aminothiazol-4-yl)-(Z)-2-(1-methoxycarbonyl cyclohexyloxyimino)acetate (90 mg) was coupled to 6β-aminopenicillanic acid as described in Example 57e, except that ethyl acetate was used in place of butan-1-ol. The title compound was obtained as a white freeze-dried solid (52 mg, 37%). $\nu_{max}$ (KBr) 3343, 2937, 1773, 1731, 1675, 1610, and 1529 cm$^{-1}$; $\delta_H$ (D$_2$O) 1.30–1.60 (6H, m), 1.58 (3H, s), 1.68 (3H, s), 1.88 (2H, m), 2.13 (2H, m), 3.82 (3H, s), 4.30 (1H, s), 5.71 (2H, d), 5.78 (2H, d), and 7.09 (1H, s).

EXAMPLE 59 a. Ethyl (Z)-2-(cis 3-methylcyclohexyl)oxyimino-3-oxobutyrate

Ethyl (Z)-2-hydroxyimino-3-oxobutyrate (3 g, 18.9 mmol) was converted into the title compound by reaction with 3-methylcyclohexanol (5.16 ml, 39.7 mmol. 60:40 cis: trans mixture) as described in Example 4a method 3, except that the reaction was complete in 2 h. After purification the title compound was obtained as a colourless oil (2.4 g; 50%); $\nu_{max}$(CHCl$_3$) 1740, 1685, and 1590 cm$^{-1}$; $\delta_H$(CDCl$_3$) 0.75–0.97 (1H, m), 0.96 (3H, d, J 6.5 Hz), 1.05 (1H, dd, J 11.7 Hz, partially obscured by d, δ 0.96), 1.32 (3H, t, J 7. 1 Hz), 1.19–1.40 (2H, m, partially obscured by t, δ 1.32), 1.40–1.73 (2H, m), 1.79–1.90 (1H, m), 2.03–2.19 (2H, m), 2.39 (3H, s), 4.23 (1H, tt, J 11.2 and 4.5 Hz), and 4.34 (2H, q, J 7.1 Hz); $\delta$13$_C$ 14.1, 22.3, 23.6, 25.1, 31.2, 31.4, 34.0, 40.1, 61.7, 85.1, 149.9 161.5, and 193.

b. Ethyl 4-bromo-(Z)-2-(cis 3-methylcyclohexyl)oxyimino-3-oxobutyrate

Ethyl (Z)-2-(cis 3-methylcyclohexyl)oxyimino-3-oxobutyrate (1.85 g; 7.2 mmol) was brominated as described in Example 4c to give the title compound as an orange oil, $\nu_{max}$ (CDCl$_3$) 1730, 1700, and 1690 cm$^{-1}$.

c. Ethyl 2-(2-aminothiazol-4-yl)-(Z)-2-(cis 3-methylcyclohexyloxyimino)acetate Ethyl 4-bromo-(Z)-2-(cis 3-methylcyclohexyl)oxyimino-3-oxobutyrate (7.2 mmol) was treated with N,N-dimethylaniline (0.91 ml; 7.2 mmol) and thiourea (0.55 g, 7.2 mmol) in ethanol as described in Example 4d, except that the reaction was worked up after 2 h. The title compound was obtained as a white crystalline solid (1.78 g; 79%) m.p. 91°–93° C. (ethyl acetate/hexane), (Found: C, 54.29; H, 6.88; N, 13.57. C$_{14}$H$_{21}$N$_3$O$_3$S requires C, 54; H, 6.79; N, 13.49%), $\nu_{max}$ (CHCl$_3$) 3480, 3400, 1730, and 1610 cm$^{-1}$; $\delta_H$ (CDCl$_3$) 0.64–1.1 (2H, m, partially obscured by d, δ 0.92), 0.92 (3H, d, J 5.5 Hz), 1.1–1.55 (3H, m, partially obscured by t, δ 1.36), 1.36 (3H, t, J 7.1 Hz), 1.55–1.70 (1H, m) 1.70–1.86 (1H, m), 2.03–2.25 (2H, m), 4.20 (1H, tt, J 11.1 and 4.3 Hz), 4.39 (2H, q, J 7.1 Hz), 5.31 (2H, broad s), and 6.7 (1H, s).

d. 2-(2-Aminothiazol-4-yl)-(Z)-2-(cis 3-methylcyclohexyloxyimino)-acetic acid Ethyl 2-(2-aminothiazol-4-yl)-(Z)-2-(cis 3-methylcyclclohexyloxyimino)acetate (1.0 g; 3.2 mmol) was hydrolysed according to the method described in Example 4e to give the title acid as a white solid (0.83 g; 86%), $\nu_{max}$ (KBr) 3800–2400, 1710, 1625, and 1530 cm$^{-1}$, $\delta_H$ [(CD$_3$)$_2$SO] 0.63–1.0 (2H, m, partially obscured by d, δ 0.91), 0.91 (3H, d, J 6.5 Hz), 1.0–2.15 (7H, m), 4.0 (1H, tt, J 11 and 4.1 Hz), 6.81 (1H, s), and 7.2 (2H, s).

e. Sodium 6β-[2-(2-aminothiazol-4-yl)-(Z)-2-(cis 3-methylcyclohexyloxyimino)acetamido]penicillanate 2-(2-Aminothiazol-4-yl)-(Z)-2-(cis 3-methylcyclohexyloxyimino)acetic acid was coupled to 6β-aminopenicillanic acid according to the method described in Example 47d to give the title compound; $\nu_{max}$ (KBr) 3650–3000, 1770, 1670, and 1610 cm$^{-1}$; $\lambda_{max}$ (H$_2$O) 228.2 (ε13,083), 290.3 nm (7,570); $\delta_H$ (D$_2$O) 0.75–1.2 (2H, m, partially obscured by d, δ 6 0.99), 0.99 (3H, d, J 6.5 Hz), 1.2–1.75 (4H, m, partially obscured by 2 x s, Δ 1.59 and 1.70 ), 1.59 and 1.70 (6H, 2 x s), δ 1.75–2.25 (3H, m), 4.25 (3H, m), 4.25 (1H, tt, J 11 and 4.3 Hz), 4.31 (1H, s), 5.63–5.78 (2H, m) and 7.06 (1H, s).

EXAMPLE 60 a. Ethyl (Z)-2-(trans 3-methylcyclohexyl)oxyimino-3-oxobutyrate

Ethyl (Z)-2hydroxyimino-3-oxobutyrate (2.65 g, 16.7 mmol) was converted into the title compound by reaction with cis 3-methylcyclohexanol (1.9 g, 16.7 mmol) as described in Example 4a method 3. After purification the title compound was obtaind as a colourless oil (0.57 g, 11%) $\nu_{max}$ (CHCl$_3$) 1735, 1680, and 1590 cm$^{-1}$; $\delta_H$ (CDCl$_3$) 0.8–1.3 (1H, m,. partially obscured by d, δ 0.9); 0.90 (3H, d, J 6.5 Hz), 1.1–1.4 (1H, m, partially obscured by t, δ 1.33 ), 1.33 (3H, t, J 7.11 Hz), 1.4–1.8 (2H, m, partially obscured by s, δ 1.55 ), 1.55 (3H, s), 1.85–2.1 (2H, m), 2.4 (3H, s), 4.36 (2H, q, J 7.1 Hz), and 4.50–4.64 (1H, m), $\delta$13$_C$(CDCl$_3$), 14.19, 20.32, 22.28, 25.13, 26.74, 29.55, 34.16, 38.13, 61.74, 81.96, 150.2, 161.51, and 193.01.

b. Ethyl 4-bromo-(Z)-2-(trans 3-methylcyclohexyl) oxyimino-3-oxobutyrate

Ethyl (Z)-2-(trans-3-methylcyclohexyl)oxyimino-3-oxobutyrate (0.57 g, 2.2 mmol), was brominated as described in Example 4b to give the title compound as an orange oil; $\nu_{max}$ (CHCl$_3$) 1735, 1700 and 1690 cm$^{-1}$.

c. Ethyl 2-(2-aminothiazol-4-yl)-(Z)-2-(trans 3-methylyclohexyloxyimino)acetate Ethyl 4-bromo-(Z)-2-(trans 3-methylcyclohexyl)oxyimino3-oxybutyrate (0.74 g, 2.2 mmol) was treated with thiourea (0.17 g; 2.2 mmol) and N,N-dimethylaniline (0.28 ml, 2.2 mmol) as described in Example 4d to give the title compound as a white crystalline solid (0.55 g, 61%); $\nu_{max}$(CHCl$_3$) 3480, 3400, 1625, 1605, 1525, and 1505 cm$^{-1}$; $\delta_H$(CDCl$_3$) 0.86 (3H, d, J 6.5 Hz), 0.8–1.3 (3H, m, partially obscured by d, $\delta$ 0.86), 1.37 (3H, t, J 7.1 Hz), 1.4–1.85 (4H, m), 1.9–2.05 (2H, m), 4.39 (2H, q, J 7.1 Hz), 4.50–4.63 (1H, m), 5.46 (2H, broad s), an 6.70 (1H, s).

d. 2-(2-Aminothiazol-4-yl)-(Z)-2-(trans 3-methylcyclohexyloxyimino)acetic acid Ethyl 2-(2-aminothiazol-4-yl)-(Z)-2-(trans 3-methylcyclohexyloxyimino)acetate (0.2 g; 0.71 mmol) was hydrolysed as described in Example 4e to give the title compound as a white solid (0.13 g, 72%); $\nu_{max}$ (KBr) 3600–2400, 1700 (sh), 1630, 1590, and 1530 cm$^{-1}$; $\delta_H$ [(CD$_3$)$_2$SO] 0.75–1.05 (1H, m, partially obscured by d, $\delta$ 0.84). 0.84 (3H, d, J 6.4 Hz), 1.05–2.0 (8H, m). 4.36 (1H, broad s), 6.83 (1H, s), and 7.22 (2H, broad s).

e. Sodium 6β-[2-(2-aminothiazol-4-yl)-(Z)-2 (trans-3-methylcyclohexyloxyimino)acetamido]penicillanate 2-(2-Aminothiazol-4-yl)-(Z)-2-(trans 3-methylcyclohexyloxyimino) acetic acid (0.1 g, 0.35 mmol) was coupled to 6β-aminopenicillanic acid as described in Example 47d to give the title compound (20 mg) as a white freeze-dried solid; $\nu_{max}$ (KBr) 1769, 1655, 1611, and 1528 cm$^{-1}$; $\nu_{max}$ (H$_2$O) 290.5 ($\epsilon$6017), 231.8 nm (9971); $\delta_H$ (D$_2$O) 0.83 and 0.85 (3H, 2 x d, J 6 Hz), 0.88–1.05 (1H, m), 1.13–1.57 (4H, m, partially obscured by s, $\delta$ 1.52), 1.52 (3H, s), 1.62 and 1.63 (3H, 2 x s), 1.57–2.02 (4H, m, partially obscured by 2 x s, $\delta$ 6 1.62 and 1.63), 4.23 (1H, broad s), 4.51 (1H, broad s), 5.63 (1H, d, J 4 Hz), 5.69 (1H, d, J 4 Hz), and 6.97 (1H, s).

EXAMPLE 61 a. tert-Butyl (Z)-2-(cis-4-acetoxycyclohexyloxyimino)-3-oxobutyrate and tert-butyl (Z)-2-(trans-4-acetoxycyclohexyloxyimino)-3-oxobutyrate tert-Butyl (Z)-2-hydroxyimino-3-oxobutyrate (8.45 g, 45 mmol), triphenylphosphine (13.09 g, 49.8 mmol) and 4-acetoxycyclohexanol (mixture of cis and trans isomers) (14.43 g, 90.9 mmol) in tetrahydrofuran (400 ml) were reacted with diethyl azodicarboxylate (8.67 g, 7.8 mmol, 49.8 mmol) using an analogous procedure to that described in Example 4 method 3 to give, after chromatography on silica gel, loading in toluene, and eluting with a gradient of ethyl acetate in hexane (5% to 10%), the less polar isomer, considered to be the trans title compound, as an oil (2..1 g; 14%). $\nu_{max}$ (KBR) 2950, 1730, 1690, 1590, 1370, 1320, and 1250 cm$^{-1}$; $\delta_H$ (250 MHz, CDCl$_3$) 1.53 (9H, s), 1.5–1.80 (4H, m), 1.85–2.30 (4H, m), 2.06 (3H, s), 2.37 (3H, s), and 4.34–4.43 (3H, s); $\delta_C$ (100 MHz, DCl$_3$) 21.30, 25.17, 26.83, 26.90, 28.14, 70.40, 81.48, 83.98, 150.82, 160.46, 170.42, and 192.94; [Mass spectrum: M$^+$ —CH$_3$ (312)]. Later fractions gave a mixture of cis and trans isomers (2.03 g; 14%), followed by the more polar isomer, considered to be the cis title compound, as a solid (2.56 g, 17%), m.p. 71°–73° C. (from EtOAc/hexane); $\nu_{max}$ (KBr) 2950, 1730, 1685, 1590, 1365, 1320 and 1235 cm$^{-1}$; $\delta_H$ (250 MHz, CDCl$_3$) 1.56 (9H, s), 1.65–1.85 (6H, m), 1.90–2.10 (2H, m), 2.05 (3H, s), 2.38 (3H, s), 4.36–4.46 (1H, m), and 4.74–4.88 (1H, m); $\delta_C$ (100 MHz, CDCl$_3$) 21.30, 25.17, 26.65, 27.34, 28.15, 70.63, 80.26, 84.01, 150.89, 160.51, 170.45, and 192.98; [Mass spectrum. Found (M$^+$—CH$_3$) 312.1450. C$_{16}$H$_{25}$NO$_6$-CH$_3$ requires 312.1447].

b. (Z)-2-(trans-4-Acetoxycyclohexyloxyimino)-4-chloro-3-oxobutyric acid tert-Butyl (Z)-2-(trans-4-acetoxycyclohexyloxyimino)3-oxobutyrate (327 mg, 1 mmol) was reacted with sulphuryl chloride (0.8 ml) in glacial acetic acid (2 ml) by an analogous procedure to that described in Example 57d to give the crude title compound.

c. Sodium (Z)-2-(trans-4-acetoxycyclohexyloxyimino)2-(2-aminothiazol-4-yl)acetate The crude (Z)-2-(trans-4-acetoxycyclohexyloxyimino)-4-chloro-3-oxobutyric acid obtained above was reacted with thiourea (76 mg, 1 mmol) and N,N-dimethylaniline (0.26 ml, 121 mg, 1 mmol) in ethanol (5 ml) as in Example 57d. Chromatography on HP20SS, eluting with water gave the title compound (119 mg, 34%); $\nu_{max}$ (KBr) 3412, 3187, 1718, 1612, 1532, 1399, 1371, 1266, and 1038 cm$^{-1}$; $\delta_H$ (250 MHz, D$_2$O) 1.54–1.72 (4H, m), 1.94–2.09 (4H, m), 2.13 (3H, s), 4.24 (1H, m), 4.85 (1H, m), and 6.88 (1H, s).

d. Sodium 6β-[(Z)-2-(trans-4-acetoxycycloh-exyloxyimino)-2-(2-aminothiazol-4-yl)acetamido]penicillanate Sodium (Z)-2-(trans-4-acetoxycyclohexyloxyimino)-2-(2-aminothiazol-4-yl)acetate (99 mg, 0.283 mmol) in N,N-dimethylformamide (2 ml) was reacted with methanesulphonyl chloride (21.9 μl, 32 mg, 0.28 mmol), followed by 6β-aminopenicillanic acid (67 mg, 0.31 mmol) and sodium hydrogen carbonate (26 mg, 0.31 mmol) in water (1.5 ml) as Example 58c to give after chromatography on HP20SS the title compound (78 mg, 50%). $\nu_{max}$ (KBr) 3326, 2947, 1769, 1723, 1669, 1610, 1527, and 1263 cm$^{-1}$; $\delta_H$ (250 MHz, D$_2$O) 1.56 (3H, s), 1.66 (3H, s), 1.6–1.8 (4H, m), 1.85–2.1 (4H, m), 4.28 (1H, s), 4.39 (1H, m), 5.67 (1H, d, J 4 Hz) 5.71 (1H, d, J 4 Hz), and 7.03 (1H, s).

EXAMPLE 62 a. (Z)-2-(cis-4-Acetoxycyclohexyloxyimino)-4-chloro-3-oxobutyric acid tert-Butyl (Z)-2-(cis-4-Acetoxycyclohexyloxyimino)-3-oxobutyrate (327 mg, 1 mmol), as prepared in Example 61a, was reacted with sulphuryl chloride (0.8 ml) in glacial acetic acid (2 ml) as described in Example 57d to give the crude title compound.

b. Sodium (Z)-2-(cis-4-acetoxycyclohexyloxyimino)-2-(2-aminothiazol-4-yl)acetate The crude (Z)-2-(cis-4-acetoxycyclohexyloxyimino)-4-chloro-3-oxobutyric acid obtained above was reacted with thiourea (76 mg, 1 mmol) and N,N-dimethylaniline (0.126 ml, 121 mg, 1 mmol) in ethanol (5 ml) as in Example 57d. Chromatography on HP20SS, eluting with water gave the title compound (64.5 mg, 19.7%); $\nu_{max}$ (KBr) 3307, 3187, 2947, 1720, 1617, 1531, 1400, and 1270 cm$^{-1}$; $\delta_H$(250 MHz, D$_2$O) 1.74–1.85 (6H, m), 1.91–2.01 (2H, m), 2.13 (3H, s), 4.33 (1H, m), 4.83 (1H, m), and 6.89 (1H, s).

c. Sodium 6β-[(Z)-2-(cis-4-acetoxycyclohexyloxyimino)-2-(2-aminothiazol-4-yl)acetamido]penicillanate Sodium (Z)-2-(cis-4-acetoxycyclohexyloxyimino)-2-(2-aminothiazol-4-yl)acetate (58.6 mg, 0.17 mmol) in N,N-dimethylformamide (2 ml) was reacted with methanesulphonyl chloride (13.3 ml, 19 mg, 0.17 mmol), followed by 6β-aminopenicillanic acid (40.3 mg. 0.19 mmol) and sodium hydrogen carbonate (15.7 mg, 0.19 mmol) in water (1 ml) as in Example 58c to give after chromatography on HP20SS, the title compound (47 mg, 50.5%). $\nu_{max}$ (KBr) 3325, 2950, 1768, 1718, 1529, and 1264 cm$^{-1}$ $\delta_H$(250 MHz, D$_2$O) 1.56 (3H, s), 1.66 (3H, s), 1.77 (6H, m), 1.99 (2H, m), 2.15 (3H, s), 4.15 (1H, s), 4.41 (1H, m), 5.69 (1H, d, J 4.1 Hz), 5.72 (1H, d, J 4.1 Hz), and 7.03 (1H, s).

EXAMPLE 63 a. Chloromethyl-4-[N-(4-nitrobenzyloxycarbonyl)glycyloxy]benzoate

Triethylamine (4 ml) was added to a suspension of N-(4-nitrobenzyloxycarbonyl)glycine (7.25 g) in dry dichloromethane at −20° C. Ethyl chloroformate (2.75 ml) was added to the resultant solution and the mixture stirred at −20° to −10° C. for 20 mins. A solution of 4-hydroxybenzoic acid (3.94 g) and triethylamine (4 ml) in dichloromethane (50 ml) was added dropwise, and stirring continued for 2.5 h after addition. The mixture was filtered, the filtrate washed with 10% aqueous citric acid (20 ml), water (20 ml), and brine (20 ml), and dried (MgSO$_4$). Evaporation under reduced pressure afforded the crude product, 4-[N-(4-nitrobenzyloxycarbonyl)glycyloxy]benzoic acid as a pale yellow foam. Without further purification, 4-[N-(4-nitrobenzyloxycarbonyl)glycyloxy]benzoic acid was treated with chloromethylchlorosulphate (5.77 g) under the conditions described in Example 55b. After work-up and chromatography as described therein, the title compound was obtained as a white crystalline solid (1.81 g), m.p. 119°–120° C. (ethylacetate/hexane); $\nu_{max}$ (CH$_2$Cl$_2$) 3450, 1780, 1740, 1610, and 1520 cm$^{-1}$; $\delta_H$(CDCl$_3$) 4.33 (2H, d, J 6 Hz), 5.33 (2H, s), 5.72 (1H, br t, J 6 Hz), 6.03 (2H, s), 7.23–7.70 (4H, m), and 8.18–8.40 (4H, m).

b. Iodomethyl-4[N-(4-nitrobenzyloxycarbonyl)glycyloxy]benzoate

Chloromethyl-4[N-(4-nitrobenzyloxycarbonyl)glycyloxy]be nzoate (1.5 g) was converted to the title compound (1.65 g, 92%) under the conditions described in Example 55c, m.p. 146°–8° C. (ethyl acetate); $\nu_{max}$ (CH$_2$Cl$_2$) 3440, 1775, 1740, 1605, and 1520 cm$^{-1}$; $\delta_H$ (CDCl$_3$/D$_6$-DMSO) 4.23 (2H, d, J 6 Hz), 5.33 (2H, s), 6.23 (2H, s), 7.25–7.73 (5H, m), and 8.08–8.37 (4H, m).

c. 4-[N-(4-Nitrobenzyloxycarbonyl)glycyloxy]benzoyloxymethyl 6β-[2-(2-aminothiazol-4-yl)-(Z)-2-(cyclohexyloxyimino)acetamido]penicillanate Iodomethyl-4-[N-(4-nitrobenzyloxycarbonyl)glycyloxy]benzoate (0.790 g) was reacted with sodium 6β-[2-(2-aminothiazol-4-yl)-(Z)-2-(cyclohexyloxyimino)acetamido]penicillanate (0.500 g) under the conditions described in Example 55d. The title compound was obtained as a pale yellow solid after trituration with ether (0.300 g, 35%), $\nu_{max}$ (CH$_2$Cl$_2$) 3450, 3400, 1790, 1775, 1740, 1690, 1605, and 1525 cm$^{-1}$; $\delta_H$ (CDCl$_3$) 1.25–2.06 (16H, m), 4.28 (2H, d, J 5.8 Hz), 4.25–4.28 (1H, m), 4.52 (1H, s), 5.18 (2H, br. s, D$_2$O exch), 5.25 (2H, s), 5.44 (1H, br. t, D$_2$O exch), 5.64 (1H, d, J 4.1 Hz), 5.88 (1H, d, J 4.2, 9.1 Hz), 7.02 (1H, s), 7.13 (1H, d, J 9.1 Hz, D$_2$O exch), 7.25 (2H, d), 7.54 (2H, d), 8.12 (2H, d), and 8.23 (2H, d).

d. 4-Glycyloxybenzoyloxymethyl 6β-[2-(2-aminothiazol-4-yl)-(Z)-2-(cyclohexyloxyimino)acetamido]penicillanate hydrochloride 4-[N-(4-Nitrobenzyloxycarbonyl)glycyloxy]benzoyloxymethyl 6β-[2-(2-aminothiazol-4-yl)-(Z)-2-(cyclohexyloxyimino)acetamido]penicillanate (0.200 g) was converted to the title compound using the procedure described in example 55e. The product was a pale yellow amorphous solid (0.065 g, 39%), $\nu_{max}$ (KBr) 3350, 2936, 1774, 1740, 1673, 1629, 1603, and 1509 cm$^{-1}$; $\delta_H$ (D$_6$-DMSO) 1.18–1.90 (16H, m), 4.04–4.10 (3H, m), 4.50 (1H, s), 5.58 (1H, d, J 4.1 Hz), 5.65 (1H, dd, J 4.0, 7.1 Hz), 6.06 (2H, ABq, J 6.0, 16.4 Hz), 6.81 (1H, s), 7.41 and 8.09 (4H, ABq, J 8.7 Hz), 8.70 (3H, br. s., D$_2$O exch) and 9.48 (1H, d, J 7.2 Hz, D$_2$O exch).

EXAMPLE 64 a. (2S,4R)-4-Hydroxy-1-(4-nitrobenzyloxycarbonyl)pyrrolidine-2-carboxylic acid (2S,4R)-(-)-4-Hydroxy-2-pyrrolidinecarboxylic acid [trans-4-hydroxy-L-proline](5.24 g, 40 mmol) in water (40 ml) was treated with 1M aqueous sodium hydroxide (40 ml), cooled in an ice-bath and then treated with 4-nitrobenzylchloroformate (8.64 g, 40 mmol) in 1,4-dioxane (40 ml), added dropwise over 20 min. The mixture was stirred at 0° C. for 3 h. Most of the 1,4-dioxane was removed by evaporation under reduced pressure and ethyl acetate (100 ml) and water (100 ml) were added. The mixture was acidified and the aqueous layer extracted a further two times with ethyl acetate (100 ml). The ethyl acetate layer was dried (MgSO$_4$) and evaporated under reduced pressure to leave an oil which crystallised after trituration under diethyl ether. The crystals were filtered off to give the title compound (8.69 g, 70%) as a mixture of conformers/rotamers, m.p. 136°–137° C. (EtOAc/hexane) (Found: C, 50.30; H, 4.43; N, 8.82 C$_{13}$H$_{14}$N$_2$O$_7$ requires C, 50.32; H, 4.55; N, 9.03%); [α]$_D$ −38° (c 1 in EtOH); ν$_{max}$ (KBr) 3319, 1737, 1663, 1607, 1518, 1456, and 1342 cm$^{-1}$; δ$_H$ (250 MHz, (CD$_3$)$_2$CO) 2.20–2.25 (1H, m), 2.25–2.50 (1H, m), 3.50–3.72 (2H, m), 4.4–4.6 (2H, m), 5.18 (d, J 14.2 Hz), 5.29 (s), 5.33 (d, J 14.2 Hz) (together 2H, OCH$_2$Ar, 2 conformers ), 7.66 (2H, m), and 8.23 (2H, m); [Mass spectrum M+ (310)].

b. 4-Nitrobenzyl (2S,4R)-4-hydroxy-1-(4-nitrobenzyloxycarbonyl)pyrrolidine-2-carboxylate (2S,4R)-4-Hydroxy-1-(4-nitrobenzyloxycarbonyl)-pyrrolidine-2-carboxylic acid (930 mg, 3 mmol), 4-nitrobenzylbromide (660 mg, 3.05 mmol) and potassium carbonate (209 mg, 1.51 mmol) were stirred together in N,N-dimethylformamide (10ml) for 3.5 h. The mixture was poured into water (100 ml)/ethyl acetate (100 ml) and the layers separated. The aqueous layer was re-extracted with ethyl acetate (50 ml). The combined organic layers were washed with water (50 ml),×4), brine (20 ml), dried (MgSO$_4$) and evaporated under reduced pressure. The residue was chromatographed on silica gel, eluting with ethyl acetate hexane mixture, followed by ethyl acetate to give the title compound (1.20 g, 90%) as a mixture of conformers/rotamers; ν$_{max}$ (CH$_2$Cl$_2$) 3610, 3470, 2960, 1735, 1710, 1610, 1535, and 1350 cm$^{-1}$; δ$_H$(400 MHz, CDCl$_3$) 1.90 (1H, broad d, J ca 7.4 Hz), 2.05–2.20 (1H, m), 2.3–2.5 (1H, m), 3.6–3.8 (2H, m), 4.58 (1H, broad d, J ca 9.3 Hz), 4.63 (1H, approx dt J 1.9, 8.1 Hz), 5.05–5.35 (4H, m,) 7.30–7.50 (4H, m), and 8.1–8.2 (4H, m); [Mass spectrum: M+ (445)].

c. tert-Butyl 3-oxo-(Z)-2-[(2S,4S)-1-(4-nitrobenzyloxycarbonyl)-2-(4-nitrobenzyloxycarbonyl)pyrrolidine-4-yloxyimino]-butyrate 4-Nitrobenzyl (2S,4R)-4-hydroxy-1-(4-nitrobenzyloxycarbonyl)pyrrolidine-2-carboxylate (3.24 g, 7.28 mmol) and triphenylphosphine (2.29 g, 8.7 mmol) in dry tetrahydrofuran (60 ml) under argon were treated with dimethyl azodicarboxylate (1.28 g, 8.7 mmol) in dry tetrahydrofuran (5 ml). After 5 min tert-butyl (Z)-2-hydroxyimino-3-oxobutyrate (2.59 g, 8.7 mmol) in dry tetrahydrofuran (10 ml) was added and the mixture was stirred under an argon atmosphere for 18 h. The tetrahydrofuran was removed and the residue taken up in ethyl acetate (150 ml) and washed with water containing a trace of acetone (100 ml,×6). The ethyl acetate layer was dried (MgSO$_4$) and evaporated under reduced pressure. The residue was chromatographed on silica gel, eluting with ethyl acetate/hexane mixture to give the title compound (2.49 g, 55%) as a mixture of two conformers/rotamers; ν$_{max}$ (CH$_2$Cl$_2$) 1735, 1710, 1605, 1525, and 1350 cm$^{-1}$; δ$_H$(250 MHz, CDCl$_3$) 1.52 (9H, s), 2.31 (3H, s), 2.40–2.80 (2H, m), 3.75–4.0 (2H, m), 4.66 (1H, approx dt, J ca 9.3, 1.5 Hz), 4.94–5.05 (1H, m), 5.1–5.4 (4H, m), 7.35–7.55 (4H, m), and 8.05–8.25 (4H, m).

d. (2-(2-Aminothiazol-4-yl)-(Z)-2-[(2S,4S)-1-(4-nitrobenzyloxycarbonyl)-2-(4-nitrobenzyloxycarbonyl)pyrrolidin-4-yloxyimino]acetic acid tert-Butyl 3-oxo-(Z)-2-[(2S,4S)-1-(4-nitrobenzyloxycarbonyl)-2-(4-nitrobenzyloxycarbonyl)pyrrolidine-4-yloxyimino]butyrate (2.19 g, 3.56 mmol) in acetic acid (7 ml) was treated with sulphuryl chloride (2.89 ml, 4.81 g, 35.6 mmol) and the mixture was heated at 50° C. for 2.75 h. The mixture was evaporated under reduced pressure, and toluene added to the residue an the solvent evaporated. The was repeated a further three times. The residue was partially dissolved in ethanol (15 ml) and thiourea (271 mg, 3.56 mmol) was added, followed by N,N-dimethylaniline (0.9 ml, 860 mg, 7.1 mmol). Ethanol (15 ml) was added and the mixture was warmed to effect dissolution, the mixture was stirred at room temperture for 1.5 h, then warmed again to dissolve the material, and stirred a further 0.5 h. The ethanol was then removed by evaporation under reduced pressure and a mixture of water/ethyl acetate/n-butanol added. The pH was adjusted to 2 and the layers separated. The aqueous layer was again extracted with n-butanol (x2). The butanol extracts were combined and evaporated under reduced pressure. Ethanol was added to the residue and removed under reduced pressure, followed by toluene (x3) to leave a solid which was dried over P$_2$O$_5$ in vacuo to give the crude title compound (2.03 g); ν$_{max}$(KBr) 3383, 1745, 1710, 1630, 1607, 1521, 1432, 1404 and 1347 cm$^{-1}$.

e. 4-Nitrobenzyl 6β-(2-(2-aminothiazol-4-yl)-(Z)-2-[(2S,4S)-1-(4-nitrobenzyloxycarbonyl)-2-(4-nitro-benzyloxycarbonyl)pyrrolidin-4-yloxyimino]acetamido)penicillanate 2-(2-Aminothiazol-4-yl)-(Z)-2-[(2S,4S)-1-(4-nitrobenzyloxycarbonyl)-2-(4-nitrobenzyloxycarbonyl) pyrrolidin-4-yl- oxyimino]acetic acid (2.05 g, 3.3 mmol) in dry N,N-dimethylformamide (DMF) (9 ml) was treated with N,N- diisopropylethylamine (0.638 ml, 473 mg, 3.67 mmol). The mixture was cooled under argon to −60° to −50° C., treated with methanesulphonyl chloride (0.284 ml, 420 mg, 3.67 mmol) and stirred in the cold for 1.75 h. 4-Nitrobenzyl 6β-aminopenicillanate (1.32 g, 3.77 mmol) and triethylamine (0.381 g, 3.77 mmol) in dry DMF (9 ml) were added and the mixture was stirred at 0° C. for 1 h. Water/ethyl acetate were added and the ethyl acetate layer was washed with water (×4), followed by brine, then dried (MgSO$_4$) and evaporated under reduced pressure. Chromatography on silica gel eluting with ethyl acetate/hexane mixtures, followed by ethyl acetate gave the title compound (965 mg) as a mixture of conformers/rotamers; ν$_{max}$ (CH$_2$Cl$_2$) 3470, 1785, 1740, 1710, 1685 (sh), 1605, 1575, and 1350 cm$^{-1}$; δ$_H$(400 MHz, CDCl$_3$) 1.39 (s), 1.41 (s) (together 3H), 1.54 (s), 1.56 (s) (together 3H), 2.40–2.48 (1H, m), 2.78 (d, J.14.4 Hz), 2.94 (d, J 14.5 Hz) (together 1H), 3.73–3.81 (1H, m), 3.98 (d, J 12.5 Hz), 4.11 (d, J 12.2 Hz) (together 1H), 4.42 (s), 4.48 (s) (together 1H), 4.61 (d, J 9.4 Hz), 4.65 (d, J 9.0 Hz) together 1H), 4.95–5.40 (7H, m), 5.44 (2H, broad s), 5.60 (d, J 4.1 Hz), 5.66 (d, J 4.3 Hz) (together 1H), 5.71 (dd, J 4.1, 8.2 Hz), 5.79 (dd, J 4.3, 8.7 Hz) (together 1H), 6.89 (s), 6.90 (s) (together 1H), 7.04 (d, J 8.5 Hz), 7.34 (d, J 8.2 Hz) (together 1H), 7.39–7.56 (6H, m), and 8.02–8.26 (6H, m).

f. Sodium 6β-(2-(2-aminothiazol-4-yl)-(Z)-2-[(2S,4S)-2-carboxypyrrolidin-4-yloxyimino]acetamido)penicillanate 10% Palladium on carbon catalyst in 1,4-dioxane (2 ml)/water(1 ml) was treated with hydrogen for 15 min. 4-Nitrobenzyl 6β-(2-(2-aminothiazol-4-yl)-(Z)-2-[(2S,4S)-1-(4-nitrobenzyloxycarbonyl)-2-(4-nitrobenzyloxycarbonyl)pyrrolidin-4-yloxyimino]acetamido)-penicillanate (48 mg) in dioxane (0.7 ml)/water (0.3 ml) was added and the mixture was hydrogenated at atmospheric pressure for 1h. 10% Pd/C catalyst (22 mg) and 1,4-dioxane (1 ml) were added and the mixture was hydrogenated a further 1.5 h. Sodium hydrogen carbonate (4 mg) was added and the mixture was filtered through Kieselguhr, the filter cake was washed with water (50 ml) and the volume of the filtrate was then reduced to ca 30 ml by evaporation under reduced pressure. The aqueous solution as washed with ethyl acetate (50 ml,×3) containing a little acetone to assist separation. The aqueous layer was then reduced in volume to ca 7 ml, sodium chloride was added and the mixture loaded onto a column of HP20SS, and the column eluted with water to give the title compound (7 mg, 26%); $\nu_{max}$ (KBr) 1764, 1604, 1553, 1398, and 1332 cm$^{-1}$; $\delta_H$(D$_2$O) 1.53 (3H, s), 2.34–2.68 (2H, m), 3.21 (1H, dd, J 4.3, 13.2 Hz), 3.63 (1H, d, J 12.9 Hz), 3.93 (1H, dd, J 5.5, 10.2 Hz), 4.26 (1H, s), 4.97 (1H, m), 5.62 (1H, d, J 3.9 Hz), 5.65 (d, J 3.9 Hz), and 7.08 (1H, s).

EXAMPLE 65 a. 2-[N-(4-Nitrobenzyloxycarbonyl)glycylamino]benzoic acid

Oxalyl chloride (1.75 ml) was added, dropwise over 2 minutes to a stirred solution of dry dimethylformamide (1.75 ml) in dry dichloromethane (30 ml) at −20° C. under dry nitrogen. The stirred mixture was allowed to attain 0° C. during 15 minutes, re-cooled to −20° C., and treated, portionwise over 1 minute , with N-(4-nitrobenzyloxycarbonyl)glycine (5.08 g). The stirred mixture was allowed to attain 0° C. during 30 minutes, re-cooled to −20° C., and treated, dropwise over 10 minutes, with a solution containing 2-aminobenzoic acid (3.74 g) and triethylamine (2.78 ml) in dry dichloromethane (20 ml). The cooling bath was removed and the mixture was stirred for 2 h [after a few minutes a semi-solid gel formed which was dispersed by the addition of dichloromethane (50 ml)]. The mixture was diluted with ethyl acetate (250 ml) and was washed with 5% citric acid (25 ml) and brine (3×25 ml). The dried (MgSO$_4$) organic layer was evaporated and the residue was triturated with ether to give the title acid as an off white solid (6.64 g), m.p. 188°–190° C. (microcrystalline solid ex acetone/hexane); $\nu_{max}$ (Nujol) 3300, 3500–2000 br, 1735, 1705, and 1680 cm$^{-1}$; $\delta_H$ [(CD$_3$)$_2$CO/(CD$_3$)$_2$SO] 3.98 (2H, d, J 6 Hz, collapses to s on exch. D$_2$O), 5.35 (2H, s), 6.8–8.6 (9H, m, 2H exch. D$_2$O), 8.85 (1H, d, J 8 Hz), and 11.95 (1H, brs, exch. D$_2$O).

b. 2-[N-(4-Nitrobenzyloxycarbonyl)glycylamino]benzoyloxymethyl 6β-[2-(2-aminothiazol-4-yl)-(Z)-2-(cyclohexyloxyimino)acetamido]penicillanate A solution of chloromethyl chlorosulphate (275 mg) in dichloromethane (1 ml) was added, dropwise over ½ minute, to a stirred mixture of 2-[N-(4-nitrobenzyloxycarbonyl)glycylamino]benzoic acid (500 mg), sodium bicarbonate (450 mg), tetrabutylammonium hydrogensulphate (70 mg), dichloromethane (10 ml), and water (10 ml). After stirring at room temperature for 1h the solid which had precipitated was redissolved by addition of dichloromethane (50 ml). The organic layer was separated and was washed with dilute brine (2×10 ml), dried (MgSO$_4$), and evaporated to give the crude product, chloromethyl 2-[N-(4-nitrobenzyloxycarbonyl)glycylamino]benzoate, as a solid. Without further purification, the crude chloromethyl ester was dissolved in dry acetone (50 ml) and was treated with sodium iodide (2.11 g). After stirring at room temperature for 24 h the mixture was evaporated. The residue was dissolved in ethyl acetate (50 ml) and was washed with water (3×10 ml), dried (MgSO$_4$), and evaporated to give the crude product, iodomethyl 2-[N-(4-nitrobenzyloxycarbonyl)glycylamino]benzoate, as a solid. Without futher purification, the crude iodomethyl ester was dissolved in dry dimethylformamide (10 ml) and treated with sodium 6β-[2-(2-aminothiazol-4-yl)-(Z)-2-(cyclohexyloxyimino)a cetamido]penicillanate (688 mg). After stirring at room temperature for 1 h the mixture was diluted with ethyl acetate (50 ml) and was washed with 5% citric acid (10 ml), brine (10 ml), saturated NaHCO$_3$ (10 ml), and brine (3×10 ml). The dried (MgSO$_4$) organic layer was evaporated and the residue chromatographed on silica gel eluting with methyl acetate/hexane mixtures to give the title compound as an amorphous solid (550 mg), $\nu_{max}$ (CHCl$_3$) 3600–3100, 1790, 1730 sh., and 1695 cm$^{-1}$; $\delta_H$ [(CD$_3$)$_2$CO] 1.20–2.00 (16H, m), 4.03 (2H, d, J 6.3 Hz, collapses to s on exch. D$_2$O), 4.05–4.25 (1H, m), 4.50 (1H, s), 5.36 (2H, s), 5.68 (1H, d, J 4.2 Hz), 5.7.9 (1H, dd, J 8.3 and 4.2 Hz, collapses to d, J 4.2 Hz on exch. D$_2$O), 6.12 and 6.17 (2H, AB q, J 6.0 Hz), 6.55 (2H, s, exch. D$_2$O), 6.83 (1H, s), 7.18–7.40 (2H, m, 1H exch. D$_2$O), 7.65–7.72 (1H, m), 7.76 (2H, d, J 8.4 Hz), 8.07 (1H, d, J 8.0 Hz), 8.12 (1H, d, J 8.3 Hz, exch. D$_2$O), 8.27 (2H, d, J 8.4 Hz), 8.76 (1H, d, J 8.4 Hz), and 11.27 (1H, s, exch. D$_2$O).

c. 2-Glycylaminobenzoyloxymethyl 6β-[2-(2-aminothiazol-4-yl)-(Z)-2-(cyclohexyloxyimino)a cetamido]penicillanate hydrochloride A solution of 2-[N-(4-nitrobenzyloxycarbonyl)glycylamino]benzoyloxymethyl 6β-[2-(2-aminothiazol-4-yl)-(Z)-2-(cyclohexyloxyimino)acetamido]penicillanate (250 mg) in a mixture of 1,4-dioxane (25 ml) and water (15 ml) was hydrogenated over 5% palladium/charcoal (375 mg) at S.T.P. for 30 minutes. The mixture was filtered through Kieselguhr and the residue was washed with 50% aqueous dioxane (2×10 ml). The combined filtrates were treated with hydrochloric acid (2.94 ml of 0.1M) and were kept at room temperature for 6 h. Work-up of the mixture as described in example 55(e) afforded the title compound as a pale yellow solid (86 mg), $\nu_{max}$ (KBr) 3700-2300, 1785, 1700, 1675, and 1630 cm$^{-1}$; $\delta_H$ (D$_2$O) 1.10-2.05 (16H, m), 4.13 (2H, s), 4.37 (1H, br s), 5.76 (2H, br s), 6.05-6.30 (2H, m), 7.15 (1H, s), 7.35-7.50 (1H, m), 7.70-7.83 (1H, m), 7.85-8.00 (1H, m), and 8.05-8.20 (1H, m).

EXAMPLE 66 a. 2-[N-(4-Nitrobenzyloxycarbonyl)glycylamino]benzoyloxymethyl 6β-[2-(2-aminothiazol-4-yl)-(Z)-2-(cyclopentyloxyimino)acetamido]penicillanate Sodium 6β-[2-(2-aminothiazol-4-yl)-(Z)-2-(cyclopentyloxyimino)acetamido]penicillanate (500 mg) was converted to the title compound, an amorphous solid (439 mg), using the procedure described in example 65(b), $\nu_{max}$ (CHCl$_3$) 3600-3100, 1790, 1730, and 1700 cm$^{-1}$; $\delta_H$ [(CD$_3$)$_2$CO] 1.25-2.10 (14H, m), 4.03 (2H, d, J 6.6 Hz), collapses to s on exch. D$_2$O), 4.49 (1H, s), 4.70-4.74 (1H, m), 5.36 (2H, s), 5.67 (1H, d, J 4.2 Hz), 5.77 (1H, dd, J 8.2 and 4.2 Hz, collapses to d, J 4.2 Hz on exch. D$_2$O), 6.12 and 6.17 (2H, ABq, J 5.9 Hz), 6.52 (1H, exch. D$_2$O), 6.83 (1H, s), 7.12-7.38 (2H, m, 1H exch. D$_2$O), 7.65-7.72 (1H, m), 7.76 (2H, d, J 8.3 Hz), 8.07 (1H, d, J 8.2 Hz), 8.13 (1H, d, J 8.2 Hz, exch. D$_2$O), 8.27 (2H, d, J 8.3 Hz), 8.76 (1H, d, 8.2 Hz), 11.28 (1H, s, exch. D$_2$O).

b. 2-Glycylaminobenzoyloxymethyl 6β-[2-(2-aminothiazol-4-yl)-(Z)-2-(cyclopentyloxyimino)acetamido]penicillanate hydrochloride 2-[N-(4-Nitrobenzyloxycarbonyl)glycylamino]benzoyloxymethyl 6β-[2-(2-aminothiazol-4-yl)-(Z)-2-(cyclopentyloxyimino) acetamido]penicillanate (250 mg) was converted to the title compound, a pale yellow solid (68 mg), using the procedure described in example 65(c), $\nu_{max}$ (KBr) 3700-2400, 1769, 1700, 1675 sh., and 1628 cm$^{-1}$; $\delta_H$ (D$_2$O) 1.30-2.00 (14H, m), 4.15 (2H, s), 5.72 (1H, d, J 4 Hz), 5.76 (1H, d, J 4 Hz), 6.12 and 6.17 (2H, ABq, J 6.1Hz), 7.15 (1H, s), 7.37-7.43 (1H, m), 7.72-7.78 (1H, m), 7.95 (1H, d, J 8.0 Hz), and 8.07 (1H, d, J 7.8 Hz).

EXAMPLE 67 a. 4-Methylene cyclohexyl benzoate

Methyl triphenylphosphonium bromide (3.6 g) was suspended in anhydrous tetrahydrofuran (20 ml) under an atmosphere of argon. Potassium tert-butoxide (1.12 g) was added and the mixture was stirred and heated under gentle reflux for 1.25 h. The orange mixture was cooled to 0° C. and a solution of (4-benzoyloxy)cyclohexanone (1.09 g; L. N. Owens and P. A. Robins, J. Chem. Soc., 1949, 320) in anhydrous tetrahydrofuran (10 ml) was added slowly. The reaction was allowed to regain room temperature and stirring was continued for 0.5 h. The mixture was diluted with ether (50 ml) and washed with water (2×25 ml) and saturated brine (25 ml), dried over anhydrous magnesium sulphate, then evaporated to dryness. Chromatography on silica afforded the olefin (0.78 g), followed by the starting ketone (0.21 g). The olefin exhibited $\nu_{max}$ (CHCl$_3$) 1710, 1650, 1610, and 1590 cm$^{-1}$; $\delta_H$ (CDCl$_3$) 1.82, 1.97, 2.21 and 2.43 (8H, 4m), 4.71 (2H, s), 5.21 (1H, m), 7.40-7.60 and 8.00-8.10 (5H, 2m). [Mass spectrum: chemical ionisation (NH$_3$), 217 (MH$^+$)].

b. 4-Methylene cyclohexanol

4-Methylene cyclohexyl benzoate (1.00 g) in ethanol (5 ml) was treated with sodium hydroxide (2M; 5 ml) and stirred at room temperature for 16 h. The resulting clear solution was diluted with water (20 ml) and extracted with ether (3×20 ml). The combined extracts were dried and evaporated to give the essentially pure alcohol (0.50 g); $\nu_{max}$ (CHCl$_3$) inter alia 3600, 3400 (br) 3075 (m), 1650, 910 (s) cm$^{-1}$; $\delta_H$ (CDCl$_3$) 1.35-1.55 (3H, m, 2H on D$_2$O exch), 1.85-2.15 and 2.25-2.45 (6H, 2m), 3.83 (1H, m), and 4.65 (2H, s). [Mass spectrum: E.I., 94 (M-H$_2$O)].

c. Ethyl (Z)-2-(4-methylenecyclohexyloxyimino)-2-(2-tritylaminothiazol-4-yl)acetate 4-Methylenecyclohexanol (412 mg), triphenylphosphine (860 mg), and ethyl (Z)-2-hydroxyimino-2-(2-tritylaminothiazol-4-yl)acetate (1.37 g) were dissolved together in anhydrous benzene (9 ml). Dimethyl azodicarboxylate (0.40 ml) was added slowly with stirring and the resulting orange solution was stored at room temperature for 65 h with exclusion of moisture. Workup and chromatography as in example 4a, method 3 afforded the title compound (174 mg), $\delta_H$ (CDCl$_3$) 1.33 (3H, t, J 7 Hz), 1.82, 2.08 and 2.31 (8H, 3m), 4.35 (2H, q, J 7 Hz), 4.51 (1H, m), 4.63 (2H, s), 6.48 (1H, s), 6.96 (1H, br s, D$_2$O exch.), and 7.30 (15H, s).

d. Ethyl (Z)-2-(4-methylenecyclohexyloxyimino)-2-(2-aminothiazol-4-yl)acetate Ethyl (Z)-2-(4-methylenecyclohexyloxyimino)-2-(2-tritylaminothiazol-4-yl)acetate (171 mg) was subjected to formic acid deprotection as in Example 1a, but with a reaction time of 1 h. After chromatography, the title compound was obtained as a white solid (74 mg) (Found M$^+$, 309.1135. C$_{14}$H$_{19}$N$_3$O$_3$S requires M, 309.1146)-, $\nu_{max\ (KBr)}$ 1724, 1650 (sh), 1624, 1540, 1461, and 1444 cm$^{-1}$; $\delta_H$ (CDCl$_3$) 1.36 (3H, t, J 7 Hz), 1.83, 2.09 and 2.32 (8H, 3m), 4.40 (2H, q, J 7 Hz), 4.48 (1H, m), 4.64 (2H, s), 5.19 (2H, br s, D$_2$O exch.), and 6.73 (1H, s).

e. Sodium 2-(2-Aminothiazol-4-yl)-(Z)-2-(4-methylenecyclohexyloxyimino)acetate Ethyl (Z)-2-(4-methylenecyclohexyloxyimino)-2-(2-aminothiazol-4-yl)acetate (70 mg) was hydrolysed with sodium hydroxide (2M; 0.34 ml) as described in Example 1b. When reaction was complete the pH was adjusted to 7.3 and solution was evaporated to dryness. Chromatography on HP20SS followed by concentration and lyophilisation of appropriate fractions afforded the sodium salt (60 mg), $\nu_{max}$ (KBr) 1670 (sh), 1617, 1529, 1398, and 1357 cm$^{-1}$; $\delta_H$ [(CD$_3$)$_2$SO]1.55, 1.80, 2.01 and 2.30 (8H, 4m), 4.06 (1H, m), 4.61 (2H, s), 6.55 (1H, s), and 7.01 (2H, br s, D$_2$O exch). [Mass spectrum: +ve ion (thioglycerol) MH$^+$ (304), M+Na-H$^+$ (325)].

f. Sodium 2-(2-aminothiazol-4-yl)-(Z)-2-(4-methylenecyclohexyloxyimino)acetamido]penicillanate Sodium 2-(2-aminothiazol-4-yl)-(Z)-2-(4-methylenecyclohexyloxyimino)acetate (50 mg) was converted to a mixed anhydride using methanesulphonyl chloride (0.015 ml) and N,N-diisopropylethylamine (0.030 ml) and subsequently reacted with 6β-aminopenicillanic acid (50 mg) as in Example 47c. Workup, chromatography on HP20SS and lyophilisation as described therein afforded the penicillin (28 mg), $\nu_{max}$ (KBr) 1768, 1660 (sh), 1609, and 1527 cm$^{-1}$; $\delta_H$ (D$_2$O) 1.55, 1.65 (6H, 2s), 1.87, 2.17, and 2.35 (8H, 3m), 4.27 (1H, s), 4.49 (1H, m), 4.75 (2H, s), 5.68 (2H, ABq), and 7.04 (1H, s).

EXAMPLE 68 a. Ethyl 2-(2-tritylaminothiazol-4-yl)-(Z)-2-(4-oxocyclohexyloxyimino)acetate 4-Hydroxycyclohexanone (570 mg; J. B. Aldersley, G. N. Burkhardt, A. E. Gillam, and N. C. Hindley, *J. Chem. Soc.*, 1940, 10) ethyl 2-(2-tritylaminothiazol-4-yl)-(Z)-2-hydroxyiminoacetate (1.37 g) and triphenylphosphine (860 mg) in anhydrous benzene (9 ml) were allowed to react with dimethyl azodicarboxylate (0.40 ml) as described in Example 67c except the reaction time was 14 days. Workup and chromatography gave the title compound (158 mg), $\nu_{max}$ (KBr) 3390, 1737, 1710, 1596, 1585, 1529, and 1491cm$^{-1}$; $\delta_H$(CDCl$_3$) 1.33 (3H, t, J 7Hz), 2.01, 2.31, and 2.55 (8H, 3m), 4.36 (2H, q, J 7z), 4.73 (1H, m), 6.52 (1H, s), 6.97 (1H, brs, D$_2$O exch.), and 7.30 (15H, br s).

b. Ethyl-2-(2-aminothiazol-4-yl)-(Z)-2-(4-oxocyclohexyloxyimino)acetate

Ethyl-2-(2-tritylaminothiazol-4-yl)-(Z)-2-(4-oxocyclohexyloxyimino)acetate (150 mg) was deprotected as in Example 1a. Chromatography gave the title compound (47 mg), $\nu_{max}$ (KBr) 3449, 1720, 1706, 1616, and 1541cm$^{-1}$; $\delta_H$(CDCl$_3$) 1.36 (3H, t, J 7 Hz), 2.03, 2.32, and 2.55 (8H, 3m), 4.41 (2H, q, J 7 Hz), 4.72 (1H, m), 5.12 (2H, brs, D$_2$O exch), and 6.77 (1H, s).

c. Sodium 2-(2-aminothiazol-4-yl)-(Z)-2-(4-oxocyclohexyloxyimino)acetate

Ethyl-2-(2-aminothiazol-4-yl)-(Z)-2-(4-oxocyclohexyloxyimino)acetate (40 mg) was hydrolysed as described in Example 1b. After adjustment to pH7 the sodium salt (36 mg) was isolated by chromatography on HP20SS, $\delta_H$[(CD$_3$)$_2$SO+D$_2$O]1.94, 2.05, 2.15, and 2.54 (8H, 4m), 4.36 (1H, m), and 6.63 (1H, s).

d. Sodium 6β-[2-(2-aminothiazol-4-yl)-(Z)-2-(4-oxocyclohexyloxyimino)acetamido]penicillanate Sodium 2-(2-aminothiazol-4-yl)-(Z)-2-(4-oxocyclohexyloxyimino)acetate (33 mg) was converted to a mixed anhydride using methanesulphonyl chloride (0.012 ml) and allowed to react with 6β-aminopenicillanic acid (34 mg) as described in Example 47c. Workup, chromatography and lyophilisation afforded the penicillin (36 mg), $\nu_{max}$ (KBr) 1767, 1700, 1663, 1609, and 1529cm$^{-1}$; $\delta_H$ (D$_2$O) 1.51 and 1.60 (6H, 2s), 2.10, 2.35, and 2.60 (8H, 3m), 4.23 (1H, s), 4.69 (1H, m), 5.67 (2H, ABq), and 7.04 (1H, s).

EXAMPLE 69 a. Ethyl (Z)-2-(terahydro-4H-thiopyran-4-yl oxyimino)-3-oxobutyrate

Ethyl (Z)-2-hydroxyimino-3-oxobutyrate (5.72 g) was reacted with tetrahydro-4H-thiopyran-4-ol as described in Example 4a. method 3 to give the title compound (1.82 g, 20%) as colourless liquid, $\nu_{max}$ (film) 2930, 1740, and 1690 cm$^{-1}$, $\delta_H$(CDCl$_3$) 1.35 (3H, t), 2.06 (2H,m), 2.21 (2H, m) 2.40 (3H, s), 2.57 (2H, m), 2.82 (2H, m), and 4.37 (3H, q+m), $\delta$c (CDCl$_3$) 14.2, 25.2, 25.3 (2C), 32.1 (2C), 62.0, 81.9, 150.5, 161.2 and 192.7. [Mass spectrum, MH$^+$(260)].

b. Ethyl 4-bromo-(Z)-2-(tetrahydro-4H-thiopyran-4-yl oxyimino)-3-oxobutyrate Bromine (0.16 ml) was added to a vigorously stirred mixture of ethyl (Z)-2-(tetrahydro-4H-thiopyran-4-yl oxyimino)-3-oxobutyrate (0.80 g), a solution of hydrogen bromide in acetic acid (0.05 ml, 45% w/v) and acetic acid (8 ml) at room temperature. After 1h the solvent was removed under reduced pressure. The residue was dissolved in ethyl acetate, washed with saturated aqueous sodium bicarbonate, dried (MgSO$_4$) and the solvent evaporated.

Flash chromatography gave the title compound (0.70. g 67%) contaminated with starting material (13%) as a colourless liquid, $\nu_{max}$ (film) 2930, 1735, and 1690 cm$^{-1}$, $\delta_H$(CDCl$_3$) 1.36 (3H, t), 2.05 (2H, m), 2.23 (2H, m), 2.56 (2H, m). 2.82 (2H, m), 4.32 (2H, s), and 4.38 (3H, q+m).

c. Ethyl 2-(2-aminothiazol-4-yl)-(Z)-2-(tetrahydro-4H-thiopyran-4-yloxyimino) acetate Ethyl 4-bromo-(Z)-2-(tetrahydro-4H-thiopyran-4-yl oxyimino)-3-oxobutyrate (0.70 g) was converted into the title compound (0.52 g, 80%) as described in Example 4d, m.p. 109°-110° C. (toluene/hexane). [Found: C, 46.0; H, 5.4; N, 13.5. C$_{12}$H$_{17}$N$_3$O$_3$S$_2$ requires C, 45.7; H, 5.4; N, 13.3%], $\nu_{max}$ (KBr) 3440, 3126, 1726, 1613, and 1536 cm$^{-1}$, $\delta$H (CDCl$_3$) 1.40 (3H, t), 2.03 (2H, m), 2.15 (2H, m), 2.5(2H, m), 2.83 (2H, m), 4.39 (1H, m), 4.42 (2H, q), 5.46 (2H, brs), and 6.72 (1H, s).

d. Sodium 2-(2-aminothiazol-4-yl)-(Z)-2-(tetrahydro-4H-thiopyran-4-yloxyimino) acetate Ethyl 2-(2-aminothiazol-4-yl)-(Z)-2-(tetrahydro-4H-thiopyran-4-yloxyimino) acetate (0.20 g) was dissolved in ethanol (7 ml); water (1.0 ml) and 1M sodium hydroxide (1.3 ml) were added and the mixture stirred at room temperature for 18h. Ethanol was removed under reduced pressure and the residue chromatographed on HP20SS to give the title compound as a white freeze-dried solid (0.19 g, 100%,) $\nu_{max}$ (KBr) 3395, 2922, 1609, 1529, and 1400cm$^{-1}$, $\delta_H$ (D$_2$O) 1.95 (2H, m), 2.11 (2H, m), 2.54 (2H, m), 2.83 (2H, m), 4.24 (1H, tt, J 7.7, 3.1 Hz, and 6.81 (1H, s).

e. Sodium 6β-[2-(2-aminothiazol-4-yl)-(Z)-2-(tetrahydro-4H-thiopyran-4-yl oxyimino)acetamido] penicillanate Sodium 2-(2-aminothiazol-4-yl)-(Z)-2-(tetrahydro-4H-thiopyran-4-yloxyimino)acetate (0.167 g) was coupled to 6β-aminopenicillanic acid as described in Example 58c. The title compound was obtained as a white freeze-dried solid (0.182 g, 66%). $\nu_{max}$ (KBr) 3326, 2926, 1767, 1669, 1609, and 1528 cm$^{-1}$, $\delta_H$ (D$_2$O) 1.51 (3H, s), 1.62 (3H, s), 2.00 (2H, m), 2.09 (2H, m), 2.54 (2H, m) 2.82 (2H, m), 4.23 (1H, s), 4.35 (1H, tt J 7.2, 3.4 Hz), 5.63 (1H, d), 5.67 (1H, d), and 6.98 (1H, s).

EXAMPLE 70

The sodium salt of 6β-[2-(2-aminothiazol-4-yl)-(Z)-2-(3-thietanyloxyimino)acetamido]penicillanic acid was prepared from 3-thietanyloxyamine using the process described in Example 54.

EXAMPLE 71

The sodium salt of 6β-[2-(2-aminothiazol-4-yl)-(Z)-2-(4-methoxyiminocyclohexyloxyimino)acetamido]-penicillanic acid was prepared from 4-methoxylminocyclohexanol using the process described in Example 68.

EXAMPLE 72

The sodium salt of 6β-[2-(2-aminothiazol-4-yl)-(Z)-2-(cis-4-hydroxycyclohexyloxyimino)acetamido]penicillanic acid was prepared from the compound of Example 62b via hydrolysis with sodium hydroxide followed by coupling using the process described in Example 58c.

EXAMPLE 73

The sodium salt of 6β-[2-(2-aminothiazol-4-yl)-(Z)-2-(1,1-dioxotetrahydro-4H-thiopyran-4-yloxyimino) acetamido]penicillanic acid was prepared using the process described in Example 69 but inserting after step a the process described in Example 43a.

| In Vitro Biological Data. MIC (μg/ml) | | |
|---|---|---|
| | example 4 | flucloxacillin |
| H. influenzae Q1 | 0.12 | 4.0 |
| H. influenzae NEMCl | 0.5 | 16.0 |
| B. catarrhalis Ravasio | 0.25 | 16.0 |
| S. aureus Oxford | 0.12 | 0.25 |
| S. aureus MB9 | 0.5 | 0.5 |
| S. aureus V573+ | 4.0 | 32.0 |
| S. epidermidis PHLN20 | 0.25 | 0.25 |

-continued

| In Vitro Biological Data. MIC (μg/ml) | | |
|---|---|---|
| | example 4 | flucloxacillin |
| S. pneumoniae 1761 | <0.03 | 0.25 |

(+ = methicillin resistant strain)

In Vivo Biological Data.
The compound of example 4 was tested in vivo in mice against experimental infections. The results of these tests are shown in the following table:

| | Total* S.C. CD$_{50}$ (mg/kg) | |
|---|---|---|
| Organism | example 4 | flucloxacillin |
| S. aureus Smith (M.I.C) | 1.5 (0.12) | 6.0 (0.25) |
| S. aureus MB9 (M.I.C) | 4.0 (0.5) | 17.0 (0.5) |

*dosed at 1 and 5 hours after infection. 5 mice/group.
(S.C. = subcutaneous)

The compound of example 4 was administered to mice (5) by the subcutaneous route at a dosage of 50 mg/kg and the blood concentration determined. The results are shown in the following table:

| Compound of example No. | Concentration μg/ml at. mins | | | | | | A.U.C μg/min/ml |
|---|---|---|---|---|---|---|---|
| | 5 | 10 | 20 | 30 | 60 | 120 | |
| 4. | 31.0 | 21.8 | 14.3 | 7.7 | 0.9 | <0.09 | 571.0 |

We claim:
1. A compound of formula (I) or a pharmaceutically acceptable salt or in-vivo hydrolysable ester thereof:

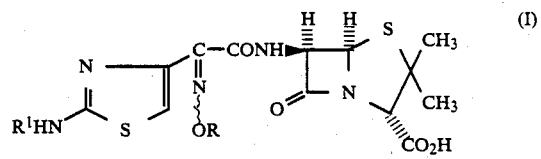

wherein R$^1$ is hydrogen or an amino protecting group and R is methyl substituted by carboxyl, esterified carboxy, carbonyl, hydroxy, alkoxy of 1 to 6 carbon atoms, alkoxyimino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; alkyl, alkenyl or alkynyl of 2 to 12 carbon atoms unsubstituted or substituted by carboxyl, esterified carboxy, carbonyl, hydroxy, alkoxy of 1 to 6 carbon atoms, alkoxyimino of 1 to 6 carbons, cyano carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; carbocyclyl unsubstituted or substituted by 1 or more of the same or different substituents selected from the group consisting of alkyl of 1 to 6 carbon atoms, alkenyl of 2 to 6 carbon atoms, alkynyl of 2 to 6 carbon atoms or exo-methylene unsubstituted or substituted by one of the substitutents specified for the alkyl, alkenyl or alkynyl groups above, alkoxycarbonyl of 1 to 6 carbon atoms; oxo, hydroxy, alkoxyimino of 1 to 6 carbon atoms in the alkoxy moiety, oxyimino, alkoxy of 1 to 6 carbon atoms, cyano, carbamoyl, N-substituted carbamoyl, aryloxy, arakoxy, mercapto, alkylthio of 1 to 6 carbon atoms in the alkyl moiety, arylthio, amino, substituted amino, halo, nitro, azido, formyl, acyl, acyloxy, pthalimido, acylamino, alkoxycarbonylamino of 1 to 6 carbon atoms in the alkoxy moiety, aralkoxycarbonylamino, aryl, heterocyclyl and carbocyclyl, aryl unsubstituted or substituted by up to 5 of the same or different substituents selected from the group consisting of halo; alkyl of 1 to 6 carbon atoms unsubstituted or substituted by carboxyl, esterified carboxy, carbonyl, hydroxy, alkoxy of 1 to 6 carbon atoms, alkoxyiminio of 1 to 6 carbon atoms, cyano, carbamoyl, N-Substituted carbamoyl, aryloxy, aralkoxy of 1 to 6 carbon atoms in the alkoxy moiety, mercapto, alkylthio of 1 to 6 carbon atoms in the alkyl moiety, arylyhio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl, carbocyclyl; alkylthio of 1 to 6 carbon atoms; acylamino; phenyl; alkoxy of 1 to 6 carbon atoms; haloalkyl of 1 to 6 carbon atoms; hydroxy; amino; nitro; carboxy; carbomoyl; N-substituted carbamoyl; alkoxycarbonyl of 1 to 6 carbons atoms in the alkoxy moiety; alkoxycarbonylalkyl of 1 to 6 carbon atoms in each of the alkoxy and alkyl moieties; alkylcarbonyloxy of 1 to 6 carbon atoms in the alkyl moiety; alkylcarbonyl of 1 to 6 carbon atoms in the alkyl moiety; and heterocyclyl; or R is heterocyclyl having a least one ring of up to four heteroatoms selected from the group consisting of oxygen, nitrogen, and sulphur, each ring being unsubstituted or substituted by up to 3 of the same or different substituents selected from the group consisting of halo, alkyl of 1 to 6 carbon atoms, carbocyclyl, alkythio of 1 to 6 carbon atoms, acylamino, alkoxy of 1 to 6 carbon atoms, haloalkyl of 1 to 6 carbon atoms, hydroxy, amino, carboxy, carbamoyl, N-substituted carbamoyl, acyl, alkoxycarbonyl of 1 to 6 carbon atoms in the alkoxy moiety, alkoxycarbonylalkyl of 1 to 6 carbon atoms in each of the alkoxy and alkyl moieties, aryl and oxo.

2. A compound according to claim 1, wherein R is carbocyclyl at least partly saturated unsubstituted or substituted by 1 or more of the same of different substituents selected from one of the group consisting of alkyl of 1 to 6 carbon atoms, unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino of 1 to 6 carbon atoms in the alkoxy moiety aralkoxycarbonylamino of 1 to 6 carbon atoms in the alkoxy moiety, aryl, heterocyclyl or carbocyclyl; alkenyl of 2 to 6 carbon atoms, unsubstituted or substituted by carboxyl, esterified carboxy, carbonyl, hydroxy, alkoxy of 1 to 6 carbon atoms, alkoxyamino of 1 to 6 carbon atoms, cyano, carbamoyl, aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino, of 1 to 6 carbon atoms in the alkoxy moiety, aralkoxycarbonylamino of 1 to 6 carbon atoms in the alkoxy moiety, aryl, heterocyclyl or carbocyclyl.

3. A compound according to claim 2, wherein R is cycloalkyl or cycloalkenyl of 5 to 10 carbon atoms having between one and four rings, unsubstituted or substituted by one or more groups selected from the group consisting of carboxy, alkyl of 1 to 6 carbon atoms, unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; alkoxycarbonyl of 1 to 6 carbon atoms in the alkoxy moiety, alkoxyimino of 1 to 6 carbon atoms, alkoxy of 1 to 6 carbon atoms, hydroxy, halo, carbamoyl, mono- or di- alkyl carbamoyl of 1 to 6 carbon atoms in each alkyl moiety, acyloxy, exo-methylene unstituted or substituted by carboxyl, esterified carboxy, carbonyl, hydroxy, alkoxy of 1 to 6 carbon atoms, alkoxyamino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyolyl or carbocyclyl, and oxo.

4. A compound according to claim 1, wherein R is alkyl, alkenyl or alkynyl of 3 to 6 carbon atoms which is attached at a secondary or tertiary carbon atom thereof said moiety being unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl.

5. A compound according to claim 1, wherein R is cyclopentyl, cyclohexyl, cycloheptyl, cyclooctyl, 4-methyl cyclohex-1-yl, 1-methyl cyclohex-1-yl, bicyclo[2.2.2]oct-1-yl, endo-bicylo [2.2.1]hept-2-yl, t-butyl, 4-t-butyl cyclohex-1-yl, adament-1-yl, tetrahydrothien-3-yl, 4-methylene cyclohex-1-yl, 4-oxocyclohex-1-yl, 1-methyl cyclohept-1-yl, 1-methyl cyclopent-1-yl, 2-methyl cyclohex-1-yl, 2-methoxycyclohex-1-yl, 4-methoxycarbonyl cyclohex-1-yl, 4-chlorocyclohex-1-yl, cyclohex-2-enyl, 2-fluorocyclohex-1-yl, 1-carboxycyclohex-1-yl, 4-(N,N-dimethylcarbamoyl)cyclohex-1-yl, 1-methoxycarbonyl cyclohex-1-yl, 3-methyl cyclohex-1-yl, 4-acetoxycyclohex-1-yl, 4-methyloxyiminocyclohex-1-yl or 4-hydroxycyclohex-1-yl.

6. A compound according to claim 1, which is the syn-isomer of formula (II):

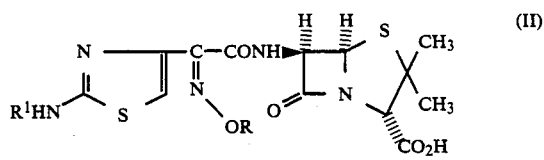

wherein R is methyl substituted by carboxyl, esterified carboxy, carbonyl, hydroxy, alkoxy of 1 to 6 carbon atoms, alkoxyimino of 1 to 6 carbon atoms, cyano, carbamoyl aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; alkyl, alkenyl or alkynyl of 2 to 12 carbon atoms unsubstituted or substituted by carboxyl, esterified carboxy, carbonyl, hydroxy, alkoxy of 1 to 6 carbon atoms, alkoxyamino of 1 to 6 carbon atoms, cyano, carbamoyl, aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; and carbocyclyl unsubstituted or substituted by 1 or more of the same or different substituents selected from the group consisting of alkyl of 1 to 6 carbon atoms, alkenyl of 2 to 6 carbon atoms, alkynyl of 2 to 6 carbon atoms or exo-methylene unsubstiuted or substituted by carboxyl, esterified carboxy, carbonyl, hydroxy, alkoxy of 1 to 6 carbon atoms, alkoxyimino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl, carbonyl, alkoxycarbonyl of 1 to 6 carbon atoms in the alkoxy moiety; oxo; hydroxy; alkoxyimino of 1 to 6 carbon atoms in the alkoxy moiety; oxyimino; alkoxy of 1 to 6 carbon atoms; cyano; carbamoyl; aryloxy; aralkoxy of 1 to 6 carbon atoms in the alkoxy moiety; mercapto; alkylthio of 1 to 6 carbon atoms in the alkyl moiety; arylthio; amino; halo; nitro; azido; formyl; acyl; acyloxy; phthalimido; acylamino; alkoxycarbonylamino of 1 to 6 carbon atoms in the alkoxy moiety; aralkoxycarbonylamino of 1 to 6 carbon atoms in the alkyl moiety; aryl; heterocyclyl; and carbocyclyl; aryl unsubstituted or substituted by up to five of the same or different substituents selected from the group consisting of alkyl of 1 to 6 carbon atoms, unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, N-substituted carbamoyal, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino, of 1 to 6 carbon atoms in the alkoxy moiety, aralkoxycarbonylamino of 1 to 6 carbon atoms in the alkoxy moiety, aryl, heterocyclyl or carbocyclyl; carbocyclyl; alkylthio of 1 to 6 carbon atoms; acylamino; phenyl; alkoxy of 1 to 6 carbon atoms; haloalkyl of 1 to 6 carbon atoms; hydroxy; amino; nitro; carboxy; carbamoyl; alkoxycarbonyl of 1 to 6 carbon atoms in the alkoxy moiety; alkoxycarbonylalkyl of 1 to 6 carbon atoms in each of the alkoxy and alkyl moietries; alkylcarbonyloxy of 1 to 6 carbon atoms in the alkyl moiety; alkylcarbonyl of 1 to 6 carbon atoms in the alkyl moiety; and heterocyclyl; or heterocyclyl having at least one ring of up to four heteroatoms selected from the group consisting of oxygen, nitrogren and sulphur, each ring being unsubstituted or substituted by up to 3 of the same or different substituents selected from the group consisting of halo, alkyl of 1 to 6 carbon atoms, carbocyclyl, alkylthio of 1 to 6 carbon atoms, acylamino, alkoxy of 1 to 6 carbon atoms, haloalkyl of 1 to 6 carbon atoms, hydroxy, amino, carboxy, carbamoyl, N-substituted carbamoyl, acyl, alkoxycarbonyl of 1 to 6 carbon atoms in the alkoxy moiety, alkoxycarbonylalkyl of 1 to 6 carbon atoms in each of the alkoxy and alkyl moieties, aryl and oxo and $R^1$ is hydrogen or an amino protecting group.

7. A compound according to claim 1 of the formula (III) or a pharmaceutically acceptable salt or in vivo hydrolysable ester thereof

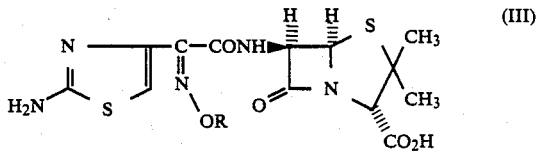

wherein R is cyclohexyl.

8. A compound according to claim 1, selected from the group consisting of
6β-[2-(2-Aminothiazol-4-yl)-(Z)-2-cyclopropylmethoxyiminoacetamido]penicillanic acid, 6β-[2-(2-aminothiazol-4-yl)-(Z)-2-ethoxyimino acetamido]penicillanic acid,
6β-[2-(2-aminothiazol-4-yl)-(Z)-2-propoxyimino acetamido]penicillanic acid,
6β-[(Z)-2-allyloxyimino-2-(2-aminothiazol-4-yl) acetamido]penicillanic acid,
6β-[2-(2-aminothiazol-4-yl)-(Z)-2-(isopropyloxyimino)acetamido]penicillanic acid,
6β-[2-(2-aminothiazol-4-yl)-(Z)-2-(tertbutyloxyimino)acetamido]penicillanic acid.
6β-[(Z)-2-(adamant-1-yloxyimino)-2-(2-aminothiazol-4-yl)acetamido]penicillanic acid,
6β-[2-(2-aminothiazol-4-yl)-(Z)-2-(1-methylcyclohex-1-yloxyimino)acetamido]penicillanic acid,
6β-[2-(2-aminothiazol-4-yl)-(Z)2-[(1S,2S,5R)5-methyl-2-isopropylcyclohex-1-yl oxyimino)acetamido]penicillanic acid,
6β-[2-(2-aminothiazol-4-yl)-(Z)-2-(2-methylpropyloxyimino)acetamido]penicillanic acid,
6β-[2-(2-aminothiazol-4-yl)-(Z)-2-(indan-2-yloxyimino)acetamido]penicillanic acid,
6β-[2-(2-aminothiazol-4-yl)-(Z)-2-(tetrahydrothien-3-yloxyimino)acetamido]pencillanic acid,
6β-[2-(2-aminothiazol-4-yl)-(Z)-2-(1-methylcyclohept-1-yloxyimino)acetamido]penicillanic acid,
6β-[2-(2-aminothiazol-4-yl)-(Z)-2-(bicyclo[2.2.2]oct-1-yloxyimino)acetamido]penicillanic acid,
6β-[2-(2-aminothiazol-4-yl)-(Z)-2-((1R,2R,5S)-5-methyl-2-isopropylcyclohex-1-yloxyimino)acetamido]penicillanic acid,
6β-[2-(2-aminothiazol-4-yl)-(Z)-2-(1-methylcyclopent-1-yloxyimino)acetamido]penicillanic acid,
6β-[2-(2-aminothiazol-4-yl)-(Z)-2-(1-(trans-4-methylcyclohexyl)-1-methylethoxyimino)acetamido]penicillanic acid,
6β-[2-(2-aminothiazol-4-yl)-(Z)-2-(3,3-dichloroprop-2-en-1-yloxyimino)acetamido]penicillanic acid,
6β-[2-(2-aminothiazol-4-yl)-(Z)-2-(1-carboxy-1-methylethoxyimino)acetamido]penicillanic acid,
6β-[2-(2-aminothiazol-4-yl)-(Z)-2-(carboxymethoxyimino) acetamido]penicillanic acid,
6β-[2-(2-aminothiazol-4-yl)-(Z)-2-(trans-2-methoxycyclohexyloxyimino)acetamido]penicillanic acid,
6β-[2-(2-aminothiazol-4-yl)-(Z)-2-(cis-2-methylcyclohexyloxyimino)acetamido]penicillanic acid,
6β-[2-(2-aminothiazol-4-yl)-(Z)-2-(trans-4-methoxycarbonylcyclohexyloxyimino)acetamido]penicillanic acid,
6β-[2-(2-aminothiazol-4-yl)-(Z)-2-(1,1-dioxotetrahydrothien-3-yloxyimino)acetamido]penicillanic acid,
6β-[2-(2-aminothiazol-4-yl)-(Z)-2-(decahydronapth-2-yloxyimino)acetamido]penicillanic acid,
6β-[2-(2-aminothiazol-4-yl)-(Z)-2-([R.S]-1-phenylethyloxyimino)acetamido]penicillanic acid,
6β-[2-(2-aminothiazol-4-yl)-(Z)-2-(2,6-dichlorobenzyloxyimino)acetamido]penicillanic acid,
6β-[2-(2-aminothiazol-4-yl)-(Z)-2-(trans-4-chlorocyclohexyloxyimino)acetamido]penicillanic acid,
6β-[2-(2-aminothiazol-4-yl)-(Z)-2-(cis-4-chlorocyclohexyloxyimino)acetamido]penicillanic acid,
6β-[2-(2-aminothiazol-4-yl)-(Z)-2-(phenoxyimino)acetamido]penicillanic acid,
6β-[2-(2-aminothiazol-4-yl)-(Z)-2-(cyclopentyloxyimino)acetamido]penicillanic acid,
6β-[2-(2-aminothiazol-4-yl)-(Z)-2-(cycloheptyloxyimino)acetamido]penicillanic acid,
6β-[2-(2-aminothiazol-4-yl)-(Z)-2-(cyclooctyloxyimino)acetamido]penicillanic acid,
6β-[2-(2-aminothiazol-4-yl)-(Z)-2-(endo-bicyclo[2.2.1]hept-2-yloxyimino)acetamido]penicillanic acid,
6β-[2-(2-aminothiazol-4-yl)-(Z)-2-(trans-4-methylcyclohexyloxyimino)acetamido]penicillanic acid,
6β-[2-(2-aminothiazol-4-yl)-(Z)-2-(cis-4-methylcyclohexyloxyimino)acetamido]penicillanic acid,
6β-[2-(2-aminothiazol-4-yl)-(Z)-2-(tetrahydro-4H-pyran4-yloxyimino)acetamido]penicillanic acid,
6β-[2-(2-aminothiazol-4-yl)-(Z)-2-(2-(1-(S)-6,6-dimethylbicyclo[3.1.1]hept-2-en-2-yl)ethoxyimino)acetamido]penicillanic acid,
6β-[2-(2-aminothiazol-4-yl)-(Z)-2-(cyclohexylmethoxyimino)acetamido]penicillanic acid,
6β-[2-(2-aminothiazol-4-yl)-(Z)-2-(n-butoxyimino)acetamido]penicillanic acid,
6β-[2-(2-aminothiazol-4-yl)-(Z)-2-(cyanomethoxyimino)acetamido]penicillanic acid,
6β-[2-(2-aminothiazol-4-yl)-(Z)-2-(trans-2-methylcyclohexyloxyimino)acetamido]penicillanic acid,
6β-[2-(2-aminothiazol-4-yl)-(Z)-2-(cyclohex-2-enyloxyimino)acetamido]penicillanic acid,
6β-[2-(2-aminothiazol-4-yl)-(Z)-2-(trans-4-t-butylcyclohexyloxyimino)acetamido]penicillanic acid,
6β-[2-(2-aminothiazol-4-yl)-(Z)-2-(trans-2-fluorocyclohexyloxyimino)acetamido]penicillanic acid,
6β-[2-(2-aminothiazol-4-yl)-(Z)-2-(2-pyrrolidon-3-yloxyimino)acetamido]penicillanic acid,
6β-[2-(2-aminothiazol-4-yl)-(Z)-2-(1-(R)-6,6-dimethylbicyclo[3.1.1]hept-2-en-2-yl)methoxyimino)acetamido]penicillanic acid,
6β-[2-(2-aminothiazol-4-yl)-(Z)-2-(1-carboxycyclohexyloxyimino)acetamido]penicillanic acid,
6β-[2-(2-aminothiazol-4-yl)-(Z)-2-(trans-4-(N,N-dimethylcarbamoyl)cyclohexyloxyimino)acetamido]penicillanic acid,
6β-[2-(2-aminothiazol-4-yl)-(Z)-2-(1-methoxycarbonylcyclohexyloxyimino)acetamido]penicillanic acid,
6β-[2-(2-aminothiazol-4-yl)-(Z)-2-(cis-3-methylcyclohexyloxyimino)acetamido]penicillanic acid,
6β-[2-(2aminothiazol-4-yl)-(Z)-2-(trans-3-methylcyclohexyloxyimino)acetamido]penicillanic acid,
6β-[2-(2-aminothiazol-4-yl)-(Z)-2-(cis-4-acetoxycyclohexyloxyimino)acetamido]penicillanic acid,
6β-[2-(2-aminothiazol-4-yl)-(Z)-2-(trans-4-acetoxycyclohexyloxyimino)acetamido]penicillanic acid,
6β-[2-(2-aminothiazol-4-yl)-(Z)-2-((2S,4S)-2-carboxypyrrolidin-4-yloxyimino)acetamido]penicillanic acid,
6β-[2-(2-aminothiazol-4-yl)-(Z)-2-(4-oxocyclohexyloxyimino)acetamido]penicillanic acid,
6β-[2-(2-aminothiazol-4-yl)-(Z)-2-(4-methylenecyclohexyloxyimino)acetamido]penicillanic acid,
6β-[2-(2-aminothiazol-4-yl)-(Z)-2-(benzyloxyimino)acetamido]penicillanic acid,
6β-[2-(2-aminothiazol-4-yl)-(Z)-2-(cyclohexyloxyimino)acetamido]penicillanic acid,
6β-[2-(2-aminothiazol-4-yl)-(Z)-2-(tetrahydro-4H-thiopyran-4-yl oxyimino)acetamido]penicillamic acid,
6β-[2-(2-aminothiazol-4-yl)-(Z)-2-(3-thietanyloxyimino) acetamido]penicillanic acid,
6β-[2-(2-aminothiazol-4-yl)-(Z)-2-4-methoxyiminocyclohexyloxyimino)acetamido] penicillanic acid,
6β-[2-(2-aminothiazol-4-yl)-(Z)-2-(cis-4-hydroxycyclohexyloxyimino)acetamido]penicillanic acid, and
6β-[2-(2-aminothiazol-4-yl)-(Z)-2-(1,1-dioxotetrahydro-4H-thiopyran-4-yloxyimino) acetamido]penicillanic acid, pharmaceutically acceptable salts and in vivo hydrolysable esters thereof.

9. A pharmaceutical composition useful for treating bacterical infections in humans and animals which comprises an antibacterially effective amount of a compound of the formula

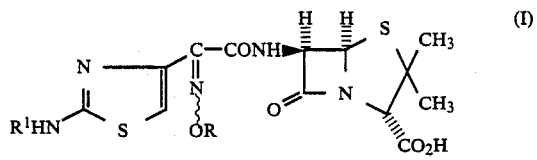

wherein $R^1$ is hydrogen or an amino protecting group and R is methyl substituted by carboxyl, esterified carboxy, carbonyl, hydroxy, alkoxy of 1 to 6 carbon atoms, alkoxyimino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocxyclyl or carbocyclyl, alkyl, alkenyl or alkynyl of 2 to 12 carbon atoms unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; carbocyclyl unsubstituted or substituted by 1 or more of the same or different substituents selected from the group consisting of alkyl of 1 to 6 carbon atoms, alkenyl of 2 to 6 carbon atoms, alkynyl of 2 to 6 carbon atoms or exo-methylene unsubstituted or substituted by one of the substituents specified for the alkyl, alkenyl or alkykyl groups above, alkoxycarbonyl of 1 to 6 carbon atoms; oxo, hydroxy, alkoxyimino of 1 to 6 carbon atoms in the alkoxy moiety, oxyimino, alkoxy of 1 to 6 carbon atoms, cyano, carbamoyl, N-substituted carbamoyl, aryloxy, aralkoxy, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino, aryl, heterocyclyl and carbocyclyl; aryl unsubstituted or substituted by up to 5 of the same or different substituents selected from the group consisting of halo; alkyl of 1 to 6 carbon atoms unsubstituted or substituted by carboxyl, esterfied carboxy, carbonyl, hydroxy, alkoxy of 1 to 6 carbon atoms, alkoxyimino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; carbocyclyl; alkylthio of 1 to 6 carbon atoms, acylamino, phenyl, alkoxy of 1 to 6 carbon atoms; haloalkyl of 1 to 6 carbon atoms; hydroxy; amino; nitro; carboxy; carbamoyl; N-substituted carbamoyl; alkoxycarbonyl of 1 to 6 carbon atoms in the alkoxy moiety; alkoxycarbonylalkyl of 1 to 6 carbon atoms in each of the alkoxy and alkyl moieties; alklcarbonyloxy of 1 to 6 carbon atoms in the alkyl moiety; alkylcarbonyl of 1 to 6 carbon atoms in the alkyl moiety; and heterocyclyl; or R is heterocyclyl having at least one ring of up to four heteroatoms selected from the group consisting of oxygen, nitrogen and sulphur, each ring being unsubstituted or substituted by up to 3 of the same or different substituents selected from the group consisting of halo, alkyl of 1 to 6 carbon atoms, carbocyclyl, alkylthio of 1 to 6 carbon atoms, acylamino, alkoxy of 1 to 6 carbon atoms, haloalkyl of 1 to 6 carbon atoms, hydroxy, amino, carboxy, carbamoyl, N-substituted carbamoyl, acyl, alkoxycarbonyl of 1 to 6 carbon atoms in the alkoxy moiety, alkoxycarbonylalkyl of 1 to 6 carbon atoms in each of the alkoxy and alkyl moieties, aryl and oxo, in combination with a pharmaceutically acceptable carrier.

10. A composition according to claim 9 wherein R is carbocyclyl, at least partly saturated, unsubstituted or substituted by 1 or more of the same or different substituents selected from the group consisting of alkyl of 1 to 6 carbon atoms, unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; alkenyl of 2 to 6 carbon atoms, unsubstituted or substituted by carboxyl, esterified carboxy, carbonyl, hydroxy, alkoxy of 1 to 6 carbon atoms, alkoxyamino of 1 to 6 carbon atoms, cyano, carbamoyl, aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino, of 1 to 6 carbon atoms in the alkoxy moiety, aralkoxycarbonylamino of 1 to 6 carbon atoms in the alkoxy moiety, aryl, heterocyclyl or carbocyclyl.

11. A composition according to claim 10 wherein R is cycloalkyl or cycloalkenyl of 5 to 10 carbon atoms having between one and four rings, unsubstituted or substituted by one or more groups selected from the group consisting of carboxy, alkyl of 1 to 6 carbon atoms, unsubstituted or substituted by carboxyl, esterified carboxy, carbonyl, hydroxy, alkoxy of 1 to 6 carbons atoms, alkoxyimino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety; arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; alkoxycarbonyl of 1 to 6 carbon atoms in the alkoxy moiety, alkoxyimino of 1 to 6 carbon atoms, alkoxy of 1 to 6 carbon atoms, hydroxy, halo, carbamoyl, mono- or di- alkyl carbamoyl of 1 to 6 carbon atoms in each alkyl moiety, acyloxy, exo-methylene unsubstituted or substituted by carboxyl, esterified carboxy, cabonyl, hydroxy, alkoxy of 1 to 6 carbon atoms, alkoxyimino of 1 to 6 carbon atoms, cyano, carbamoyl, aryloxy, aralkoxy of 1 to 6 carbon atoms in the alkoxy moiety, mercapto, alkylthio of 1 to 6 carbons in the alkyl moiety, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl, and oxo.

12. A composition according to claim 9 wherein R is alkyl, alkenyl or alkynyl of 3 to 6 carbon atoms which is attached at a secondary or tertiary carbon atom thereof said moiety being unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl.

13. A composition according to claim 13 wherein R is cyclopentyl, cyclohexyl, cycloheptyl, cyclooctyl, 4-methyl cyclohex-1-yl, 1-methylcyclohex-1-yl, bicyclo[2.2.2]oct-1-yl, endo-bicyclo[2.2.1]hept-2-yl, t-butyl, 4-t-butylcyclohex-1-yl, adamant-1-yl, tetrahydrothien-3-yl, 4-methylenecyclohex-1-yl, 4-oxocyclohex-1-yl, 1-methylcyclohept-1-yl, 1-methyl cyclopent-1-yl, 1-methylcyclopent-1-yl, 2-methylcyclohex-1-yl,
2-methoxycyclohex-1-y1,4-methoxycarbonylcyclohex-1-yl, 4-chlorocyclohex-1-yl, cyclohex-2-eny1,2-fluorocyclohex-1-yl, 1-carboxycyclohex-1-yl, 4-(N,N-dimethylcarbamoyl)cyclohex-1-yl, 1-methoxycarbonylcyclohex-1-yl, 3-methylcyclohex-1-yl, 4-acetoxycyclohex-1-yl, 4-methoxyiminocyclohex-1-yl, or 4-hydroxycyclohex-1-yl.

14. A composition according to claim 9 wherein the compound is the syn-isomer of the formula (II):

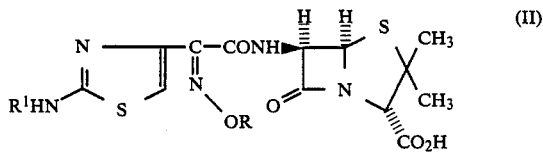

(II)

wherein R is methyl substituted by carboxyl, esterified carboxy, carbonyl, hydroxy, alkoxy of 1 to 6 carbon atoms, alkoxyimino of 1 to 6 carbon atoms, cyano, carbamoyl, aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; alkyl, alkenyl or alkynyl of 2 to 12 carbon atoms unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; and carbocyclyl unsubstituted or substituted by 1 or more of the same or different substituents selected from the group consisting of alkyl of 1 to 6 carbon atoms, alkenyl of 2 to 6 carbon atoms, alkynyl of 2 to 6 carbon atoms or exo-methylene unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; carboxyl; alkoxycarbonyl of 1 to 6 carbon atoms in the alkoxy moiety; oxo; hydroxy; alkoxyimino of 1 to 6 carbon atoms in the alkoxy moiety; oxyimino; alkoxy of 1 to 6 carbon atoms; cyano; carbamoyl; aryloxy; aralkoxy of 1 to 6 carbon atoms in the alkoxy moiety; mercapto; alkylthio of 1 to 6 carbon atoms in the alkyl moiety; arylthio; amino; halo; nitro; azido; formyl; acyl; acyloxy; phthalimido; acylamino; alkoxycarbonylamino of 1 to 6 carbon atoms in the alkoxy moiety; aralkoxycarbonylamino of 1 to 6 carbon atoms in the alkyl moiety; aryl; heterocyclyl; and carbocyclyl; aryl unsubstituted or substituted by up to 5 of the same or different substituents selected from the group consisting of alkyl of 1 to 6 carbon atoms, unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; carbocyclyl; alkylthio of 1 to 6 carbon atoms; acylamino; phenyl; alkoxy of 1 to 6 carbon atoms; haloalkyl of 1 to 6 carbon atoms; hydroxy; amino; nitro; carboxy; carbamoyl; alkoxycarbonyl of 1 to 6 carbon atoms in the alkoxy moiety; alkoxycarbonylalkyl of 1 to 6 carbon atoms in each of the alkoxy and alkyl moieties; alkylcarbonyloxy of 1 to 6 carbon atoms in the alkyl moiety; alkylcarbonyl of 1 to 6 carbon atoms in the aklyl moiety; and heterocyclyl; or heterocyclyl having at least one ring of up to four heteroatoms selected from the group consisting of oxygen, nitrogen and sulphur, each ring being unsubstituted or substituted by up to 3 of the same or different substituents selected from the group consisting of halo, alkyl of 1 to 6 carbon atoms, carbocyclyl, alkylthio of 1 to 6 carbon atoms, acylamino, alkoxy of 1 to 6 carbon atoms, haloalkyl of 1 to 6 carbon atoms, hydroxy, amino, carboxy, carbamoyl, N-substituted carbamoyl, acyl, alkoxycarbonyl of 1 to 6 carbon atoms in the alkoxy moiety, alkoxycarbonylalkyl of 1 to 6 carbon atoms in each of the alkoxy and alkyl moieties, aryl and oxo and $R^1$ is hydrogen or an amino protecting group.

15. A composition according to claim 9 wherein the compound is of the formula (III) or a pharmaceutically acceptable salt or in vivo hydrolysable ester thereof

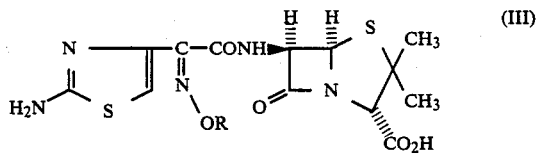

wherein R is cyclohexyl.

16. A composition according to claim 9 wherein the compound is selected from the group consisting of
6β-[2-(2-Aminothiazol-4-yl)-(Z)-2-cyclopropylmethoxyiminoacetamido]penicillanic acid,
6β-[2-(2-aminothiazol-4-yl)-(Z)-2-ethoxyimino acetamido]penicillanic acid,
6β-[2-(2-aminothiazol-4-yl)-(Z)-2-propoxyimino acetamido]penicillanic acid,
6β-[(Z)-2-allyloxyimino-2-(2-aminothiazol-4-yl) acetamido]penicillanic acid,
6β-[2-(2-aminothiazol-4-yl)-(Z)-2-(isopropyloxyimino)acetamido]penicillanic acid,
6β-[2-(2-aminothiazol-4-yl)-(Z)-2-(tertbutyloxyimino)acetamido]penicillanic acid.
6β-[(Z)-2-(adamant-1-yloxyimino)-2-aminothiazol-4-yl)acetamido]penicillanic acid,
6β-[2-(2-aminothiazol-4-yl)-(Z)-2-(1-methylcyclohex-1-yloxyimino) acetamido]penicillanic acid,
6β-[2-(2-aminothiazol-4-yl)-(Z)2-[(1S,2S,5R) 5-methyl-2-isopropylcyclohex-1-yl oxyimino)acetamido]penicillanic acid,
6β-[2-(2-aminothiazol-4-yl)-(Z)-2-(2-methylpropyloxyimino)acetamido]penicillanic acid,
6β-[2-(2-aminothiazol-4-yl)-(Z)-2-(indan-2-yloxyimino)acetamido]penicillanic acid,
6β-[2-(2-aminothiazol-4-yl)-(Z)-2-(tetrahydrothien-3-yloxyimino)acetamido]pencillanic acid,
6β-[2-(2-aminothiazol-4-yl)-(Z)-2-(1-methylcyclohept-1-yloxyimino) acetamido]penicillanic acid,
6β-[2-(2-aminothiazol-4-yl)-(Z)-2-(bicyclo[2.2.2]oct-1-yloxyimino) acetamido]penicillanic acid,
6β-[2-(2-aminothiazol-4-yl)-(Z)-2-((1R,2R,5S)-5-methyl-2-isopropylcyclohex -1-yloxyimino)acetamido]penicillanic acid,
6β-[2-(2-aminothiazol-4-yl)-(Z)-2-(1-methylcyclopent-1-yloxyimino) acetamido]penicillanic acid,
6β-[2-(2-aminothiazol-4-yl)-(Z)-2-(1-(trans-4-methylcyclohexyl)-1-methylethoxyimino) acetamido]penicillanic acid,
6β-[2-(2-aminothiazol-4-yl)-(Z)-2-(3,3-dichloroprop-2-en-1-yloxyimino) acetamido]penicillanic acid,
6β-[2-(2-aminothiazol-4-yl)-(Z)-2-(1-carboxy-1-methylethoxyimino) acetamido]penicillanic acid,
6β-[2-(2-aminothiazol-4-yl)-(Z)-2-(carboxymethoxyimino) acetamido]penicillanic acid,
6β-[2-(2-aminothiazol-4-yl)-(Z)-2-(trans-2-methoxycyclohexyloxyimino) acetamido]penicillanic acid,
6β-[2-(2-aminothiazol-4-yl)-(Z)-2-(cis-2-methylcyclohexyloxyimino) acetamido]penicillanic acid,
6β-[2-(2-aminothiazol-4-yl)-(Z)-2-(trans-4-methoxycarbonylcyclohexyloxyimino) acetamido]penicillanic acid,
6β-[2-(2-aminothiazol-4-yl)-(Z)-2-(1,1-dioxotetrahydrothien-3-yloxyimino) acetamido]penicillanic acid,
6β-[2-(2-aminothiazol-4-yl)-(Z)-2-(decahydronapth-2-yloxyimino) acetamido]penicillanic acid,
6β-[2-(2-aminothiazol-4-yl)-(Z)-2-([R.S]-1-phenylethyloxiimino) acetamido]penicillanic acid,
6β-[2-(2-aminothiazol-4-yl)-(Z)-2-(2,6-dichlorobenzyloxyimino) acetamido]penicillanic acid,
6β-[2-(2-aminothiazol-4-yl)-(Z)-2-(trans-4-chlorocyclohexyloxyimino) acetamido]penicillanic acid,
6β-[2-(2-aminothiazol-4-yl)-(Z)-2-(cis-4-chlorocyclohexyloxyimino) acetamido]penicillanic acid,
6β-[2-(2-aminothiazol-4-yl)-(Z)-2-(phenoxyimino)-acetamido]penicillanic acid,
6β-[2-(2-aminothiazol4-yl)-(Z)-2-(cyclopentyloxyimino) acetamido]penicillanic acid,
6β-[2-(2-aminothiazol-4-yl)-(Z)-2-(cycloheptyloxyimino) acetamido]penicillanic acid,
6β[2-(2-aminothiazol-4-yl)-(Z)-2-(cyclooctyloxyimino) acetamido]penicillanic acid,
6β-[2-(2-aminothiazol-4-yl)-(Z)-2-(endo-bicyclo[2.2.1]-hept-2-yloxyimino) acetamido]penicillanic acid,
6β-8-[2-(2-aminothiazol-4-yl)-(Z)-2-(trans-4-methylcyclohexyloxyimino) acetamido]penicillanic acid,
6β-[2-(2-aminothiazol-4-yl)-(Z)-2-(cis-4-methylcyclohexyloxyimino) acetamido]penicillanic acid,
6β-[2-(2-aminothiazol-4-yl)-(Z)-2-(tetrahydro-4H-pyran-4-yloxyimino) acetamido]penicillanic acid,
6β-[2-(2-aminothiazol-4-yl)-(Z)-2-(2-(1-(S)-6,6-dimethylbicyclo [3.1.1]hept-2-en-2-yl)ethoxyimino)acetamido]penicillanic acid,
6β-[2-(2-aminothiazol-4-yl)-(Z)-2-(cyclohexylmethoxyimino) acetamido]penicillanic acid,
6β-[2-(2-aminothiazol-4-yl)-(Z)-2-(n-butoxyimino) acetamido]penicillanic acid,
6β-[2-(2-aminothiazol-4-yl)-(Z)-2-(cyanomethoxyimino) acetamido]penicillanic acid,
6β-[2-(2-aminothiazol-4-yl)-(Z)-2-(trans-2-methylcyclohexyloxyimino) acetamido]penicillanic acid,
6β-[2-(2-aminothiazol-4-yl)-(Z)-2-(cyclohex-2-enyloxyimino) acetamido]penicillanic acid,
6β-[2-(2-aminothiazol-4-yl)-(Z)-2-(trans-4-t-butylcyclohexyloxyimino) acetamido]penicillanic acid,
6β-[2-(2-aminothiazol-4-yl)-(Z)-2-(trans-2-fluorocyclohexyloxyimino) acetamido]penicillanic acid,
6β-[2-(2-aminothiazol-4-yl)-(Z)-2-(2-pyrrolidon-3-yloxyimino) acetamido]penicillanic acid,
6β-[2-(2-aminothiazol-4-yl)-(Z)-2-(1-(R)-6,6-dimethylbicyclo [3.1.1]hept-2-en-2-yl)methoxyimino)acetamido]penicillanic acid, 6β-[2-(2-aminothiazol-4-yl)-(Z)-2-(1-carboxycyclohexyloxyimino) acetamido]penicillanic acid,
6β-[2-(2-aminothiazol-4-yl)-(Z)-2-(trans-4-(N,N-dimethylcarbamoyl) cyclohexyloxyimino)acetamido]penicillanic acid,
6β-[2-(2-aminothiazol-4-yl)-(Z)-2-(1-methoxycarbonyl-cyclohexyloxyimino) acetamido]penicillanic acid,
6β-[2-(2-aminothiazol-4-yl)-(Z)-2-(cis-3-methylcyclohexyloxyimino) acetamido]penicillanic acid,
6β-[2-(2-aminothiazol-4-yl)-(Z)-2-(trans-3-methylcyclohexyloxyimino) acetamido]penicillanic acid,
6β-[2-(2-aminothiazol-4-yl)-(Z)-2-(cis-4-acetoxycyclohexyloxyimino) acetamido]penicillanic acid,
6β-[2-(2-aminothiazol-4-yl)-(Z)-2-(trans-4-acetoxycyclohexyloxyimino) acetamido]penicillanic acid,
6β-[2-(2-aminothiazol-4-yl)-(Z)-2-((2S,4S)-2-carboxypyrrolidin-4-yloxyimino) acetamido]penicillanic acid,
6β-[2-(2-aminothiazol-4-yl)-(Z)-2-(4-oxocyclohexyloxyimino) acetamido]penicillanic acid,
6β-[2-(2-aminothiazol-4-yl)-(Z)-2-(4-methylenecyclohexyloxyimino) acetamido]penicillanic acid,
6β-[2-(2-aminothiazol-4-yl)-(Z)-2-(benzyloxyimino)acetamido]penicillanic acid,
6β-[2-(2-aminothiazol-4-yl)-(Z)-2-(cyclohexyloxyimino) acetamido]penicillanic acid,
6β-[2-(2-aminothiazol-4-yl)-(Z)-2-(tetrahydro-4H-thiopyran-4-yl oxyimino)acetamido]penicillanic acid,
6β-[2-(2-aminothiazol-4-y)-(Z)-2-(3-thietanyloxyimino) acetamido]penicillanic acid,
6β-[2-(2-aminothiazol-4-yl)-(Z)-2-4-methoxyiminocyclohexyloxyimino) acetamido]penicillanic acid,
6β-[2-(2-aminothiazol-4-yl)-(Z)-2-(cis-4-hydroxycyclohexyloxyimino) acetamido]penicillanic acid, and
6β-[2-(2-aminothiazol-4-yl)-(Z)-2-(1,1-dioxotetrahydro-4H-thiopyran-4-yloxyimino) acetamido]penicillanic acid, pharmaceutically, acceptable salts and in vivo hydrolysable esters thereof.

17. A method of treating bacterial infections in humans and animals which comprises administering to a human or animal in need thereof a antibacterially effective amount of a compound of the formula

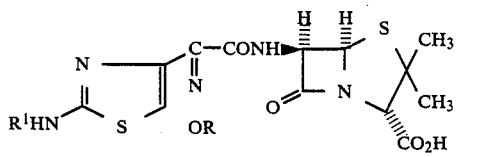

wherein $R^1$ is hydrogen or an amino protecting group and R is methyl substituted by carboxyl, esterified carboxy, carbonyl, hydroxy, alkoxy of 1 to 6 carbon atoms, alkoxyimino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; alkyl, alkenyl or alkynyl of 2 to 12 carbon atoms unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; carbocyclyl unsubstituted or substituted by 1 or more of the same or different substituents selected from the group consisting of alkyl of 1 to 6 carbon atoms, alkenyl of 2 to 6 carbon atoms, alkynyl of 2 to 6 carbon atoms or exo-methylene unsubstituted or substitued by one of the substitutents specified for the alkyl, alkenyl or alkynyl groups above, alkoxycarbonyl of 1 to 6 carbon atoms; oxo, hydroxy, alkoxyimino of 1 to 6 carbon atoms in the alkoxy moiety, oxyimino, alkoxy of 1 to 6 carbon atoms, cyano, carbamoyl, N-substituted carbamoyl, aryloxy, aralkoxy, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino, aryl, heterocyclyl and carbocyclyl; aryl unsubstituted or substituted by up to 5 of the same or different substituents selected from the group consisting of halo; alkyl of 1 to 6 carbon atoms unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; carbocyclyl; alkylthio of 1 to 6 carbon atoms; acylamino; phenyl; alkoxy of 1 to 6 carbon atoms; haloalkyl of 1 to 6 carbon atoms; hydroxy; amino; nitro; carboxy; carbamoyl; N-substituted carbamoyl; alkoxycarbonyl of 1 to 6 carbon atoms in the alkoxy moiety; alkoxycarbonylalkyl of 1 to 6 carbon atoms in each of the alkoxy and alkyl moieties; alkylcarbonyloxy of 1 to 6 carbon atoms in the alkyl moiety; alkylcarbonyl of 1 to 6carbon atoms in the alkyl moiety; and heterocyclyl; or R is heterocyclyl having at least one ring of up to four heterotoms selected from the group consisting of oxygen, nitrogen and sulphur, each ring being unsubstituted or substituted by up to 3 of the same or different substituents selected from the group consisting of halo, alkyl of 1 to 6 carbon atoms, carbocyclyl, alkylthio of 1 to 6 carbon atoms, acylamino, alkoxy of 1 to 6 carbon atoms, haloalkyl of 1 to 6 carbon atoms, hydroxy, amino, carboxy, carbamoyl, N-substituted carbamoyl, acyl, alkoxycarbonyl of 1 to 6 carbon atoms in the alkoxy moiety, alkoxycarbonylalkyl of 1 to 6 carbon atoms in each of the alkoxy and alkyl moieties, aryl and oxo, in combination with a pharmaceutically acceptable carrier.

18. A method according to claim 17 wherein R is carbocyclyl at least partly saturated unsubstituted or substituted by 1 or more of the same or different substituents selected from the group consisting of alkyl of 1 to 6 carbon atoms, unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino, of 1 to 6 carbon atoms in the alkoxy moiety, aralkoxycarbonylamino of 1 to 6 carbon atoms in the alkoxy moiety, aryl, heterocyclyl or carbocyclyl; alkenyl of 2 to 6 carbon atoms, unsubstituted or substituted by carboxyl, esterified carboxy, carbonyl, hydroxy, alkoxy of 1 to 6 carbon atoms, alkoxyamino of 1 to 6 carbon atoms, cyano, carbamoyl, aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino, of 1 to 6 carbon atoms in the alkoxy moiety, aralkoxycarbonylamino of 1 to 6 carbon atoms in the alkoxy moiety, aryl, heterocyclyl or carbocyclyl.

19. A method according to claim 18 wherein R is cycloalkyl or cycloalkenyl of 5 to 10 carbon atoms having between one and four rings, unsubstituted or substituted by one or more groups selected from the group consisting of carboxy, alkyl of 1 to 6 carbon atoms, unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; alkoxycarbonyl of 1 to 6 carbon atoms in the alkoxy moiety, alkoxyimino of 1 to 6 carbon atoms, alkoxy of 1 to 6 carbon atoms, hydroxy, halo, carbamoyl, mono- or di- alkyl carbamoyl of 1 to 6 carbon atoms in each alkyl moiety, acyloxy, exo-methylene unsubstituted or substituted by carboxyl, esterified carboxy, carbonyl, hydroxy, alkoxy of 1 to 6 carbon atoms, alkoxyamino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl, and oxo.

20. A method according to claim 17 wherein R is alkyl, alkenyl or alkynyl of 3 to 6 carbon atoms which is attached at a secondary or tertiary carbon atom thereof said moiety being unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino, of 1 to 6 carbon atoms in the alkoxy moiety, aralkoxycarbonylamino of 1 to 6 carbon atoms in the alkoxy moiety, aryl, heterocyclyl or carbocyclyl.

21. A method according to claim 17 wherein R is cyclopentyl, cyclohexyl, cycloheptyl, cyclooctyl, 4-methyl cyclohex-1-yl, 1-methylcyclohex-1-yl, bicyclo[2.2.2]oct-1-yl, endo-bicyclo[2.2.1]hept-2-yl, t-butyl, 4-t-butylcyclohex-1-yl, adamant-1-yl, tetrahydrothien-3-yl, 4-methylenecyclohex-1-yl, 4-oxocyclohex-1-yl, 1-methylcyclohept-1-yl, 1-methyl cyclopent-1-yl, 1-methylcyclopent-1-yl, 2-methylcyclohex-1-yl, 2-methoxycyclohex-1-y1,4-methoxycarbonylcyclohex-1-yl, 4-chlorocyclohex-1-yl, cyclohex-2-eny1,2-fluorocyclohex-1-yl, 1-carboxycyclohex-1-yl, 4-(N,N-dimethylcarbamoyl)cyclohex-1-yl, 1-methoxycarbonylcyclohex-1-yl, 3-methylcyclohex-1-yl, 4-acetoxycyclohex-1-yl, 4-methoxyiminocyclohex-1-yl, or 4-hydroxycyclohex-1-yl.

22. A method according to claim 17 wherein the is the syn-isomer of the formula (II):

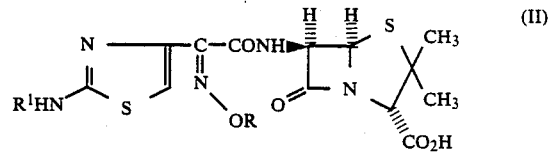

wherein R is methyl substituted by carboxyl, esterified carboxy, carbonyl, hydroxy, alkoxy of 1to 6 carbon atoms, alkoxyimino of 1 to 6 carbon atoms, cyano, carbamoyl, aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; alkyl, alkenyl or alkynyl of 2 to 12 carbon atoms unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, aryloxy, aralkoxy of 1 to 6 carbon atoms in the alkoxy moiety, mercapto, alkylthio of 1 to 6 carbon atoms in the alkyl moiety, arylthio, amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; and carbocyclyl unsubstituted or substituted by 1 or more of the same or different substituents selected from the group consisting of alkyl of 1 to 6 carbon atoms, alkenyl of 2 to 6 carbon atoms, alkynyl of 2 to 6 carbon atoms or exo-methylene unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; carboxyl; alkoxycarbonyl of 1 to 6 carbon atoms in the alkoxy moiety; oxo; hydroxy; alkoxyimino of 1 to 6 carbon atoms in the alkoxy moiety; oxyimino; alkoxy of 1 to 6 carbon atoms; cyano; carbamoyl; aryloxy; aralkoxy of 1 to 6 carbon atoms in the alkoxy moiety; mercapto; alkylthio of 1 to 6 carbon atoms in the alkyl moiety; arylthio; amino; halo; nitro; azido; formyl; acyl; acyloxy; phthalimido; acylamino; alkoxycarbonylamino of 1 to 6 carbon atoms in the alkoxy moiety; aralkoxycarbonylamino of 1 to 6 carbon atoms in the alkyl moiety; aryl; heterocyclyl; and carbocyclyl; aryl unsubstituted or substituted by up to five of the same or different substituents selected from the group consisting of alkyl of 1 to 6 carbon atoms, unsubstituted or substituted by carboxyl, esterified carboxy, carbonyl, hydroxy, alkoxy of 1 to 6 carbon atoms, alkoxyimino of 1 to 6 carbon atoms, cyano, carbamoyl, N-substituted carbamoyl, aryloxy, aralkoxy of 1 to 6 carbon atoms in the alkoxy moiety, mercapto, alkylthio of 1 to 6 carbon atoms in the alkyl moiety, arylthio, amino, substituted amino, halo, nitro, azido, formyl, acyl, acyloxy, phthalimido, acylamino, alkoxycarbonylamino of 1 to 6 carbon atoms in the alkoxy moiety, aralkoxycarbonylamino of 1 to 6 carbon atoms in the alkoxy moiety, aryl, heterocyclyl or carbocyclyl; carbocyclyl; alkylthio of 1 to 6 carbon atoms; acylamino; phenyl; alkoxy of 1 to 6 carbon atoms; haloalkyl of 1 to 6 carbon atoms; hydroxy; amino; nitro; carboxy; carbamoyl; alkoxycarbonyl of 1 to 6 carbon atoms in the alkoxy moiety; alkylcarbonylalkyl of 1 to 6 carbon atoms in each of the alkoxy and alkyl moieties; alkylcarbonyloxy of 1 to 6 carbon atoms in the alkyl moiety; alkylcarbonyl of 1 to 6 carbon atoms in the alkyl moiety; and heterocyclyl; or heterocyclyl having at least one ring of up to four heteroatoms selected from the group consisting of oxygen, nitrogen and sulphur, each ring being unsubstituted or substituted by up to 3 of the same or different substituents selected from the group consisting of halo, alkyl of 1 to 6 carbon atoms, carbocyclyl, alkylthio of 1 to 6 carbon atoms, acylamino, alkoxy of 1 to 6 carbon atoms, haloalkyl of 1 to 6 carbon atoms, hydroxy, amino, carboxy, carbamoyl, N-substituted carbamoyl, acyl, alkoxycarbonyl of 1 to 6 carbon atoms in the alkoxy moiety, alkoxycarbonylalkyl of 1 to 6 carbon atoms in each of the alkoxy and alkyl moieties, aryl and oxo and $R^1$ is hydrogen or an amino protecting group.

23. A method according to claim 17 wherein the compound is of the formula (III) or a pharmaceutically acceptable salt or in vivo hydrolysable ester thereof

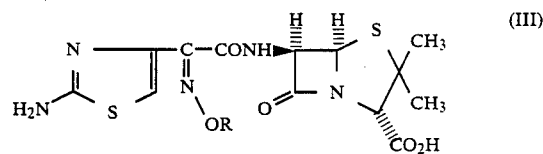

wherein R is cyclohexyl.

24. A method according to claim 17 wherein the compound is selected from the group consisting of
6β-[2-(2-Aminothiazol-4-yl)-(Z)-2-cyclopropylmethoxyiminoacetamido]penicillanic acid,
6β-[2-(2-aminothiazol-4-yl)-(Z)-2-ethoxyimino acetamido]penicillanic acid,
6β-[2-(2-aminothiazol-4-yl)-(Z)-2-propoxyimino acetamido]penicillanic acid,
6β-[(Z)-2-allyloxyimino-2-(2-aminothiazol-4-yl) acetamido]penicillanic acid,
6β-[2-(2-aminothiazol-4-yl)-(Z)-2-(iso-propyloxyimino) acetamido]penicillanic acid,
6β-[2-(2-aminothiazol-4-yl)-(Z)-2-(tertbutyloxyimino) acetamido]penicillanic acid.
6β-[(Z)-2-(adamant-1-yloxyimino)-2-(2-aminothiazol-4-yl) acetamido]penicillanic acid,
6β-[2-(2-aminothiazol-4-yl)-(Z)-2-(1-methylcyclohex-1-yloxyimino) acetamido]penicillanic acid,
6β-[2-(2-aminothiazol-4-yl)-(Z)2-[(1S,2S,5R) 5-methyl-2-isopropylcyclohex-1yl oxyimino)acetamido]penicillanic acid,
6β-[2-(2-aminothiazol-4-yl) -(Z)-2-(2-methylpropyloxyimino)acetamido]penicillanic acid,
6β-[2-(2-aminothiazol-4-yl)-(Z)-2-(indan-2-yloxyimino) acetamido]penicillanic acid,
6β-[2-(2-aminothiazol-4-yl)-(Z)-2-(tetrahydrothien-3-yloxyimino) acetamido]pencillanic acid,
6β-[2-(2-aminothazol-4-yl)-(Z)-2-(1-methylcyclohept-1-yloxyimino) acetamido]penicillanic acid,
6β-[2-(2-aminothiazol-4-yl)-(Z)-2-(bicyclo[2.2.2]oct-1-yloxyimino)acetamido]penicillanic acid,
6β-[2-(2-aminothiazol-4-yl)-(Z)-2-((1R,2R,5S)-5-methyl-2-isopropylcyclohex-1-yloxyimino)acetamido]penicillanic acid,
6β-[2-(2-aminothiazol-4-yl)-(Z)-2-(1-methylcyclopent-1-yloxyimino) acetamido]penicillanic acid,
6β-[2-(2-aminothiazol-4-yl)-(Z)-2-(1-(trans-4-methylcyclohexyl)-1-methylethoxyimino)acetamido]penicillanic acid,
6β-[2-(2-aminothiazol-4-yl)-(Z)-2-(3,3-dichloroprop-2-en-1-yloxyimino) acetamido]penicillanic acid,
6β-[2-(2-aminothiazol-4-yl)-(Z)-2-(1-carboxy-1-methylethoxyimino) acetamido]penicillanic acid,
6β-[2-(2-aminothiazol-4-yl)-(Z)-2-(carboxymethoxyimino) acetamido]penicillanic acid,
6β-[2-(2-aminothiazol-4-yl)-(Z)-2-(trans-2-methoxycyclohexyloxyimino) acetamido]penicillanic acid,
6β-[2-(2-aminothiazol-4-yl)-(Z)-2-(cis-2-methylcyclohexyloxyimino) acetamido]penicillanic acid,
6β-[2-(2-aminothiazol-4-yl)-(Z)-2-(trans-4-methoxycarbonylcyclohexyloxyimino) acetamido]penicillanic acid,
6β-[2-(2-aminothiazol-4-yl)-(Z)-2-(1,1-dioxotetrahydrothien-3-yloxyimino) acetamido]penicillanic acid,
6β-[2-(2-aminothiazol-4-yl)-(Z)-2-(decahydronapth-2-yloxyimino) acetamido]penicillanic acid,
6β-[2-(2-aminothiazol-4-yl)-(Z)-2-([R.S]-1-phenylethyloxyimino) acetamido]penicillanic acid, 6β-[2-(2-aminothiazol-4-yl)-(Z)-2-(2,6-dichlorobenzyloxyimino) acetamido]penicillanic acid,
6β-[2-(2-aminothiazol-4-yl)-(Z)-2-(trans-4-chlorocyclohexyloxyimino) acetamido]penicillanic acid,
6β-[2-(2-aminothiazol-4-yl)-(Z)-2-(cis-4-chlorocyclohexyloxyimino) acetamido]penicillanic acid,
6β-[2-(2-aminothiazol-4-yl)-(Z)-2-(phenoxyimino) acetamido]penicillanic acid,
6β-[2-(2-aminothiazol4-yl)-(Z)-2-(cyclopentyloxyimino) acetamido]penicillanic acid,
6β-[2-(2-aminothiazol-4-yl)-(Z)-2-(cycloheptyloxyimino) acetamido]penicillanic acid,
6β-[2-(2-aminothiazol-4-yl)-(Z)-2-(cyclooctyloxyimino) acetamido]penicillanic acid,
6β-[2-(2-aminothiazol-4-yl)-(Z)-2-(endo-bicyclo [2.2.1]-hept-2-yloxyimino)acetamido]penicillanic acid,
6β-[2-(2-aminothiazol-4-yl)-(Z)-2-(trans-4-methylcyclohexyloxyimino) acetamido]penicillanic acid,
6β-[2-(2-aminothiazol-4-yl)-(Z)-2-(cis-4-methylcyclohexyloxyimino) acetamido]penicillanic acid,
6β-[2-(2-aminothiazol-4-yl)-(Z)-2-(tetrahydro-4H-pyran-4-yloxyimino)acetamido]penicillanic acid,
6β-[2-(2-aminothiazol-4-yl)-(Z)-2-(2-(1-(S)-6,6-dimethylbicyclo [3.1.1]hept-2-en-2-yl)ethoxyimino)-acetamido]penicillanic acid,
6β-[2-(2-aminothiazol-4-yl)-(Z)-2-(cyclohexylmethoxyimino) acetamido]penicillanic acid,
6β-[2-(2-aminothiazol-4-yl)-(Z)-2-(n-butoxyimino)-acetamido]penicillanic acid,
6β-[2-(2-aminothiazol-4-yl)-(Z)-2-(n-butoxyimino)-acetamido]penicillanic acid,
6β-[2-(2-aminothiazol-4-yl)-(Z)-2-(cyanomethoxyimino) acetamido]penicillanic acid,
6β-[2-(2-aminothiazol-4-yl)-(Z)-2-(trans-2-methylcyclohexyloxyimino) acetamido]penicillanic acid,
6β-[2-(2-aminothiazol-4-yl)-(Z)-2-(cyclohex-2-enyloxyimino) acetamido]penicillanic acid,
6β-[2-(2-aminothiazol4-yl)-(Z)-2-(trans-4-t-butylcyclohexyloxyimino) acetamido]penicillanic acid,
68-[2-(2-aminothiazol-4-yl)-(Z)-2-(trans-2-fluorocyclohexyloxyimino) acetamido]penicillanic acid,
6β-[2-(2-aminothiazol-4-yl)-(Z)-2-(2-pyrrolidon-3-yloxyimino) acetamido]penicillanic acid,
6β-[2-(2-aminothiazol-4-yl)-(Z)-2-(1-(R)-6,6-dimethylbicyclo [3.1.1]hept-2-en-2-yl)methoxyimino) acetamido]penicillanic acid,
6β-[2-(2-aminothiazol-4-yl)-(Z)-2-(1-carboxycyclohexyloxyimino) acetamido]penicillanic acid,
6β-[2-(2-aminothiazol-4-yl)-(Z)-2-(trans-4-(N,N-dimethylcarbamoyl) cyclohexyloxyimino)acetamido]penicillanic acid,
6β-[2-(2-aminothiazol-4-yl)-(Z)-2-(1-methoxycarbonylcyclohexyloxyimino) acetamido]penicillanic acid,
6β-[2-(2-aminothiazol-4-yl)-(Z)-2-(cis-3-methylcyclohexyloxyimino) acetamido]penicillanic acid,
6β-[2-(2-aminothiazol-4-yl)-(Z)-2-(trans-3-methylcyclohexyloxyimino) acetamido]penicillanic acid,
6β-[2-(2-aminothiazol-4-yl)-(Z)-2-(cis-4-acetoxycyclohexyloxyimino) acetamido]penicillanic acid,
6β-[2-(2-aminothiazol-4-yl)-(Z)-2-(trans-4-acetoxycyclohexyloxyimino) acetamido]penicillanic acid,
6β-[2-(2-aminothiazol-4-yl)-(Z)-2-((2S,4S)-2-carboxypyrrolidin-4-yloxyimino) acetamido]penicillanic acid,
6β-[2-(2-aminothiazol-4-yl)-(Z)-2-(4-oxocyclohexyloxyimino) acetamido]penicillanic acid,
6β-[2-(2-aminothiazol-4-yl)-(Z)-2-(4-methylenecyclohexyloxyimino) acetamido]penicillanic acid,
6β-[2-(2-aminothiazol-4-yl)-(Z)-2-(benzyloxyimino) acetamido]penicillanic acid,
6β-[2-(2-aminothiazol-4-yl)-(Z)-2-(cyclohexyloxyimino) acetamido]penicillanic acid,
65-[2-(2-aminothiazol-4-yl)-(Z) 2-(tetrahydro-4H-thiopyran-4-yl oxyimino)acetamido]penicillanic acid,
6β-[2-(2-aminothiazol-4-yl)-(Z)-2-(3-thietanyloxyimino) acetamido]penicillanic acid,
6β-[2-(2-aminothiazol-4-yl)-(Z)-2-4-methoxyiminocyclohexyloxyimino) acetamido]penicillanic acid,
6β-[2-(2-aminothiazol-4-yl)-(Z)-2-(cis-4-hydroxycyclohexyloxyimino) acetamido]penicillanic acid, and
6β-[2-(2-aminothiazol-4-yl)-(Z)-2-(1,1-dioxotetrahydro-4H-thiopyran-4-yloxyimino)acetamido]penicillanic acid, pharmaceutically acceptable salts and in vivo hydrolysable esters thereof.

* * * * *